United States Patent
Miller et al.

(10) Patent No.: US 11,773,058 B2
(45) Date of Patent: *Oct. 3, 2023

(54) SULFONAMIDE CARBOXAMIDE COMPOUNDS

(71) Applicant: Inflazome Limited, Dublin (IE)

(72) Inventors: David Miller, Cambridge (GB); Angus MacLeod, Cambridge (GB); Jimmy Van Wiltenburg, Groningen (NL); Stephen Thom, Nottingham (GB); Stephen St-Gallay, Nottingham (GB); Jonathan Shannon, Nottingham (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/638,646

(22) PCT Filed: Aug. 15, 2018

(86) PCT No.: PCT/EP2018/072133
§ 371 (c)(1),
(2) Date: Feb. 12, 2020

(87) PCT Pub. No.: WO2019/034696
PCT Pub. Date: Feb. 21, 2019

(65) Prior Publication Data
US 2020/0331850 A1    Oct. 22, 2020

(30) Foreign Application Priority Data

Aug. 15, 2017 (GB) ..................... 1713079
Aug. 15, 2017 (GB) ..................... 1713082
(Continued)

(51) Int. Cl.
*C07C 311/55* (2006.01)
*C07D 205/04* (2006.01)
(Continued)

(52) U.S. Cl.
CPC .......... *C07C 311/55* (2013.01); *C07D 205/04* (2013.01); *C07D 205/12* (2013.01);
(Continued)

(58) Field of Classification Search
None
See application file for complete search history.

(56) References Cited

U.S. PATENT DOCUMENTS 2,979,437 A * 4/1961 McLamore et al. . C07D 333/08
514/332
4,723,991 A 2/1988 Holyoke, Jr. et al.
(Continued)

FOREIGN PATENT DOCUMENTS

CN  105906535 A * 8/2016 ............ A01N 25/32
CN  105906535 A   8/2016
(Continued)

OTHER PUBLICATIONS

Li et al., Journal of Agricultural and Food Chemistry (2005), 53(6), pp. 2202-2206. (Year: 2005).*
Moss et al., Pure & Appl. Chem., vol. 67, Nos. 8/9, pp. 1307-1375, 1995. (Year: 1995).*
Kessler et al., "Synthesis of N-substituted methanedisulfonamides and N'-substituted methanedisulfonylureas", Journal of Pharmaceutical Sciences, 50(10):842-844, (1961).
Luckhurst et al., "A convenient synthesis of sulfonylureas from carboxylic acids and sulfonamides via an in situ Curtius rearrangement", Tetrahedron Letters, 48(50):8878-8882, (2007).
WIPO Application No. PCT/EP2018/0721 33, PCT Internationai Preliminary Report on Patentability dated Feb. 27, 2020.
WIPO Application No. PCT/EP2018/072133, PCT Internationai Search Report dated Oct. 18, 2018.
(Continued)

*Primary Examiner* — Laura L Stockton
(74) *Attorney, Agent, or Firm* — Alston & Bird LLP

(57) ABSTRACT

The present invention relates to compounds of formula (I): Formula (I) wherein Q is selected from O or S; L is a saturated or unsaturated, optionally substituted $C_1$-$C_{12}$ hydrocarbylene group optionally including one or more heteroatoms N, O or S; $R^1$ is —$NR^3R^4$, —$OR^5$, —(C=$NR^6$)$R^7$, —(CO)$R^8$, —CN, —$N_3$, a quaternary ammonium group or an optionally substituted heterocycle; $R^3$, $R^4$, $R^5$, $R^6$, $R^7$ and $R^8$ are each independently hydrogen or a saturated or unsaturated, optionally substituted $C_1$-$C_{10}$ hydrocarbyl group optionally including one or more heteroatoms N, O or S; wherein optionally L and $R^3$, or L and $R^4$, or $R^3$ and $R^4$, or L and $R^5$, or L and $R^6$, or L and $R^7$, or $R^6$ and $R^7$, or L and $R^8$ together with the atom(s) to which they are attached may form a 3- to 12-membered, saturated or unsaturated, optionally substituted cyclic group; and $R^2$ is a cyclic group substituted at the a-position, wherein $R^2$ may optionally be further substituted; provided that the atom of L which is attached to the sulfur atom of the sulfonylurea group is a carbon atom and is not a ring atom of a heterocyclic or aromatic group. The present invention further relates to salts, solvates and prodrugs of such compounds, to pharmaceutical compositions comprising such compounds, and to the use of such compounds in the treatment and prevention of medical disorders and diseases, most especially by the inhibition of $NLRP_3$.

Formula (I)

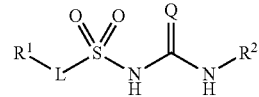

20 Claims, No Drawings

(30) Foreign Application Priority Data

| Aug. 15, 2017 | (GB) | 1713083 |
|---|---|---|
| Nov. 9, 2017 | (GB) | 1718561 |
| Nov. 9, 2017 | (GB) | 1718563 |
| Nov. 9, 2017 | (GB) | 1718564 |
| Dec. 22, 2017 | (GB) | 1721726 |
| Jul. 4, 2018 | (GB) | 1810983 |
| Jul. 26, 2018 | (GB) | 1812225 |

(51) Int. Cl.
C07D 205/12 (2006.01)
C07D 207/09 (2006.01)
C07D 211/24 (2006.01)
C07D 211/58 (2006.01)
C07D 213/34 (2006.01)
C07D 213/40 (2006.01)
C07D 231/12 (2006.01)
C07D 295/088 (2006.01)

(52) U.S. Cl.
CPC .......... C07D 207/09 (2013.01); C07D 211/24 (2013.01); C07D 211/58 (2013.01); C07D 213/34 (2013.01); C07D 213/40 (2013.01); C07D 231/12 (2013.01); C07D 295/088 (2013.01)

(56) References Cited

U.S. PATENT DOCUMENTS

| 4,725,679 | A | * | 2/1988 | Willms | C07D 295/092 540/546 |
|---|---|---|---|---|---|
| 4,802,908 | A | | 2/1989 | Hillemann | |
| 5,216,026 | A | | 6/1993 | Howbert | |
| 2016/0185815 | A1 | | 6/2016 | Wang et al. | |
| 2020/0216389 | A1 | * | 7/2020 | Miller | C07D 213/46 |
| 2020/0291003 | A1 | * | 9/2020 | Cooper | C07D 405/04 |
| 2020/0361895 | A1 | * | 11/2020 | Cooper | C07D 405/14 |

FOREIGN PATENT DOCUMENTS

| EP | 0125864 A1 | 11/1984 |
|---|---|---|
| EP | 0615859 A1 | 9/1994 |
| EP | 1236468 A1 | 9/2002 |
| JP | H 04-234353 A | 8/1992 |
| JP | 2000/053649 A | 2/2000 |
| WO | WO 1993/04046 A1 | 3/1993 |
| WO | WO 1998/032733 A1 | 7/1998 |
| WO | WO 2001/019390 A1 | 3/2001 |
| WO | WO 2002/06246 A1 | 1/2002 |
| WO | WO 2003/035076 A1 | 5/2003 |
| WO | WO 2006/085815 A1 | 8/2006 |
| WO | WO 2009/065096 A1 | 5/2009 |
| WO | WO 2009/086835 A1 | 7/2009 |
| WO | WO 2016/131098 A1 | 8/2016 |
| WO | WO 2016/187308 A1 | 11/2016 |
| WO | WO 2017/129897 A1 | 8/2017 |
| WO | WO 2017/140778 A1 | 8/2017 |
| WO | WO 2018/093579 A1 | 5/2018 |
| WO | WO 2018/097945 A1 | 5/2018 |
| WO | WO 2008/090382 A1 | 7/2018 |
| WO | WO 2018/136890 A1 | 7/2018 |
| WO | WO 2018/215818 A1 | 11/2018 |
| WO | WO 2019/008025 A1 | 1/2019 |
| WO | WO 2019/008029 A1 | 1/2019 |
| WO | WO 2019/034686 A1 | 2/2019 |
| WO | WO 2019/034688 A1 | 2/2019 |
| WO | WO 2019/034690 A1 | 2/2019 |
| WO | WO 2019/034692 A1 | 2/2019 |
| WO | WO 2019/034693 A1 | 2/2019 |
| WO | WO 2019/034696 A1 | 2/2019 |
| WO | WO 2019/034697 A1 | 2/2019 |
| WO | WO 2019/043610 A1 | 3/2019 |
| WO | WO 2019/068772 A1 | 4/2019 |
| WO | WO 2019/092170 A1 | 5/2019 |
| WO | WO 2019/092171 A1 | 5/2019 |
| WO | WO 2019/092172 A1 | 5/2019 |
| WO | WO 2019/166619 A1 | 9/2019 |
| WO | WO 2019/166621 A1 | 9/2019 |
| WO | WO 2019/166623 A1 | 9/2019 |
| WO | WO 2019/166624 A1 | 9/2019 |
| WO | WO 2019/166627 A1 | 9/2019 |
| WO | WO 2019/166628 A1 | 9/2019 |
| WO | WO 2019/166629 A1 | 9/2019 |
| WO | WO 2019/166632 A1 | 9/2019 |
| WO | WO 2019/166633 A1 | 9/2019 |
| WO | WO 2019/206871 A1 | 10/2019 |
| WO | WO 2019/211463 A1 | 11/2019 |
| WO | WO 2020/035464 A1 | 2/2020 |
| WO | WO 2020/035465 A1 | 2/2020 |
| WO | WO 2020/035466 A1 | 2/2020 |
| WO | WO 2020/079207 A1 | 4/2020 |
| WO | WO 2020/104657 A1 | 5/2020 |
| WO | WO 2020/208249 A1 | 10/2020 |
| WO | WO 2021/032588 A1 | 2/2021 |
| WO | Wo 2021/032591 A1 | 2/2021 |
| WO | WO 2021/043966 A1 | 3/2021 |
| WO | WO 2021/089768 A2 | 5/2021 |
| WO | WO 2021/089769 A1 | 5/2021 |
| WO | WO 2021/089776 A1 | 5/2021 |
| WO | WO 2021/089781 A1 | 5/2021 |
| WO | WO 2021/089782 A1 | 5/2021 |
| WO | WO 2021/089783 A1 | 5/2021 |

OTHER PUBLICATIONS

WIPO Application No. PCT/EP2018/072133, PCT Written Opinion of the International Searching Authority dated Oct. 18, 2018.

Baldwin et al., "Inhibiting the inflammasome: a chemical perspective", Journal of Medicinal Chemistry, 59(5): 1691-1710, (2016).

Brown, "Bioisosteres in Medicinal Chemistry" Published by Wiley-VCH Verlag GmbH & Co. KGaA, Weinheim, Germany, (2012).

CAS 210826-40-7; STN Entry Date: Sep. 3, 1998; CN Compound Name: 2-Furansulfonamide, N-[[(1,2,3,5,6,7-hexahydro-s-indacen-4-yl)amino]carbonyl]-4-(1-hydroxy-1-methylethyl)- (CA Index Name).

CAS 344752-79-0; STN Entry Date: Jul. 6, 2001; CN Compound Name: 2H-1-Benzopyran-8-sulfonamide, N-[[(2,4-dinitrophenyl)amino]carbonyl]-4a,8a-dihydro-4,5,7-trimethy1-2-oxo- (CA Index Name).

CAS 345942-69-0; STN Entry Date: Jul. 15, 2001; CN Compound Name: 2H-1-Benzopyran-8-sulfonamide, 4a,8a-dihydro-4,5,7-trimethyl-N-[[(2-methylphenyl)amino]carbonyl]-2-oxo- (CA Index Name).

CAS 345944-26-5; STN Entry Date: Jul. 15, 2001; CN Compound Name: 2H-1-Benzopyran-8-sulfonamide, N-[[(2,3-dibromophenyl)amino]carbonyl]-4a,8a-dihydro-4,5,7- trimethyl-2-oxo- (CA Index Name).

CAS 345944-27-6; STN Entry Date: Jul. 15, 2001; CN Compound Name: 2H-1-Benzopyran-8-sulfonamide, 4a,8a-dihydro-N-[[(2-methoxyphenyl)amino]carbonyl]-4,5,7-trimethyl-2-oxo- (CA Index Name).

CAS 345944-28-7; STN Entry Date: Jul. 15, 2001; CN Compound Name: 2H-1-Benzopyran-8-sulfonamide, N-[[(2,4-dichlorophenyl)amino]carbonyl]-4a,8a-dihydro-4,5,7-trimethyl-2-oxo- (CA Index Name).

Coll, "In their own words . . . 2012 IEIIS Young Investigator Awardees," Endotoxin Newsletter, vol. 19, No. 1, Editor Jerold Weiss, PhD, Dept. of Internal Medicine, University of Iowa, (Oct. 2013).

Coll, et al., "Correction: The Cytokine Release Inhibitory Drug CRID3 Targets ASC Oligomerisation in the NLRP3 and AIM2 Inflammasomes," PloS ONE, 6(12):e29539, (Feb. 27, 2013).

Coll, et al., "The Cytokine Release Inhibitory Drug CRID3 Targets ASC Oligomerisation in the NLRP3 and AIM2 Inflammasomes," PloS ONE, 6(12): e29539, (Dec. 2011).

Dalvie, et al., "Biotransformation Reactions of Five-Membered Aromatic Heterocyclic Rings," Chem. Res. Toxicol., 15(3): 269-299 (2002).

(56) References Cited

OTHER PUBLICATIONS

Dempsey, et al., "Cytokine release inhibitor drug, CRID3, inhibits the NLRP3 inflammasome in glia," Journal of Neuroimmunology, 275(1-2): 147, (2014).
Email from CAS Customer Center <help@cas.org>, Subject: RE: Case #00345503: question of indexing, Sent: Oct. 9, 2020.
Febbraio, "Role of interleukins in obesity: implications for metabolic disease," Trends in Endocrinology and Metabolism, 25(6): 312-319, (Jun. 2014).
Guo, et al., "Inflammasomes: mechanism of action, role in disease, and therapeutics," Nature Medicine, 21(7): 677-687, (Jul. 2015).
Haneklaus, et al., "Modulatory mechanisms controlling the NLRP3 inflammasome in inflammation: recent developments," Current Opinion in Immunology, 25(1): 40-45, (2013).
Li et al., Journal of Agricultural and Food Chemistry, 2005, 53(6): 2202-2206.
Mullen, et al., "Pattern recognition receptors as potential therapeutic targets in inflammatory rheumatic disease," Arthritis Research & Therapy, 17:122, (2015).
St Jean, et al., "Mitigating Heterocycle Metabolism in Drug Discovery," Journal of Medicinal Chemistry, 55: 6002-6020, (2012).
Stocks, et al., "On Chemistry, On Medical Chemistry," Published in Great Britain by Sci-Ink Limited, ISBN 978-0-9550072-3-1, pp. 214-215, (2007).
Balant, ed in Wolff et al. Burger's Medicinal Chemistry and drug discovery, 5th Ed., vol. 1. Principles and practice, pp. 949-982, 1995.
Banker, et al., Prodrugs, Modern Pharmaceutics, 3rd edition, Revised and Expanded, pp. 451 and 596.
Belikov, "Pharmaceutical chemistry", chapter 2.6 "The interconnection between chemical structure, properties of substances and their effect on the body", MEDpress-inform, Moscow, 2007, p. 27-29, Brief Statement of Relevance.
Bundgaard, Design of Prodrugs, Chapter 1, p. 1, 1985.
Disease—Wikipedia, retrieved from the internet on Feb. 2, 2022 at: https://en.wikipedia.org/wiki/Disease.
Ettmayer, et al., "Lessons learned from marketed and investigational prodrugs" J. Med. Chem., 47(10):2394-2404 (2004).
Han, "Targeted prodrug design to optimize drug delivery" AAPS Pharmsci. 2(1) Article 6: 1-11, (2000).
Hill et al., "Sulfonylureas as Concomitant Insulin Secretagogues and NLRP3 Inflammasome Inhibitors," ChemMedChem, 12, 1449-1457, (2017).
Himiceskij, Chemical Encyclopedia, (1983), p. 130-131, Brief Statement of Relevance.
Parajuli, et al., Prodrug as a novel approach of drug delivery—a review, Journal of Drug Delivery & Therapeutics, 2015, 5(3), pp. 5-9.
Silverman, Prodrugs and drug delivery systems, The organic chemistry of drug design and drug action, Chapter 8, pp. 352-400, 1992.
Solvation—Wikipedia, retrieved from the internet on Jan. 15, 2022 at: https://en.wikipedia.org/wiki/Solvation.
Stella, "Prodrugs as theraputics" Expert Opinion of theraputic patents, 14(3): 277-280 (2004).
Testa, "Prodrug Research: futile or fertile?" Biochemical Pharmacology, 68 (2004) 2097-2106.
Zawilska, et al., "Prodrugs: a challenge for the drug development," Pharmacological Reports, 2013, vol. 65, No. 1, pp. 1-14.
Alikhan, et al., "Hidradenitis suppurativa: A comprehensive review," J AM Acad Dermatol, vol. 60, No. 4, pp. 539-561, (Apr. 2009).
Allen, et al., "The NLRP3 inflammasome functions as a negative regulator of tumorigenesis during colitis-associated cancer," J Exp Med, vol. 207, No. 5, pp. 1045-1056, (Apr. 2010).
Amsler, et al., "The inflammasome as a target of moduiation by DNA viruses," Future Virol., 8(4), pp. 357-370, (2013).
Basiorka, et al., The NLRP3 inflammasome functions as a driver of the myelodysplastic syndrom phenotype, Blood, vol. 128, No. 25, pp. 2960-2975, (Dec. 2016).

Braddock et al., "Targeting IL-1 In Inflammatory Disease: New Opportunities for Thereapeutic Intervention," Nature Reviews, vol. 3, (Apr. 2004).
Cook, et al., "The NLRP3 inflammasome, a target for therapy in diverse disease states," Eur. J. Immunol, 40: 595-653, (2010).
Coll, et al., "A small-molecule inhibitor of the NLRP3 inflammasome for the treatment of inflammatory diseases", Nature Medicine, 21(3): 248-255, (2015).
Dempsey, et al, "Inhibiting the NLRP3 inflammasome with MCC950 promotes non-phlogistic clearance of amyloidβ and cognitive function in APP/PS1 mice," Brain, Behavior, and Immunity, 61, 306-316, (2017).
DeNardo, et al., "New Insights into Mechanisms Controlling the NLRP3 Inflammasome and Its Role in Lung Disease," the American Journal of Pathology, vol. 184, No. 1, pp. 42-54, (Jan. 2014).
Doyle, et al., "NLRP3 has a protective role in age-related macular degeneration through the induction of IL-18 by drusen componets," Nature Medicine, vol. 18, No. 5, pp. 791-498, (May 2012).
Duewell, et al., "NLRP3 inflammasomes are required for atherogenesis and activated by cholesterol crystals," Nature Letters, vol. 464, doi:10.1038/nature08938, (Apr. 2010).
Fang, et al., "Increased expression of NLRP3 inflammasome componets and interleukin-18 in patients with bullous pemphigoid," Journal of Dermatological Science, 83, 116-123, (2016).
Granata, et al., "NLRP3 Inflammasome Activation in Dialyzed Chronic Kidney Disease Patients," PLoS ONE, 10(3): e0122272, (2015).
Henao-Mejia, et al., "Inflammasome-mediated dysbiosis regulates progression of NAFLD and obesity," Nature, vol. 482, pp. 170-185, (Feb. 2012).
Hu, et al., "Inflammation-induced tumorigenesis in the colon is regulated by caspase-1 and NLR4," PNAS, vol. 107, No. 50, pp. 21635-21640, (Dec. 2010).
Huang, et al., "NLRP3 inflammasome activation promotes inflammation-induced carcinogenesis in head and neck squamous cell carcinoma," Journal of Experimental & Clinical Cancer Research, 36:116, (2017).
Iannitti, et al., "IL-1 receptor antagonist ameliorates inflammasome-dependent inflammation in murine and human cystic fibrosis," Nature Communications, 7:10791, doi:10.1038/ncomms10791, (Mar. 2016).
Inoue, et al., "The role of interferon-β in the treatment of multiple sclerosis and experimental autoimmune encephalomyelitis—in the perspective of inflammasomes," Immunology, 139, 11-18, (2013).
Jager, et al., "Key Role of NLrp3 Inflammasome Activation In Granduloma Generation of Sarcoidosis," AM J Respir Crit Care Med, 191, A5816, (2015).
Kim, et al., "Role for NLRP3 inflammasome-mediated, IL-1β-Dependent Responses in Severe, Steroid-Resistant Asthma," American Journal of Respiratory and Critical Care Medicine, vol. 196, No. 3, pp. 283-297, (Aug. 2017).
Lazaridis, et al., "Acitvation of NLRP3 Inflammasome in Inflammatory Bowel Disease: Differences Between Crohn's Disease and Ulcerative Colitis," Dig Dis Sci, 62:2348-2356, (2017).
Li, et al., "Dysregulation of the NLRP3 inflammasome complex and related cytokines in patients with multiple myeloma," Hematology, vol. 21, No. 3, pp. 144-151, (2016).
Li, et al., "Aging-related gene signature regulated by NLrp3 predicts glioma progression," Am J Cancer Res., 5(1) 442-449, (2015).
Loukovaara, et ai., "NLRP3 inflammasome activation is associated with proliferative diabetic retinopathy," Acta Ophthalmol, 95: 803-808, (2017).
Masters, "Specific inflammasomes in complex diseases," Clinical Immunology, http://dx.doi.org/10.1016/j.clim.2012.12.006, (2013).
Menu et al., "The NLRP3 inflammasome in health and disease: the good, the bad and the ugly," Clinical and Experimental Immunology, 166: 1-15, (Jun. 2011).
Mridha, et al., "NLRP3 inflammasome blockade reduces liver inflammation and fibrosis in experimenal NASH in mice," Journal of Hepatology, http://dx.doi.org/10.1016/j.jhep.2017.01.022, (2017).
Neudecker, et al., "Myeloid-derived miR-223 regulates intestinal inflammation via repression of the NLRP3 inflammasome," JEM,

(56) References Cited

OTHER PUBLICATIONS published online May 9, 2017 at http://doi.org/10.1084/jem.20160462, downloaded on (Jun. 2019).

Niebuhr, et al., "Impaired NLRP3 inflammasome expressison and function in atopic dermatitis due to Th2 milieu," Allergy, 69: 1058-1067, (2014).

Ozaki, et al., "Targeting the NLRP3 inflammasome in chronic inflammatory diseases: current perspectives," Journal of Inflammation Research, 8, 15-27, (Jan. 2015).

Primiano, et al., "Effiacy and Pharmacology of the NLRP3 Inflammasome Inhibitor CP-456,773 (CRID3) in Murine Models of Dermal and Plumonary Inflammation," The Journal of Immunology, 197: 2421-2433, (2016).

Puyang, et al., "Retinal Ganglion Cell Loss is Delayed Following Opti Nerve Crush in NLRP3 Knockout Mice," Scientific Reports, 6:20998, (Feb. 2016).

Qin, et al., "Propionibacterium acnes induces IL-1β secretion via the NLRP3 inflammasome in human monocytes," J Invest Dermatol, 134(2): 381-388, (Feb. 2014).

Ridker, et al., "Effect of interleukin-1β inhibition with canakinumab on incident lung cancer in patients with atherosclerosis: exploratory results from a randomised, double-blind, plaebo-controlled trial," Lancet, 390: 1833-42, (2017).

Sano, et al., "Tet2-Mediated Clonal Hematopoiesis Accelerates Heart Failure Through a Mechanism Involoving the IL-1β/NLRP3 Inflammasome," The Journal of the American College of Cardiology, vol. 71, No. 8, pp. 875-886, (Feb. 2018).

Schroder, et al., "The Inflammasomes," Cell, 140, 821-832, (Mar. 2010).

Scott, et al., "A randomised trial evaluating anakinra in early active rheumatoid arthritis," Clinical and Experimental Reheumatology, 34: 88-93, (2016).

Strowig, et al., "Inflammasomes in health and disease," Nature, vol. 481, pp. 278-286, (Jan. 2012).

Tarallo, et al., "DICER1 Loss and Alu RNA Induce Age-Related Macular Degeneration via the NLRP3 Inflammasome and MyD88," Cell, 149, 847-859, (May 2012).

vanHout, et al., "The selective NLRP3-inflammasome inhibitor MCC950 reduces infarct size and preserves cardiac function in a pig model of myocardial infarction," European Heart Journal, 38, 828-836, (2017).

Walsh, et al., "Inflammasomes in the CNS," Nature Reviews, vol. 15, pp. 84-97, (Feb. 2014).

Wang, et al., "Activation of NLRP3 inflammasome enhances the proliferation and migration of A549 lung cancer cells," Onccology Reports, 35: 2053-2064, (2016).

Wen, et al., "A role for the NLRP3 inflammasome in metabolic diseases—did Warburg miss inflammation?" Nature Immunology, vol. 13, No. 4, pp. 352-357, (Apr. 2012).

Wu, et al., "NLRP3 Nucleotide Oligomerization Domain-Like Receptor Family, Pyrin Domain Containing 3)-Caspase-1 Inflammasome Degrades Contractile Proteins," Arterioscler Thromb Vasc Biol., 37:694-706, (Apr. 2017).

Ridker, et al., "Antiinflammatory Therapy with Canakinumab for Atherosclerotic Disease," The New England Journal of Medicine, DOI:10.1056/NEJMoa1707914, (Aug. 2017).

* cited by examiner

SULFONAMIDE CARBOXAMIDE COMPOUNDS

CROSS-REFERENCE TO RELATED APPLICATION

This application is the US national stage of PCT/EP2018/072133 filed Aug. 15, 2018, which claims priority to GB 1713079.0 filed Aug. 15, 2017; GB 1713082.4 filed Aug. 15, 2017; GB 1713083.2 filed Aug. 15, 2017; GB 1718561.2 filed Nov. 9, 2017; GB 1718563.8 filed Nov. 9, 2017; GB 1718564.6 filed Nov. 9, 2017; GB 1721726.6 filed Dec. 22, 2017; GB 1810983.5 filed Jul. 4, 2018; and GB 1812225.9 filed Jul. 26, 2018.

FIELD OF THE INVENTION

The present invention relates to sulfonylureas and sulfonylthioureas comprising a hydrocarbyl group comprising at least one nitrogen or oxygen atom attached to the sulfur atom of the sulfonylurea group and an α-substituted cyclic group attached to the nitrogen atom of the urea group, and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NO-MID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlr3−/− mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/015445 A1 and WO 2018/136890 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

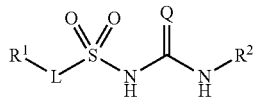

Formula (I)

wherein:
- Q is selected from O or S;
- L is a saturated or unsaturated $C_1$-$C_{12}$ hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;
- $R^1$ is —$NR^3R^4$, —$OR^5$, —$(C=NR^6)R^7$, —$(CO)R^8$, —CN, —$N_3$, a quaternary ammonium group or an optionally substituted heterocycle;
- $R^3$, $R^4$, $R^5$, $R^6$, $R^7$ and $R^8$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
- wherein optionally L and $R^3$, or L and $R^4$, or $R^3$ and $R^4$ together with the nitrogen atom to which they are attached may form a 3- to 12-membered saturated or unsaturated cyclic group, wherein the cyclic group may optionally be substituted;
- wherein optionally L and $R^5$ together with the oxygen atom to which they are attached may form a 3- to 12-membered saturated or unsaturated cyclic group, wherein the cyclic group may optionally be substituted;
- wherein optionally L and $R^6$, or L and $R^7$, or $R^6$ and $R^7$ together with the —(C=N)— group to which they are attached may form a 3- to 12-membered saturated or unsaturated cyclic group, wherein the cyclic group may optionally be substituted;
- wherein optionally L and $R^8$ together with the —(C=O)— group to which they are attached may form a 3- to 12-membered saturated or unsaturated cyclic group, wherein the cyclic group may optionally be substituted;
- $R^2$ is a cyclic group substituted at the α-position, wherein $R^2$ may optionally be further substituted;
- provided that the atom of L which is attached to the sulfur atom of the sulfonylurea group is a carbon atom and is not a ring atom of a heterocyclic or aromatic group.

The first aspect of the invention also provides a compound of formula (I):

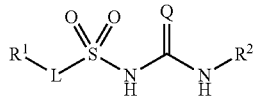

Formula (I)

wherein:
- Q is selected from O or S;
- L is a saturated or unsaturated $C_1$-$C_{12}$ hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;
- $R^1$ is —$NR^3R^4$, —$OR^5$, —$(C=NR^6)R^7$, —$(CO)R^8$, —CN or —$N_3$;
- $R^3$, $R^4$, $R^5$, $R^6$, $R^7$ and $R^8$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
- wherein optionally L and $R^3$, or L and $R^4$, or $R^3$ and $R^4$ together with the nitrogen atom to which they are attached may form a 3- to 12-membered saturated or unsaturated cyclic group, wherein the cyclic group may optionally be substituted;
- wherein optionally L and $R^5$ together with the oxygen atom to which they are attached may form a 3- to 12-membered saturated or unsaturated cyclic group, wherein the cyclic group may optionally be substituted;
- wherein optionally L and $R^6$, or L and $R^7$, or $R^6$ and $R^7$ together with the —(C=N)— group to which they are attached may form a 3- to 12-membered saturated or unsaturated cyclic group, wherein the cyclic group may optionally be substituted;
- wherein optionally L and $R^8$ together with the —(C=O)— group to which they are attached may form a 3- to 12-membered saturated or unsaturated cyclic group, wherein the cyclic group may optionally be substituted;
- $R^2$ is a cyclic group substituted at the α-position, wherein $R^2$ may optionally be further substituted;
- provided that the atom of L which is attached to the sulfur atom of the sulfonylurea group is a carbon atom and is not a ring atom of a heterocyclic or aromatic group.

In one embodiment the compound is not:

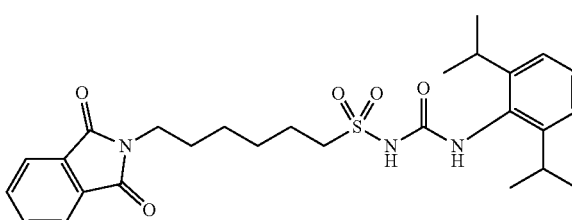

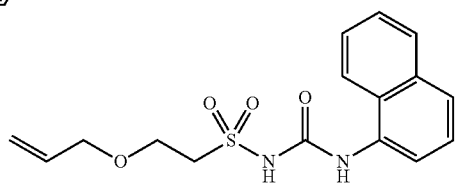

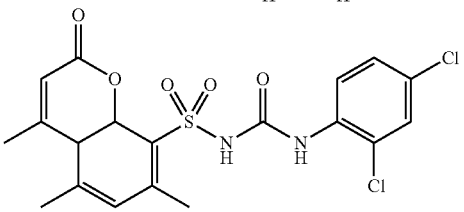

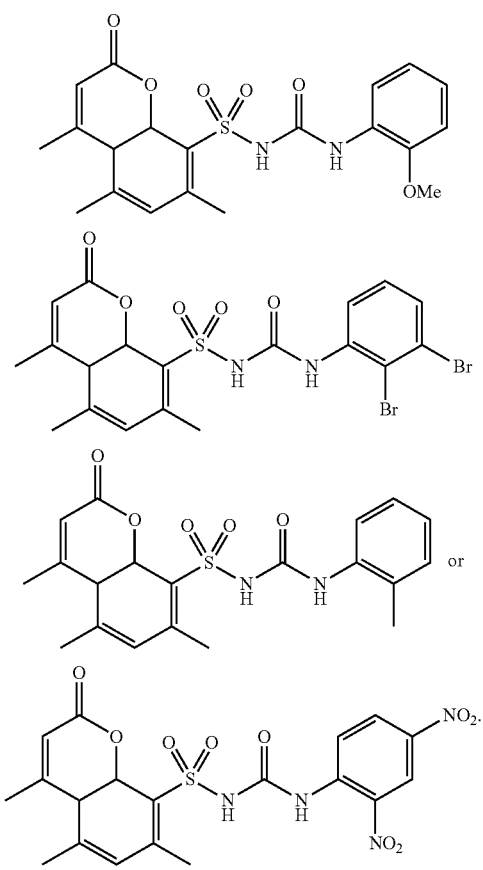

In one embodiment the compound is not:

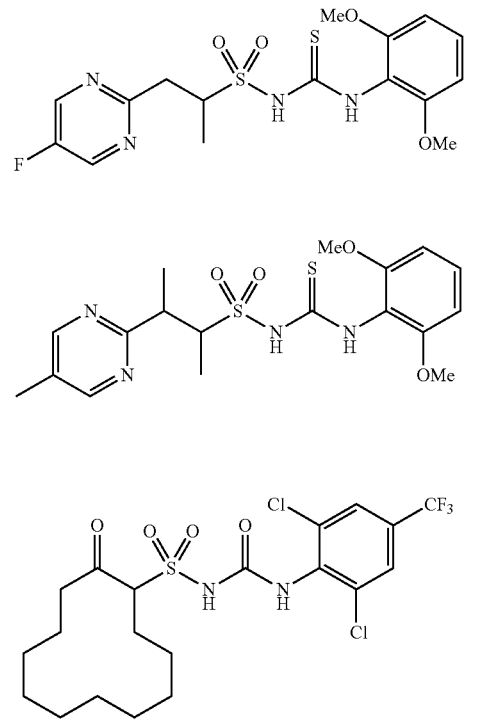

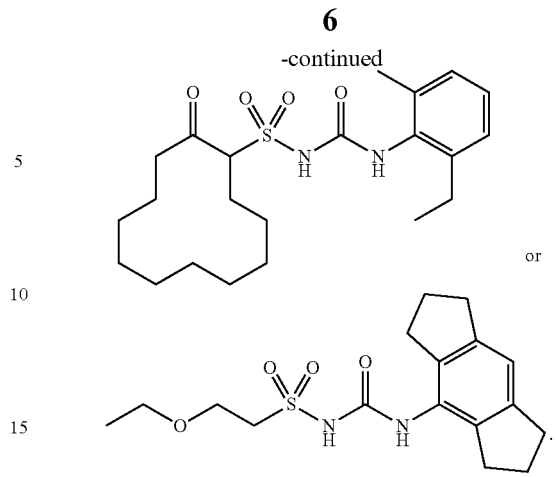

In one embodiment of the first aspect of the invention, there is provided a compound of formula (I):

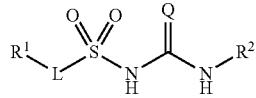

Formula (I)

wherein:
Q is selected from O or S;
L is a saturated or unsaturated $C_1$-$C_{12}$ hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;
$R^1$ is —$NR^3R^4$, —$OR^5$, —(C=$NR^6$)$R^7$, —(CO)$R^8$, —CN or —$N_3$;
$R^3$, $R^4$, $R^5$, $R^6$, $R^7$ and $R^8$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
wherein optionally L and $R^3$, or L and $R^4$, or $R^3$ and $R^4$ together with the nitrogen atom to which they are attached may form a 3- to 12-membered saturated or unsaturated cyclic group, wherein the cyclic group may optionally be substituted;
wherein optionally L and $R^5$ together with the oxygen atom to which they are attached may form a 3- to 12-membered saturated or unsaturated cyclic group, wherein the cyclic group may optionally be substituted;
wherein optionally L and $R^6$, or L and $R^7$, or $R^6$ and $R^7$ together with the —(C=N)— group to which they are attached may form a 3- to 12-membered saturated or unsaturated cyclic group, wherein the cyclic group may optionally be substituted;
wherein optionally L and $R^8$ together with the —(C=O)— group to which they are attached may form a 3- to 12-membered saturated or unsaturated cyclic group, wherein the cyclic group may optionally be substituted;

R² is a cyclic group substituted at the α and α' positions, wherein R² may optionally be further substituted;

provided that the atom of L which is attached to the sulfur atom of the sulfonylurea group is a carbon atom and is not a ring atom of a heterocyclic or aromatic group.

In one embodiment the compound is not:

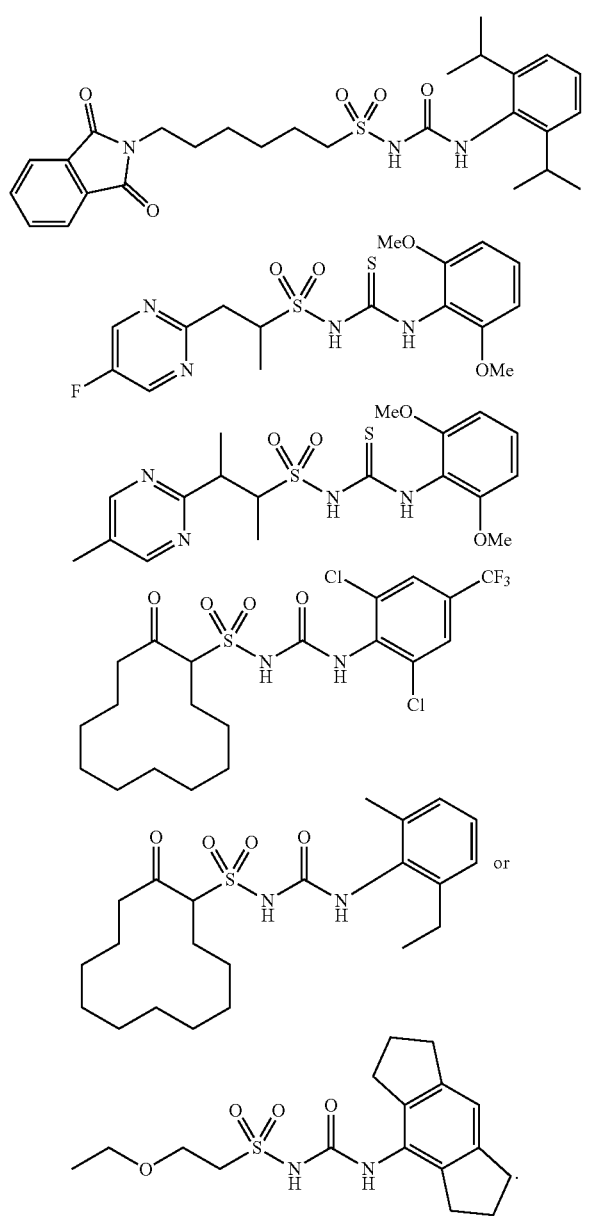

In another embodiment of the first aspect of the invention, there is provided a compound of formula (I):

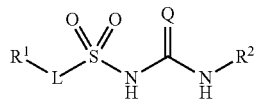

Formula (I)

wherein:
Q is selected from O or S;
L is a saturated or unsaturated $C_1$-$C_{12}$ hydrocarbylene group, wherein the hydrocarbylene group may be straight-chained or branched, or be or include cyclic groups, wherein the hydrocarbylene group may optionally be substituted, and wherein the hydrocarbylene group may optionally include one or more heteroatoms N, O or S in its carbon skeleton;
R¹ is —NR³R⁴, —OR⁵, —(C=NR⁶)R⁷, —(CO)R⁸, —CN or —N₃;
R³, R⁴, R⁵, R⁶, R⁷ and R⁸ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;
wherein optionally L and R³, or L and R⁴, or R³ and R⁴ together with the nitrogen atom to which they are attached may form a 3- to 12-membered saturated or unsaturated cyclic group, wherein the cyclic group may optionally be substituted;
wherein optionally L and R⁵ together with the oxygen atom to which they are attached may form a 3- to 12-membered saturated or unsaturated cyclic group, wherein the cyclic group may optionally be substituted;
wherein optionally L and R⁶, or L and R⁷, or R⁶ and R⁷ together with the —(C=N)— group to which they are attached may form a 3- to 12-membered saturated or unsaturated cyclic group, wherein the cyclic group may optionally be substituted;
wherein optionally L and R⁸ together with the —(C=O)— group to which they are attached may form a 3- to 12-membered saturated or unsaturated cyclic group, wherein the cyclic group may optionally be substituted;
R² is a cyclic group substituted at the α and α' positions, wherein R² may optionally be further substituted;
provided that the atom of L which is attached to the sulfur atom of the sulfonylurea group is a carbon atom and is not a ring atom of a cyclic group.

In one embodiment the compound is not:

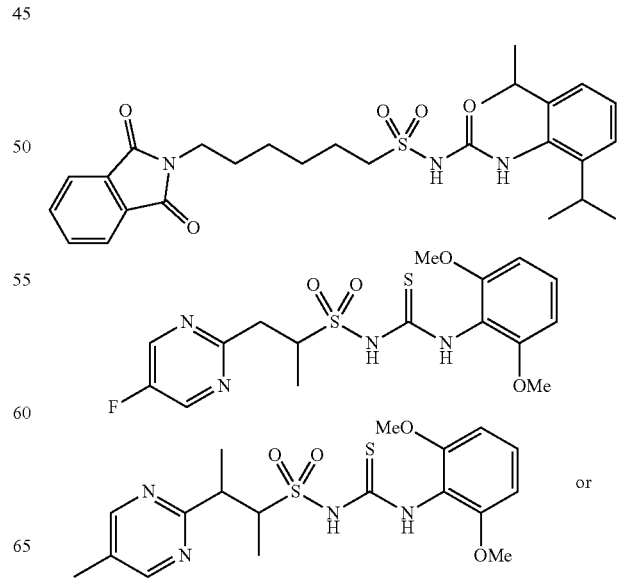

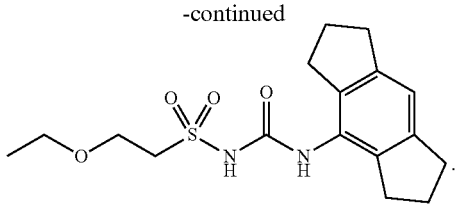

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{12}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be straight-chained or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl and thiomorpholinyl groups, typically such as azetidinyl, azetinyl, tetrahydrofuranyl, pyrrolidinyl, tetrahydrothiophenyl, tetrahydropyranyl, piperidinyl, piperazinyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

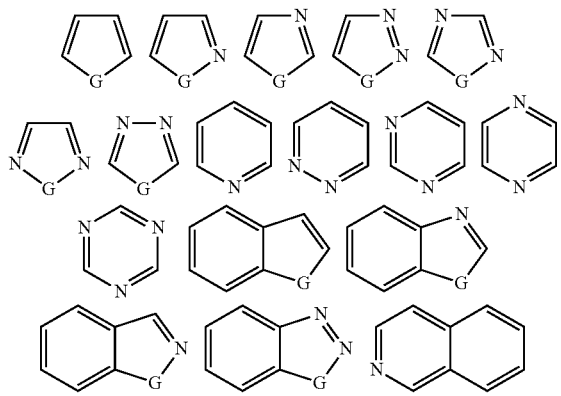

-continued

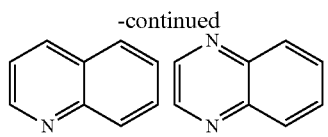

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:

(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or (ii) any two hydrogen atoms attached to the same atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)R$^\beta$ group, what is intended is:

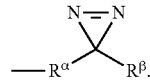

Typically, in an optionally substituted group or moiety:
(i) each hydrogen atom may optionally be replaced by a group independently selected from halo; —CN; —NO$_2$; —N$_3$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$; and/or (ii) any two hydrogen atoms attached to the same carbon atom may optionally be replaced by a π-bonded substituent independently selected from oxo (=O), =S, =NH or =NR$^β$; and/or
(iii) any two hydrogen atoms attached to the same or different atoms, within the same optionally substituted group or moiety, may optionally be replaced by a bridging substituent independently selected from —O—, —S—, —NH—, —N(R$^β$)— or —R$^α$—;
wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^β$ groups; and
wherein each —R$^β$ is independently selected from a C$_1$-C$_6$ alkyl, C$_2$-C$_6$ alkenyl, C$_2$-C$_6$ alkynyl or C$_2$-C$_6$ cyclic group, and wherein any —R$^β$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH or oxo (=O) groups.

Typically, in an optionally substituted group or moiety:
(i) each hydrogen atom may optionally be replaced by a group independently selected from halo; —CN; —NO$_2$; —N$_3$; —R$^β$; —OH; —OR$^β$; —SH; —SR$^β$; —SOR$^β$; —SO$_2$H; —SO$_2$R$^β$; —SO$_2$NH$_2$; —SO$_2$NHR$^β$; —SO$_2$N(R$^β$)$_2$; —R$^α$—SH; —R$^α$—SR$^β$; —R$^α$—SOR$^β$; —R$^α$—SO$_2$H; —R$^α$—SO$_2$R$^β$; —R$^α$—SO$_2$NH$_2$; —R$^α$—SO$_2$NHR$^β$; —R$^α$—SO$_2$N(R$^β$)$_2$; —NH$_2$; —NHR$^β$; —N(R$^β$)$_2$; —R$^α$—NH$_2$; —R$^α$—NHR$^β$; —R$^α$—N(R$^β$)$_2$; —CHO; —COR$^β$; —COOH; —COOR$^β$; —OCOR$^β$; —R$^α$—CHO; —R$^α$—COR$^β$; —R$^α$—COOH; —R$^α$—COOR$^β$; or —R$^α$—OCOR$^β$; and/or
(ii) any two hydrogen atoms attached to the same carbon atom may optionally be replaced by a π-bonded substituent independently selected from oxo (=O), =S, =NH or =NR$^β$; and/or
(iii) any two hydrogen atoms attached to the same or different atoms, within the same optionally substituted group or moiety, may optionally be replaced by a bridging substituent independently selected from —O—, —S—, —NH—, —N(R$^β$)— or —R$^α$—;
wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^β$ groups; and
wherein each —R$^β$ is independently selected from a C$_1$-C$_6$ alkyl, C$_2$-C$_6$ alkenyl, C$_2$-C$_6$ alkynyl or C$_2$-C$_6$ cyclic group, and wherein any —R$^β$ may optionally be substituted with one or more C$_1$-C$_4$ alkyl or halo groups.

Typically, in an optionally substituted group or moiety:
(i) each hydrogen atom may optionally be replaced by a group independently selected from halo; —CN; —NO$_2$; —N$_3$; —R$^β$; —OH; —OR$^β$; —SH; —SR$^β$; —SOR$^β$; —SO$_2$H; —SO$_2$R$^β$; —SO$_2$NH$_2$; —SO$_2$NHR$^β$; —SO$_2$N(R$^β$)$_2$; —R$^α$—SH; —R$^α$—SR$^β$; —R$^α$—SOR$^β$; —R$^α$—SO$_2$H; —R$^α$—SO$_2$R$^β$; —R$^α$—SO$_2$NH$_2$; —R$^α$—SO$_2$NHR$^β$; —R$^α$—SO$_2$N(R$^β$)$_2$; —NH$_2$; —NHR$^β$; —N(R$^β$)$_2$; —R$^α$—NH$_2$; —R$^α$—NHR$^β$; —R$^α$—N(R$^β$)$_2$; —CHO; —COR$^β$; —COOH; —COOR$^β$; —OCOR$^β$; —R$^α$—CHO; —R$^α$—COR$^β$; —R$^α$—COOH; —R$^α$—COOR$^β$; or —R$^α$—OCOR$^β$; and/or
(ii) any two hydrogen atoms attached to the same carbon atom may optionally be replaced by a π-bonded substituent independently selected from oxo (=O), =S, =NH or =NR$^β$; and/or
(iii) any two hydrogen atoms attached to the same or different atoms, within the same optionally substituted group or moiety, may optionally be replaced by a bridging substituent independently selected from —O—, —S—, —NH—, —N(R$^β$)— or —R$^α$—;
wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^β$ groups; and
wherein each —R$^β$ is independently selected from a C$_1$-C$_6$ alkyl, C$_2$-C$_6$ alkenyl, C$_2$-C$_6$ alkynyl or C$_2$-C$_6$ cyclic group, and wherein any —R$^β$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH or oxo (=O) groups.

Typically, in an optionally substituted group or moiety:
(i) each hydrogen atom may optionally be replaced by a group independently selected from halo; —CN; —NO$_2$; —N$_3$; —R$^β$; —OH; —OR$^β$; —SH; —SR$^β$; —SOR$^β$; —SO$_2$H; —SO$_2$R$^β$; —SO$_2$NH$_2$; —SO$_2$NHR$^β$; —SO$_2$N(R$^β$)$_2$; —R$^α$—SH; —R$^α$—SR$^β$; —R$^α$—SOR$^β$; —R$^α$—SO$_2$H; —R$^α$—SO$_2$R$^β$; —R$^α$—SO$_2$NH$_2$; —R$^α$—SO$_2$NHR$^β$; —R$^α$—SO$_2$N(R$^β$)$_2$; —NH$_2$; —NHR$^β$; —N(R$^β$)$_2$; —R$^α$—NH$_2$; —R$^α$—NHR$^β$; —R$^α$—N(R$^β$)$_2$; —CHO; —COR$^β$; —COOH; —COOR$^β$; —OCOR$^β$; —R$^α$—CHO; —R$^α$—COR$^β$; —R$^α$—COOH; —R$^α$—COOR$^β$; or —R$^α$—OCOR$^β$; and/or
(ii) any two hydrogen atoms attached to the same carbon atom may optionally be replaced by a π-bonded substituent independently selected from oxo (=O), =S, =NH or =NR$^β$; and/or
(iii) any two hydrogen atoms attached to the same or different atoms, within the same optionally substituted group or moiety, may optionally be replaced by a bridging substituent independently selected from —O—, —S—, —NH—, —N(R$^β$)— or —R$^α$—;
wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^β$ groups; and
wherein each —R$^β$ is independently selected from a C$_1$-C$_6$ alkyl, C$_2$-C$_6$ alkenyl, C$_2$-C$_6$ alkynyl or C$_2$-C$_6$ cyclic group, and wherein any —R$^β$ may optionally be substituted with one or more C$_1$-C$_4$ alkyl or halo groups.

Typically a substituted group comprises 1, 2, 3 or 4 substituents, more typically 1, 2 or 3 substituents, more typically 1 or 2 substituents, and more typically 1 substituent.

Unless stated otherwise, any divalent bridging substituent (e.g. —O—, —S—, —NH—, —N(R$^β$)—, —N(O)(R$^β$)—, —N$^+$(R$^β$)$_2$— or —R$^α$—) of an optionally substituted group or moiety (e.g. L) must only be attached to the specified group or moiety and may not be attached to a second group or moiety (e.g. R$^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

is replaced by

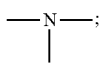

—CH$_2$— is replaced by —NH—, —O— or —S—;
—CH$_3$ is replaced by —NH$_2$—, —OH, or —SH;
—CH═ is replaced by —N═;
CH$_2$═ is replaced by NH═, O═ or S═; or
CH≡ is replaced by N≡;
provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:
—CH$_2$— is replaced by

or
—CH$_2$— is replaced by

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are counted as carbon atoms when calculating the number of carbon atoms in a $C_x$-$C_y$ group. For example, a morpholinyl group is to be considered a $C_6$ heterocyclic group, not a $C_4$ heterocyclic group.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group (C═O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

L is a saturated or unsaturated $C_1$-$C_{12}$ hydrocarbylene group, wherein the hydrocarbylene group may be straight-chained or branched, or be or include cyclic groups, wherein the hydrocarbylene group may optionally be substituted, and wherein the hydrocarbylene group may optionally include one or more (such as one, two or three) heteroatoms N, O or S in its carbon skeleton.

In one embodiment, L is a saturated or unsaturated $C_1$-$C_{10}$ hydrocarbylene group, wherein the hydrocarbylene group may be straight-chained or branched, or be or include cyclic groups, wherein the hydrocarbylene group may optionally include one heteroatom N, O or S in its carbon skeleton, and wherein the hydrocarbylene group may optionally be substituted with one or more substituents (such as one, two or three substituents) independently selected from halo, —CN, —N(R$^9$)$_2$, —OR$^9$ or oxo (═O) groups, wherein R$^9$ is independently selected from a hydrogen atom or a $C_1$-$C_3$ alkyl group.

In one embodiment, L is a saturated or unsaturated $C_1$-$C_8$ hydrocarbylene group, wherein the hydrocarbylene group may be straight-chained or branched, or be or include cyclic groups, and wherein the hydrocarbylene group may optionally be substituted with one or more substituents (such as one, two or three substituents) independently selected from halo, —CN, —N(R$^9$)$_2$, —OR$^9$ or oxo (═O) groups, wherein R$^9$ is independently selected from a hydrogen atom or a $C_1$-$C_3$ alkyl group.

In one embodiment, L is a saturated $C_1$-$C_6$ hydrocarbylene group, wherein the hydrocarbylene group may be straight-chained or branched, or be or include cyclic groups, and wherein the hydrocarbylene group may optionally be substituted with one or more substituents (such as one, two or three substituents) independently selected from halo, —CN, —N(R$^9$)$_2$, —OR$^9$ or oxo (═O) groups, wherein R$^9$ is independently selected from a hydrogen atom or a $C_1$-$C_3$ alkyl group.

In one embodiment, L is a saturated $C_1$-$C_5$ hydrocarbylene group, wherein the hydrocarbylene group may be straight-chained or branched, or be or include cyclic groups, and wherein the hydrocarbylene group may optionally be substituted with one or more substituents (such as one, two or three substituents) independently selected from halo, —CN, —N(R$^9$)$_2$, —OR$^9$ or oxo (═O) groups, wherein R$^9$ is independently selected from a hydrogen atom or a $C_1$-$C_3$ alkyl group.

In one embodiment, L is a saturated or unsaturated $C_1$-$C_{10}$ hydrocarbylene group, wherein the hydrocarbylene group may be straight-chained or branched, or be or include cyclic groups, and wherein the hydrocarbylene group does not include any heteroatoms in its carbon skeleton.

In one embodiment, L is a $C_1$-$C_{10}$ alkylene group which may be straight-chained or branched or be or include a cycloalkyl or cycloalkylene group. Typically, L is a $C_1$-$C_8$ alkylene group which may be straight-chained or branched or be or include a cycloalkyl or cycloalkylene group. Typically, L is a $C_1$-$C_6$ alkylene group which may be straight-chained or branched or be or include a cycloalkyl or cycloalkylene group. Typically, L is a $C_1$-$C_6$ alkylene group which may be straight-chained or branched or include a cycloalkyl or cycloalkylene group, wherein the atom of L which is attached to the sulfur atom of the sulfonylurea group is not a ring atom of any cyclic group.

In one embodiment, L is a $C_1$-$C_{12}$ arylalkylene group wherein $R^1$ may be attached to the aryl part or to the alkylene part of the arylalkylene group. Typically, L is a phenyl-($C_1$-$C_3$ alkylene)- group, wherein $R^1$ may be attached to the phenyl part or to the alkylene part of the phenyl-($C_1$-$C_3$ alkylene)- group.

In one embodiment, $R^1$ is —$NR^3R^4$, and the compound has the formula (IA):

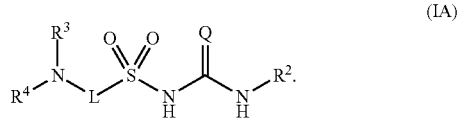

(IA)

$R^3$ and $R^4$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and optionally L and $R^3$, or L and $R^4$, or $R^3$ and $R^4$ together with the nitrogen atom to which they are attached may form a 3- to 12-membered saturated or unsaturated cyclic group, wherein the cyclic group may optionally be substituted, and wherein the cyclic group may optionally include one or more further heteroatoms N, O or S in its carbon skeleton.

In one embodiment, $R^3$ and $R^4$ are each independently hydrogen or a saturated or unsaturated $C_1$-$C_8$ hydrocarbyl group, wherein the hydrocarbyl group may be straight-chained or branched, or be or include cyclic groups, wherein the hydrocarbyl group may optionally include one heteroatom N, O or S in its carbon skeleton, and wherein the hydrocarbyl group may optionally be substituted with one or more substituents (such as one, two or three substituents) independently selected from halo, —CN, —$N(R^9)_2$, —$OR^9$ or oxo (═O) groups, wherein $R^9$ is independently selected from a hydrogen atom or a $C_1$-$C_3$ alkyl group.

In one embodiment, $R^3$ and $R^4$ are each independently selected from a hydrogen atom or a $C_1$-$C_6$ alkyl, $C_2$-$C_6$ alkenyl, $C_2$-$C_6$ alkynyl, —O($C_1$-$C_6$ alkyl), —CO($C_1$-$C_6$ alkyl), —COO($C_1$-$C_6$ alkyl), —CHO, $C_1$-$C_6$ cycloalkyl, phenyl or benzyl group, each of which may optionally be substituted with one or more substituents (such as one, two or three substituents) independently selected from halo, —CN, —$N(R^9)_2$, —$OR^9$ or oxo (═O) groups, wherein $R^9$ is independently selected from a hydrogen atom or a $C_1$-$C_3$ alkyl group.

In one embodiment, $R^3$ and $R^4$ are each independently hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group, each of which may optionally be substituted with one or more substituents (such as one, two or three substituents) independently selected from halo, —CN, —$N(R^9)_2$, —$OR^9$ or oxo (═O) groups, wherein $R^9$ is independently selected from a hydrogen atom or a $C_1$-$C_3$ alkyl group.

In one embodiment, L and $R^3$, or L and $R^4$, or $R^3$ and $R^4$ together with the nitrogen atom to which they are attached form a 3- to 7-membered saturated or unsaturated cyclic group, wherein the cyclic group may optionally include one or two further heteroatoms N, O or S in its carbon skeleton, and wherein the cyclic group may optionally be substituted with one or more substituents (such as one, two or three substituents) independently selected from halo, —CN, —$N(R^9)_2$, —$OR^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

In one embodiment, L and $R^3$, or L and $R^4$, or $R^3$ and $R^4$ together with the nitrogen atom to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —$N(R^9)_2$, —$OR^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

In one embodiment, $R^3$ and $R^4$ together with the nitrogen atom to which they are attached form a 4-, 5- or 6-membered saturated or unsaturated cyclic group selected from an azetidinyl, azetinyl, pyrrolidinyl, pyrazolidinyl, imidazolidinyl, piperidinyl, piperazinyl, morpholinyl, thiomorpholinyl or 6-oxa-2-azaspiro[3.4]octanyl group, each of which may optionally be substituted with one or two substituents independently selected from a halo, $C_1$-$C_6$ alkyl, $C_1$-$C_6$ haloalkyl, —CN, —$N(R^9)_2$, —$OR^9$ or saturated 4- to 6-membered heterocyclic group, wherein $R^9$ is independently selected from a hydrogen atom or a $C_1$-$C_3$ alkyl group.

In one embodiment, $R^3$ and $R^4$ together with the nitrogen atom to which they are attached form a 4-, 5- or 6-membered saturated cyclic group selected from an azetidinyl, pyrrolidinyl, piperidinyl or morpholinyl group, each of which may optionally be substituted with one or two substituents independently selected from a halo, $C_1$-$C_6$ alkyl, $C_1$-$C_6$ haloalkyl, —CN, —$N(R^9)_2$, —$OR^9$ or saturated 4- to 6-membered heterocyclic group, wherein $R^9$ is independently selected from a hydrogen atom or a $C_1$-$C_3$ alkyl group.

In one embodiment, $R^1$ is —$OR^5$, and the compound has the formula (IB):

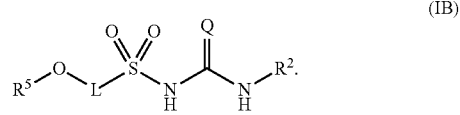

(IB)

$R^5$ is hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and optionally L and $R^5$ together with the oxygen atom to which they are attached may form a 3- to 12-membered saturated or unsaturated cyclic group, wherein the cyclic group may optionally be substituted, and wherein the cyclic group may optionally include one or more further heteroatoms N, O or S in its carbon skeleton.

In one embodiment, $R^5$ is hydrogen or a saturated or unsaturated $C_1$-$C_8$ hydrocarbyl group, wherein the hydrocarbyl group may be straight-chained or branched, or be or include cyclic groups, wherein the hydrocarbyl group may optionally include one heteroatom N, O or S in its carbon skeleton, and wherein the hydrocarbyl group may optionally be substituted with one or more substituents (such as one, two or three substituents) independently selected from halo, —CN, —N($R^9$)$_2$, —O$R^9$ or oxo (═O) groups, wherein $R^9$ is independently selected from a hydrogen atom or a $C_1$-$C_3$ alkyl group.

In one embodiment, $R^5$ is hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group, each of which may optionally be substituted with one or more substituents (such as one, two or three substituents) independently selected from halo, —CN, —N($R^9$)$_2$, —O$R^9$ or oxo (═O) groups, wherein $R^9$ is independently selected from a hydrogen atom or a $C_1$-$C_3$ alkyl group.

In one embodiment, $R^5$ is hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group. In one embodiment, $R^5$ is hydrogen or a $C_1$-$C_6$ alkyl group. In one embodiment, $R^5$ is a $C_1$-$C_3$ alkyl group.

In one embodiment, $R^5$ is not —CH$_2$CH$_2$OCH$_2$CH$_3$.

In one embodiment, L and $R^5$ together with the oxygen atom to which they are attached form a 3- to 7-membered saturated or unsaturated cyclic group, wherein the cyclic group may optionally include one or two further heteroatoms N, O or S in its carbon skeleton, and wherein the cyclic group may optionally be substituted with one or more substituents (such as one, two or three substituents) independently selected from halo, —CN, —N($R^9$)$_2$, —O$R^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

In one embodiment, L and $R^5$ together with the oxygen atom to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —N($R^9$)$_2$, —O$R^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

In one embodiment, $R^1$ is —(C═N$R^6$)$R^7$, and the compound has the formula (IC):

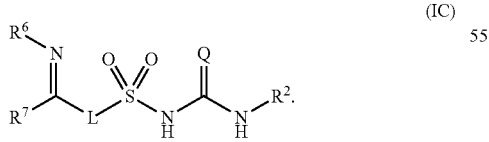

(IC)

$R^6$ and $R^7$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and optionally L and $R^6$, or L and $R^7$, or $R^6$ and $R^7$ together with the —(C═N)— group to which they are attached may form a 3- to 12-membered saturated or unsaturated cyclic group, wherein the cyclic group may optionally be substituted, and wherein the cyclic group may optionally include one or more further heteroatoms N, O or S in its carbon skeleton.

In one embodiment, $R^6$ and $R^7$ are each independently hydrogen or a saturated or unsaturated $C_1$-$C_8$ hydrocarbyl group, wherein the hydrocarbyl group may be straight-chained or branched, or be or include cyclic groups, wherein the hydrocarbyl group may optionally include one heteroatom N, O or S in its carbon skeleton, and wherein the hydrocarbyl group may optionally be substituted with one or more substituents (such as one, two or three substituents) independently selected from halo, —CN, —N($R^9$)$_2$, —O$R^9$ or oxo (═O) groups, wherein $R^9$ is independently selected from a hydrogen atom or a $C_1$-$C_3$ alkyl group.

In one embodiment, $R^6$ and $R^7$ are each independently hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group, each of which may optionally be substituted with one or more substituents (such as one, two or three substituents) independently selected from halo, —CN, —N($R^9$)$_2$, —O$R^9$ or oxo (═O) groups, wherein $R^9$ is independently selected from a hydrogen atom or a $C_1$-$C_3$ alkyl group.

In one embodiment, L and $R^6$, or L and $R^7$, or $R^6$ and $R^7$ together with the —(C═N)— group to which they are attached form a 3- to 7-membered saturated or unsaturated cyclic group, wherein the cyclic group may optionally include one or two further heteroatoms N, O or S in its carbon skeleton, and wherein the cyclic group may optionally be substituted with one or more substituents (such as one, two or three substituents) independently selected from halo, —CN, —N($R^9$)$_2$, —O$R^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

In one embodiment, L and $R^6$, or L and $R^7$, or $R^6$ and $R^7$ together with the —(C═N)— group to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —N($R^9$)$_2$, —O$R^9$, $C_1$-$C_3$ alkyl, $C_1$-$C_3$ alkylene or oxo (═O) groups, wherein $R^9$ is independently selected from a hydrogen atom or a $C_1$-$C_3$ alkyl group.

For example, L and $R^7$ together with the —(C═N$R^6$)— group to which they are attached may form a group

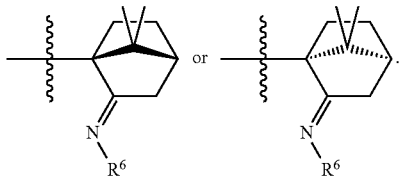

In one embodiment, $R^1$ is —(CO)$R^8$, and the compound has the formula (ID):

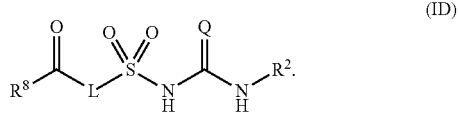

(ID)

$R^8$ is hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and optionally L and $R^8$ together with the —(C=O)— group to which they are attached may form a 3- to 12-membered saturated or unsaturated cyclic group, wherein the cyclic group may optionally be substituted, and wherein the cyclic group may optionally include one or more heteroatoms N, O or S in its carbon skeleton.

In one embodiment, $R^8$ is hydrogen or a saturated or unsaturated $C_1$-$C_8$ hydrocarbyl group, wherein the hydrocarbyl group may be straight-chained or branched, or be or include cyclic groups, wherein the hydrocarbyl group may optionally include one heteroatom N, O or S in its carbon skeleton, and wherein the hydrocarbyl group may optionally be substituted with one or more substituents (such as one, two or three substituents) independently selected from halo, —CN, —N($R^9$)$_2$, —OR$^9$ or oxo (=O) groups, wherein $R^9$ is independently selected from a hydrogen atom or a $C_1$-$C_3$ alkyl group.

In one embodiment, $R^8$ is hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group, each of which may optionally be substituted with one or more substituents (such as one, two or three substituents) independently selected from halo, —CN, —N($R^9$)$_2$, —OR$^9$ or oxo (=O) groups, wherein $R^9$ is independently selected from a hydrogen atom or a $C_1$-$C_3$ alkyl group.

In one embodiment, $R^8$ is hydrogen or a $C_1$-$C_6$ alkyl, —N($R^{19}$)$_2$ or —OR$^{19}$ group, wherein $R^{19}$ is independently selected from a hydrogen atom or a $C_1$-$C_3$ alkyl group.

In one embodiment, L and $R^8$ together with the —(C=O)— group to which they are attached form a 3- to 7-membered saturated or unsaturated cyclic group, wherein the cyclic group may optionally include one or two further heteroatoms N, O or S in its carbon skeleton, and wherein the cyclic group may optionally be substituted with one or more substituents (such as one, two or three substituents) independently selected from halo, —CN, —N($R^9$)$_2$, —OR$^9$, $C_1$-$C_3$ alkyl, $C_1$-$C_3$ alkylene or oxo (=O) groups, wherein $R^9$ is independently selected from a hydrogen atom or a $C_1$-$C_3$ alkyl group.

In one embodiment, L and $R^8$ together with the —(C=O)— group to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —N($R^9$)$_2$, —OR$^9$, $C_1$-$C_3$ alkyl, $C_1$-$C_3$ alkylene or oxo (=O) groups, wherein $R^9$ is independently selected from a hydrogen atom or a $C_1$-$C_3$ alkyl group.

For example, L and $R^8$ together with the —(C=O)— group to which they are attached may form a group

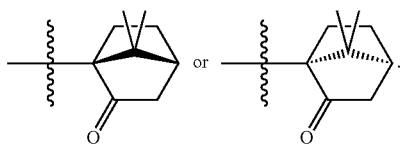 [SMILES: *[C@]12CC[C@H](CC1=O)C2(C)C ; *[C@@]12CC[C@@H](CC1=O)C2(C)C]

In one embodiment, $R^1$ is a quaternary ammonium group and the compound has the formula (IE):

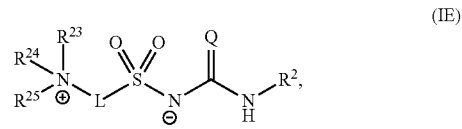

wherein $R^{23}$, $R^{24}$ and $R^{25}$ are each independently a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton, or wherein $R^{23}$ and $R^{24}$, or $R^{23}$ and $R^{25}$, or $R^{24}$ and $R^{25}$, or $R^{23}$ and $R^{24}$ and $R^{25}$, together with the nitrogen atom to which they are attached, form a cyclic group such as a saturated $C_5$-$C_8$ cyclic group.

In one embodiment, $R^{23}$, $R^{24}$ and $R^{25}$ are each independently a $C_1$-$C_6$ alkyl, $C_2$-$C_6$ alkenyl, $C_2$-$C_6$ alkynyl, $C_1$-$C_6$ cycloalkyl, phenyl or benzyl group. In one embodiment, $R^{23}$, $R^{24}$ and $R^{25}$ are each independently a $C_1$-$C_6$ alkyl group. In one embodiment, $R^{23}$, $R^{24}$ and $R^{25}$ are each methyl.

In one embodiment, $R^1$ is an optionally substituted heterocycle. In one embodiment, $R^1$ is an optionally substituted heterocycle comprising one, two or three heteroatoms N and/or O and no further heteroatoms in the ring structure. In one embodiment, $R^1$ is an optionally substituted monocyclic heterocycle comprising one, two or three heteroatoms N and/or O and no further heteroatoms in the ring structure. In one embodiment, $R^1$ is an optionally substituted heteroaryl group or an optionally substituted non-aromatic heterocyclic group.

In one embodiment, $R^1$ is an optionally substituted heterocycle selected from a diazirinyl, azetidinyl, azetinyl, oxetanyl, thietanyl, pyrrolidinyl, tetrahydrofuranyl, tetrahydrothiophenyl, pyrazolidinyl, imidazolidinyl, dioxolanyl, oxathiolanyl, piperidinyl, tetrahydropyranyl, thianyl, piperazinyl, dioxanyl, morpholinyl, thiomorpholinyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl or 6-oxa-2-azaspiro[3.4]octanyl group, each of which may optionally be substituted with one or two substituents independently selected from a halo, $C_1$-$C_6$ alkyl, —CN, —N($R^9$)$_2$, —OR$^9$ or saturated 4- to 6-membered heterocyclic group, wherein $R^9$ is independently selected from a hydrogen atom or a $C_1$-$C_3$ alkyl group.

In one embodiment, $R^1$ is an optionally substituted heterocycle selected from a diazirinyl, azetidinyl, azetinyl, oxetanyl, pyrrolidinyl, tetrahydrofuranyl, pyrazolidinyl, imidazolidinyl, dioxolanyl, oxathiolanyl, piperidinyl, tetrahydropyranyl, piperazinyl, dioxanyl, morpholinyl, thiomorpholinyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl or 6-oxa-2-azaspiro[3.4]octanyl group, each of which may optionally be substituted with one or two substituents independently selected from a halo, $C_1$-$C_6$ alkyl, —CN, —N($R^9$)$_2$, —OR$^9$ or saturated 4- to 6-membered heterocyclic group, wherein $R^9$ is independently selected from a hydrogen atom or a $C_1$-$C_3$ alkyl group.

In one embodiment, $R^1$ is an optionally substituted heterocycle selected from a diazirinyl, azetidinyl, pyrrolidinyl, piperidinyl, morpholinyl, pyridinyl, pyrazolyl or 6-oxa-2-azaspiro[3.4]octanyl group, each of which may optionally be substituted with one or two substituents independently selected from a halo, $C_1$-$C_6$ alkyl, —CN, —N($R^9$)$_2$, —OR$^9$ or saturated 4- to 6-membered heterocyclic group, wherein $R^9$ is independently selected from a hydrogen atom or a $C_1$-$C_3$ alkyl group.

The atom of L which is attached to the sulfur atom of the sulfonylurea group is a carbon atom and is not a ring atom of a heterocyclic or aromatic group. In one embodiment, the atom of L which is attached to the sulfur atom of the sulfonylurea group is a carbon atom and is not a ring atom of a heterocyclic group, an aromatic group, or a spiro cyclic group. In one embodiment, the atom of L which is attached to the sulfur atom of the sulfonylurea group is a carbon atom and is not a ring atom of any cyclic group.

In one embodiment, L is attached to the sulfur atom of the sulfonylurea group by a —CH$_2$— group. For the avoidance of doubt, it is noted that this —CH$_2$— group is a part of L.

In one aspect of any of the above embodiments, -L-NR$^3$R$^4$, -L-OR$^5$, -L-(C=NR$^6$)R$^7$ or -L-(CO)R$^8$ contains from 2 to 30 atoms other than hydrogen, more typically from 3 to atoms other than hydrogen, more typically from 4 to 20 atoms other than hydrogen.

In one aspect of any of the above embodiments, where $R^1$ is a quaternary ammonium group or an optionally substituted heterocycle, -L-R$^1$ contains from 2 to 30 atoms other than hydrogen, more typically from 3 to 25 atoms other than hydrogen, more typically from 4 to 20 atoms other than hydrogen.

In one aspect of any of the above embodiments, -L-R$^1$ contains from 2 to 30 atoms other than hydrogen. More typically, -L-R$^1$ contains from 2 to 25 atoms other than hydrogen. More typically, -L-R$^1$ contains from 2 to 20 atoms other than hydrogen.

$R^2$ is a cyclic group substituted at the α-position, wherein $R^2$ may optionally be further substituted. For the avoidance of doubt, it is noted that it is a ring atom of the cyclic group of $R^2$ that is directly attached to the nitrogen atom of the urea or thiourea group, not any substituent.

As used herein, the nomenclature α, β, α', β' refers to the position of the atoms of a cyclic group, such as —R$^2$, relative to the point of attachment of the cyclic group to the remainder of the molecule. For example, where —R$^2$ is a 1,2,3,5,6,7-hexahydro-s-indacen-4-yl moiety, the α, β, α' and β' positions are as follows:

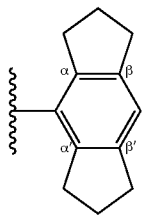 [SMILES: *c1c2c(cc3c1CCC3)CCC2]

For the avoidance of doubt, where it is stated that a cyclic group, such as an aryl or a heteroaryl group, is substituted at the α and/or α' positions, it is to be understood that one or more hydrogen atoms at the α and/or α' positions respectively are replaced by one or more substituents, such as any optional substituent as defined above. Unless stated otherwise, the term 'substituted' does not include the replacement of one or more ring carbon atoms by one or more ring heteroatoms.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is a phenyl or a 5- or 6-membered heteroaryl group, wherein the phenyl or the heteroaryl group is substituted at the α-position, and wherein $R^2$ may optionally be further substituted. Typically, $R^2$ is an aryl or a heteroaryl group, wherein the aryl or the heteroaryl group is substituted at the α and α' positions, and wherein $R^2$ may optionally be further substituted. Typically, $R^2$ is a phenyl or a 5- or 6-membered heteroaryl group, wherein the phenyl or the heteroaryl group is substituted at the α and α' positions, and wherein $R^2$ may optionally be further substituted. For example, $R^2$ may be a phenyl group substituted at the 2- and 6-positions or a phenyl group substituted at the 2-, 4- and 6-positions.

In one embodiment, the parent phenyl or 5- or 6-membered heteroaryl group of $R^2$ may be selected from phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl. Typically, the parent phenyl or 5- or 6-membered heteroaryl group of $R^2$ may be selected from phenyl, pyridinyl, pyridazinyl, pyrimidinyl, pyrrolyl, pyrazolyl, imidazolyl or triazolyl. Typically, the parent phenyl or 5- or 6-membered heteroaryl group of $R^2$ may be selected from phenyl, pyridinyl, pyridazinyl, pyrimidinyl or pyrazolyl.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions of the parent cyclic group of $R^2$ may be independently selected from —R$^δ$, —OR$^δ$ or —COR$^δ$ groups, wherein each R$^δ$ is independently selected from a $C_1$-$C_6$ alkyl, $C_2$-$C_6$ alkenyl, $C_2$-$C_6$ alkynyl or $C_2$-$C_6$ cyclic group and wherein each R$^δ$ is optionally further substituted with one or more halo groups. More typically, the substituents at the α and/or α' positions are independently selected from alkyl or cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the aryl or heteroaryl group across the α,β positions.

Typically, the aryl or heteroaryl group is also substituted at the α' position, for example with a substituent selected from —R$^{43}$, —OR$^{43}$ and —COR$^{43}$, wherein each R$^{43}$ is independently selected from a C$_1$-C$_6$ alkyl, C$_2$-C$_6$ alkenyl, C$_2$-C$_6$ alkynyl or C$_2$-C$_6$ cyclic group and wherein each R$^{43}$ is optionally further substituted with one or more halo groups. Typically in such an embodiment, R$^2$ is bicyclic or tricyclic.

More typically, R$^2$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein R$^2$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure. Typically, the phenyl or the 5- or 6-membered heteroaryl group is also substituted at the α' position, for example with a substituent selected from —R$^{43}$, —OR$^{43}$ and —COR$^{43}$, wherein each R$^{43}$ is independently selected from a C$_1$-C$_6$ alkyl, C$_2$-C$_6$ alkenyl, C$_2$-C$_6$ alkynyl or C$_2$-C$_6$ cyclic group and wherein each R$^{43}$ is optionally further substituted with one or more halo groups. Typically in such an embodiment, R$^2$ is bicyclic or tricyclic.

In another embodiment, R$^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein R$^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, R$^2$ is tricyclic.

In yet another embodiment, R$^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein R$^2$ may optionally be further substituted. Typically in such an embodiment, R$^2$ is tricyclic.

More typically, R$^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α',β' positions so as to form a second 4- to 6-membered fused ring structure, wherein R$^2$ may optionally be further substituted. Typically in such an embodiment, R$^2$ is tricyclic.

In one embodiment, —R$^2$ has a formula selected from:

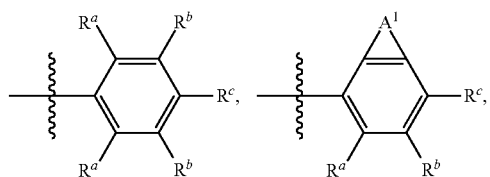

-continued

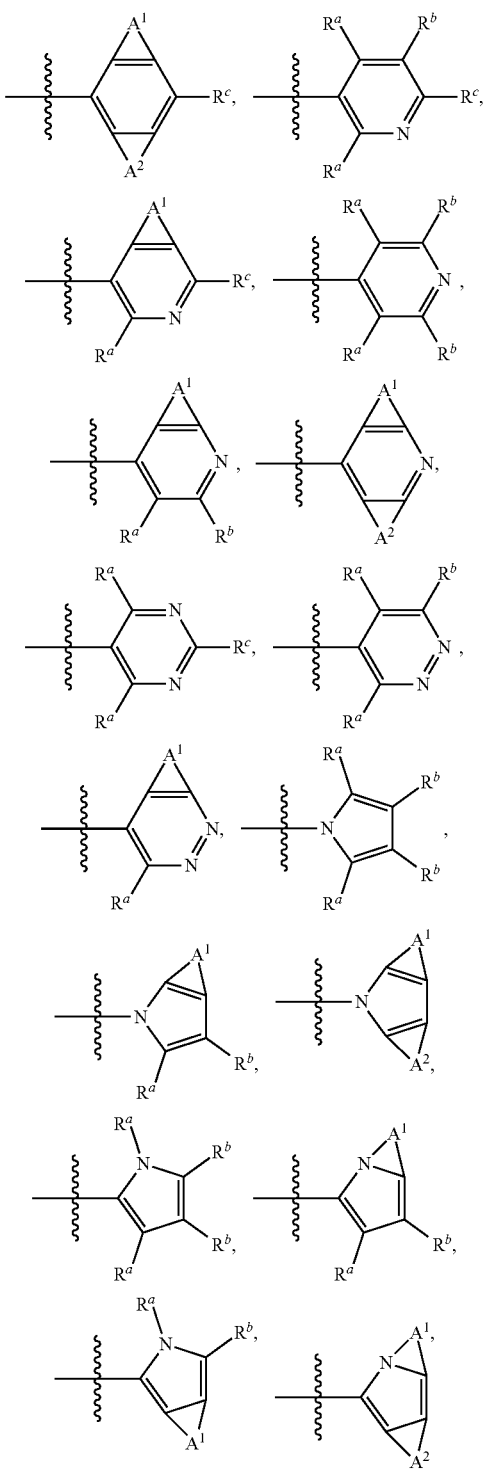

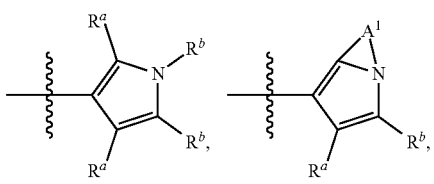

wherein:
A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S;
each R$^a$ is independently selected from —R$^{aa}$, —OR$^{aa}$ or —COR$^{aa}$;
each R$^b$ is independently selected from hydrogen, halo, —NO$_2$, —CN, —R$^{aa}$, —OR$^{aa}$ or —COR$^{aa}$;
provided that any R$^a$ or R$^b$ that is directly attached to a ring nitrogen atom is not halo, —NO$_2$, —CN or —OR$^{aa}$;
each R$^c$ is independently selected from hydrogen, halo, —OH, —NO$_2$, —CN, —R$^{cc}$, —OR$^{cc}$, —COR$^{cc}$, —COOR$^{cc}$, —CONH$_2$, —CONHR$^{cc}$ or —CON(R$^{cc}$)$_2$;
each R$^{aa}$ is independently selected from a C$_1$-C$_6$ alkyl, C$_2$-C$_6$ alkenyl, C$_2$-C$_6$ alkynyl or a 3- to 7-membered cyclic group, wherein each R$^{aa}$ is optionally substituted; and
each R$^{cc}$ is independently selected from a C$_1$-C$_6$ alkyl, C$_2$-C$_6$ alkenyl, C$_2$-C$_6$ alkynyl or a 3- to 7-membered cyclic group, or any two R$^{cc}$ attached to the same nitrogen atom may, together with the nitrogen atom to which they are attached, form a 3- to 7-membered heterocyclic group, wherein each R$^{cc}$ is optionally substituted.

Typically, any ring containing A$^1$ or A$^2$ is a 5- or 6-membered ring. Typically, A$^1$ and A$^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A$^1$ and A$^2$ are each independently selected from an optionally substituted straight-chained alkylene group, wherein one carbon atom in the backbone of the alkylene group may optionally be replaced by an oxygen atom. Typically, no heteroatom in A$^1$ or A$^2$ is directly attached to another ring heteroatom. Typically, A$^1$ and A$^2$ are unsubstituted or substituted with one or more substituents independently selected from halo, —OH, —CN, —NO$_2$, C$_1$-C$_4$ alkyl, C$_1$-C$_4$ haloalkyl, —O(C$_1$-C$_4$ alkyl) or —O(C$_1$-C$_4$ haloalkyl). More typically, A$^1$ and A$^2$ are unsubstituted or substituted with one or more fluoro and/or chloro groups. Where R$^2$ contains both A and A$^2$ groups, A$^1$ and A$^2$ may be the same or different. Typically, A$^1$ and A$^2$ are the same.

Where R$^{aa}$ is a substituted C$_1$-C$_6$ alkyl, C$_2$-C$_6$ alkenyl or C$_2$-C$_6$ alkynyl group, typically the C$_1$-C$_6$ alkyl, C$_2$-C$_6$ alkenyl or C$_2$-C$_6$ alkynyl group is substituted with one or more (e.g. one or two) substituents independently selected from halo, —OH, —CN, —NO$_2$, —O(C$_1$-C$_4$ alkyl) or —O(C$_1$-C$_4$ haloalkyl).

Where R$^{aa}$ is a substituted 3- to 7-membered cyclic group, typically the 3- to 7-membered cyclic group is substituted with one or more (e.g. one or two) substituents independently selected from halo, —OH, —NH$_2$, —CN, —NO$_2$, —B$^1$, —OB$^1$, —NHB$^1$, —N(B$^1$)$_2$, —CONH$_2$, —CONHB$^1$, —CON(B$^1$)$_2$, —NHCOB$^1$, —NB$^1$COB$^1$, or —B$^{11}$—;
  wherein each B$^1$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B$^1$ may optionally be halo-substituted and/or substituted with one or two substituents independently selected from —OH, —NH$_2$, —OB$^{12}$, —NHB$^{12}$ or —N(B$^{12}$)$_2$;
  wherein each B$^{11}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and
  wherein each B$^{12}$ is independently selected from a C$_1$-C$_3$ alkyl or C$_1$-C$_3$ haloalkyl group. Typically, any divalent group —B$^{11}$— forms a 4- to 6-membered fused ring.

Typically, each R$^a$ is —R$^{aa}$. More typically, each R$^a$ is independently selected from a C$_1$-C$_6$ alkyl (in particular C$_3$-C$_6$ branched alkyl) or C$_3$-C$_6$ cycloalkyl group, wherein each R$^a$ is optionally further substituted with one or more halo groups. More typically, each R$^a$ is independently selected from a C$_1$-C$_4$ alkyl, C$_1$-C$_4$ haloalkyl, C$_3$-C$_4$ cycloalkyl or C$_3$-C$_4$ halocycloalkyl group. Where a group R$^a$ is present at both the α- and α'-positions, each R$^a$ may be the same or different. Typically, each R$^a$ is the same.

Typically, each R$^b$ is independently selected from hydrogen or halo. More typically, each R$^b$ is hydrogen.

Typically, each $R^c$ is independently selected from hydrogen, halo, —OH, —NO$_2$, —CN, —R$^{cc}$ or —OR$^{cc}$. More typically, each $R^c$ is independently selected from hydrogen, halo, —CN, C$_1$-C$_3$ alkyl, C$_1$-C$_3$ haloalkyl, cyclopropyl or halocyclopropyl. Most typically, each $R^c$ is independently selected from hydrogen or halo.

Typically, each $R^{cc}$ is independently selected from a C$_1$-C$_4$ alkyl or C$_3$-C$_6$ cycloalkyl group, or any two $R^{cc}$ attached to the same nitrogen atom may, together with the nitrogen atom to which they are attached, form a 3- to 6-membered saturated heterocyclic group, wherein each $R^{cc}$ is optionally substituted. Where $R^c$ is substituted, typically $R^{cc}$ is substituted with one or more halo, —OH, —CN, —NO$_2$, —O(C$_1$-C$_4$ alkyl) or —O(C$_1$-C$_4$ haloalkyl) groups. More typically, each $R^{cc}$ is independently selected from a C$_1$-C$_4$ alkyl, C$_1$-C$_4$ haloalkyl, C$_3$-C$_4$ cycloalkyl or C$_3$-C$_4$ halocycloalkyl group.

In one embodiment, —R$^2$ has a formula selected from:

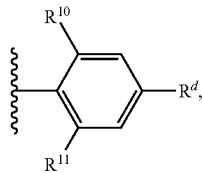

wherein $R^{10}$ and $R^{11}$ are independently selected from C$_1$-C$_4$ alkyl, C$_1$-C$_4$ haloalkyl, C$_3$-C$_4$ cycloalkyl and C$_3$-C$_4$ halocycloalkyl, and $R^d$ is hydrogen, halo, —OH, —NO$_2$, —CN, —R$^{dd}$, —OR$^{dd}$, —COR$^{dd}$, —COOR$^{dd}$, —CONH$_2$, —CONHR$^{dd}$ or —CON(R$^{dd}$)$_2$, wherein each —R$^{dd}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, $R^{10}$ and $R^{11}$ are independently selected from C$_1$-C$_4$ alkyl, and $R^d$ is hydrogen, halo, —CN, C$_1$-C$_3$ alkyl, C$_1$-C$_3$ haloalkyl, cyclopropyl or halocyclopropyl. More typically, $R^{10}$ and $R^{11}$ are independently selected from C$_1$-C$_4$ alkyl, and $R^d$ is hydrogen or halo.

Typically, —R$^2$ has a formula selected from:

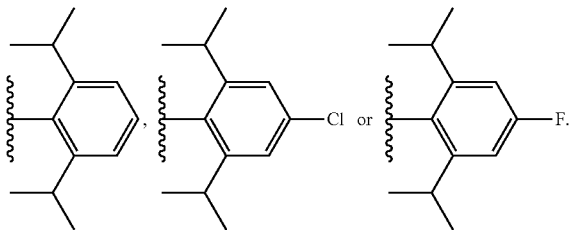

In one embodiment, —R$^2$ has a formula selected from:

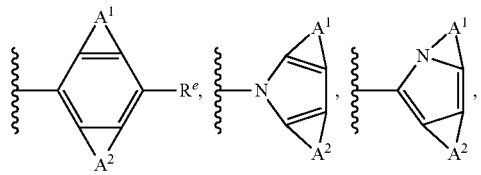

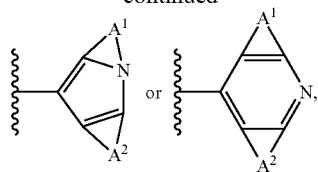

wherein A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S, and wherein $R^e$ is hydrogen or any optional substituent. $R^e$ and any optional substituent attached to A$^1$ or A$^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to A$^1$ and any optional substituent attached to A$^2$ may also together with the atoms to which they are attached form a further fused cycloalkyl, cycloalkenyl, non-aromatic heterocyclic, aryl or heteroaryl ring which may itself be optionally substituted.

In one embodiment, $R^e$ is hydrogen, halo, —OH, —NO$_2$, —CN, —R$^{ee}$, —OR$^{ee}$, —COR$^{ee}$, —COOR$^{ee}$, —CONH$_2$, —CONHR$^{ee}$ or —CON(R$^{ee}$)$_2$, wherein each —R$^{ee}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, $R^e$ is hydrogen or a halo, hydroxyl, —CN, —NO$_2$, —R$^{ee}$ or —OR$^{ee}$ group, wherein $R^{ee}$ is a C$_1$-C$_4$ alkyl group which may optionally be halo-substituted. More typically, $R^e$ is hydrogen or halo.

Typically, any ring containing A$^1$ or A$^2$ is a 5- or 6-membered ring.

Typically, A$^1$ and A$^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A$^1$ and A$^2$ are each independently selected from an optionally substituted straight-chained alkylene group, wherein one carbon atom in the backbone of the alkylene group may optionally be replaced by an oxygen atom. Typically, no heteroatom in A$^1$ or A$^2$ is directly attached to another ring heteroatom. Typically, A$^1$ and A$^2$ are unsubstituted or substituted with one or more halo, hydroxyl, —CN, —NO$_2$, —B$^3$ or —OB$^3$ groups, wherein B$^3$ is a C$_1$-C$_4$ alkyl group which may optionally be halo-substituted. More typically, A$^1$ and A$^2$ are unsubstituted or substituted with one or more fluoro and/or chloro groups. Where R$^2$ contains both A$^1$ and A$^2$ groups, A$^1$ and A$^2$ may be the same or different. Typically, A$^1$ and A$^2$ are the same.

In a further embodiment, —R$^2$ has a formula selected from:

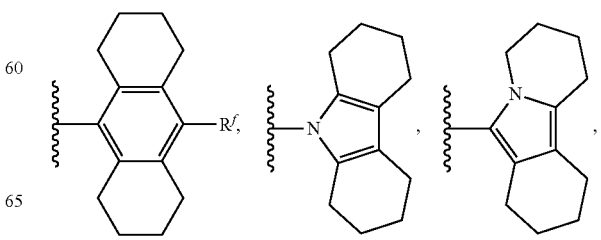

-continued
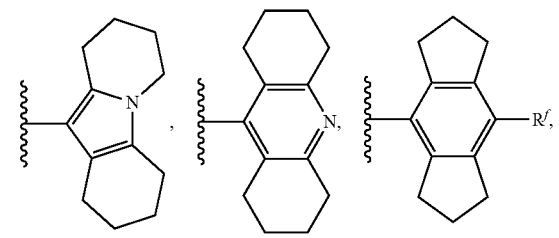
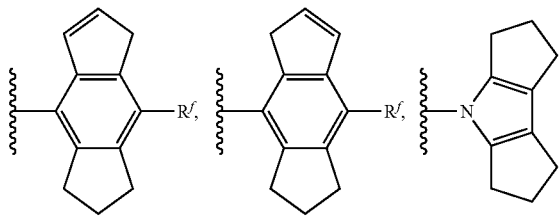
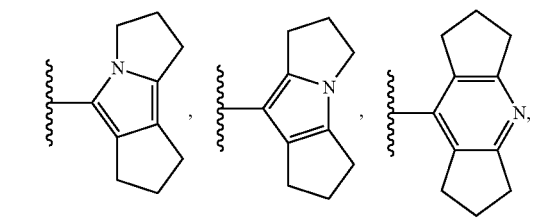
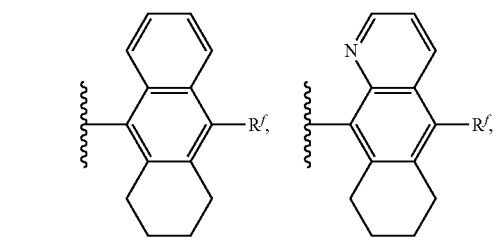
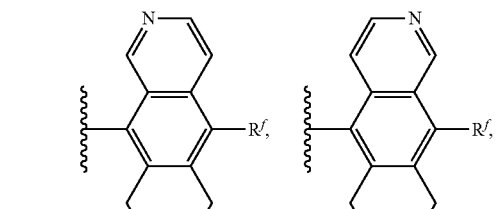
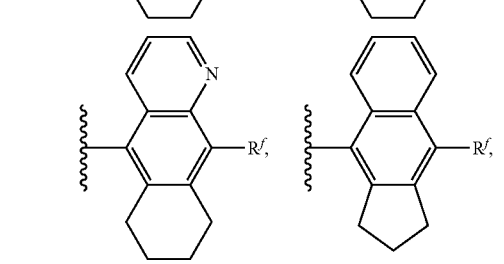
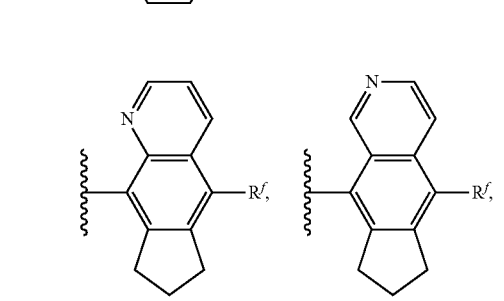
-continued
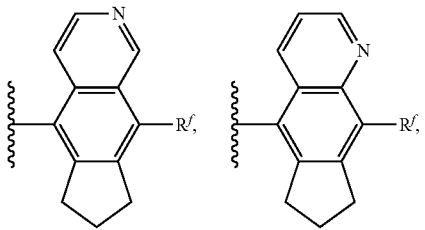
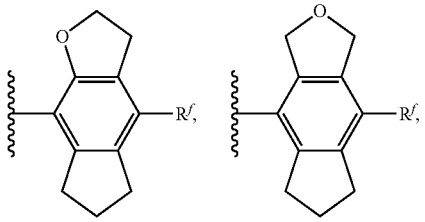
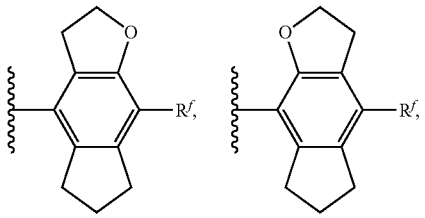
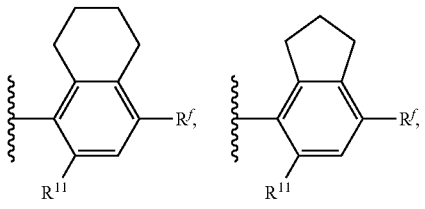
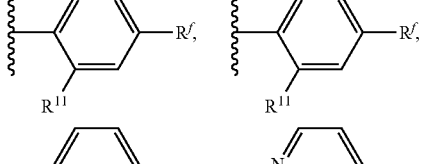
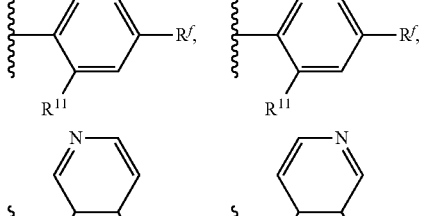
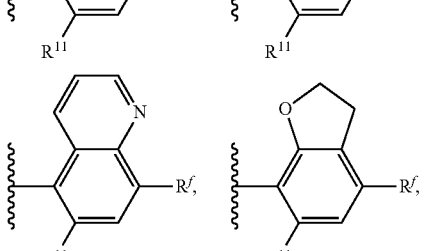

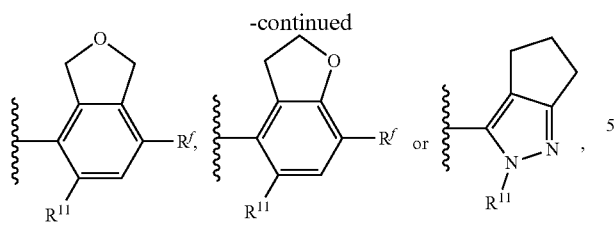

wherein $R^{11}$ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —NO$_2$, —CN, —R$^{\textit{ff}}$, —OR$^{\textit{ff}}$, —COR$^{\textit{ff}}$, —COOR$^{\textit{ff}}$, —CONH$_2$, —CONHR$^{\textit{ff}}$ or —CON(R$^{\textit{ff}}$)$_2$, wherein each —R$^{\textit{ff}}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, $R^{11}$ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, $R^{11}$ is $C_1$-$C_4$ alkyl, and $R^f$ is hydrogen or halo.

Typically, —R$^2$ has a formula selected from:

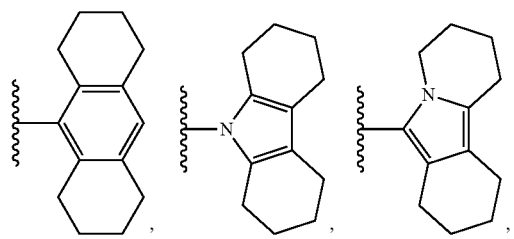

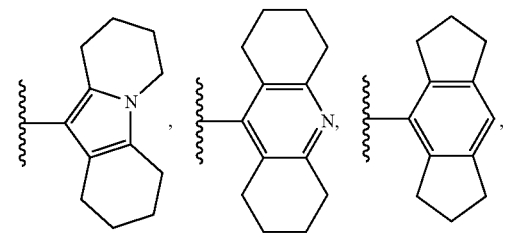

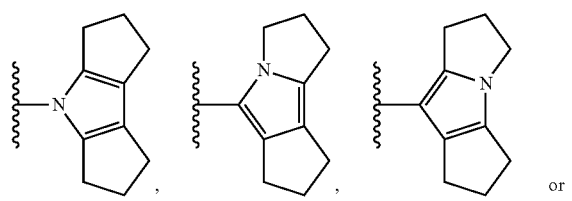

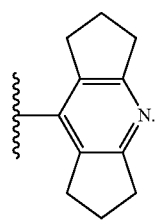

More typically, —R$^2$ has the formula:

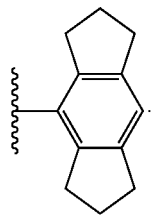 [SMILES: *c1c2c(cc3c1CCC3)CCC2]

Yet other typical substituents at the α-position of the parent cyclic group of R$^2$ may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such R$^2$ groups are described in greater detail below.

In one embodiment, the α-substituted parent cyclic group of R$^2$ is a 5- or 6-membered cyclic group, wherein the cyclic group may optionally be further substituted. In one embodiment, the α-substituted parent cyclic group of R$^2$ is an aryl or a heteroaryl group, all of which may optionally be further substituted. In one embodiment, the α-substituted parent cyclic group of R$^2$ is a phenyl or a 5- or 6-membered heteroaryl group, all of which may optionally be further substituted. In one embodiment, the α-substituted parent cyclic group of R$^2$ is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl or isothiazolyl group, all of which may optionally be further substituted. In one embodiment, the α-substituted parent cyclic group of R$^2$ is a phenyl or pyrazolyl group, both of which may optionally be further substituted. In one embodiment, the α-substituted parent cyclic group of R$^2$ is a phenyl group, which may optionally be further substituted.

In one embodiment, the α-substituted parent cyclic group of R$^2$ is substituted at the α and α' positions, and may optionally be further substituted. For example, the α-substituted parent cyclic group of R$^2$ may be a phenyl group substituted at the 2- and 6-positions, or a phenyl group substituted at the 2-, 4- and 6-positions.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, piperazinyl, 1,4-dioxanyl, thianyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH$_2$, —CN, —NO$_2$, —B$^4$, —OB$^4$, —NHB$^4$, —N(B$^4$)$_2$, —CONH$_2$, —CONHB$^4$, —CON(B$^4$)$_2$, —NHCOB$^4$, —NB$^4$COB$^4$, or —B$^{44}$—;
- wherein each B$^4$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^4$ together with the nitrogen atom to which they are attached may form a 4- to 6-membered heterocyclic group containing one or two ring heteroatoms N and/or O, wherein any B$^4$ may optionally be halo-substituted and/or substituted with one or two substituents independently selected from —OH, —NH$_2$, —OB$^{45}$, —NHB$^{45}$ or —N(B$^{45}$)$_2$;
- wherein each B$^{44}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{45}$, —NHB$^{45}$ or —N(B$^{45}$)$_2$; and
- wherein each B$^{45}$ is independently selected from a C$_1$-C$_3$ alkyl or C$_1$-C$_3$ haloalkyl group.

Typically, any divalent group —B$^{44}$— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^4$ or —N(B$^4$)$_2$, wherein B$^4$ is independently selected from C$_1$-C$_4$ alkyl which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^4$ or —N(B$^4$)$_2$, wherein B$^4$ is independently selected from C$_1$-C$_4$ alkyl which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^4$ or —N(B$^4$)$_2$, wherein B$^4$ is independently selected from C$_1$-C$_4$ alkyl which may optionally be halo-substituted. Alternatively, any of these monovalent phenyl or heterocyclic groups at the α-position may optionally be substituted with one or two substituents independently selected from halo, —OH, —NH$_2$, —CN, —NO$_2$, —B$^4$, —OB$^4$, —NHB$^4$ or —N(B$^4$)$_2$, wherein each B$^4$ is independently selected from a C$_1$-C$_4$ alkyl, C$_2$-C$_4$ alkenyl or C$_2$-C$_4$ alkynyl group all of which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of R$^2$. Such further substituents may be independently selected from halo, —R$^γ$, —OR$^γ$ or —COR$^γ$ groups, wherein each R$^γ$ is independently selected from a C$_1$-C$_6$ alkyl, C$_2$-C$_6$ alkenyl, C$_2$-C$_6$ alkynyl or C$_2$-C$_6$ cyclic group and wherein each R$^γ$ is optionally further substituted with one or more halo groups. Typically, such further substituents on the α-substituted parent cyclic group of R$^2$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

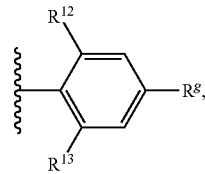

wherein R$^{12}$ is C$_1$-C$_4$ alkyl, C$_1$-C$_4$ haloalkyl, C$_3$-C$_6$ cycloalkyl or C$_3$-C$_6$ halocycloalkyl, R$^{13}$ is a 5- or 6-membered, optionally substituted heterocyclic or aromatic group, and R$^g$ is hydrogen, halo, —OH, —NO$_2$, —CN, —R$^{gg}$, —OR$^{gg}$, —COR$^{gg}$, —COOR$^{gg}$, —CONH$_2$, —CONHR$^{gg}$ or —CON(R$^{gg}$)$_2$, wherein each —R$^{gg}$ is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B$^5$, —B⁵, —NHB⁵, —N(B⁵)₂, —CONH₂, —CONHB⁵, —CON(B⁵)₂, —NHCOB⁵, —NB⁵COB⁵, or —B⁵⁵—;

wherein each $B^5$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^5$ together with the nitrogen atom to which they are attached may form a 4- to 6-membered heterocyclic group containing one or two ring heteroatoms N and/or O, wherein any $B^5$ may optionally be halo-substituted and/or substituted with one or two substituents independently selected from —OH, —NH₂, —OB⁵⁶, —NHB⁵⁶ or —N(B⁵⁶)₂;

wherein each $B^{55}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁵⁶, —NHB⁵⁶ or —N(B⁵⁶)₂; and wherein each $B^{56}$ is independently selected from a $C_1$-$C_3$ alkyl or $C_1$-$C_3$ haloalkyl group.

Typically, any divalent group —B⁵⁵— forms a 4- to 6-membered fused ring. Typically, $R^{12}$ is $C_1$-$C_4$ alkyl, $R^{13}$ is a 5- or 6-membered, optionally substituted heterocyclic or aromatic group, and $R^g$ is hydrogen, halo, —CN, $C_1$-$C_3$ alkyl, $C_1$-$C_3$ haloalkyl, cyclopropyl or halocyclopropyl. More typically, $R^{12}$ is $C_1$-$C_4$ alkyl, $R^{13}$ is a 5- or 6-membered, optionally substituted heterocyclic or aromatic group, and $R^g$ is hydrogen or halo. In one embodiment, the optional substituents on the heterocyclic or aromatic group are independently selected from halo, —OH, —NH₂, —CN, —NO₂, —B⁵, —B⁵, —NHB⁵ or —N(B⁵)₂, wherein each $B^5$ is independently selected from a $C_1$-$C_4$ alkyl, $C_2$-$C_4$ alkenyl or $C_2$-$C_4$ alkynyl group all of which may optionally be halo-substituted. In one embodiment, the optional substituents on the heterocyclic or aromatic group are selected from halo, —OH, —NH₂, —CN, $C_1$-$C_4$ alkyl, $C_2$-$C_4$ alkenyl, $C_2$-$C_4$ alkynyl, $C_1$-$C_4$ haloalkyl, —OB⁵ or —N(B⁵)₂, wherein $B^5$ is independently selected from $C_1$-$C_4$ alkyl which may optionally be halo-substituted.

Typically, —R² has a formula selected from:

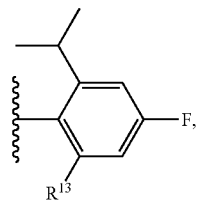

wherein $R^{13}$ is a 5- or 6-membered, optionally substituted heterocyclic or aromatic group. In one embodiment, the optional substituents on the heterocyclic or aromatic group are independently selected from halo, —OH, —NH₂, —CN, —NO₂, —B⁶, —B⁶, —NHB⁶, —N(B⁶)₂, —CONH₂, —CONHB⁶, —CON(B⁶)₂, —NHCOB⁶, —NB⁶COB⁶, or —B⁶⁶—;

wherein each $B^6$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^6$ together with the nitrogen atom to which they are attached may form a 4- to 6-membered heterocyclic group containing one or two ring heteroatoms N and/or O, wherein any $B^6$ may optionally be halo-substituted and/or substituted with one or two substituents independently selected from —OH, —NH₂, —OB⁶⁷, —NHB⁶⁷ or —N(B⁶⁷)₂;

wherein each $B^{66}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁶⁷, —NHB⁶⁷ or —N(B⁶⁷)₂; and wherein each $B^{67}$ is independently selected from a $C_1$-$C_3$ alkyl or $C_1$-$C_3$ haloalkyl group.

Typically, any divalent group —B⁶⁶— forms a 4- to 6-membered fused ring. Typically, the optional substituents on the heterocyclic or aromatic group are independently selected from halo, —OH, —NH₂, —CN, —NO₂, —B⁶, —OB⁶, —NHB⁶ or —N(B⁶)₂, wherein each $B^6$ is independently selected from a $C_1$-$C_4$ alkyl, $C_2$-$C_4$ alkenyl or $C_2$-$C_4$ alkynyl group all of which may optionally be halo-substituted. Typically, the optional substituents on the heterocyclic or aromatic group are selected from halo, —OH, —NH₂, —CN, $C_1$-$C_4$ alkyl, $C_2$-$C_4$ alkenyl, $C_2$-$C_4$ alkynyl, $C_1$-$C_4$ haloalkyl, —OB⁶ or —N(B⁶)₂, wherein $B^6$ is independently selected from $C_1$-$C_4$ alkyl which may optionally be halo-substituted.

In one embodiment, R² is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of R² also include cycloalkyl, cycloalkenyl, non-aromatic heterocyclic, aryl or heteroaryl rings which are fused to the α-substituted parent cyclic group of R². Typically, the cycloalkyl, cycloalkenyl, non-aromatic heterocyclic, aryl or heteroaryl rings are ortho-fused to the α-substituted parent cyclic group of R², i.e. each fused cycloalkyl, cycloalkenyl, non-aromatic heterocyclic, aryl or heteroaryl ring has only two atoms and one bond in common with the α-substituted parent cyclic group of R². Typically, the cycloalkyl, cycloalkenyl, non-aromatic heterocyclic, aryl or heteroaryl rings are ortho-fused to the α-substituted parent cyclic group of R² across the α',β' positions.

In one embodiment, —R² has a formula selected from:

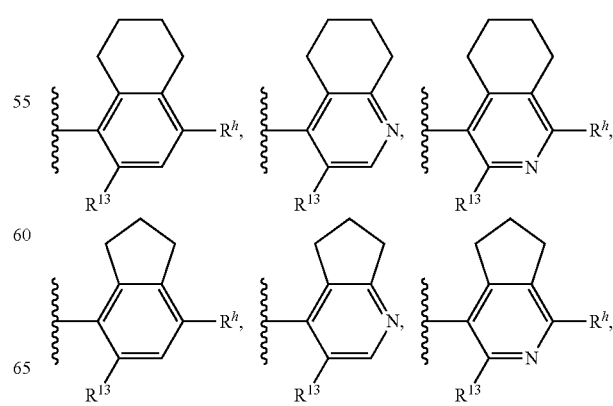

-continued

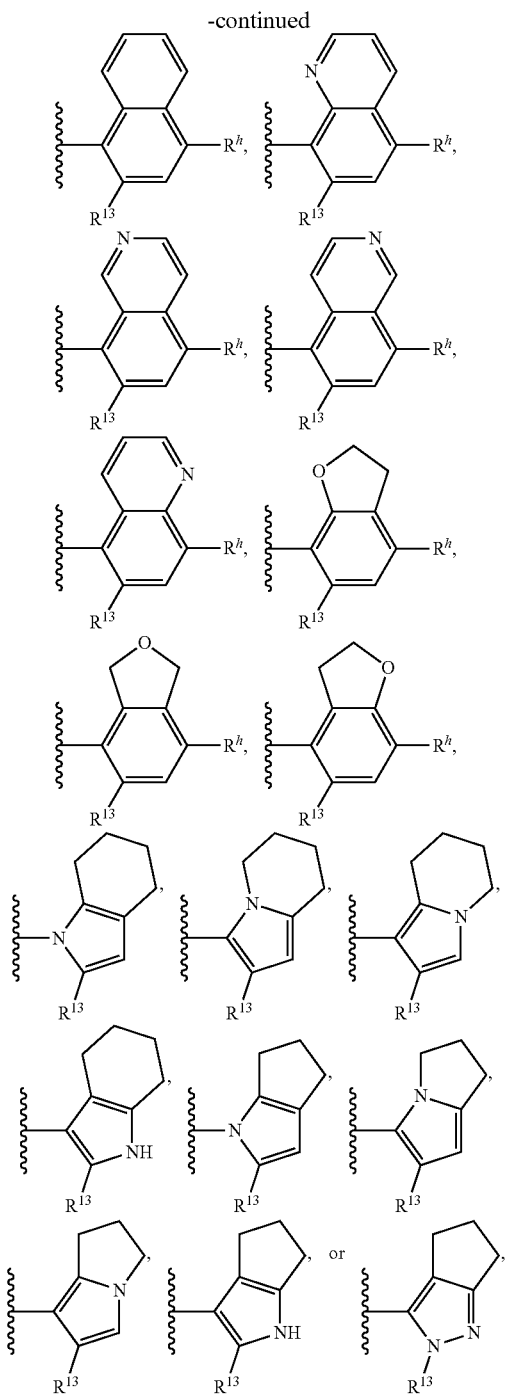

wherein R[13] is a 5- or 6-membered, optionally substituted heterocyclic or aromatic group, and R[h] is hydrogen, halo, —OH, —NO$_2$, —CN, —R[hh], —OR[hh], —COR[hh], —CO-OR[hh], —CONH$_2$, —CONHR[hh] or —CON(R[hh])$_2$, wherein each —R[hh] is independently selected from C$_1$-C$_4$ alkyl, C$_1$-C$_4$ haloalkyl, C$_3$-C$_4$ cycloalkyl and C$_3$-C$_4$ halocycloalkyl. In one embodiment, the optional substituents on the heterocyclic or aromatic group are independently selected from halo, —OH, —NH$_2$, —CN, —NO$_2$, —B[7], —OB[7], —NHB[7], —N(B[7])$_2$, —CONH$_2$, —CONHB[7], —CON(B[7])$_2$, —NHCOB[7], —NB[7]COB[7], or —B[77]—;
wherein each B[7] is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B[7] together with the nitrogen atom to which they are attached may form a 4- to 6-membered heterocyclic group containing one or two ring heteroatoms N and/or O, wherein any B[7] may optionally be halo-substituted and/or substituted with one or two substituents independently selected from —OH, —NH$_2$, —OB[78], —NHB[78] or —N(B[78])$_2$;
wherein each B[77] is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB[78], —NHB[78] or —N(B[78])$_2$; and
wherein each B[78] is independently selected from a C$_1$-C$_3$ alkyl or C$_1$-C$_3$ haloalkyl group.

Typically, any divalent group —B[77]— forms a 4- to 6-membered fused ring. Typically, R[h] is hydrogen, halo, —CN, C$_1$-C$_3$ alkyl, C$_1$-C$_3$ haloalkyl, cyclopropyl or halocyclopropyl. More typically, R[h] is hydrogen or halo. Typically, the optional substituents on the heterocyclic or aromatic group are independently selected from halo, —OH, —NH$_2$, —CN, —NO$_2$, —B[7], —OB[7], —NHB[7] or —N(B[7])$_2$, wherein each B[7] is independently selected from a C$_1$-C$_4$ alkyl, C$_2$-C$_4$ alkenyl or C$_2$-C$_4$ alkynyl group all of which may optionally be halo-substituted. Typically, the optional substituents on the heterocyclic or aromatic group are selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB[7] or —N(B[7])$_2$, wherein B[7] is independently selected from C$_1$-C$_4$ alkyl which may optionally be halo-substituted.

In one embodiment, —R[2] has a formula selected from:

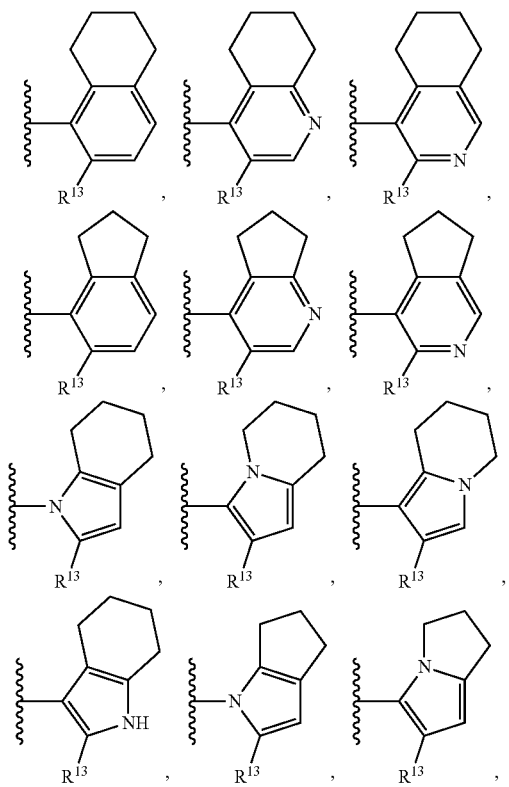

-continued

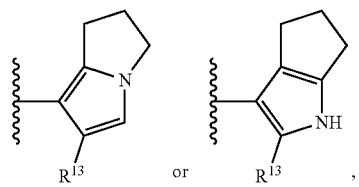

wherein $R^{13}$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^8$, —B$^8$, —NHB$^8$, —N(B$^8$)$_2$, —CONH$_2$, —CONHB$^8$, —CON(B$^8$)$_2$, —NHCOB$^8$, —NB$^8$COB$^8$, or —B$^{88}$—;

wherein each B$^8$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^8$ together with the nitrogen atom to which they are attached may form a 4- to 6-membered heterocyclic group containing one or two ring heteroatoms N and/or O, wherein any B$^8$ may optionally be halo-substituted and/or substituted with one or two substituents independently selected from —OH, —NH$_2$, —OB$^{89}$, —NHB$^{89}$ or —N(B$^{89}$)$_2$;

wherein each B$^{88}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{89}$, —NHB$^{89}$ or —N(B$^{89}$)$_2$; and wherein each B$^{89}$ is independently selected from a $C_1$-$C_3$ alkyl or $C_1$-$C_3$ haloalkyl group.

Typically, any divalent group —B$^{88}$— forms a 4- to 6-membered fused ring. Typically, the optional substituents on the heterocyclic or aromatic group are independently selected from halo, —OH, —NH$_2$, —CN, —NO$_2$, —B$^8$, —OB$^8$, —NHB$^8$ or —N(B$^8$)$_2$, wherein each B$^8$ is independently selected from a $C_1$-$C_4$ alkyl, $C_2$-$C_4$ alkenyl or $C_2$-$C_4$ alkynyl group all of which may optionally be halo-substituted. Typically, the optional substituents on the heterocyclic or aromatic group are selected from halo, —OH, —NH$_2$, —CN, $C_1$-$C_4$ alkyl, $C_2$-$C_4$ alkenyl, $C_2$-$C_4$ alkynyl, $C_1$-$C_4$ haloalkyl, —OB$^8$ or —N(B$^8$)$_2$, wherein B$^8$ is independently selected from $C_1$-$C_4$ alkyl which may optionally be halo-substituted.

Typically, —R$^2$ has a formula selected from:

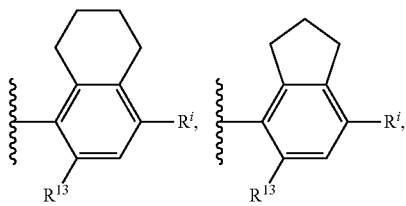

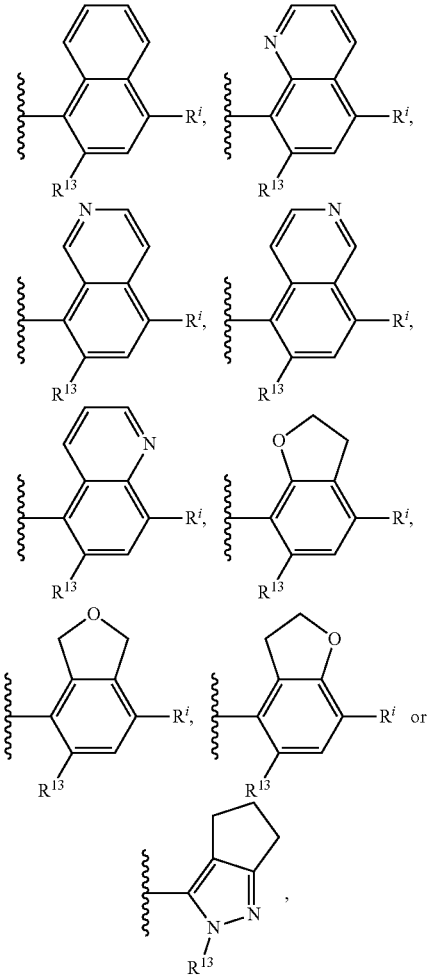

wherein $R^{13}$ is a 5- or 6-membered, optionally substituted heterocyclic or aromatic group, and $R^i$ is hydrogen, halo, —OH, —NO$_2$, —CN, —R$^{ii}$, —OR$^{ii}$, —COR$^{ii}$, —COOR$^{ii}$, —CONH$_2$, —CONHR$^{ii}$ or —CON(R$^{ii}$)$_2$, wherein each —R$^{ii}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH$_2$, —CN, —NO$_2$, —B$^9$, —OB$^9$, —NHB$^9$, —N(B$^9$)$_2$, —CONH$_2$, —CONHB$^9$, —CON(B$^9$)$_2$, —NHCOB$^9$, —NB$^9$COB$^9$, or —B$^{99}$—;

wherein each B$^9$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B$^9$ together with the nitrogen atom to which they are attached may form a 4- to 6-membered heterocyclic group containing one or two ring heteroatoms N and/or O, wherein any B$^9$ may optionally be halo-substituted and/or substituted with one or two substituents independently selected from —OH, —NH$_2$, —OB$^{98}$, —NHB$^{98}$ or —N(B$^{98}$)$_2$;

wherein each B$^{99}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{98}$, —NHB$^{98}$ or —N(B$^{98}$)$_2$; and wherein each B$^{98}$ is independently selected from a C$_1$-C$_3$ alkyl or C$_1$-C$_3$ haloalkyl group.

Typically, any divalent group —B$^{99}$— forms a 4- to 6-membered fused ring. Typically, R$^i$ is hydrogen, halo, —CN, C$_1$-C$_3$ alkyl, C$_1$-C$_3$ haloalkyl, cyclopropyl or halocyclopropyl. More typically, R$^i$ is hydrogen or halo. Typically, the optional substituents on the heterocyclic or aromatic group are independently selected from halo, —OH, —NH$_2$, —CN, —NO$_2$, —B$^9$, —OB$^9$, —NHB$^9$ or —N(B$^9$)$_2$, wherein each B$^9$ is independently selected from a C$_1$-C$_4$ alkyl, C$_2$-C$_4$ alkenyl or C$_2$-C$_4$ alkynyl group all of which may optionally be halo-substituted. Typically, the optional substituents on the heterocyclic or aromatic group are selected from halo, —OH, —NH$_2$, —CN, C$_1$-C$_4$ alkyl, C$_2$-C$_4$ alkenyl, C$_2$-C$_4$ alkynyl, C$_1$-C$_4$ haloalkyl, —OB$^9$ or —N(B$^9$)$_2$, wherein B$^9$ is independently selected from C$_1$-C$_4$ alkyl which may optionally be halo-substituted.

In one embodiment, R$^2$ is phenyl or a 5- or 6-membered heteroaryl group (such as phenyl, pyridinyl, pyridazinyl, pyrimidinyl or pyrazinyl); wherein (i) the phenyl or 5- or 6-membered heteroaryl group is substituted at the α position with a substituent selected from —R$^{43}$, —OR$^{43}$ and —COR$^{43}$, wherein R$^{43}$ is selected from a C$_1$-C$_6$ alkyl, C$_2$-C$_6$ alkenyl, C$_2$-C$_6$ alkynyl or C$_2$-C$_6$ cyclic group and wherein R$^{43}$ is optionally substituted with one or more halo groups; and optionally the phenyl or 5- or 6-membered heteroaryl group is further substituted at the α' position with a substituent selected from —R$^{44}$, —OR$^{44}$ and —COR$^{44}$, wherein R$^{44}$ is selected from a C$_1$-C$_6$ alkyl, C$_2$-C$_6$ alkenyl, C$_2$-C$_6$ alkynyl or C$_2$-C$_6$ cyclic group and wherein R$^{44}$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —R$^{43}$, —OR$^{43}$ and —COR$^{43}$, wherein R$^{43}$ is selected from a C$_1$-C$_6$ alkyl, C$_2$-C$_6$ alkenyl, C$_2$-C$_6$ alkynyl or C$_2$-C$_6$ cyclic group and wherein R$^{43}$ is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{17}$—OR$^{18}$, —R$^{17}$—N(R$^{18}$)$_2$, —R$^{17}$—CN or —R$^{17}$—C≡CR$^{18}$, and wherein a ring atom of the monovalent heterocyclic or aromatic group is directly attached to the α-ring atom of the parent phenyl or 5- or 6-membered heteroaryl group; wherein R$^{17}$ is independently selected from a bond or a C$_1$-C$_3$ alkylene group; and R$^{18}$ is independently selected from hydrogen or a C$_1$-C$_3$ alkyl or C$_1$-C$_3$ haloalkyl group; and optionally the phenyl or 5- or 6-membered heteroaryl group is further substituted at the α' position with a substituent selected from —R$^{43}$, —OR$^{43}$ and —COR$^{43}$, wherein R$^{43}$ is selected from a C$_1$-C$_6$ alkyl, C$_2$-C$_6$ alkenyl, C$_2$-C$_6$ alkynyl or C$_2$-C$_6$ cyclic group and wherein R$^{43}$ is optionally substituted with one or more halo groups; and optionally the phenyl or 5- or 6-membered heteroaryl group is further substituted (typically with one, two or three substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{17}$—OR$^{18}$, —R$^{17}$—N(R$^{18}$)$_2$, —R$^{17}$—CN or —R$^{17}$—C≡CR$^{18}$, and wherein a ring atom of the monovalent heterocyclic or aromatic group is directly attached to the α-ring atom of the parent phenyl or 5- or 6-membered heteroaryl group; wherein R$^{17}$ is independently selected from a bond or a C$_1$-C$_3$ alkylene group; and R$^{18}$ is independently selected from hydrogen or a C$_1$-C$_3$ alkyl or C$_1$-C$_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —NO$_2$, —CN, —COOR$^{15}$, —CONH$_2$, —CONHR$^{15}$ or —CON(R$^{15}$)$_2$, wherein each —R$^{15}$ is independently selected from a C$_1$-C$_4$ alkyl or C$_1$-C$_4$ haloalkyl group).

In the embodiment directly above, where a group or moiety is optionally substituted with one or more halo groups, it may be substituted for example with one, two, three, four, five or six halo groups.

In one aspect of any of the above embodiments, R$^2$ contains from 15 to 50 atoms. More typically, R$^2$ contains from 20 to 40 atoms. Most typically, R$^2$ contains from 25 to 35 atoms.

In another aspect of any of the above embodiments, R$^2$ contains from 10 to 50 atoms other than hydrogen. More typically, R$^2$ contains from 10 to 40 atoms other than hydrogen. More typically, R$^2$ contains from 10 to 35 atoms other than hydrogen. Most typically, R$^2$ contains from 12 to 30 atoms other than hydrogen.

Q is selected from O or S. In one embodiment of the first aspect of the invention, Q is O.

In one embodiment, the invention provides a compound of formula (I), wherein:

Q is O;
L is —(CHR$^{14}$)$_n$—, wherein n is 1, 2, 3, 4 or 5, and R$^{14}$ is independently selected from hydrogen, methyl or ethyl;
R$^1$ is a 3-, 4-, 5-, 6- or 7-membered heterocycle comprising at least one nitrogen or oxygen ring atom, wherein the heterocycle may optionally be substituted with one, two or three substituents independently selected from halo, C$_1$-C$_3$ alkyl, C$_1$-C$_3$ haloalkyl, —CN, —N$_3$, —NO$_2$, —N(R$^5$)$_2$, —OR$^{15}$, —COR$^{15}$, —COOR$^{15}$ or oxo (=O), wherein R$^{15}$ is independently selected from hydrogen or C$_1$-C$_3$ alkyl; and
R$^2$ is a cyclic group substituted at the α-position, wherein R$^2$ may optionally be further substituted. In one embodiment, R$^2$ is a cyclic group substituted at the α and α' positions. In one embodiment, n is 1, 2 or 3. In one embodiment, the heterocycle of R$^1$ is a saturated heterocycle such as azetidine, oxetane, thietane, pyrrolidine, tetrahydrofuran, tetrahydrothiophene, piperidine, tetrahydropyran, thiane, piperazine, dioxane, morpholine and thiomorpholine. In another embodiment, the heterocycle of R$^1$ is an aromatic heterocycle such as pyridine, pyridazine, pyrimidine, pyrazine, pyrrole, furan, thiophene, pyrazole, imidazole, oxazole, isoxazole, thiazole, isothiazole or triazole.

In another embodiment, the invention provides a compound of formula (I), wherein:

Q is O;
L is a saturated or unsaturated C$_1$-C$_8$ hydrocarbylene group, wherein the hydrocarbylene group may be straight-chained or branched, or be or include cyclic groups, wherein the hydrocarbylene group may optionally be substituted with one, two or three substituents independently selected from halo, C$_1$-C$_3$ haloalkyl, —CN, —N$_3$, —NO$_2$, —N(R$^5$)$_2$, —OR$^{15}$, —COR$^{15}$, —COOR$^{15}$ or oxo (=O);
R$^1$ is —NR$^3$R$^4$;
R$^3$ and R$^4$ are each independently selected from hydrogen, C$_1$-C$_3$ alkyl, phenyl or benzyl, wherein the C$_1$-C$_3$ alkyl group may optionally be substituted with one, two or three substituents independently selected from halo, —CN, —N$_3$, —NO$_2$, —N(R$^5$)$_2$, —OR$^{15}$, —COR$^{15}$, —COOR$^{15}$ or oxo (=O), and wherein the phenyl or benzyl group may optionally be substituted with one, two or three substituents independently selected from halo, C$_1$-C$_3$ alkyl, C$_1$-C$_3$ haloalkyl, —CN, —N$_3$, —NO$_2$, —N(R$^5$)$_2$, —OR$^{15}$, —COR$^{15}$, —COOR$^{15}$ or oxo (=O);
R$^{15}$ is independently selected from hydrogen or C$_1$-C$_3$ alkyl; and
R$^2$ is a cyclic group substituted at the α-position, wherein R$^2$ may optionally be further substituted;
provided that the atom of L which is attached to the sulfur atom of the sulfonylurea group is not a ring atom of an aromatic group. In one embodiment, R$^2$ is a cyclic group substituted at the α and α' positions. In one embodiment, the atom of L which is attached to the sulfur atom of the sulfonylurea group is not a ring atom of a heterocyclic or aromatic group. In one embodiment, the atom of L which is attached to the sulfur atom of the sulfonylurea group is not a ring atom of any cyclic group.

In another embodiment, the invention provides a compound of formula (I), wherein:

Q is O;
L is —(CHR$^{14}$)$_n$—, wherein n is 1, 2, 3, 4 or 5, and R$^{14}$ is independently selected from hydrogen, methyl or ethyl;
R$^1$ is —NR$^3$R$^4$;
R$^3$ and R$^4$ are each independently selected from hydrogen, C$_1$-C$_3$ alkyl, phenyl or benzyl, wherein the C$_1$-C$_3$ alkyl group may optionally be substituted with one, two or three substituents independently selected from halo, —CN, —N$_3$, —NO$_2$, —N(R$^5$)$_2$, —OR$^{15}$, —COR$^{15}$, —COOR$^{15}$ or oxo (=O), and wherein the phenyl or benzyl group may optionally be substituted with one, two or three substituents independently selected from halo, C$_1$-C$_3$ alkyl, C$_1$-C$_3$ haloalkyl, —CN, —N$_3$, —NO$_2$, —N(R$^5$)$_2$, —OR$^{15}$, —COR$^{15}$, —COOR$^{15}$ or oxo (=O);
R$^{15}$ is independently selected from hydrogen or C$_1$-C$_3$ alkyl; and
R$^2$ is a cyclic group substituted at the α-position, wherein R$^2$ may optionally be further substituted. In one embodiment, R$^2$ is a cyclic group substituted at the α and α' positions. In one embodiment, n is 1, 2 or 3.

In another embodiment, the invention provides a compound of formula (I), wherein:

Q is O;
L is a saturated or unsaturated C$_1$-C$_8$ hydrocarbylene group, wherein the hydrocarbylene group may be straight-chained or branched, or be or include cyclic groups, wherein the hydrocarbylene group may optionally be substituted with one, two or three substituents independently selected from halo, C$_1$-C$_3$ haloalkyl, —CN, —N$_3$, —NO$_2$, —N(R$^{15}$)$_2$, —OR$^{15}$, —COR$^{15}$, —COOR$^{15}$ or oxo (=O);
R$^1$ is —OR$^5$;
R$^5$ is selected from hydrogen, C$_1$-C$_3$ alkyl, phenyl or benzyl, wherein the C$_1$-C$_3$ alkyl group may optionally be substituted with one, two or three substituents independently selected from halo, —CN, —N$_3$, —NO$_2$, —N(R$^{15}$)$_2$, —OR$^{15}$, —COR$^{15}$, —COOR$^{15}$ or oxo (═O), and wherein the phenyl or benzyl group may optionally be substituted with one, two or three substituents independently selected from halo, $C_1$-$C_3$ alkyl, $C_1$-$C_3$ haloalkyl, —CN, —$N_3$, —$NO_2$, —$N(R^{15})_2$, —$OR^{15}$, —$COR^{15}$, —$COOR^{15}$ or oxo (═O);

$R^{15}$ is independently selected from hydrogen or $C_1$-$C_3$ alkyl; and $R^2$ is a cyclic group substituted at the α-position, wherein $R^2$ may optionally be further substituted;

provided that the atom of L which is attached to the sulfur atom of the sulfonylurea group is not a ring atom of an aromatic group. In one embodiment, $R^2$ is a cyclic group substituted at the α and α' positions. In one embodiment, the atom of L which is attached to the sulfur atom of the sulfonylurea group is not a ring atom of a heterocyclic or aromatic group. In one embodiment, the atom of L which is attached to the sulfur atom of the sulfonylurea group is not a ring atom of any cyclic group.

In another embodiment, the invention provides a compound of formula (I), wherein:

Q is O;

L is —$(CHR^{14})_n$—, wherein n is 1, 2, 3, 4 or 5, and $R^{14}$ is independently selected from hydrogen, methyl or ethyl;

$R^i$ is —$OR^5$;

$R^5$ is selected from hydrogen, $C_1$-$C_3$ alkyl, phenyl or benzyl, wherein the $C_1$-$C_3$ alkyl group may optionally be substituted with one, two or three substituents independently selected from halo, —CN, —$N_3$, —$NO_2$, —$N(R^5)_2$, —$OR^{15}$, —$COR^{15}$, —$COOR^{15}$ or oxo (═O), and wherein the phenyl or benzyl group may optionally be substituted with one, two or three substituents independently selected from halo, $C_1$-$C_3$ alkyl, $C_1$-$C_3$ haloalkyl, —CN, —$N_3$, —$NO_2$, —$N(R^5)_2$, —$OR^{15}$, —$COR^{15}$, —$COOR^{15}$ or oxo (═O);

$R^{15}$ is independently selected from hydrogen or $C_1$-$C_3$ alkyl; and $R^2$ is a cyclic group substituted at the α-position, wherein $R^2$ may optionally be further substituted. In one embodiment, $R^2$ is a cyclic group substituted at the α and α' positions. In one embodiment, n is 1, 2 or 3.

In another embodiment, the invention provides a compound of formula (I), wherein:

Q is O;

-L-$R^1$ is a saturated or unsaturated $C_1$-$C_{12}$ hydrocarbyl group substituted with oxo (═O), wherein the hydrocarbyl group may be straight-chained or branched, or be or include cyclic groups, and wherein the hydrocarbyl group may optionally be further substituted with one, two or three substituents independently selected from halo, $C_1$-$C_3$ haloalkyl, —CN, —$N_3$, —$NO_2$, —$N(R^5)_2$, —$OR^{15}$, —$COR^{15}$, —$COOR^{15}$ or oxo (═O);

$R^{15}$ is independently selected from hydrogen or $C_1$-$C_3$ alkyl; and $R^2$ is a cyclic group substituted at the α-position, wherein $R^2$ may optionally be further substituted;

provided that the atom of L which is attached to the sulfur atom of the sulfonylurea group is not a ring atom of an aromatic group. In one embodiment, $R^2$ is a cyclic group substituted at the α and α' positions. In one embodiment, the atom of L which is attached to the sulfur atom of the sulfonylurea group is not a ring atom of a heterocyclic or aromatic group. In one embodiment, the atom of L which is attached to the sulfur atom of the sulfonylurea group is not a ring atom of any cyclic group.

In another embodiment, the invention provides a compound of formula (I), wherein:

Q is O;

-L-$R^1$ is —$(CHR^{14})_n$—$R^{16}$;

n is 1, 2, 3, 4 or 5;

$R^{14}$ is independently selected from hydrogen, methyl or ethyl;

$R^{16}$ is a 5- or 6-membered cyclic group substituted with one substituent selected from —CN, —$N(R^5)_2$, —$OR^{15}$, —$COR^{15}$, —$COOR^{15}$ or oxo (═O), and optionally further substituted with one, two or three substituents independently selected from halo, $C_1$-$C_3$ alkyl, $C_1$-$C_3$ haloalkyl, —CN, —$N_3$, —$NO_2$, —$N(R^5)_2$, —$OR^{15}$, —$COR^{15}$, —$COOR^{15}$ or oxo (═O);

$R^{15}$ is independently selected from hydrogen or $C_1$-$C_3$ alkyl; and $R^2$ is a cyclic group substituted at the α-position, wherein $R^2$ may optionally be further substituted. In one embodiment, $R^2$ is a cyclic group substituted at the α and α' positions. In one embodiment, n is 1, 2 or 3.

In another embodiment, the invention provides a compound of formula (I), wherein:

Q is O;

-L-$R^1$ is —$(CHR^{14})_n$—$R^{16}$;

n is 1, 2 or 3;

$R^{14}$ is independently selected from hydrogen or methyl;

$R^{16}$ is phenyl or a 5- or 6-membered heteroaryl group, wherein the phenyl or 5- or 6-membered heteroaryl group is substituted with one substituent selected from —CN, —$N(R^5)_2$, —$OR^{15}$, —$COR^{15}$, —$COOR^{15}$ or oxo (═O), and optionally further substituted with one, two or three substituents independently selected from halo, $C_1$-$C_3$ alkyl, $C_1$-$C_3$ haloalkyl, —CN, —$N_3$, —$NO_2$, —$N(R^{15})_2$, —$OR^{15}$, —$COR^{15}$, —$COOR^{15}$ or oxo (═O);

$R^{15}$ is independently selected from hydrogen or $C_1$-$C_3$ alkyl; and $R^2$ is a cyclic group substituted at the α-position, wherein $R^2$ may optionally be further substituted. In one embodiment, $R^2$ is a cyclic group substituted at the α and α' positions.

In one specific embodiment, the invention provides a compound of formula (I):

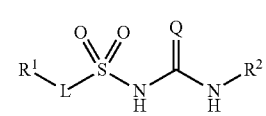

Formula (I)

wherein:

Q is O;

L is a $C_1$-$C_{10}$ alkylene group which may be straight-chained or branched or be or include a cycloalkyl or cycloalkylene group; or L is a $C_1$-$C_{12}$ arylalkylene group wherein $R^1$ may be attached to the aryl part or to the alkylene part of the arylalkylene group;

$R^1$ is —$NR^3R^4$, —$OR^5$, —(C═$NR^6$)$R^7$, —(CO)$R^8$, —CN, —$N_3$, —$NR^{23}R^{24}R^{25+}$ or an optionally substituted heterocycle; wherein the optionally substituted heterocycle is selected from a diazirinyl, azetidinyl, azetinyl, oxetanyl, pyrrolidinyl, tetrahydrofuranyl, pyrazolidinyl, imidazolidinyl, dioxolanyl, oxathiolanyl, piperidinyl, tetrahydropyranyl, piperazinyl, dioxanyl, morpholinyl, thiomorpholinyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl or 6-oxa-2-azaspiro[3.4]octanyl group, each of which may optionally be substituted with one or two substituents independently selected from a halo, $C_1$-$C_6$ alkyl, —CN, —N($R^9$)$_2$, —$OR^9$ or saturated 4- to 6-membered heterocyclic group, wherein $R^9$ is independently selected from a hydrogen atom or a $C_1$-$C_3$ alkyl group;

$R^3$ and $R^4$ are each independently selected from a hydrogen atom or a $C_1$-$C_6$ alkyl, $C_2$-$C_6$ alkenyl, $C_2$-$C_6$ alkynyl, —O($C_1$-$C_6$ alkyl), —CO($C_1$-$C_6$ alkyl), —COO($C_1$-$C_6$ alkyl), —CHO, $C_1$-$C_6$ cycloalkyl, phenyl or benzyl group, each of which may optionally be substituted with one or more substituents (such as one, two or three substituents) independently selected from halo, —CN, —N($R^9$)$_2$, —$OR^9$ or oxo (=O) groups, wherein $R^9$ is independently selected from a hydrogen atom or a $C_1$-$C_3$ alkyl group; or $R^3$ and $R^4$ together with the nitrogen atom to which they are attached form a 4-, 5- or 6-membered saturated or unsaturated cyclic group selected from an azetidinyl, azetinyl, pyrrolidinyl, pyrazolidinyl, imidazolidinyl, piperidinyl, piperazinyl, morpholinyl, thiomorpholinyl or 6-oxa-2-azaspiro[3.4]octanyl group, each of which may optionally be substituted with one or two substituents independently selected from a halo, $C_1$-$C_6$ alkyl, $C_1$-$C_6$ haloalkyl, —CN, —N($R^9$)$_2$, —$OR^9$ or saturated 4- to 6-membered heterocyclic group, wherein $R^9$ is independently selected from a hydrogen atom or a $C_1$-$C_3$ alkyl group;

$R^5$ is hydrogen or a $C_1$-$C_6$ alkyl group;

$R^6$ and $R^7$ are each independently hydrogen or a $C_1$-$C_6$ alkyl, $C_2$-$C_6$ alkenyl, $C_2$-$C_6$ alkynyl, $C_1$-$C_6$ cycloalkyl, phenyl or benzyl group, each of which may optionally be substituted with one or more substituents (such as one, two or three substituents) independently selected from halo, —CN, —N($R^9$)$_2$, —$OR^9$ or oxo (=O) groups, wherein $R^9$ is independently selected from a hydrogen atom or a $C_1$-$C_3$ alkyl group; or L and $R^6$, or L and $R^7$, or $R^6$ and $R^7$ together with the —(C=N)— group to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —N($R^9$)$_2$, —$OR^9$, $C_1$-$C_3$ alkyl, $C_1$-$C_3$ alkylene or oxo (=O) groups, wherein $R^9$ is independently selected from a hydrogen atom or a $C_1$-$C_3$ alkyl group;

$R^8$ is hydrogen or a $C_1$-$C_6$ alkyl, —N($R^{19}$)$_2$ or —$OR^{19}$ group, wherein $R^{19}$ is independently selected from a hydrogen atom or a $C_1$-$C_3$ alkyl group; or L and $R^8$ together with the —(C=O)— group to which they are attached form a 4-, 5- or 6-membered saturated cyclic group, wherein the cyclic group may optionally include one further heteroatom N, O or S in its carbon skeleton, and wherein the cyclic group may optionally be substituted with one or more substituents (such as one, two or three substituents) independently selected from halo, —CN, —N($R^9$)$_2$, —$OR^9$, $C_1$-$C_3$ alkyl, $C_1$-$C_3$ alkylene or oxo (=O) groups, wherein $R^9$ is independently selected from a hydrogen atom or a $C_1$-$C_3$ alkyl group;

$R^{23}$, $R^{24}$ and $R^{25}$ are each independently a $C_1$-$C_6$ alkyl group; and $R^2$ is phenyl or a 5- or 6-membered heteroaryl group; wherein (i) the phenyl or 5- or 6-membered heteroaryl group is substituted at the α position with a substituent selected from —$R^3$, —$OR^{30}$ and —$COR^{30}$, wherein $R^{30}$ is selected from a $C_1$-$C_6$ alkyl, $C_2$-$C_6$ alkenyl, $C_2$-$C_6$ alkynyl or $C_2$-$C_6$ cyclic group and wherein $R^{30}$ is optionally substituted with one or more halo groups; and optionally the phenyl or 5- or 6-membered heteroaryl group is further substituted at the α' position with a substituent selected from —$R^{33}$, —$OR^{33}$ and —$COR^{33}$, wherein $R^{33}$ is selected from a $C_1$-$C_6$ alkyl, $C_2$-$C_6$ alkenyl, $C_2$-$C_6$ alkynyl or $C_2$-$C_6$ cyclic group and wherein $R^{33}$ is optionally substituted with one or more halo groups; and optionally the phenyl or 5- or 6-membered heteroaryl group is further substituted (typically with one, two or three substituents independently selected from halo, —$NO_2$, —CN, —$COOR^{34}$, —$CONH_2$, —$CONHR^{34}$ or —$CON(R^{34})_2$, wherein each —$R^{34}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —$R^{30}$, —$OR^{30}$ and —$COR^{30}$, wherein $R^{30}$ is selected from a $C_1$-$C_6$ alkyl, $C_2$-$C_6$ alkenyl, $C_2$-$C_6$ alkynyl or $C_2$-$C_6$ cyclic group and wherein $R^{30}$ is optionally substituted with one or more halo groups; and optionally the phenyl or 5- or 6-membered heteroaryl group is further substituted (typically with one or two substituents independently selected from halo, —$NO_2$, —CN, —$COOR^{34}$, —$CONH_2$, —$CONHR^{34}$ or —$CON(R^{34})_2$, wherein each —$R^{34}$ is independently selected from a $C_1$-$C_4$ alkyl or $C_1$-$C_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —$NO_2$, —CN, —$COOR^{34}$, —$CONH_2$, —$CONHR^{34}$ or

51

—CON(R$^{34}$)$_2$, wherein each —R$^{34}$ is independently selected from a C$_1$-C$_4$ alkyl or C$_1$-C$_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{31}$—OR$^{32}$, —R$^{31}$—N(R$^{32}$)$_2$, —R$^{31}$—CN or —R$^{31}$—C≡CR$^{32}$, and wherein a ring atom of the monovalent heterocyclic or aromatic group is directly attached to the α-ring atom of the parent phenyl or 5- or 6-membered heteroaryl group; wherein R$^{31}$ is independently selected from a bond or a C$_1$-C$_3$ alkylene group; and R$^{32}$ is independently selected from hydrogen or a C$_1$-C$_3$ alkyl or C$_1$-C$_3$ haloalkyl group; and optionally the phenyl or 5- or 6-membered heteroaryl group is further substituted at the α' position with a substituent selected from —R$^{30}$, —OR$^{30}$ and —COR$^{30}$, wherein R$^{30}$ is selected from a C$_1$-C$_6$ alkyl, C$_2$-C$_6$ alkenyl, C$_2$-C$_6$ alkynyl or C$_2$-C$_6$ cyclic group and wherein R$^{30}$ is optionally substituted with one or more halo groups; and optionally the phenyl or 5- or 6-membered heteroaryl group is further substituted (typically with one, two or three substituents independently selected from halo, —NO$_2$, —CN, —COOR$^{34}$, —CONH$_2$, —CONHR$^{34}$ or —CON(R$^{34}$)$_2$, wherein each —R$^{34}$ is independently selected from a C$_1$-C$_4$ alkyl or C$_1$-C$_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{31}$—OR$^{32}$, —R$^{31}$—N(R$^{32}$)$_2$, —R$^{31}$—CN or —R$^{31}$—C≡CR$^{32}$, and wherein a ring atom of the monovalent heterocyclic or aromatic group is directly attached to the α-ring atom of the parent phenyl or 5- or 6-membered heteroaryl group; wherein R$^{31}$ is independently selected from a bond or a C$_1$-C$_3$ alkylene group; and R$^{32}$ is independently selected from hydrogen or a C$_1$-C$_3$ alkyl or C$_1$-C$_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —NO$_2$, —CN, —COOR$^{34}$, —CONH$_2$, —CONHR$^{34}$ or —CON(R$^{34}$)$_2$, wherein each —R$^{34}$ is independently selected from a C$_1$-C$_4$ alkyl or C$_1$-C$_4$ haloalkyl group).

In this specific embodiment directly above, the parent phenyl or 5- or 6-membered heteroaryl group of R$^2$ may be selected from phenyl, pyridinyl, pyridazinyl, pyrimidinyl or pyrazinyl.

52

In this specific embodiment directly above, where a group or moiety is optionally substituted with one or more halo groups, it may be substituted for example with one, two, three, four, five or six halo groups.

In one aspect of any of the above embodiments, the compound of formula (I) has a molecular weight of from 200 to 2,000 Da. Typically, the compound of formula (I) has a molecular weight of from 235 to 1,400 Da. Typically, the compound of formula (I) has a molecular weight of from 270 to 1,000 Da. Typically, the compound of formula (I) has a molecular weight of from 300 to 700 Da. More typically, the compound of formula (I) has a molecular weight of from 300 to 600 Da.

A second aspect of the invention provides a compound selected from the group consisting of:

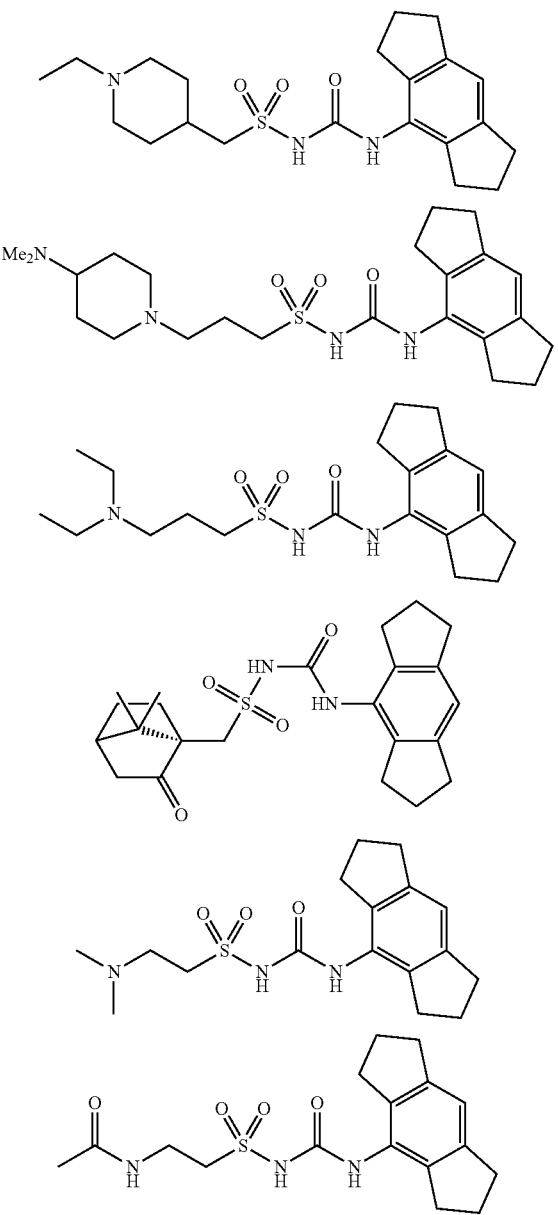

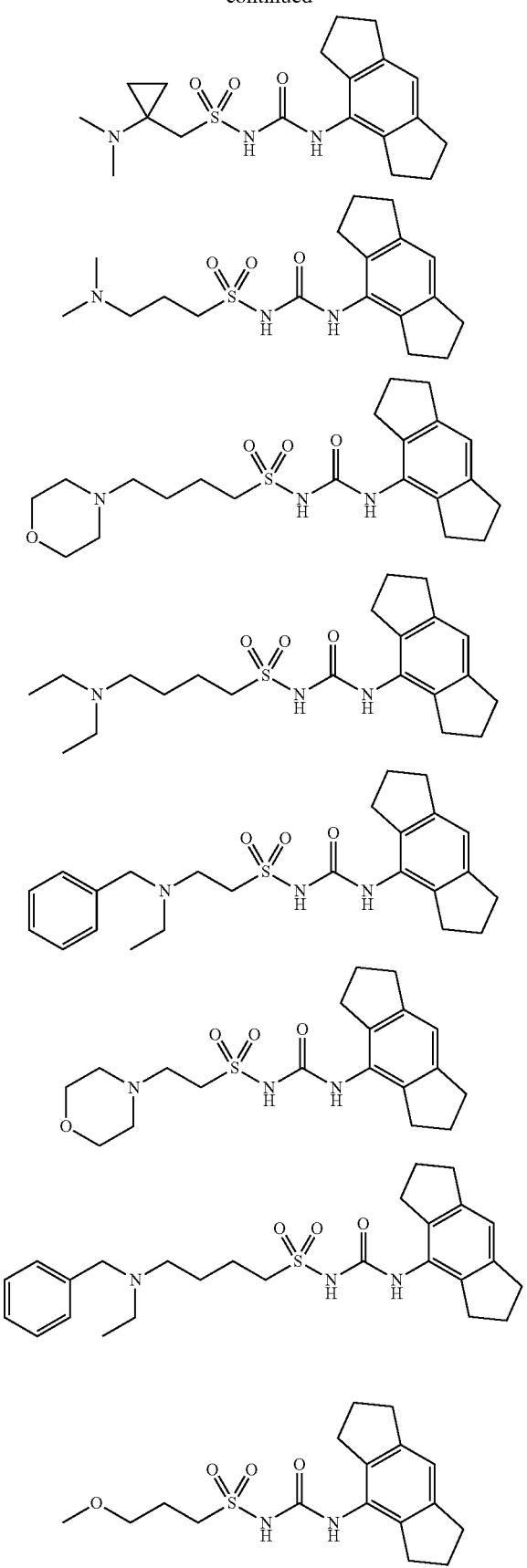
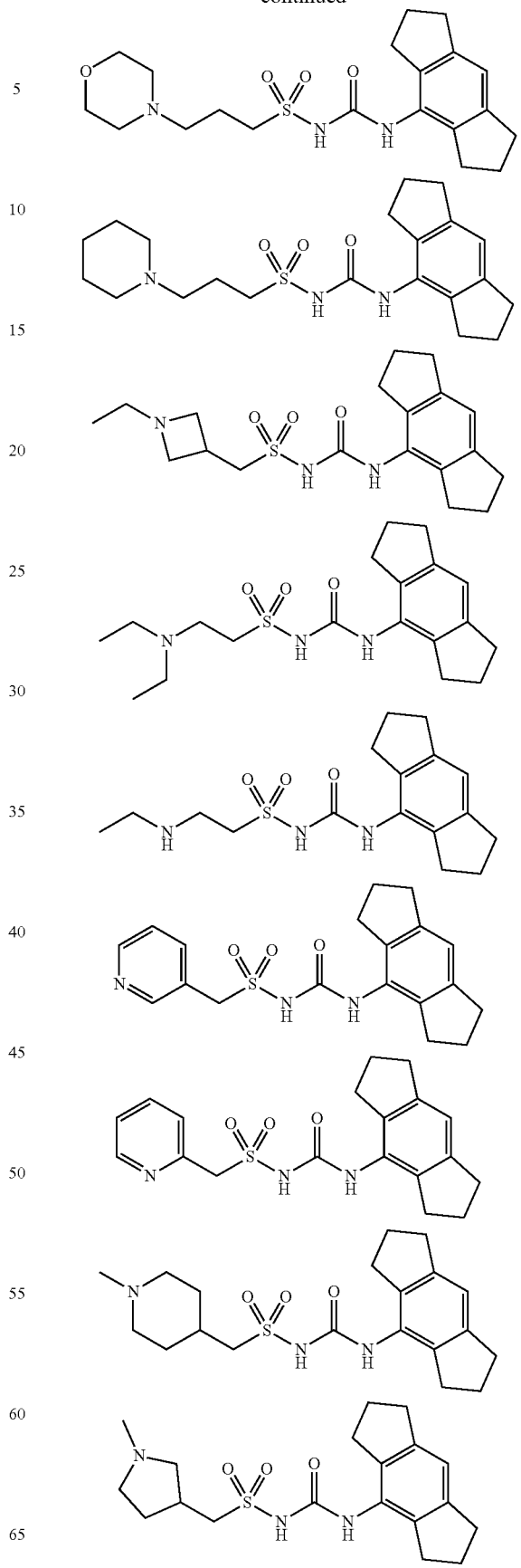

55
-continued
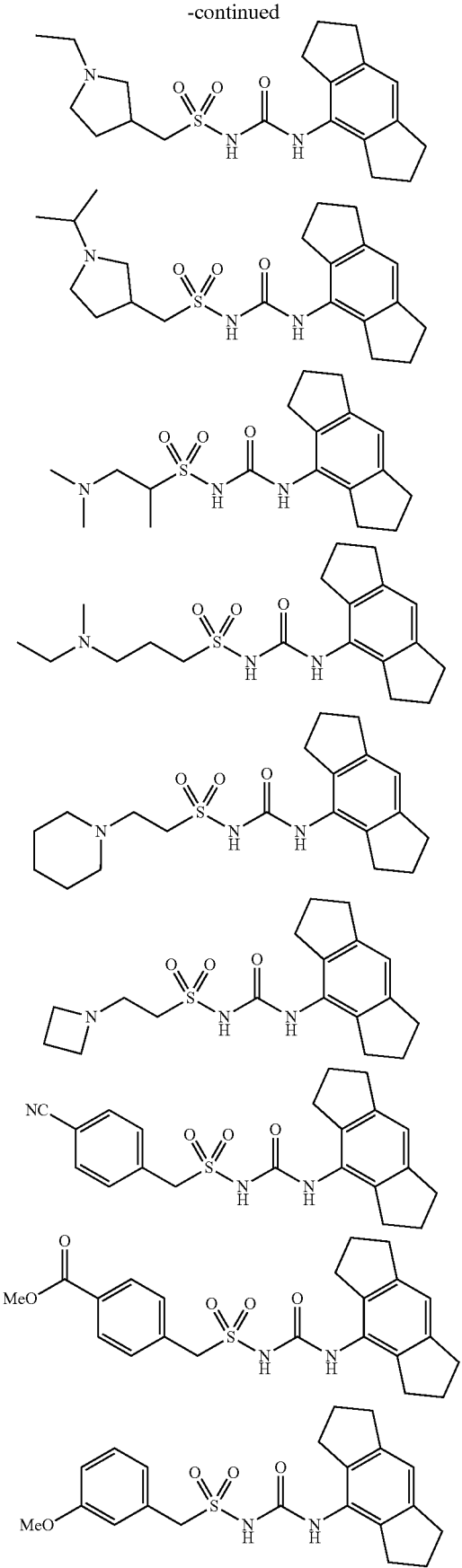
56
-continued
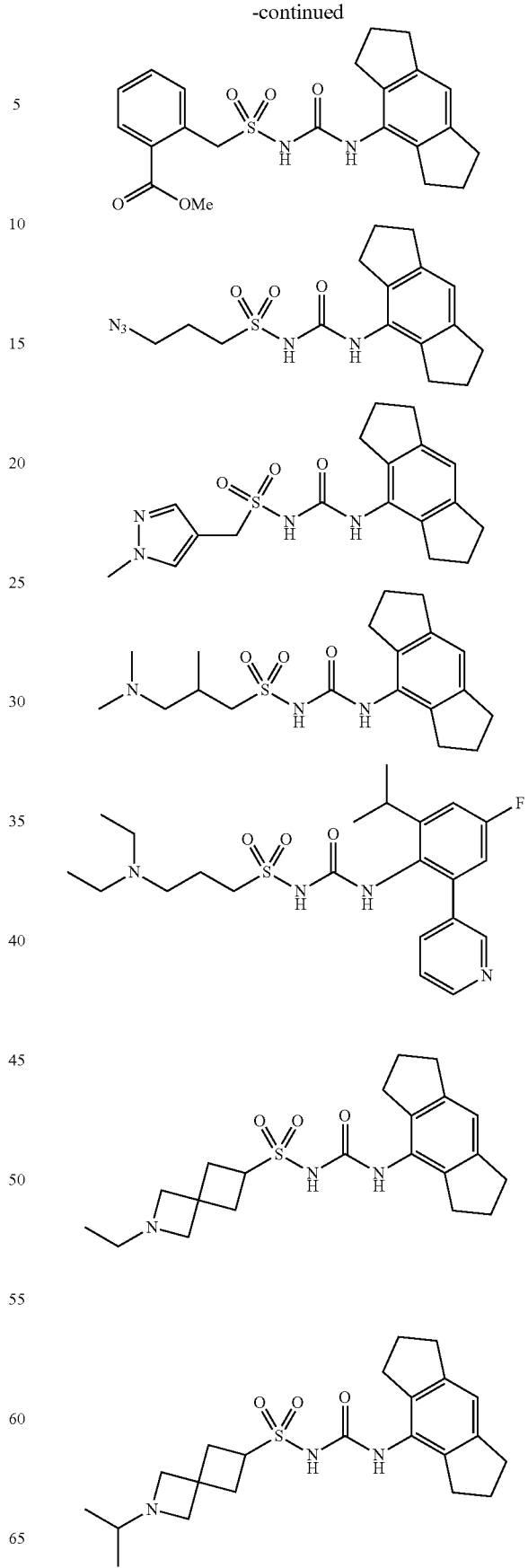

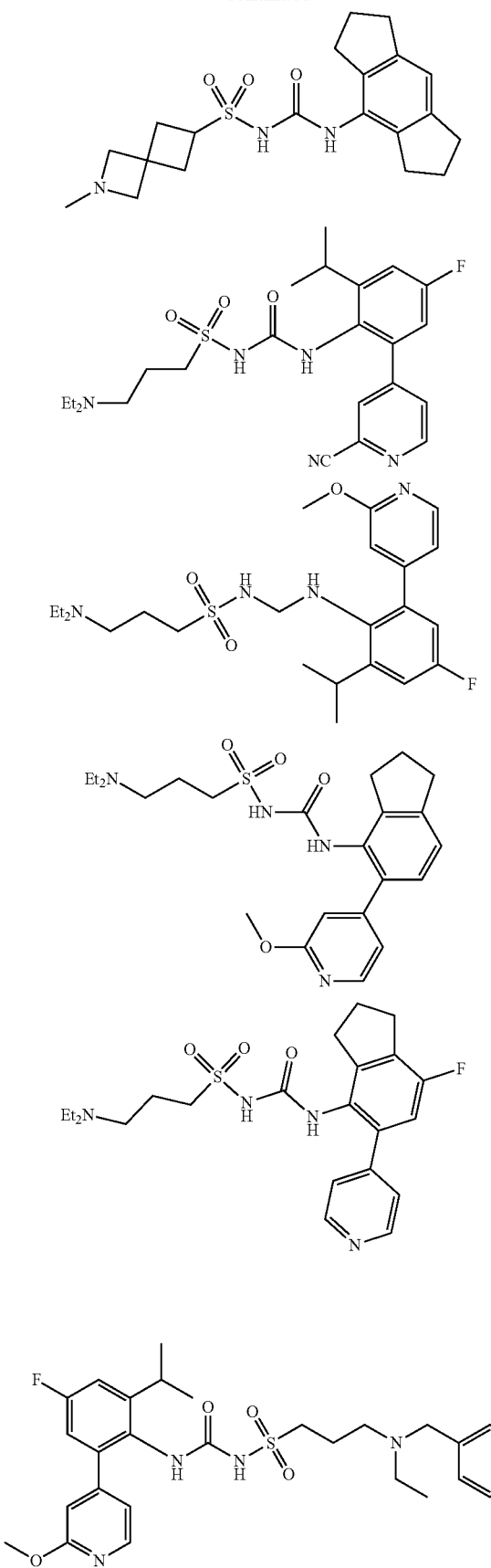
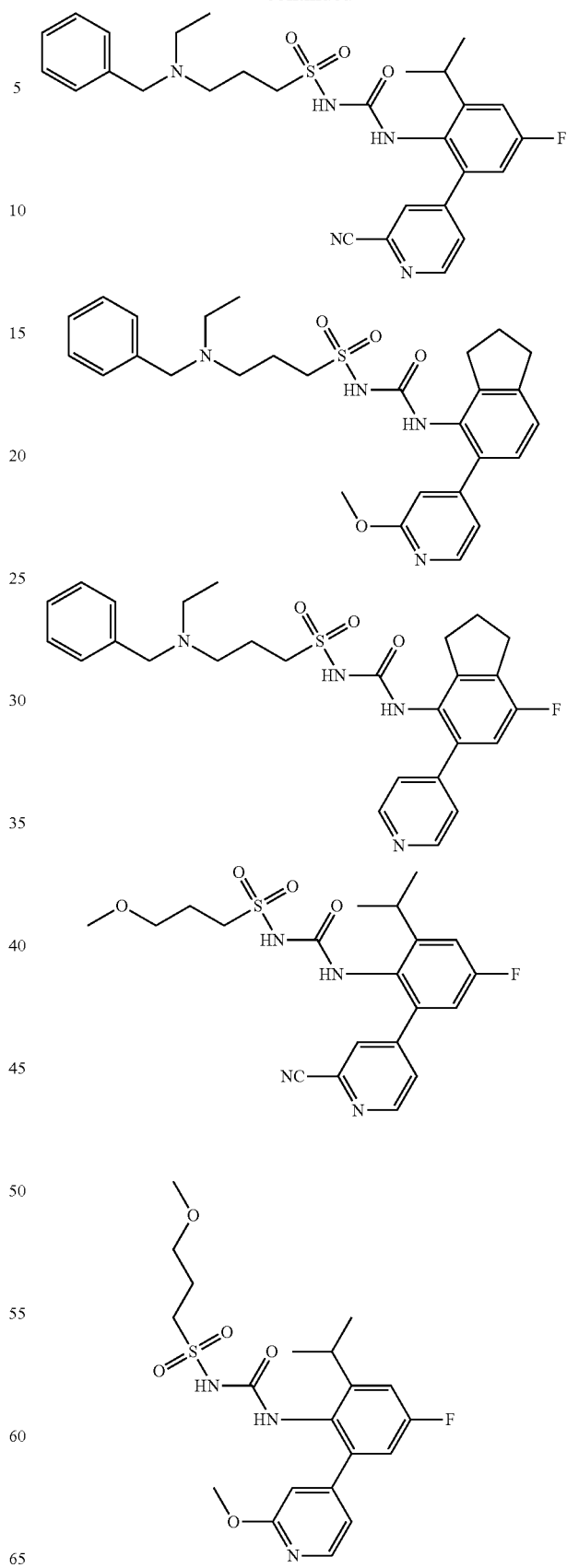

59
-continued
60
-continued
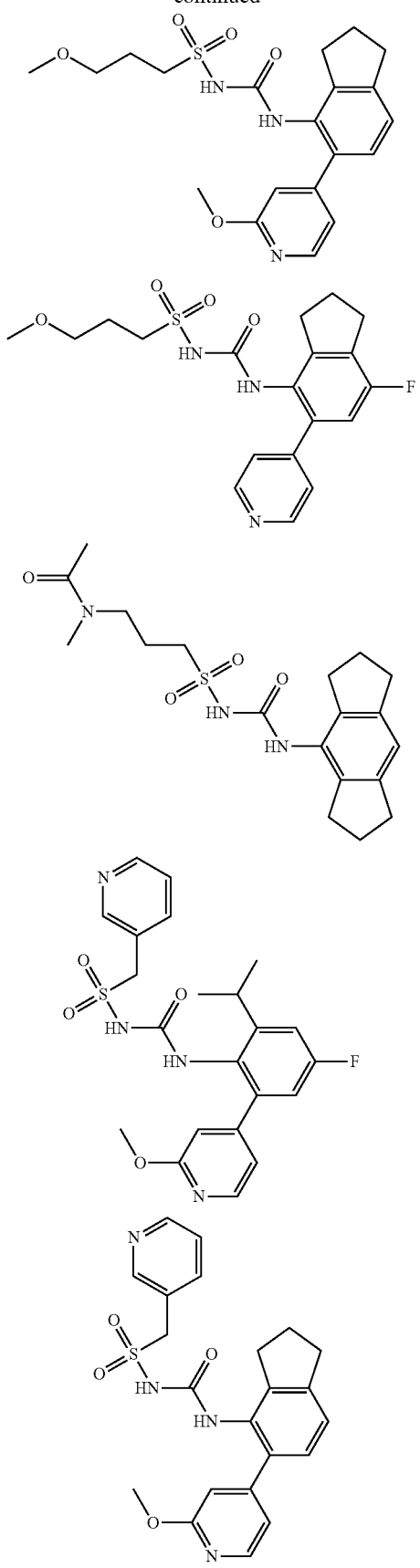
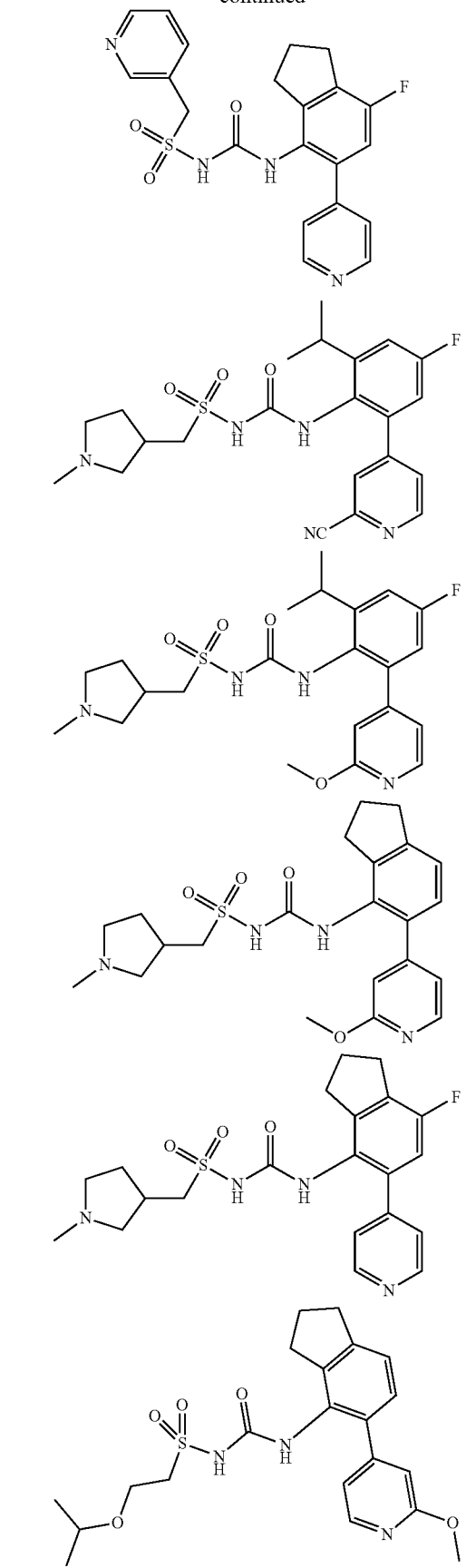

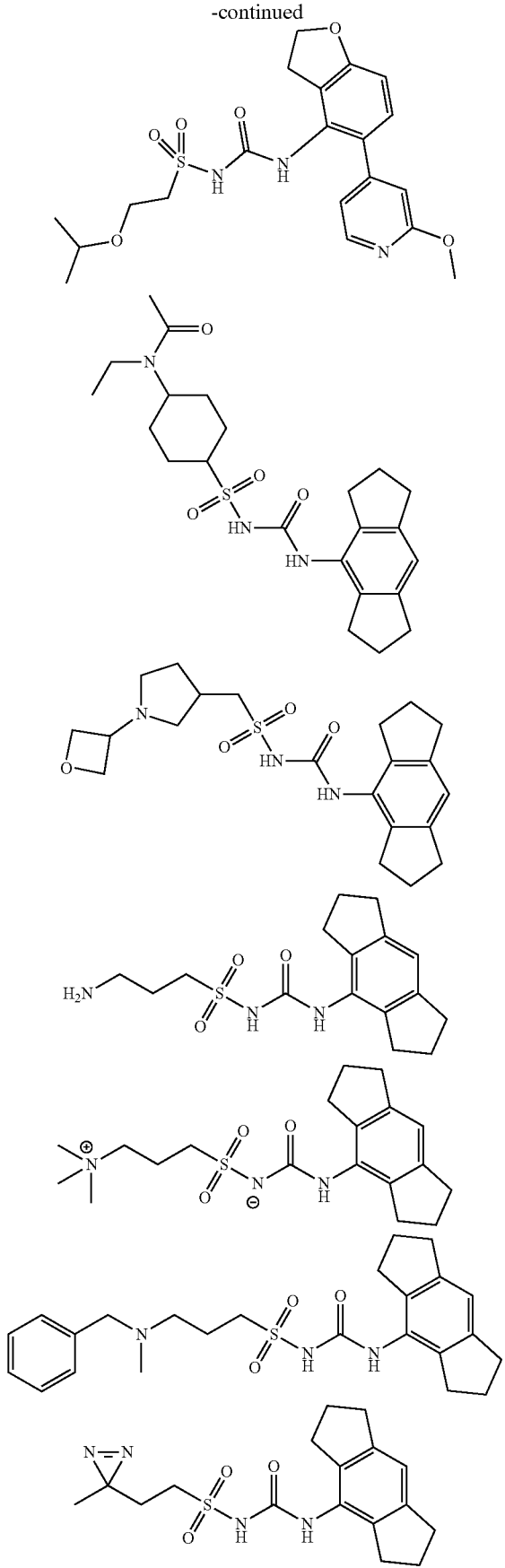
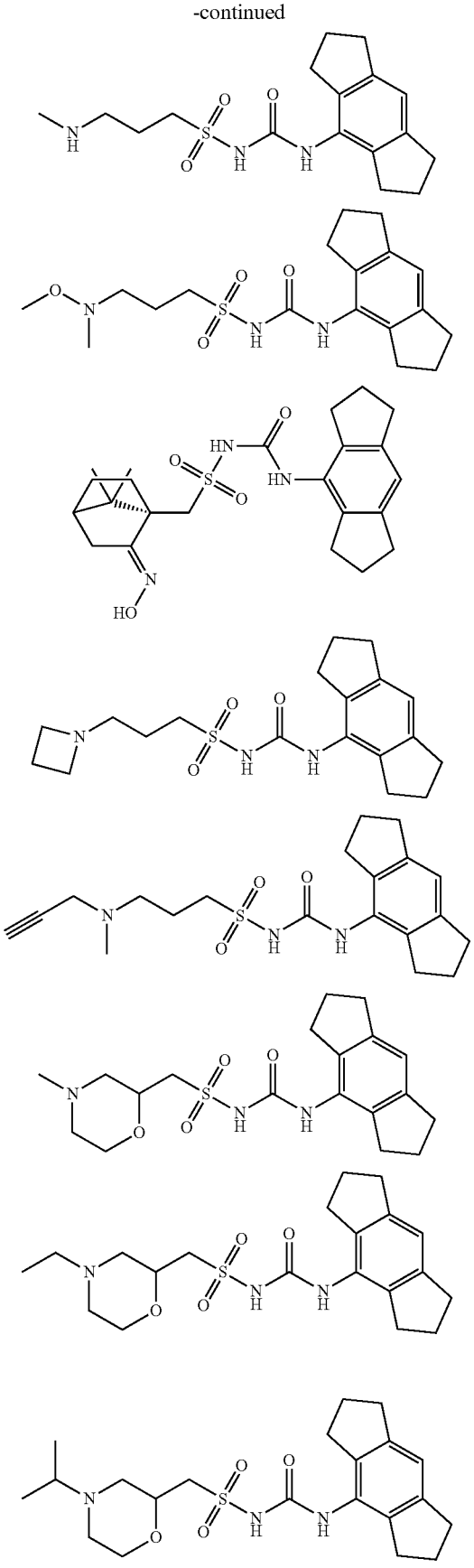

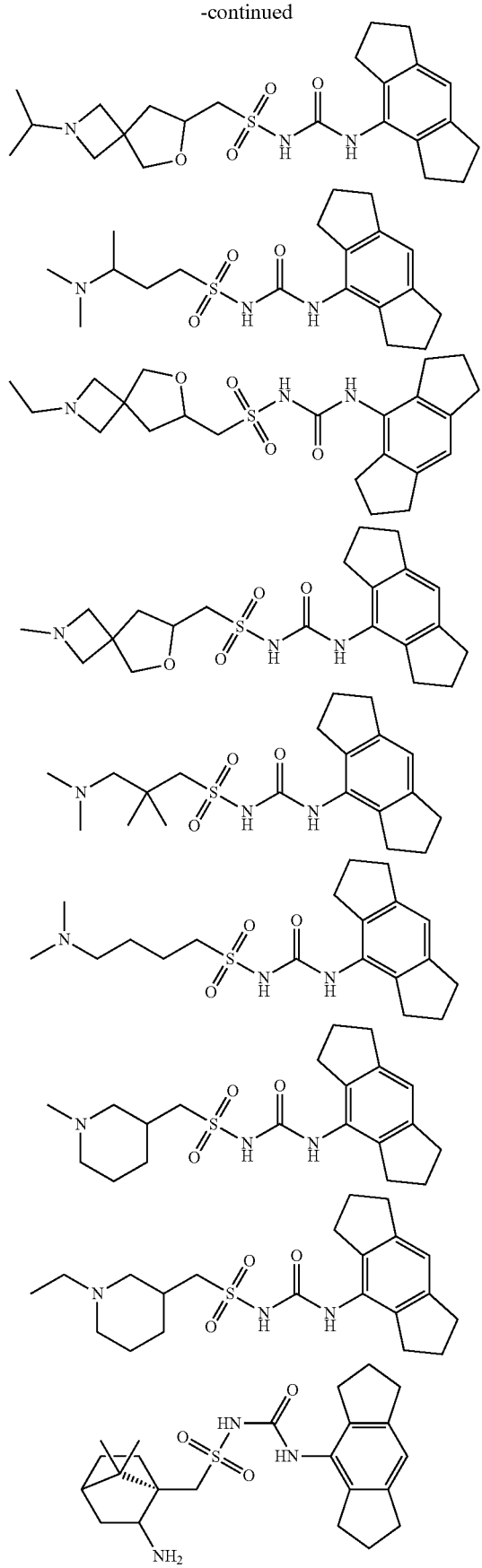
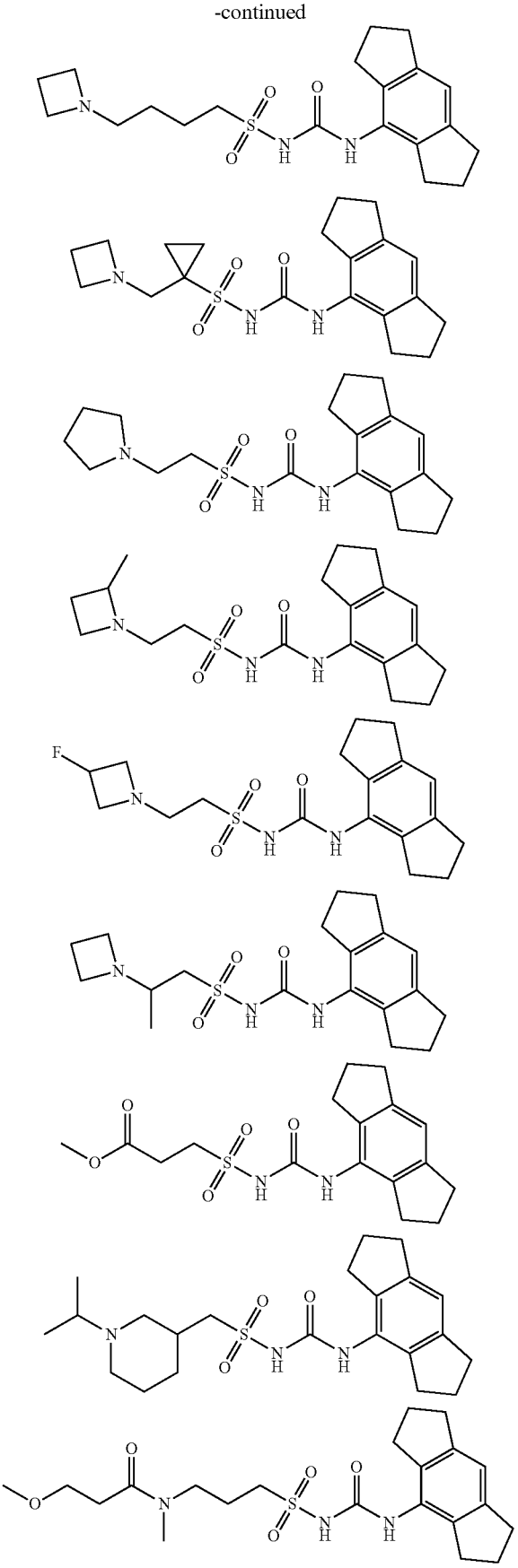

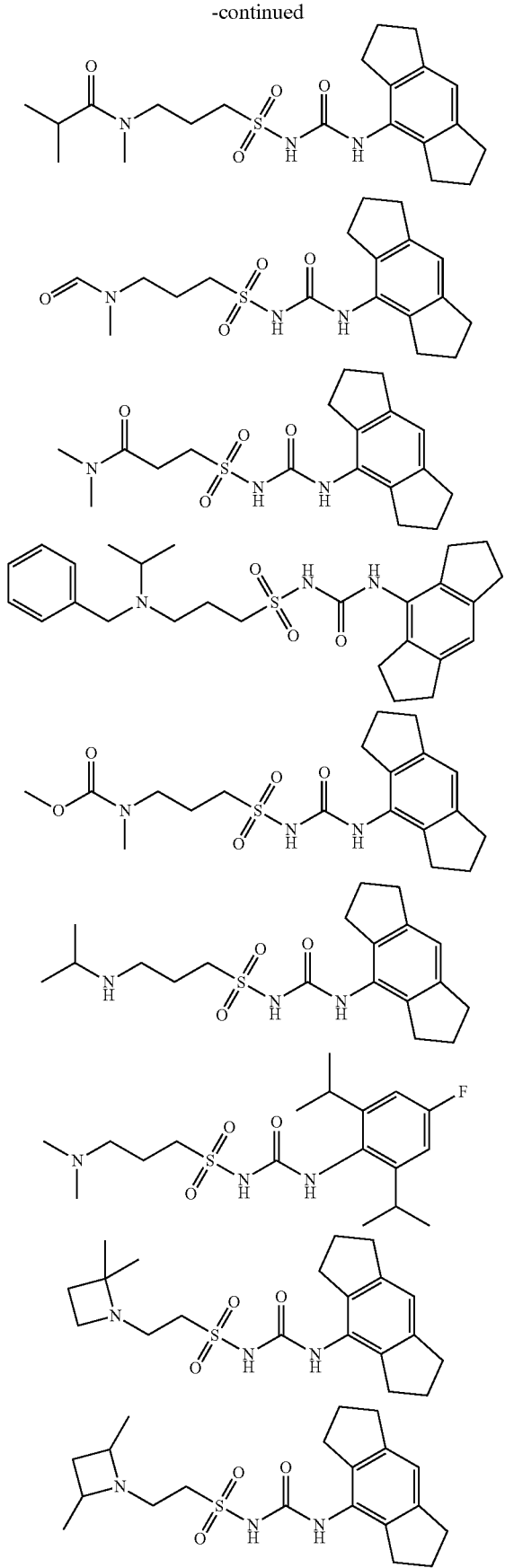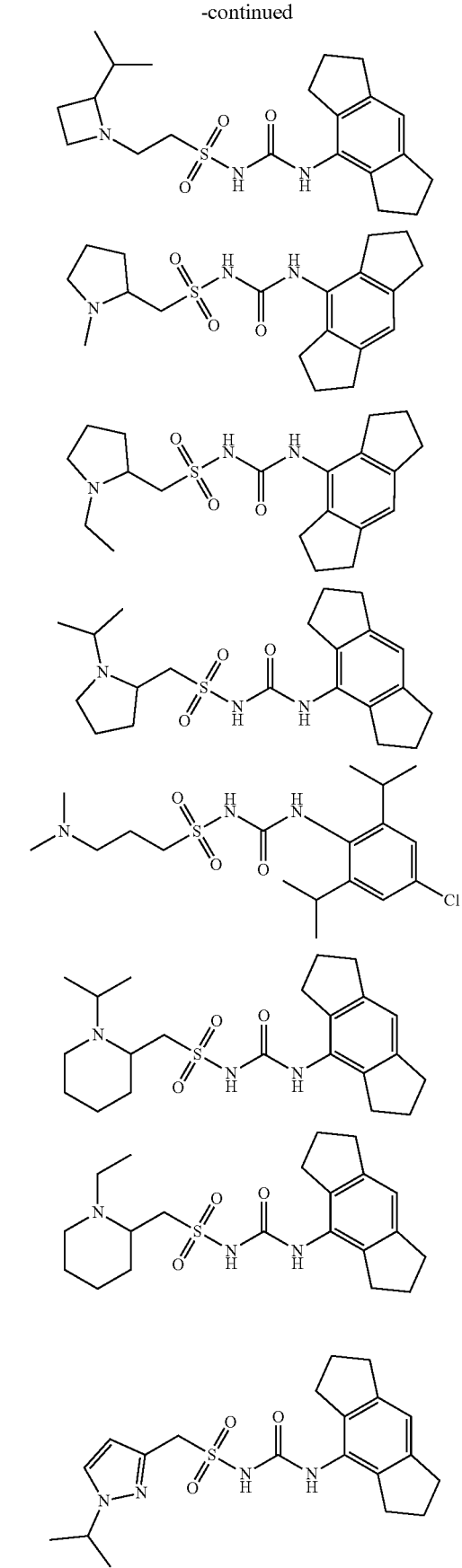

67
-continued
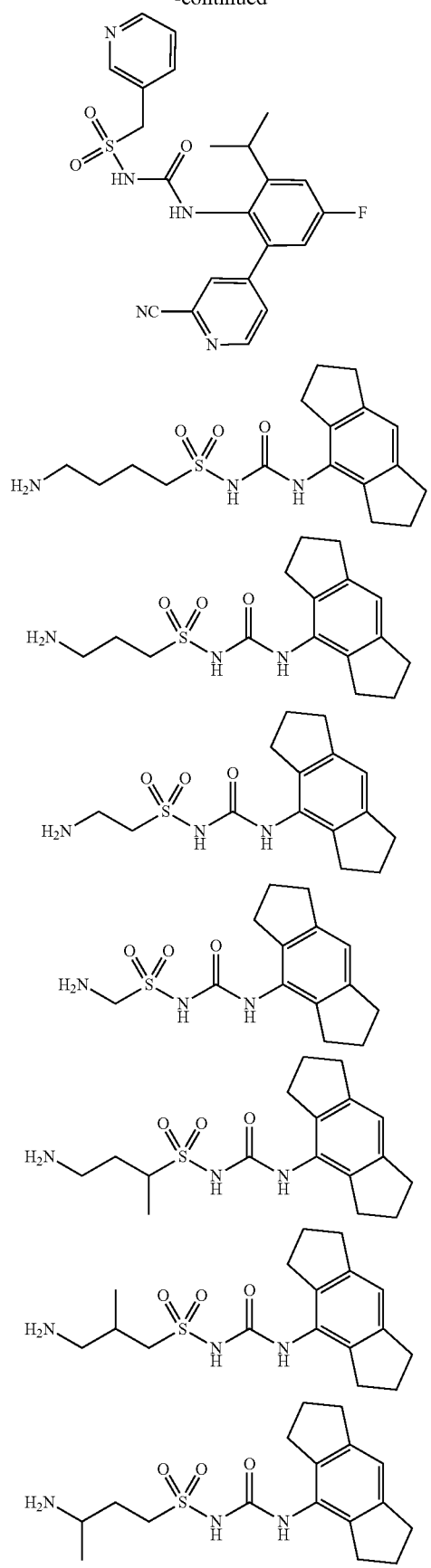
68
-continued
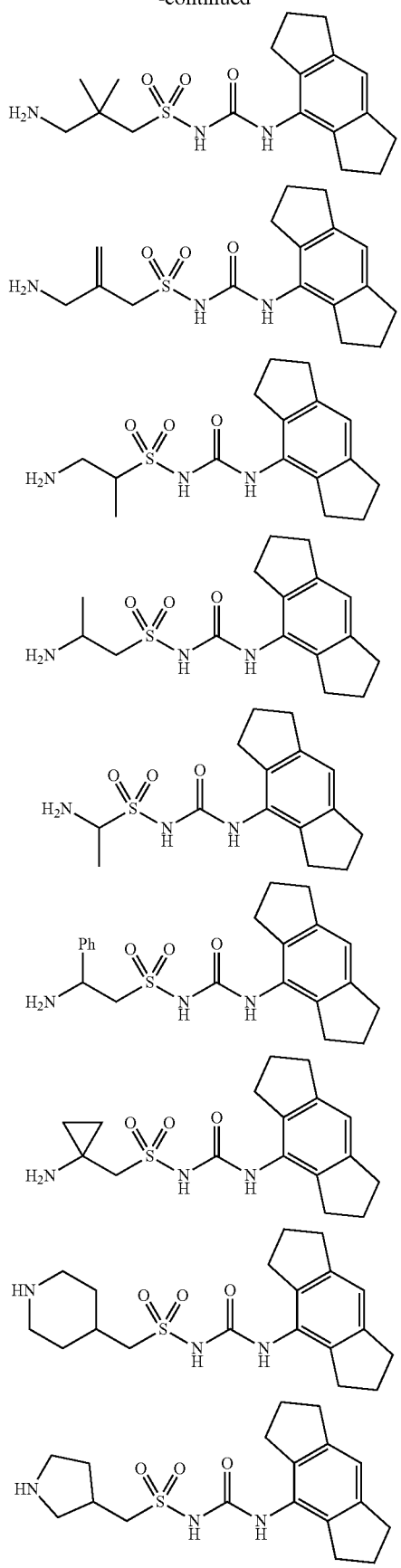

69
-continued
70
-continued
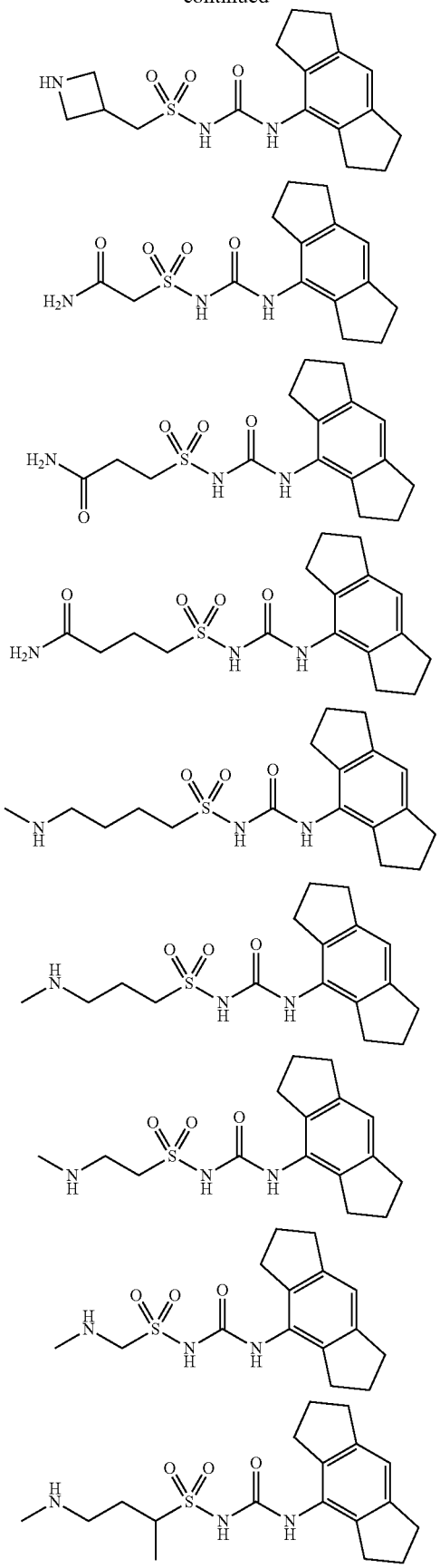
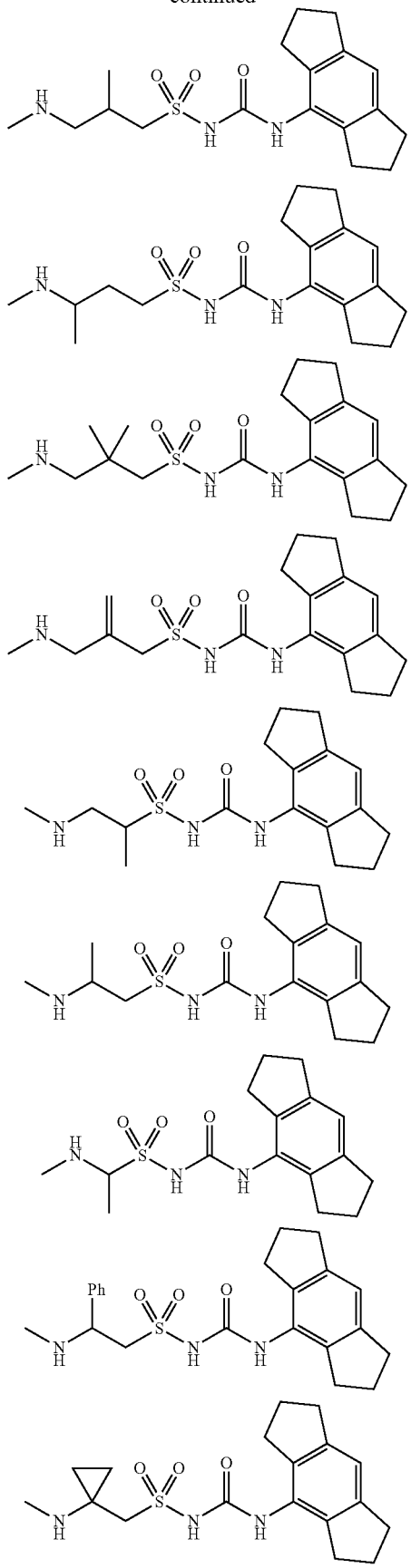

71
-continued
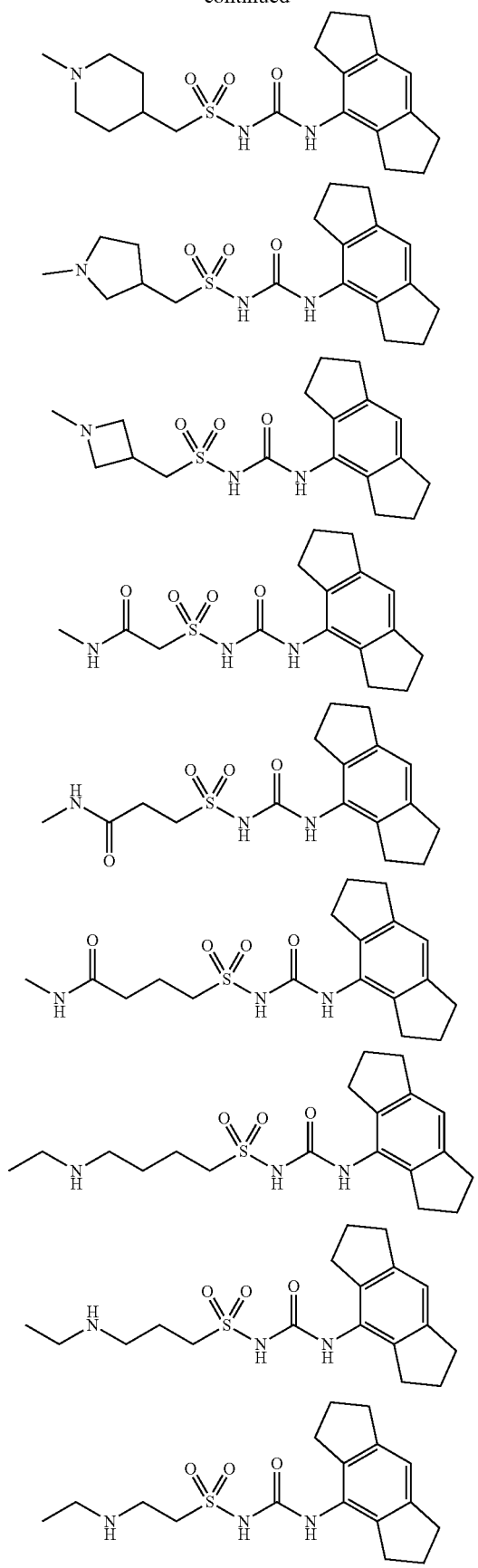
72
-continued
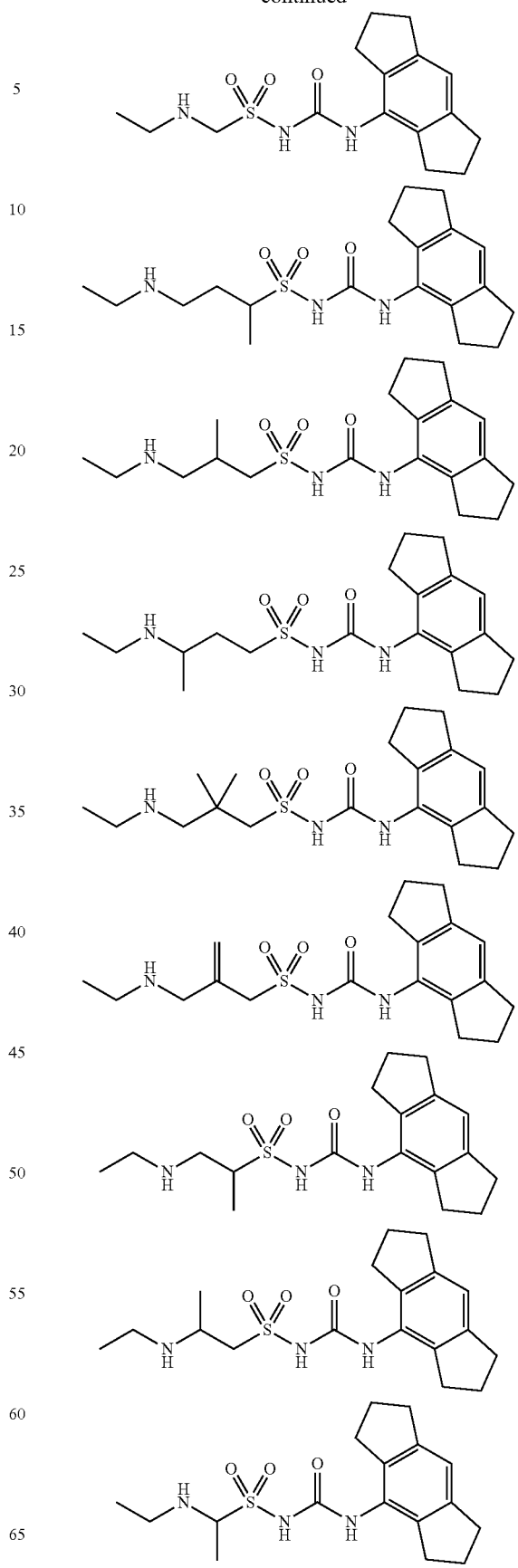

73
-continued
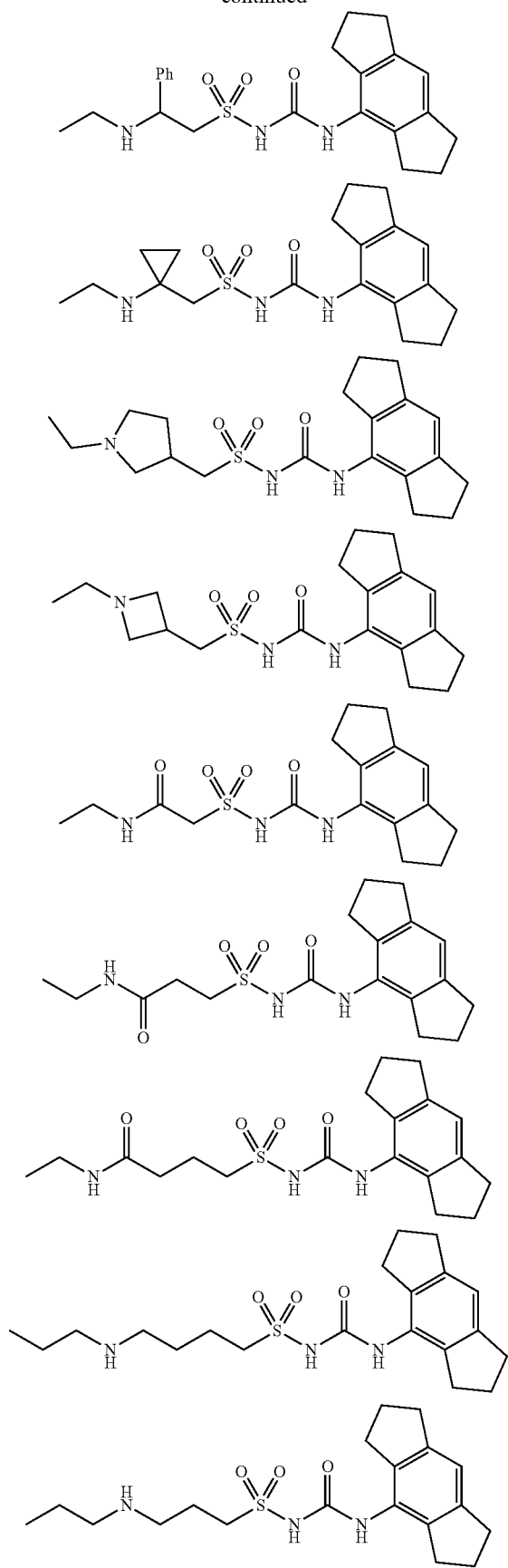
74
-continued
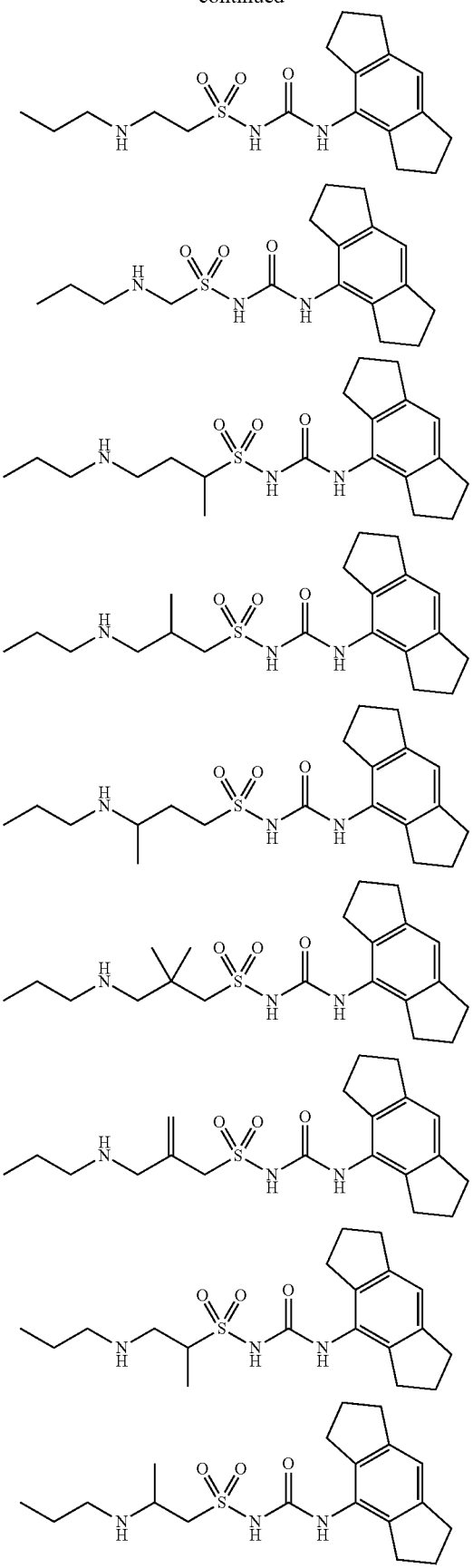

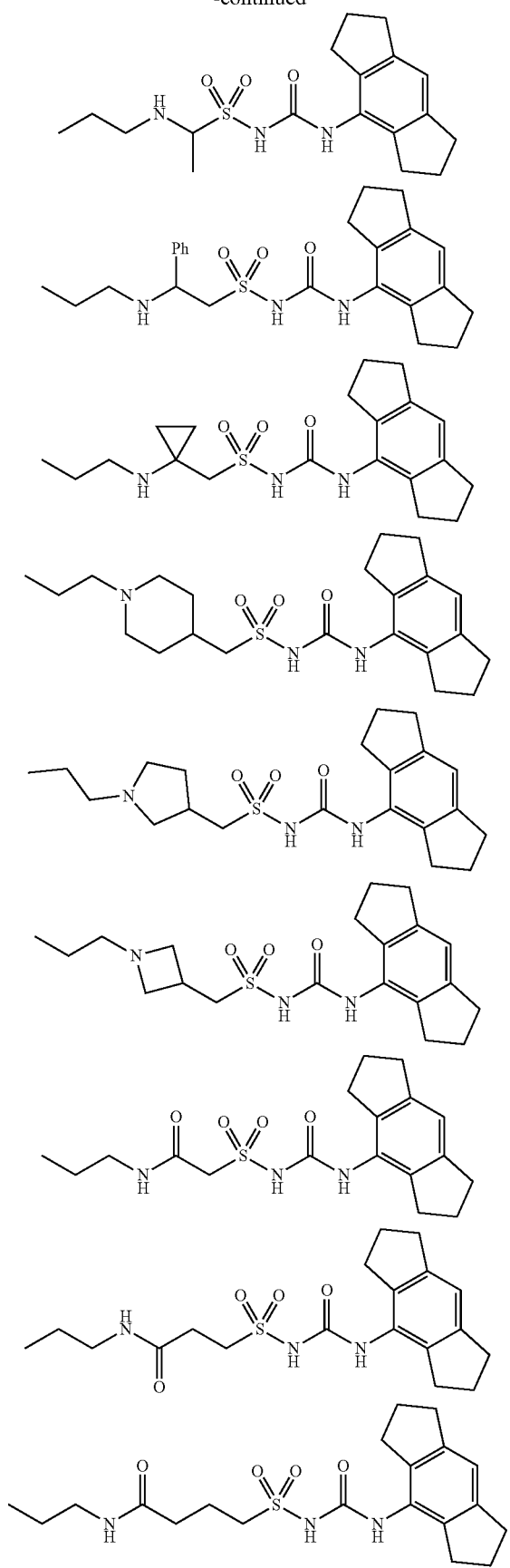
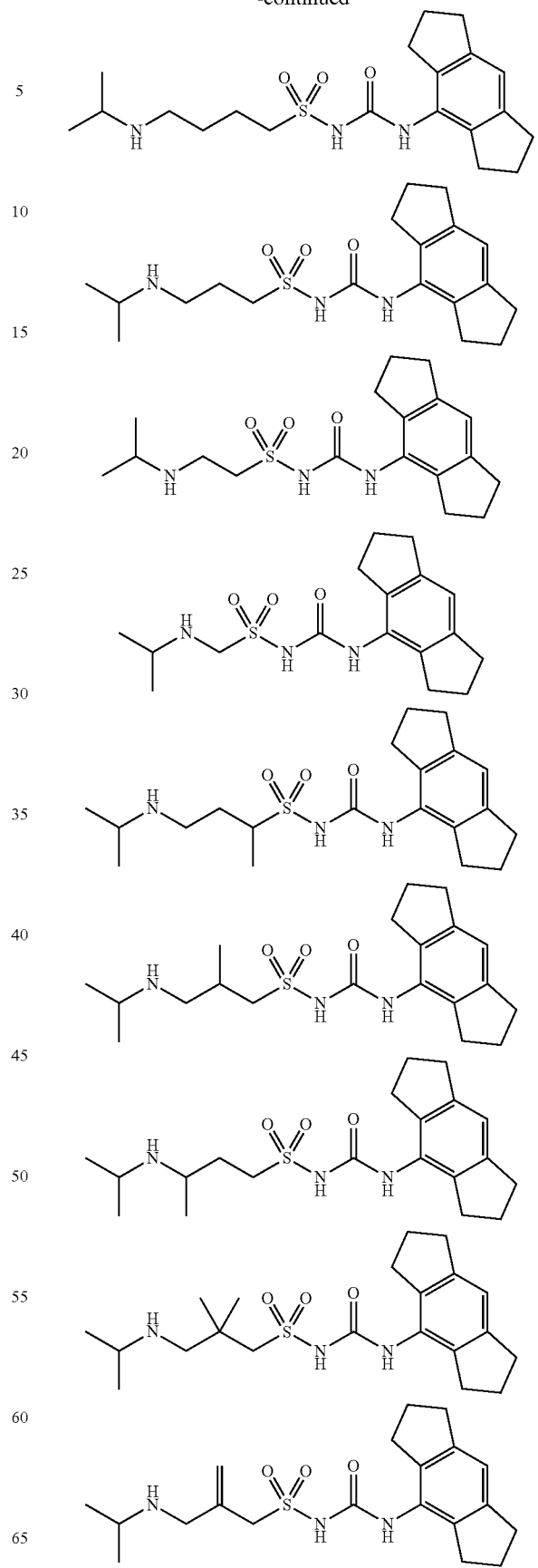

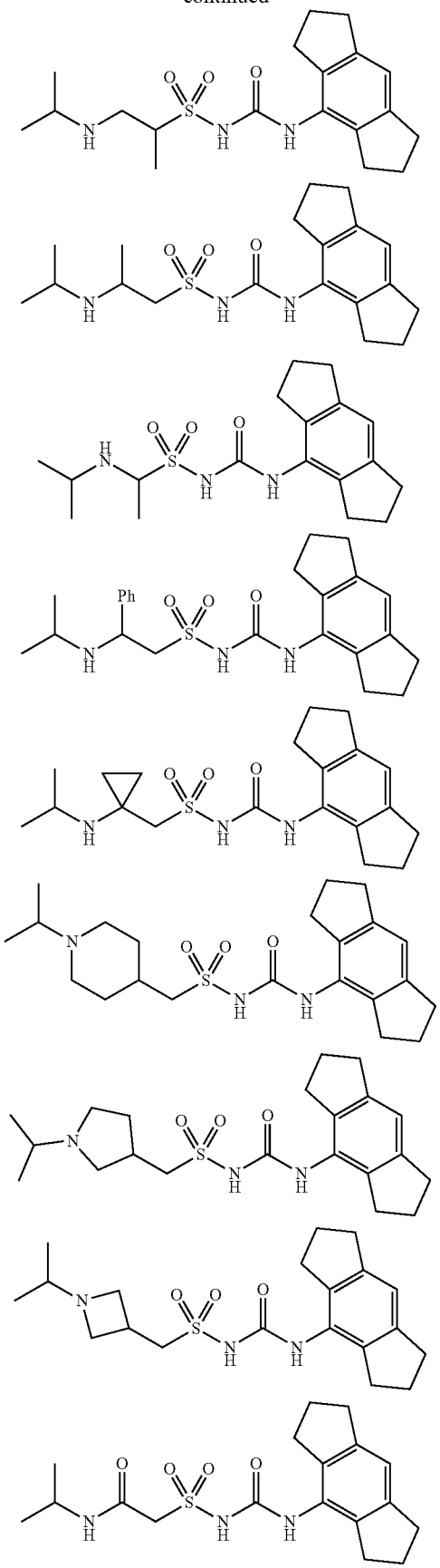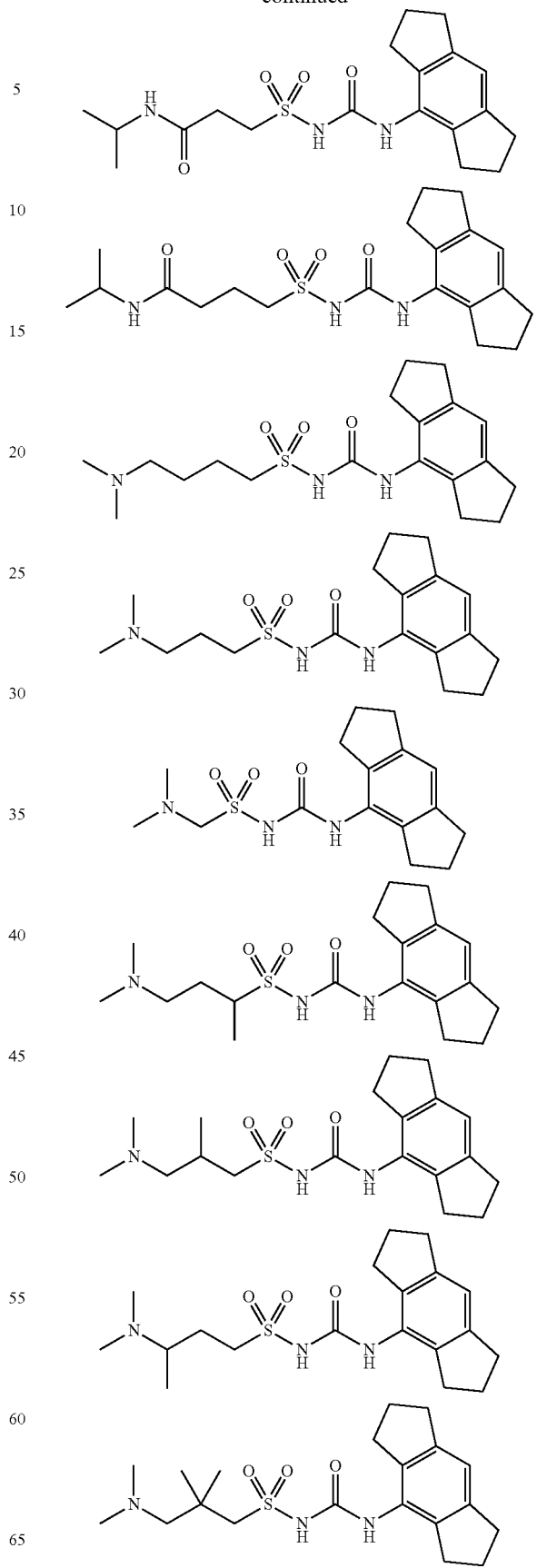

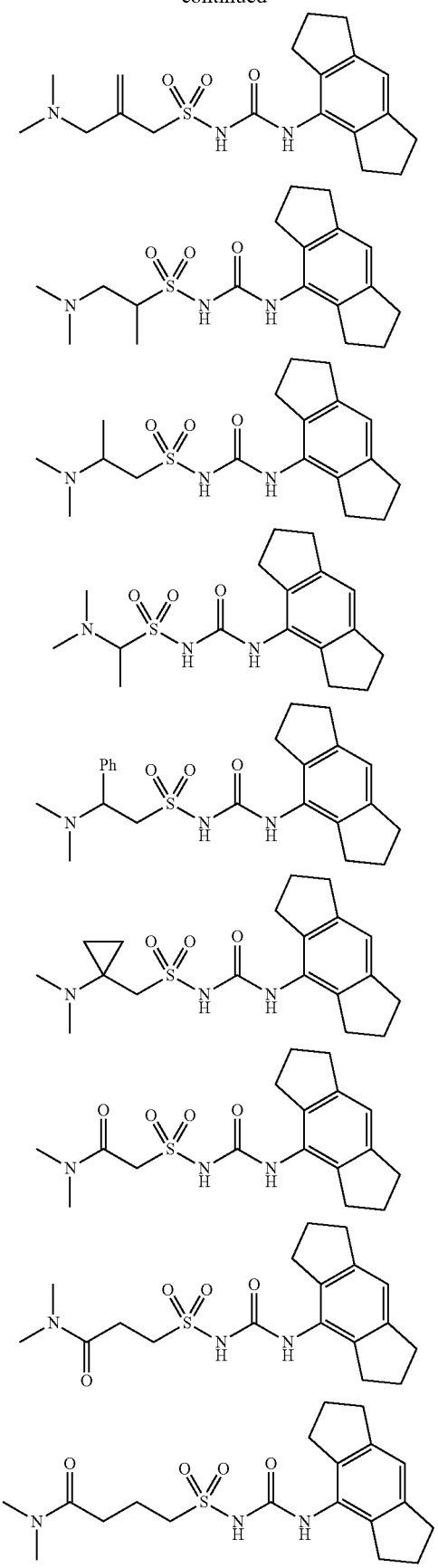
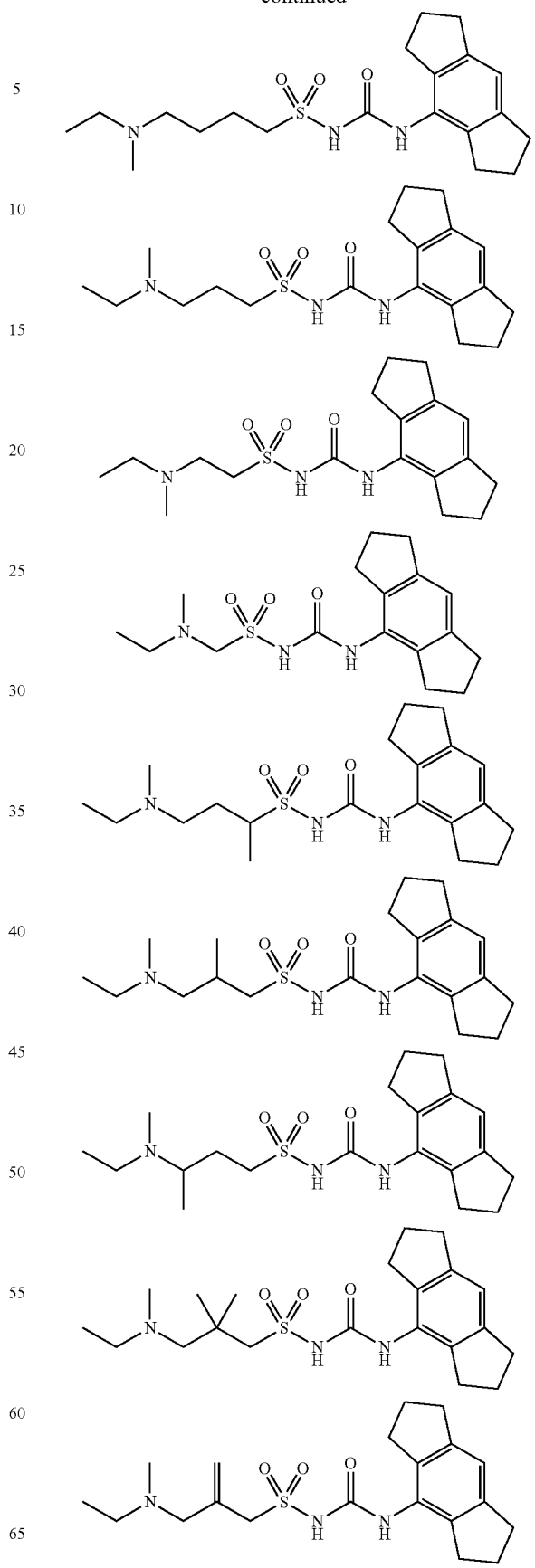

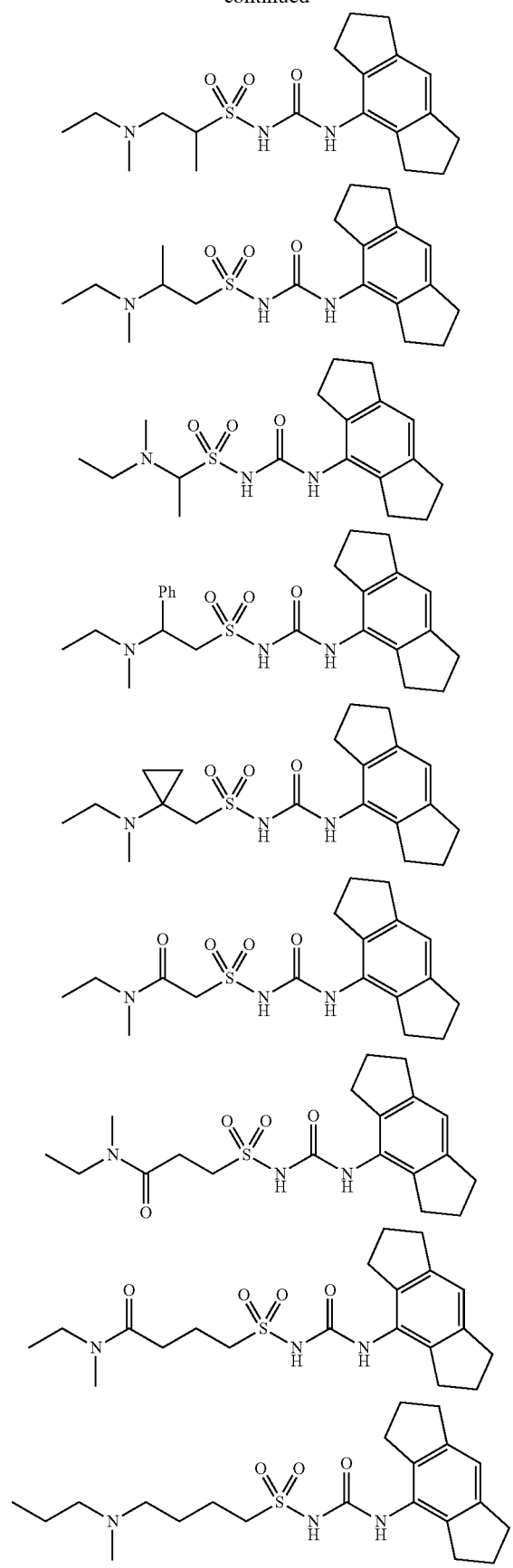
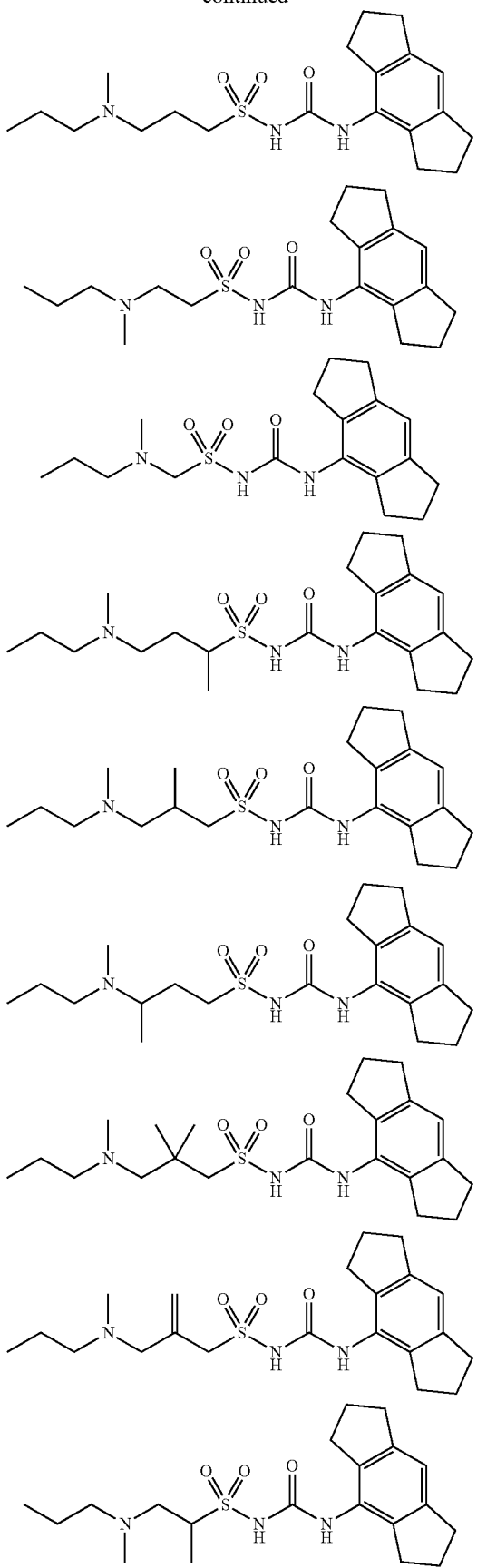

83
-continued
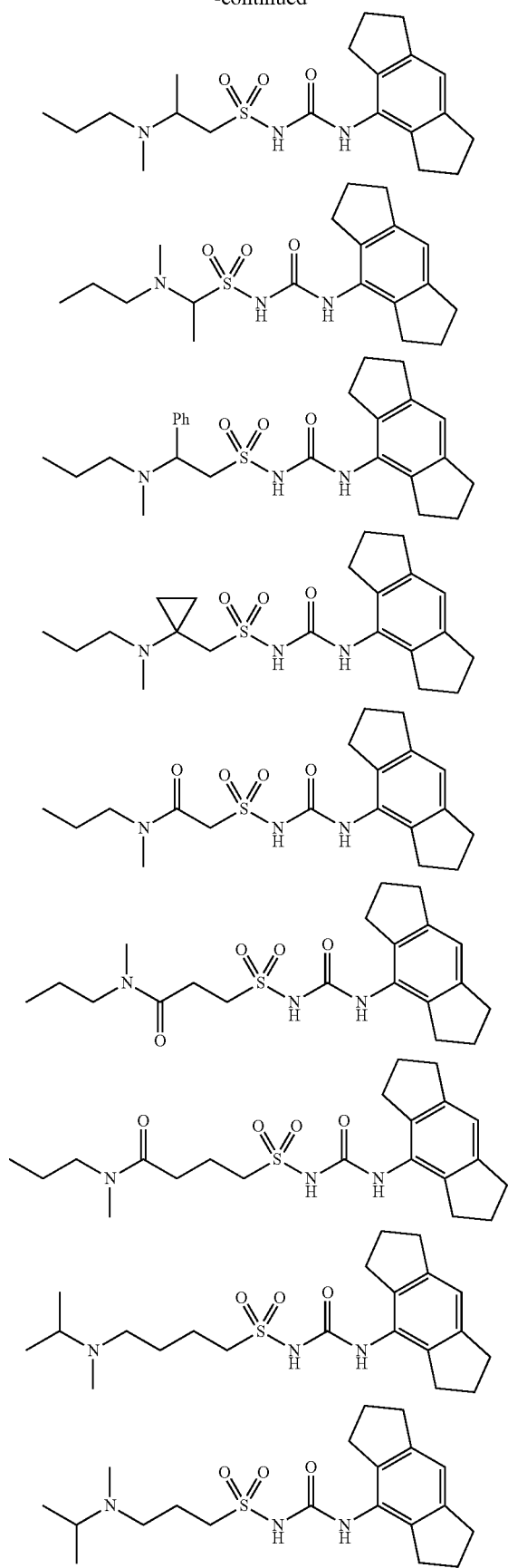
84
-continued
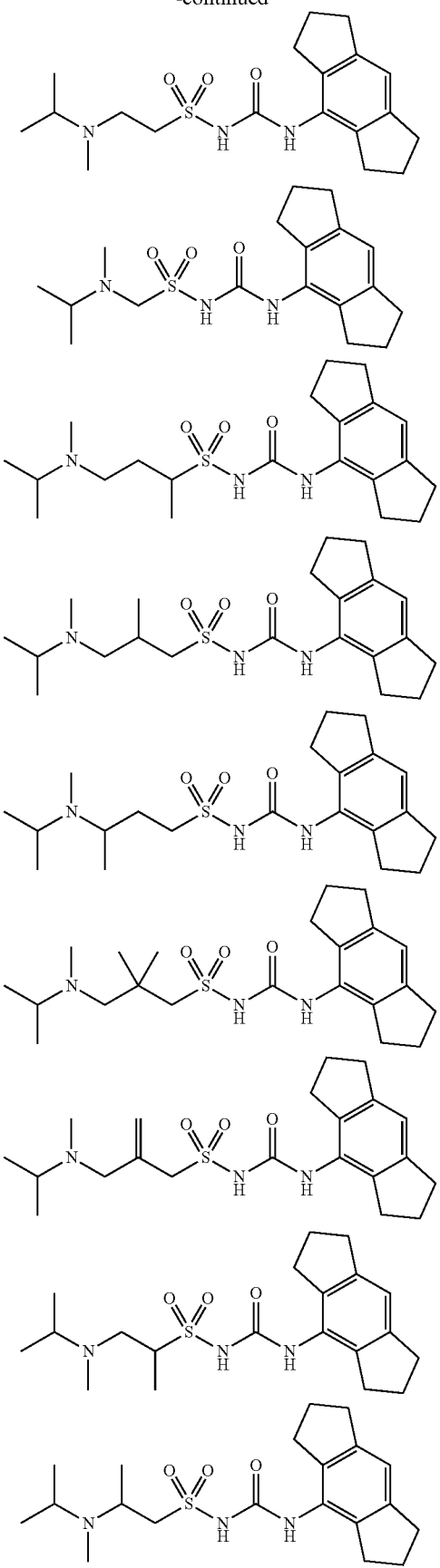

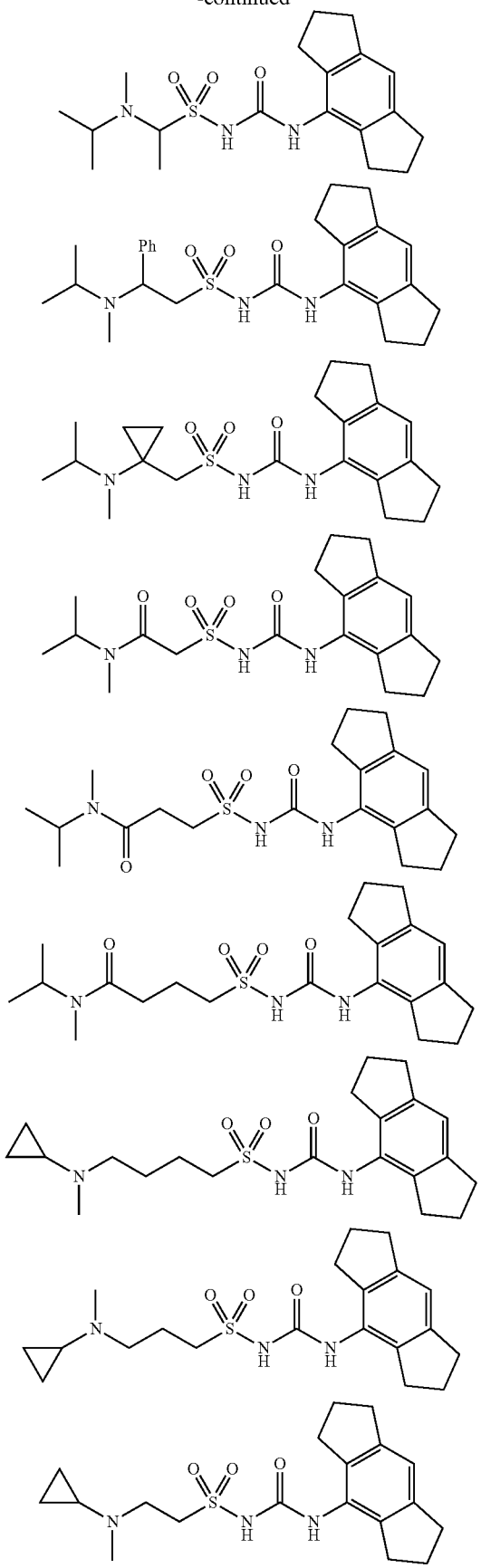
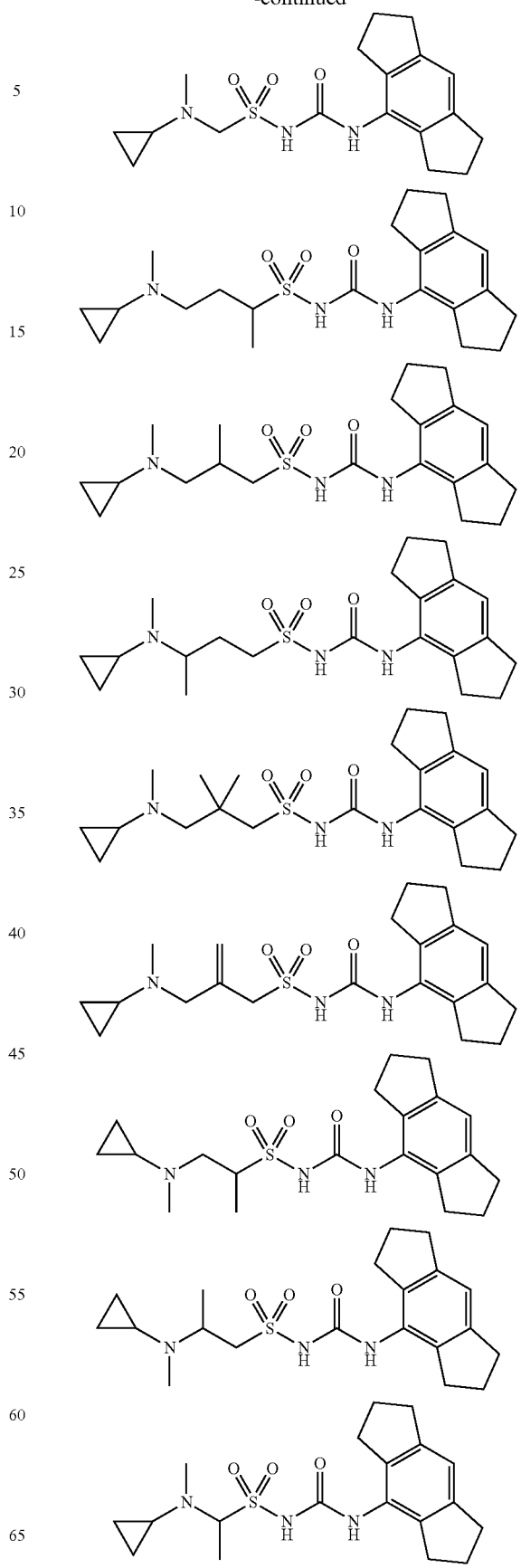

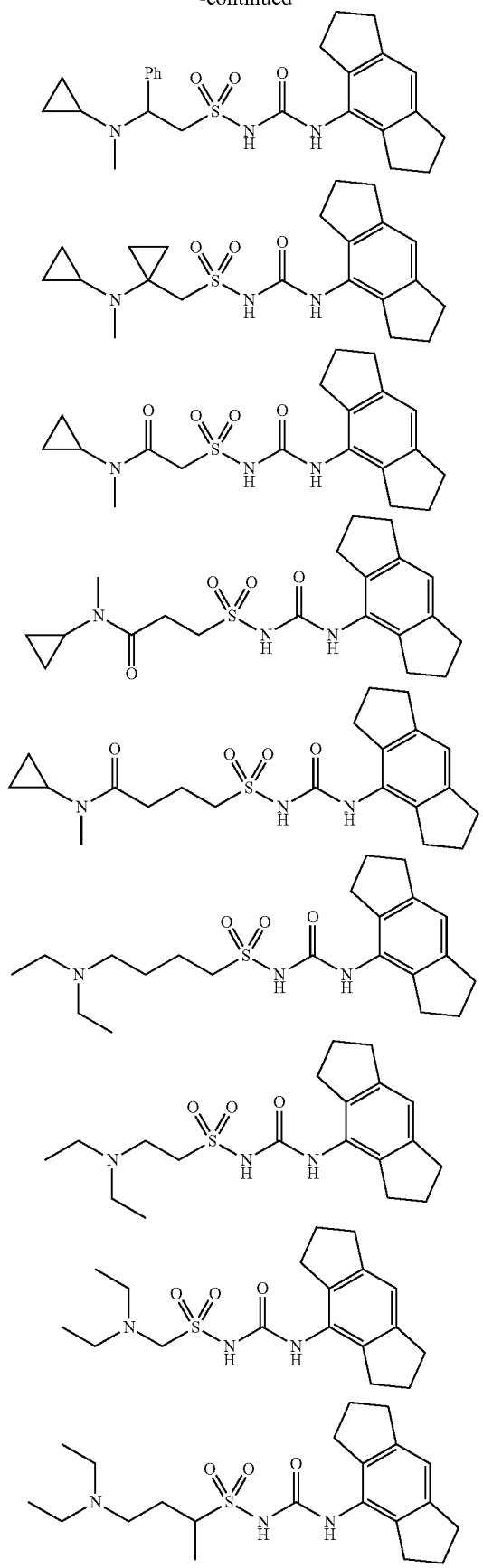
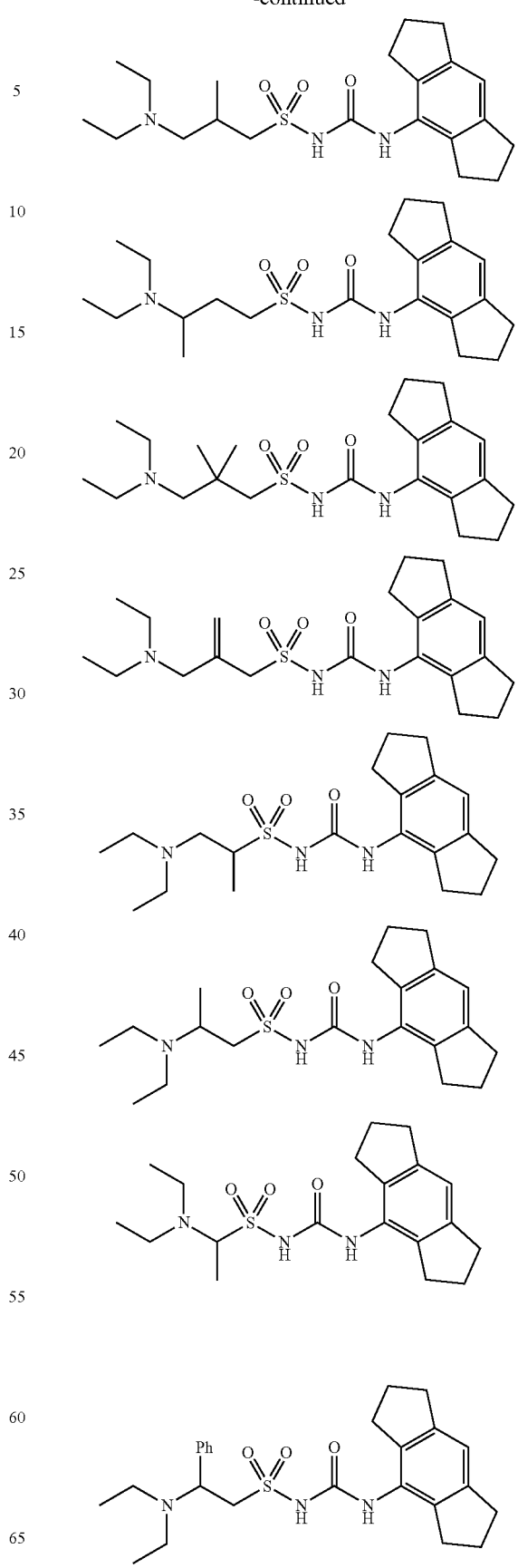

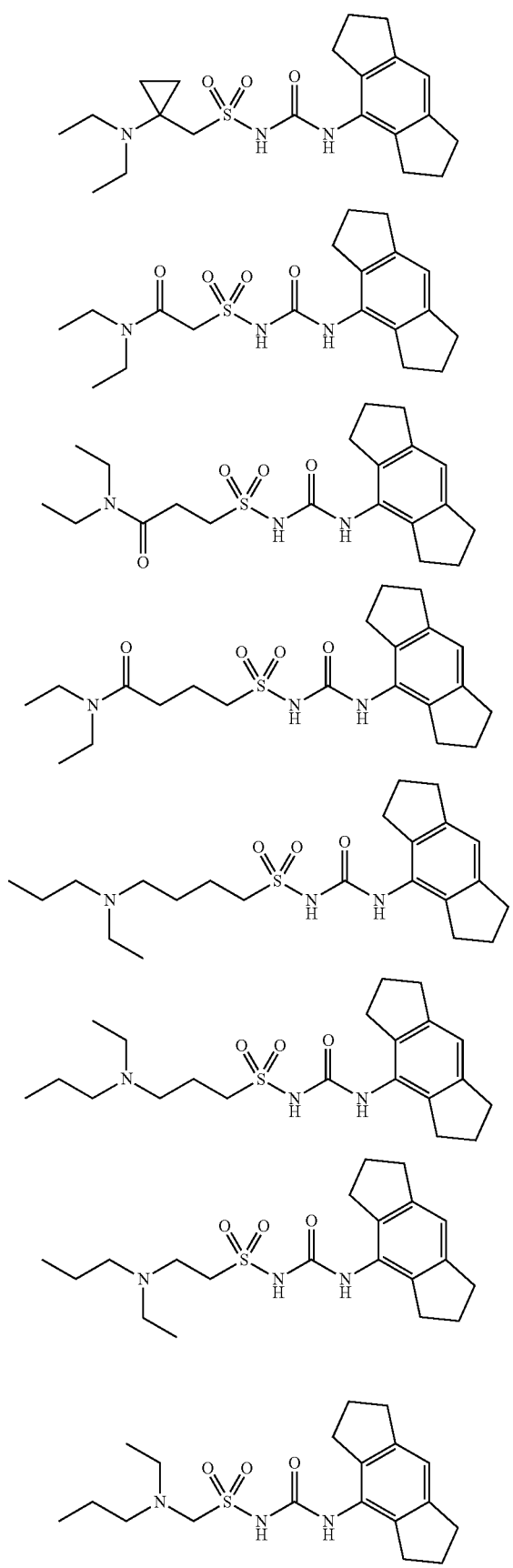
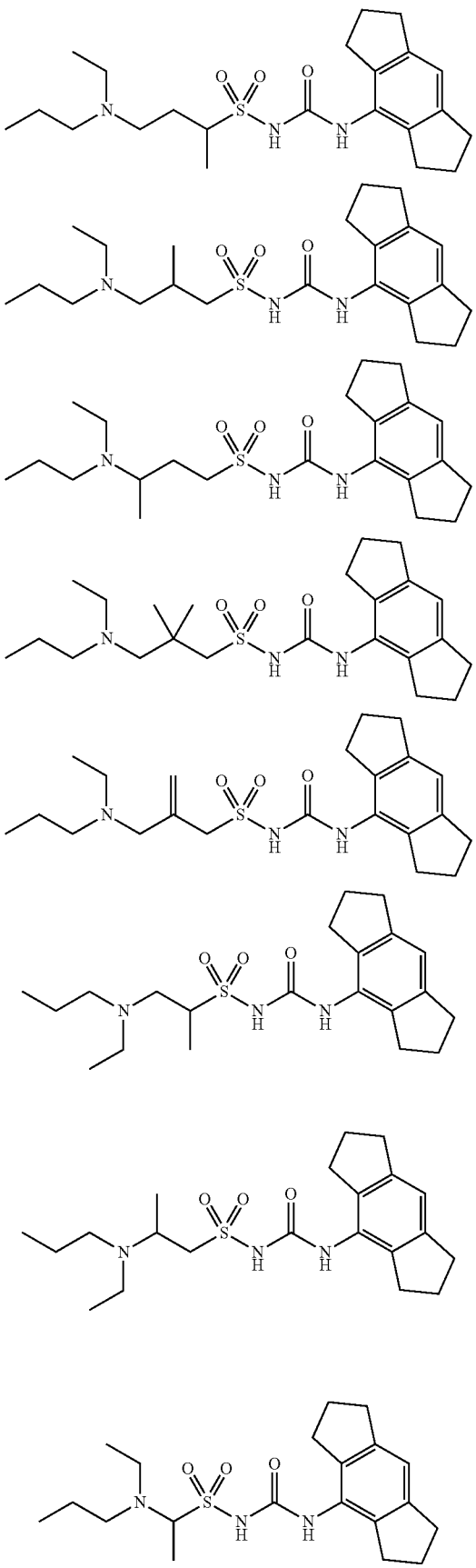

91
-continued
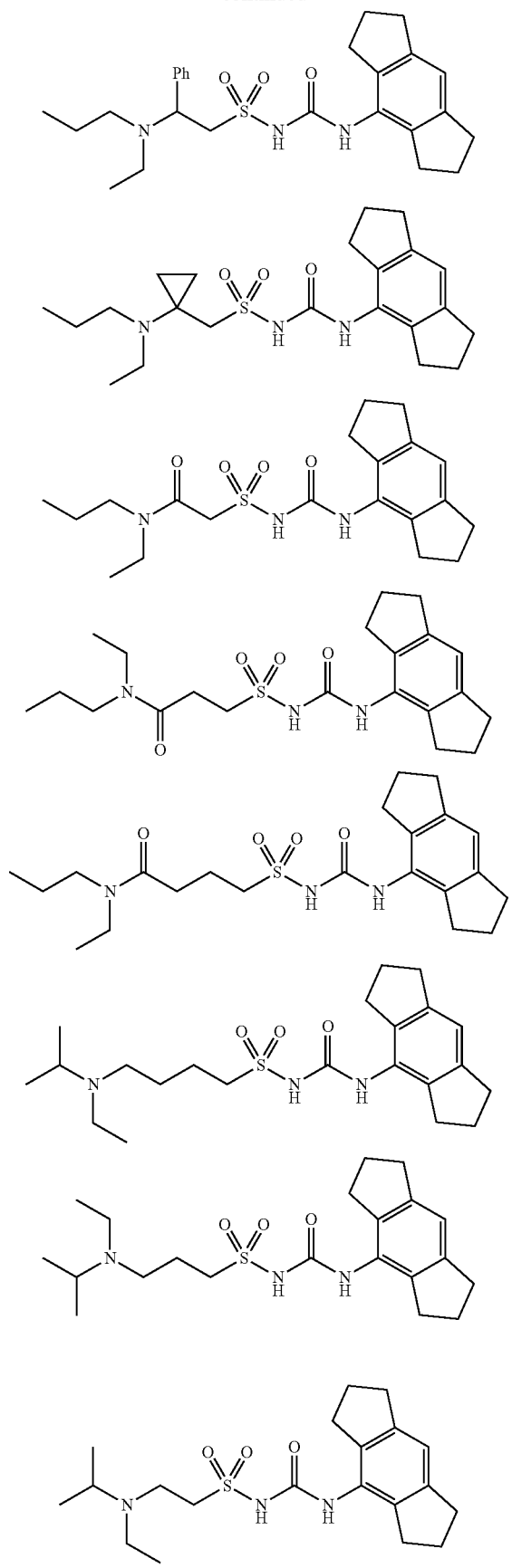
92
-continued
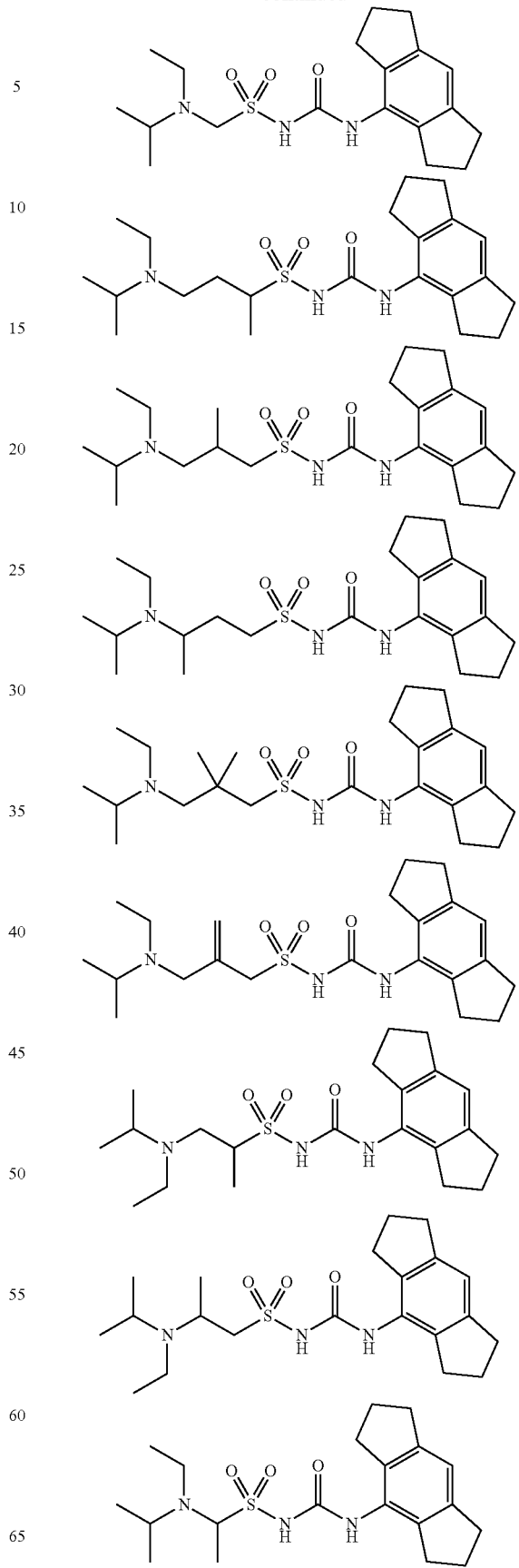

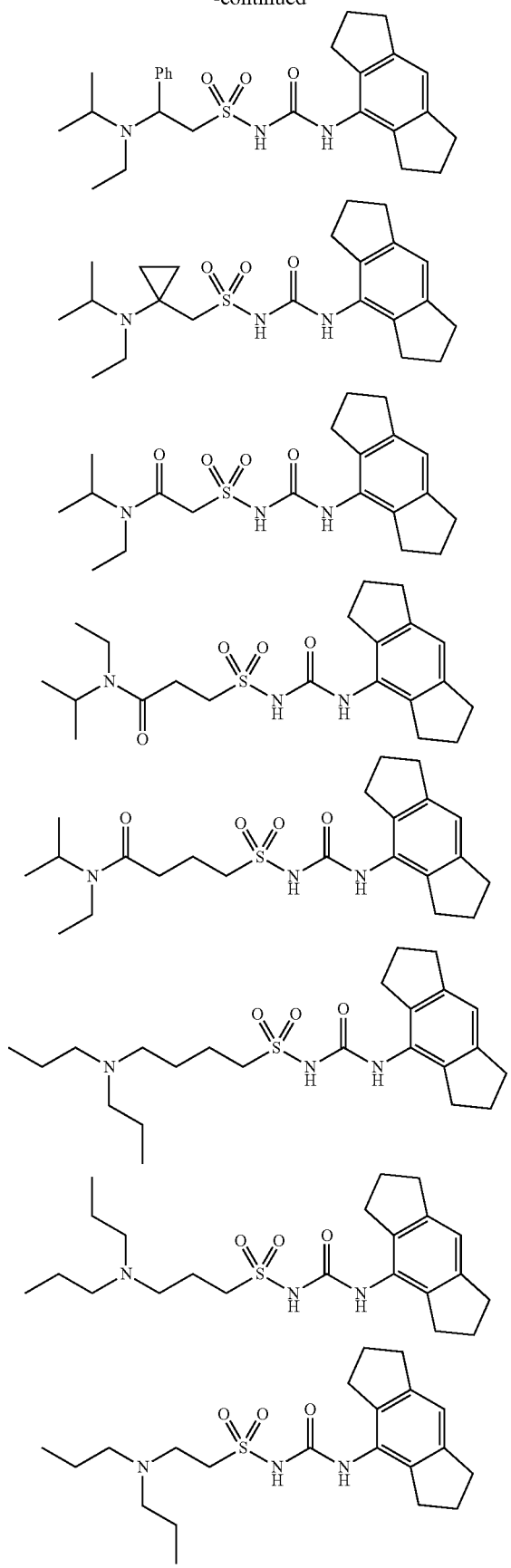
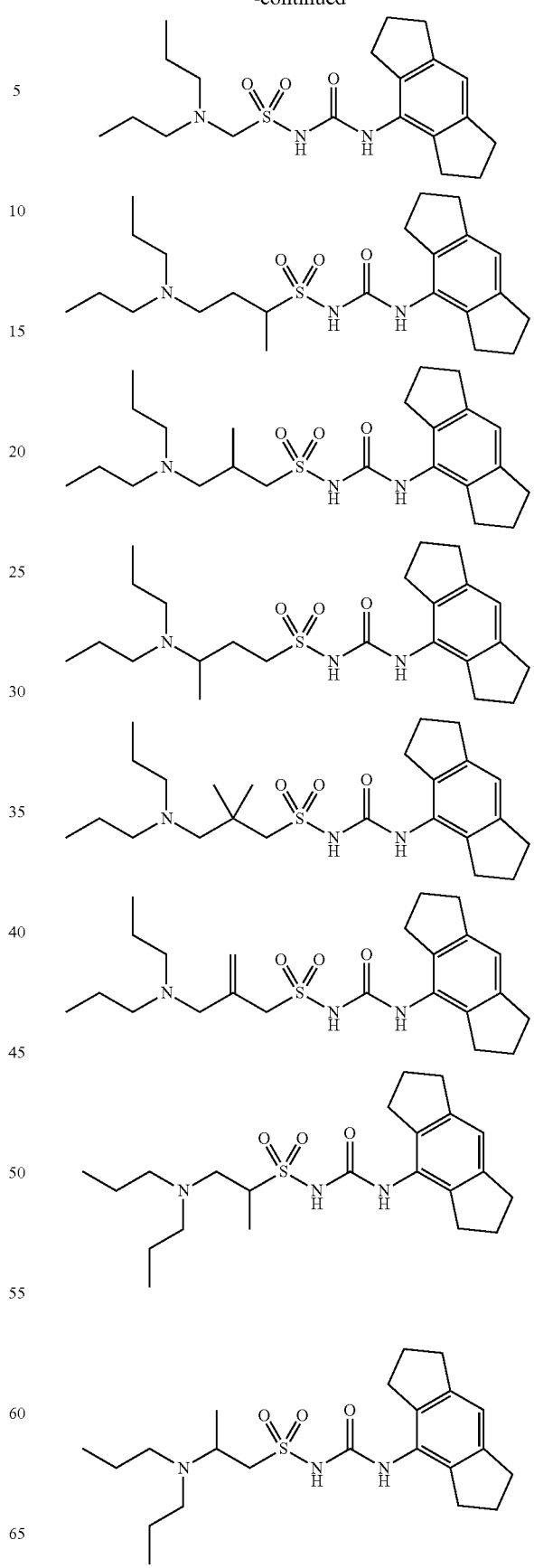

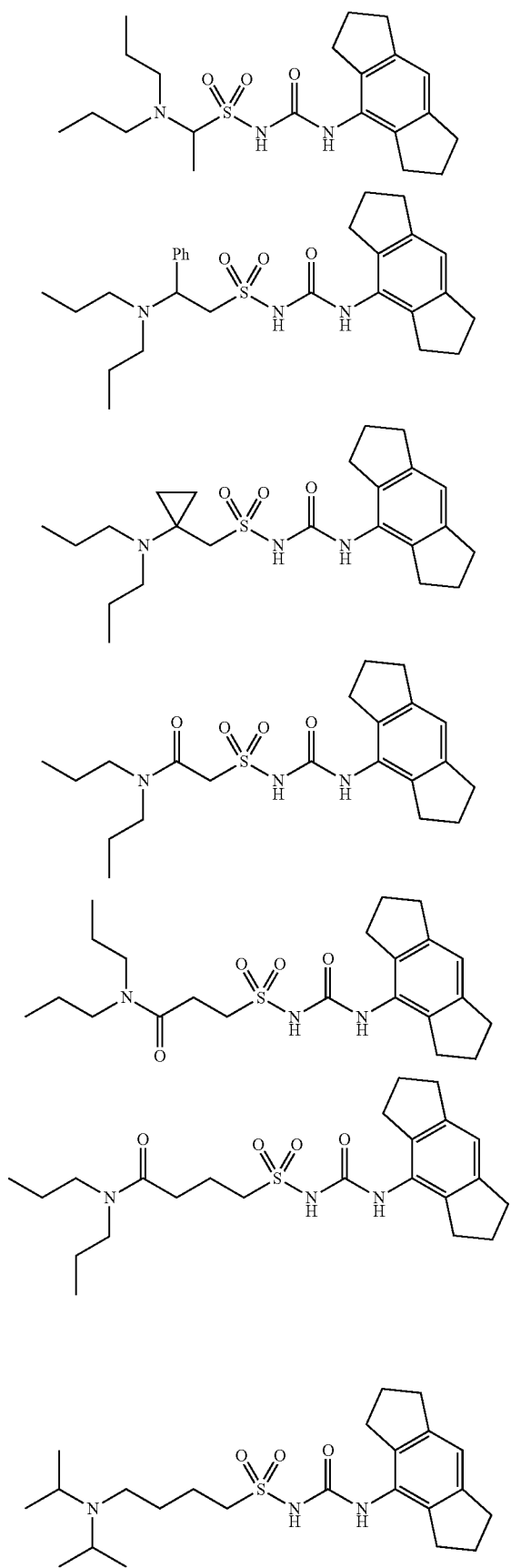
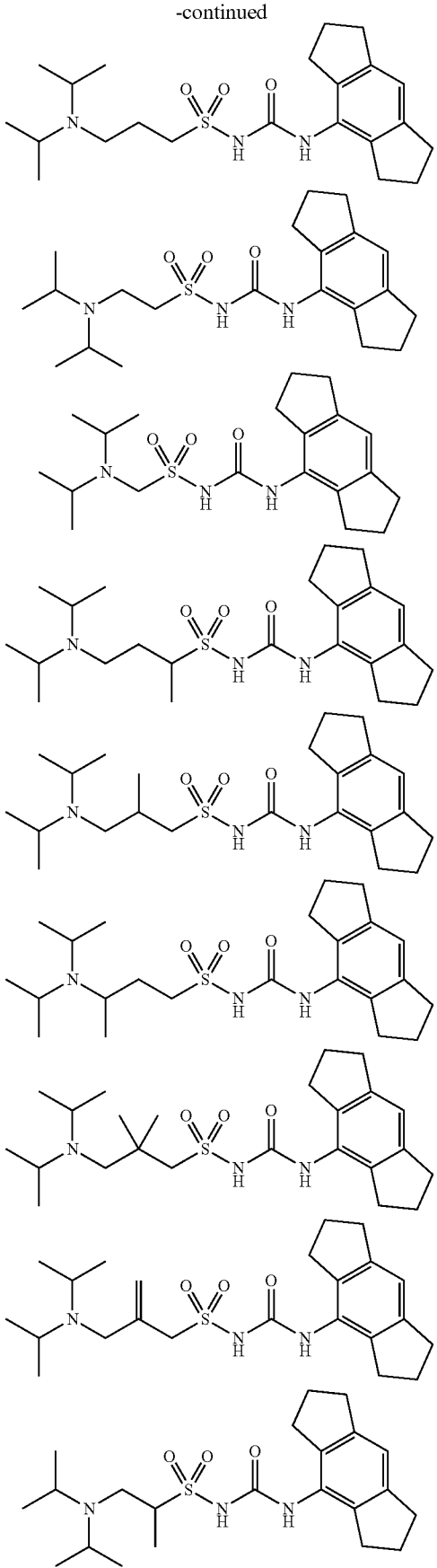

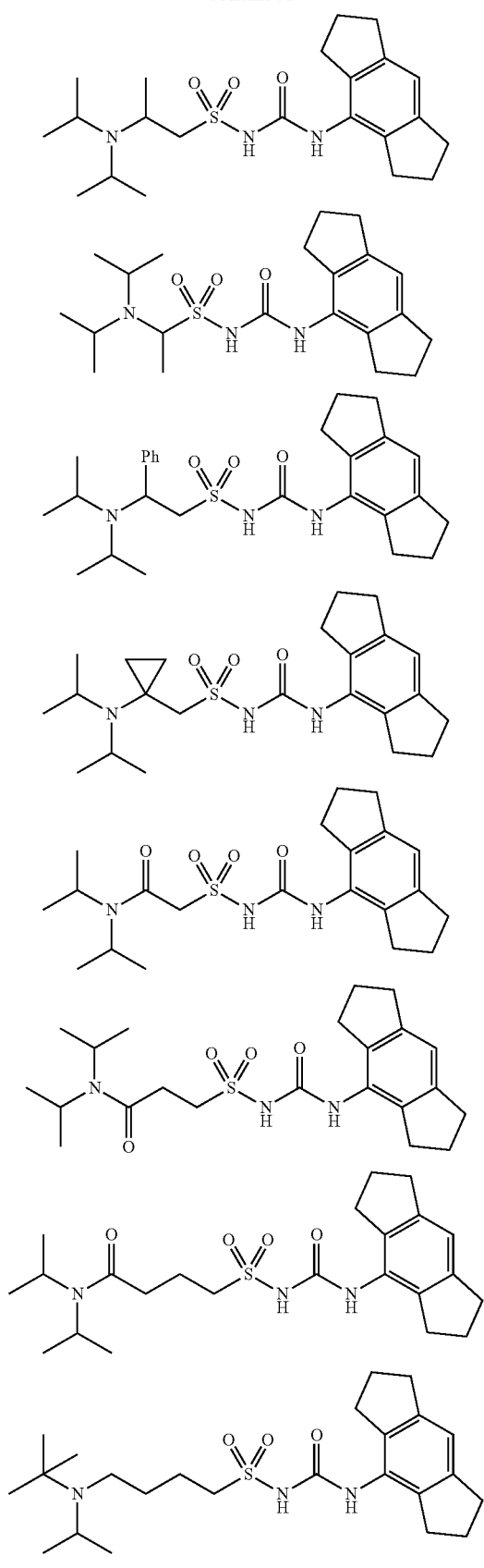
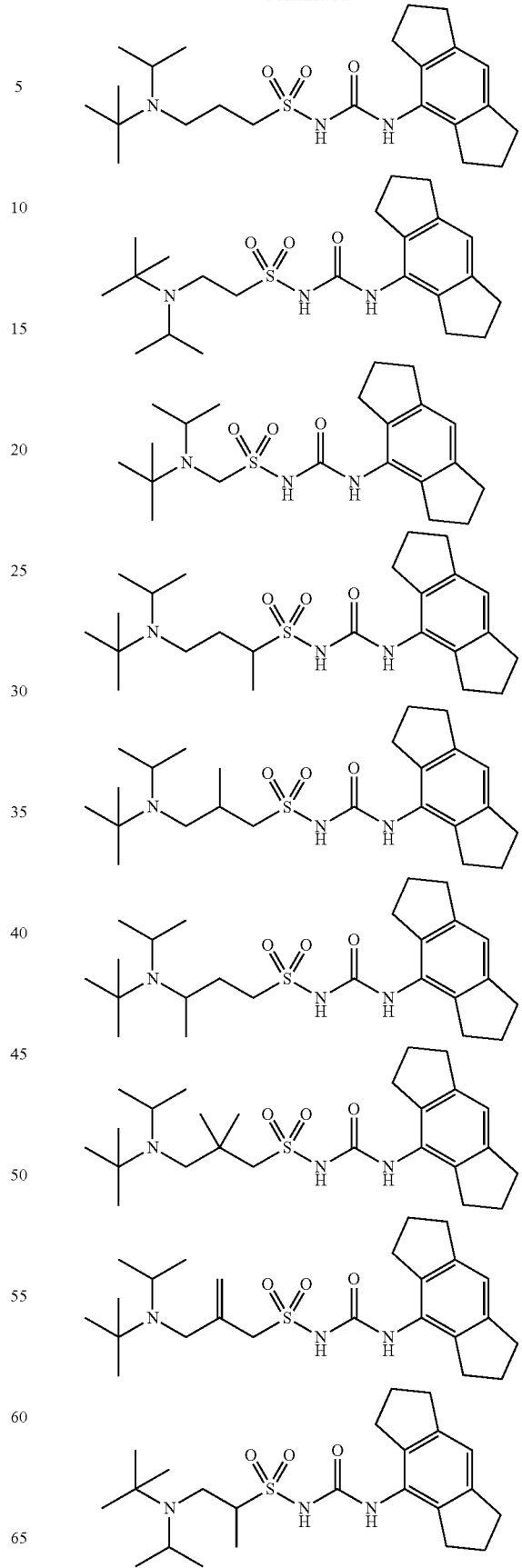

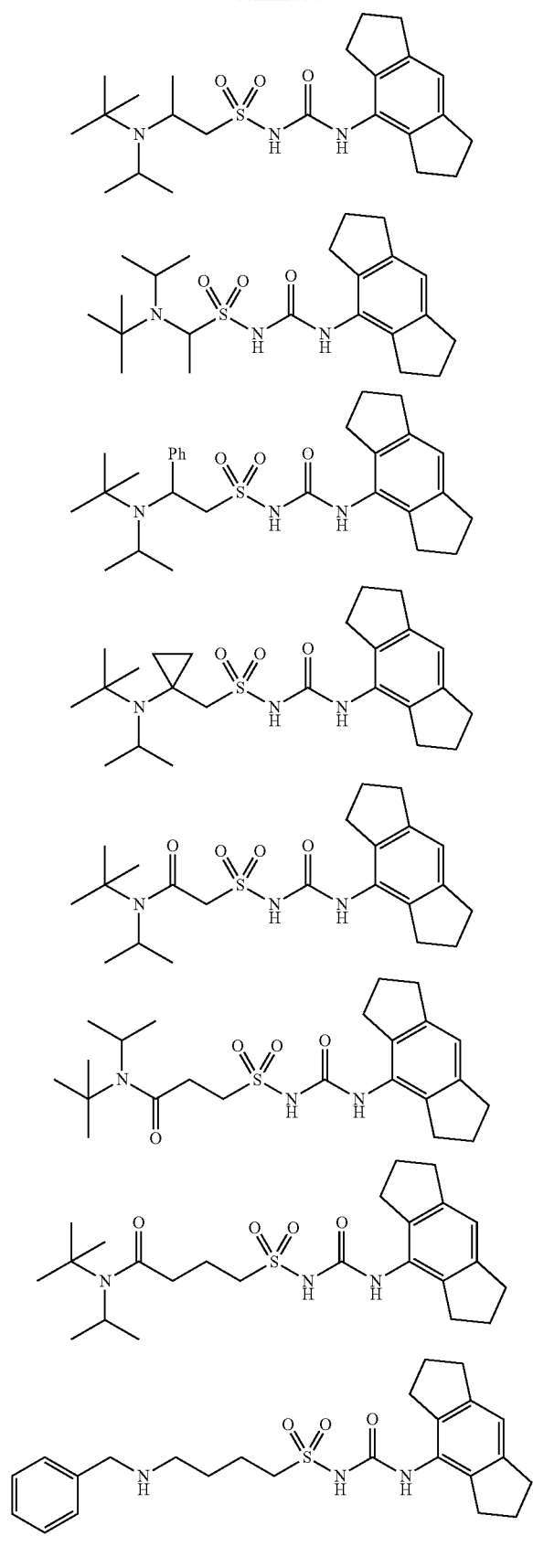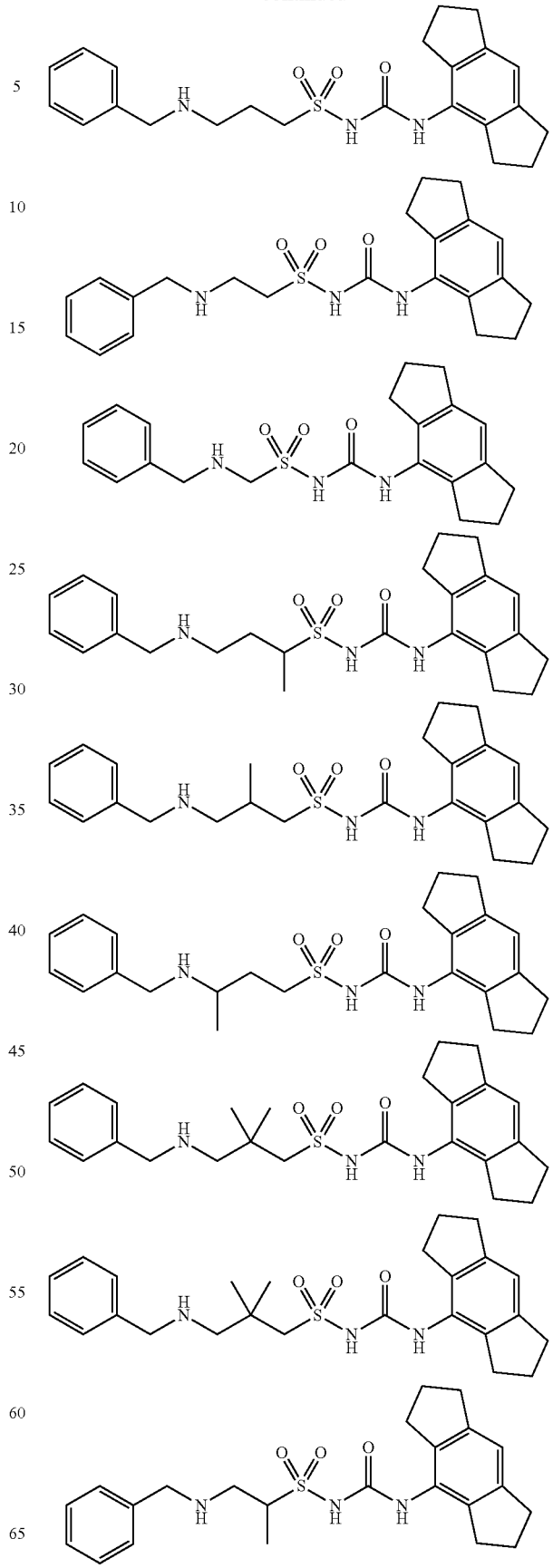

101
-continued
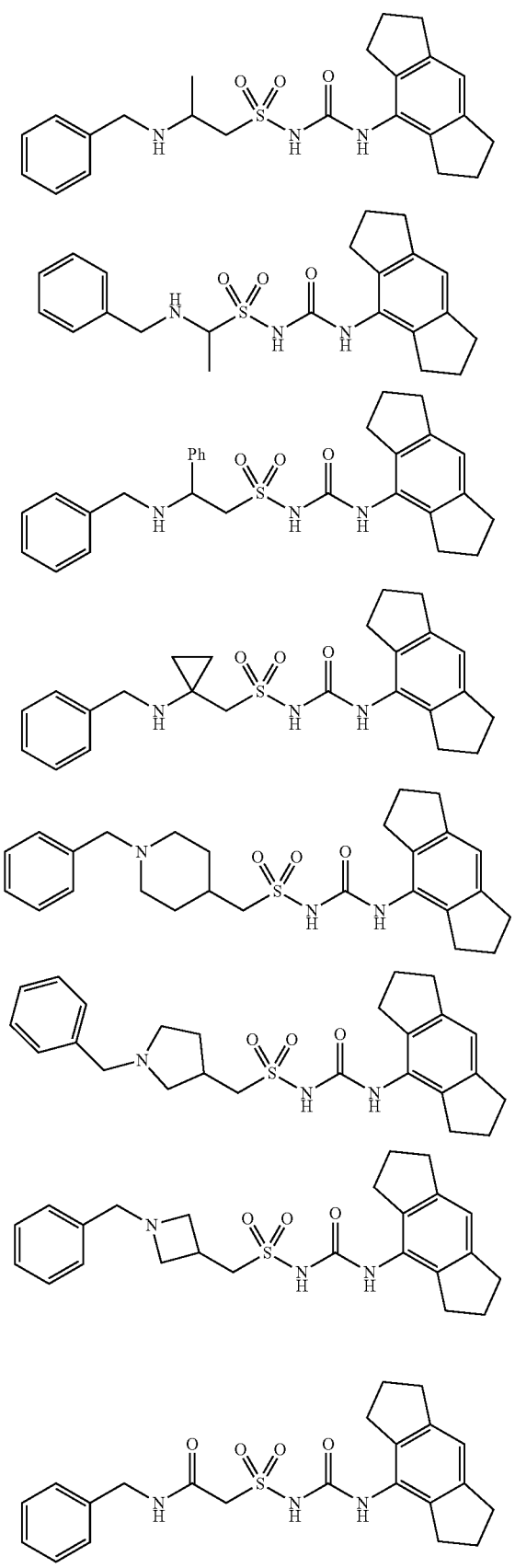
102
-continued
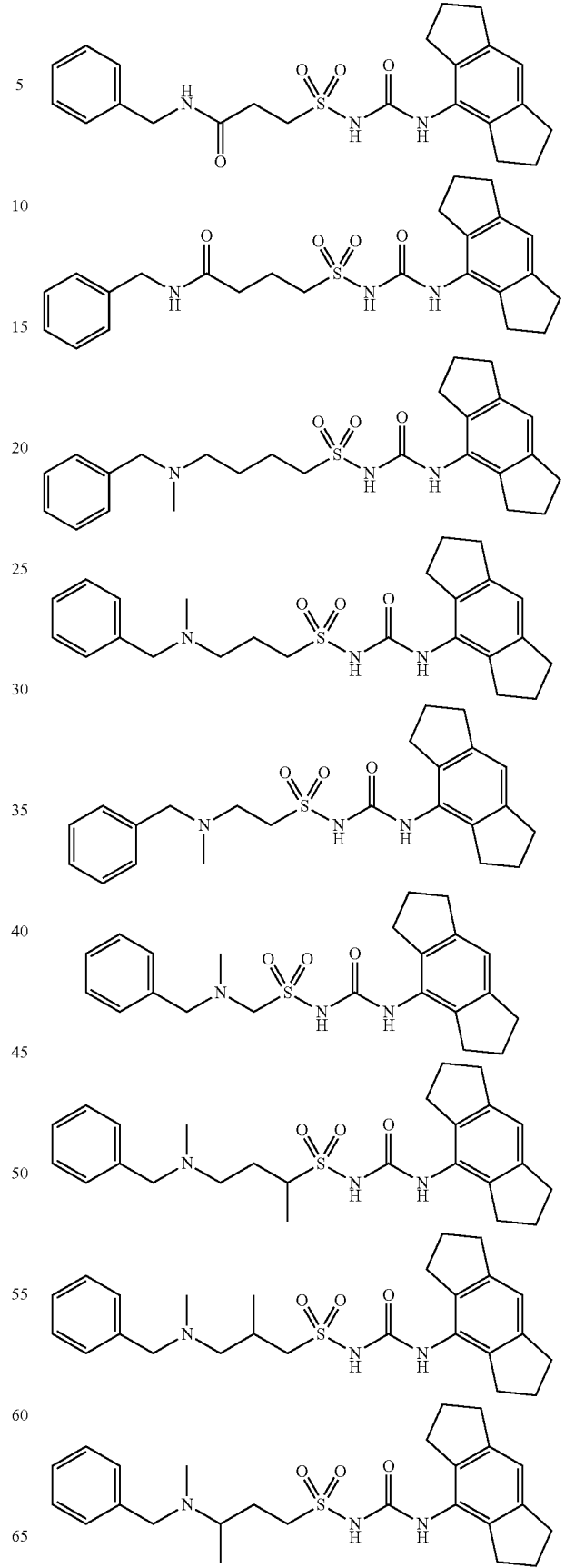

103
-continued
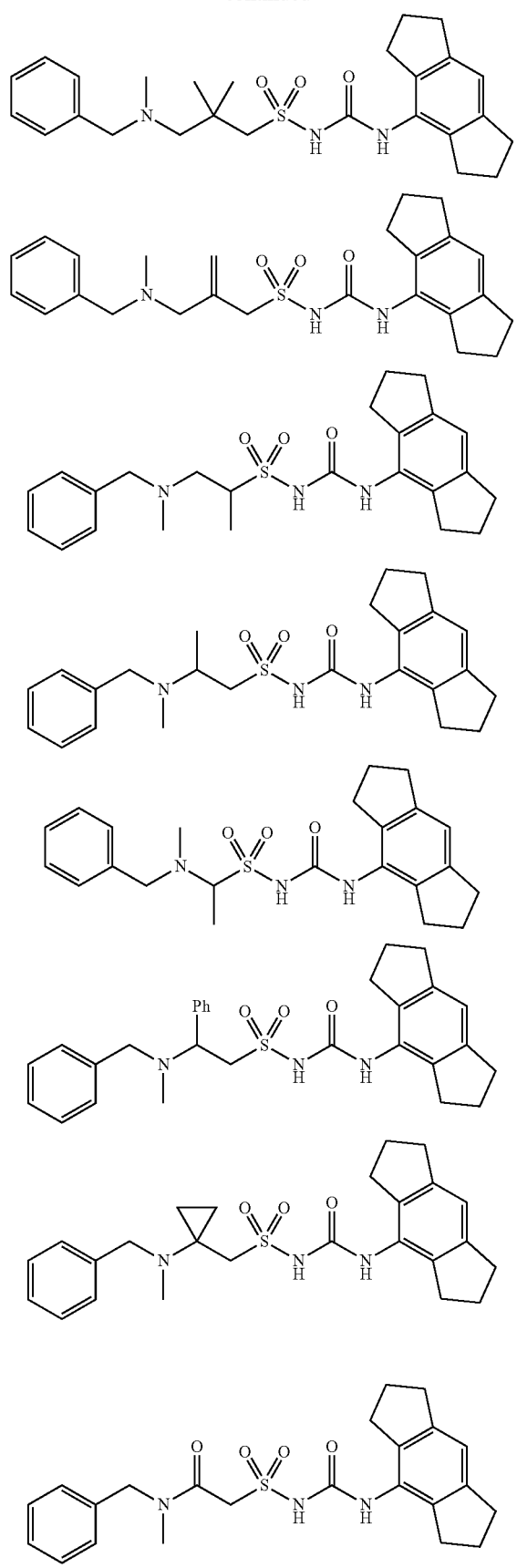
104
-continued
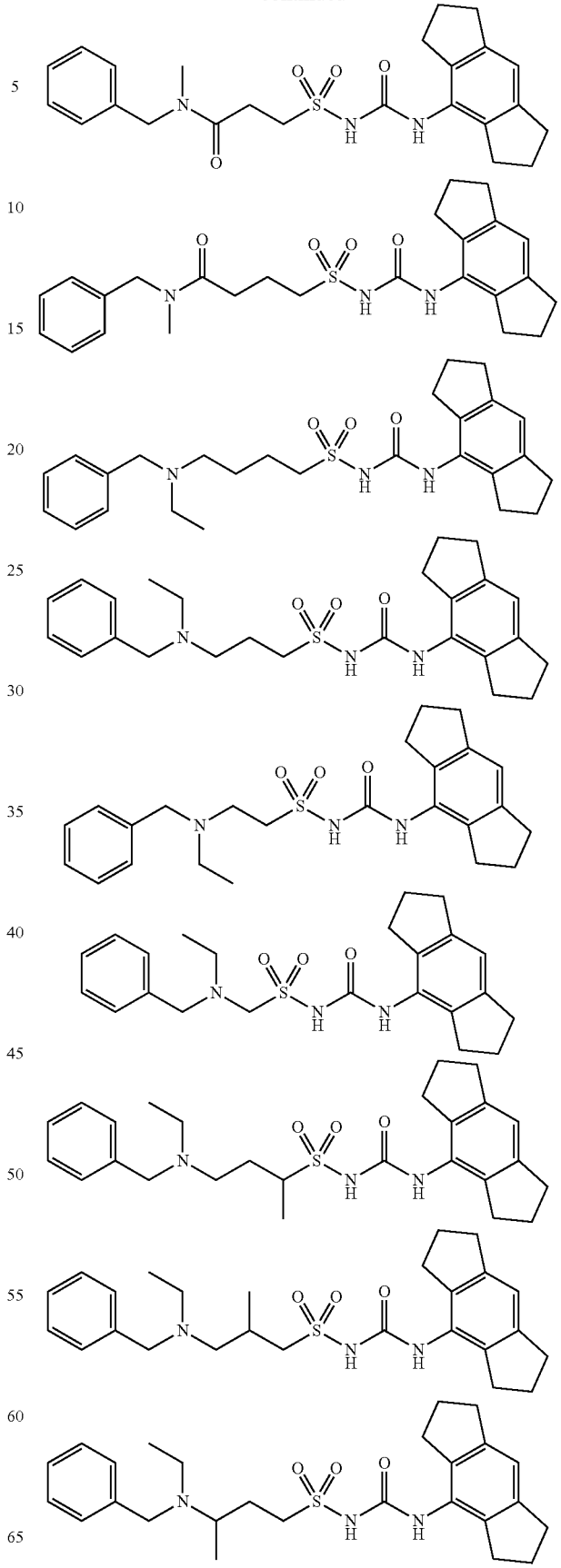

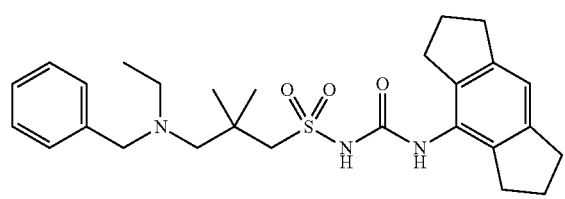
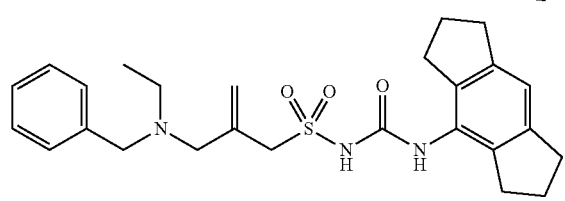
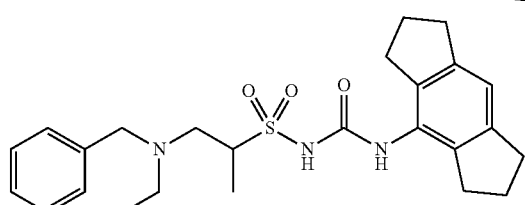
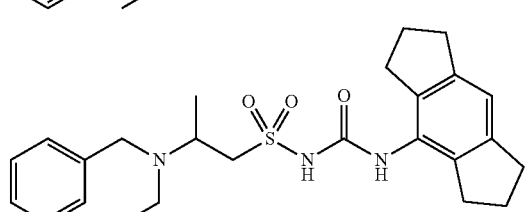
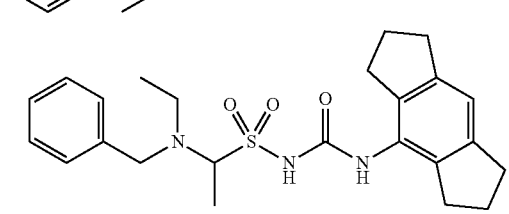
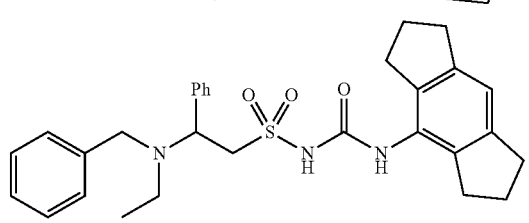
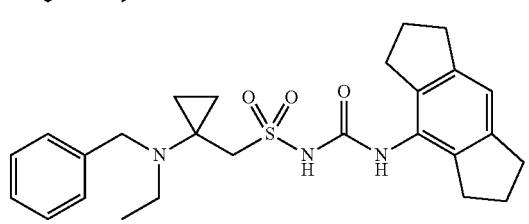
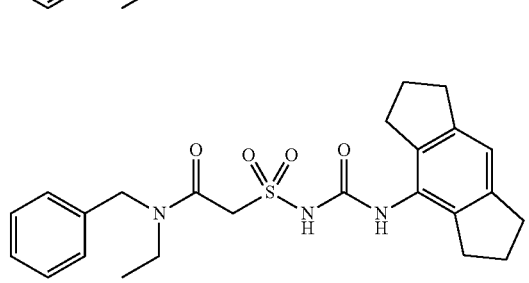
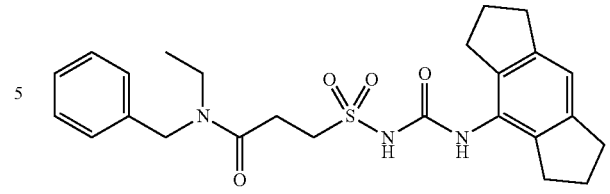
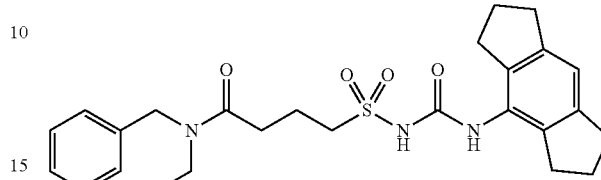
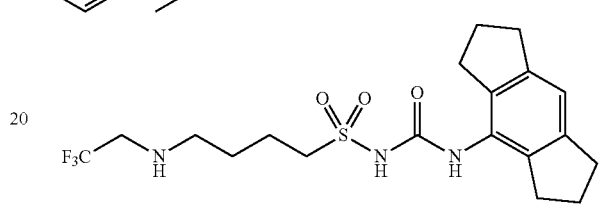
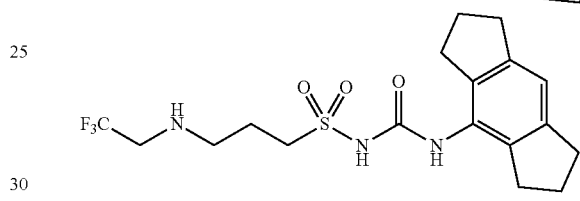
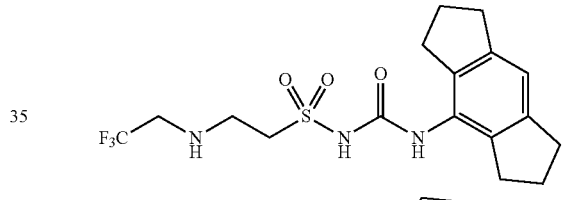
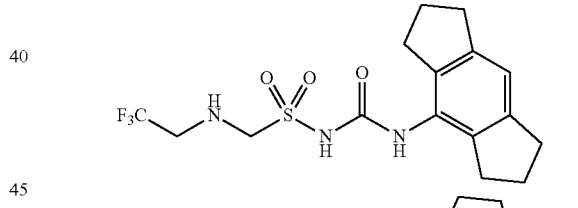
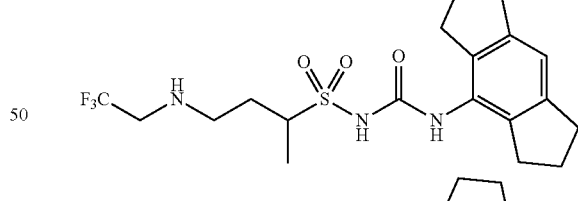
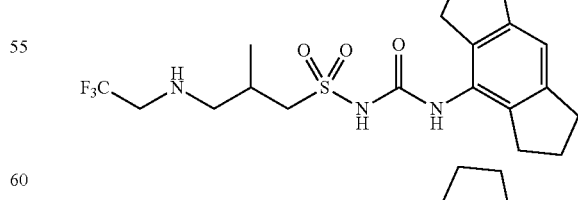
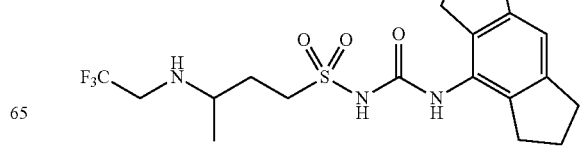

107
-continued
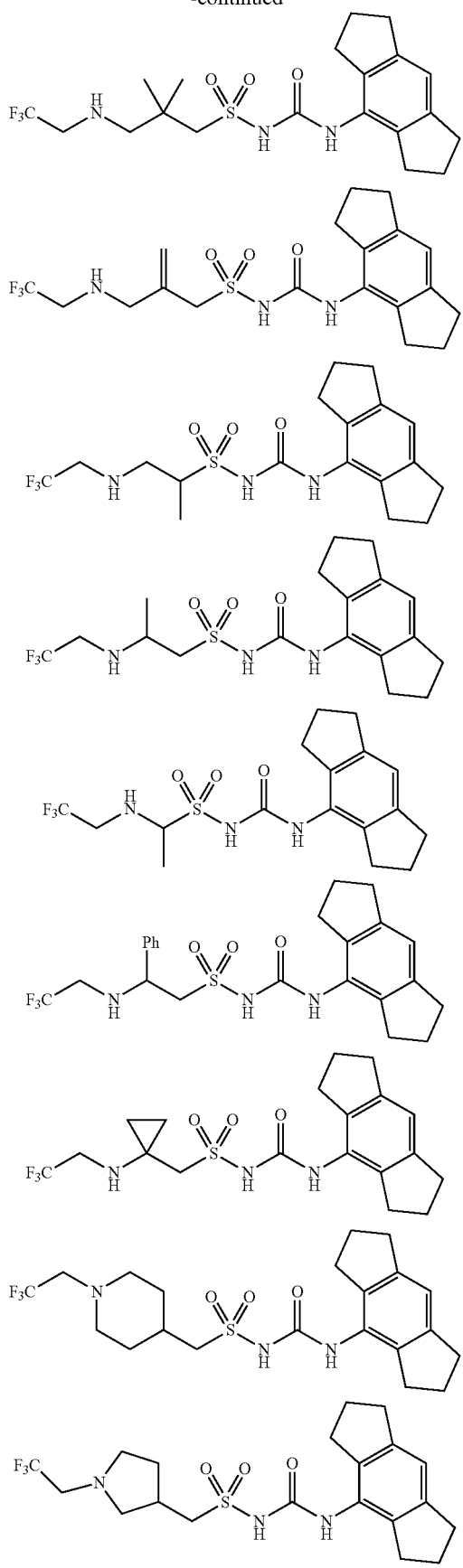
108
-continued
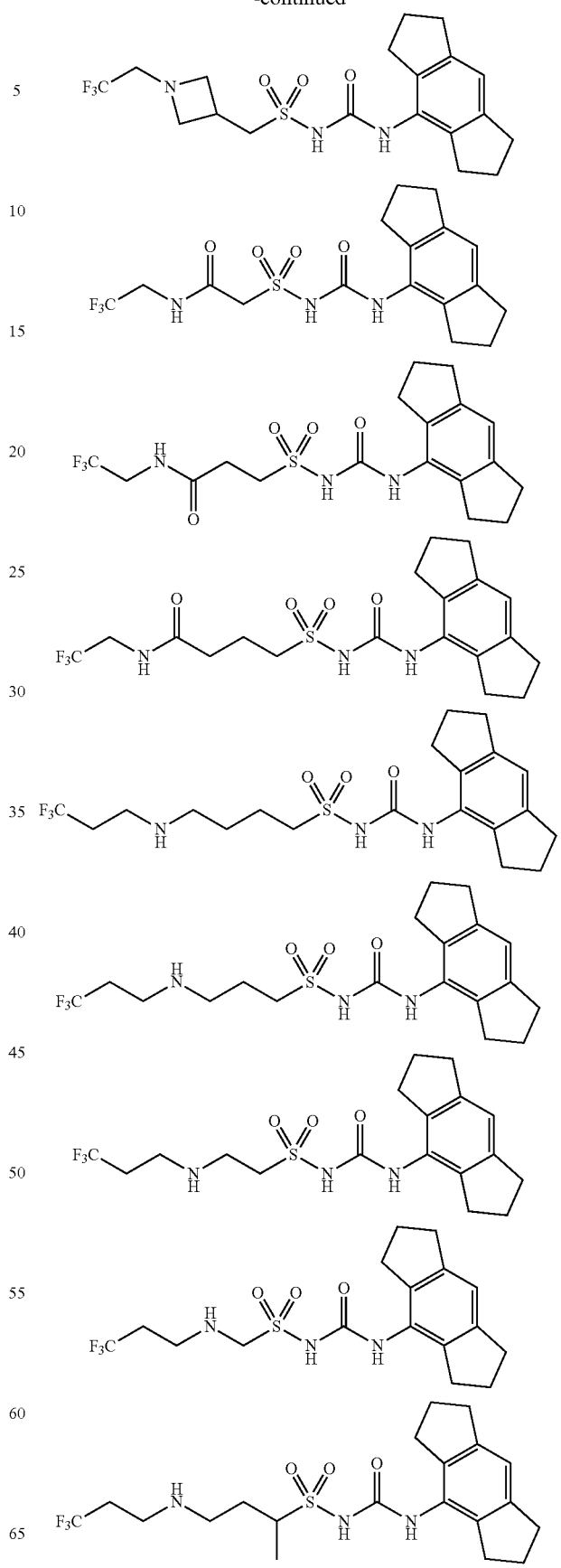

109
-continued
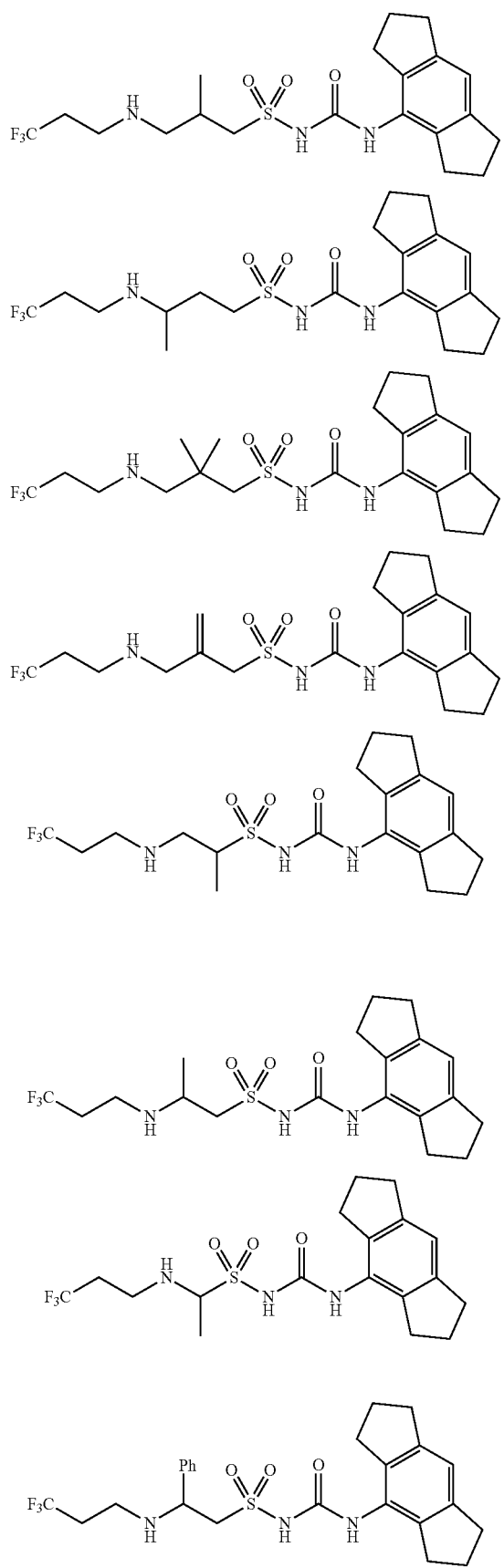
110
-continued
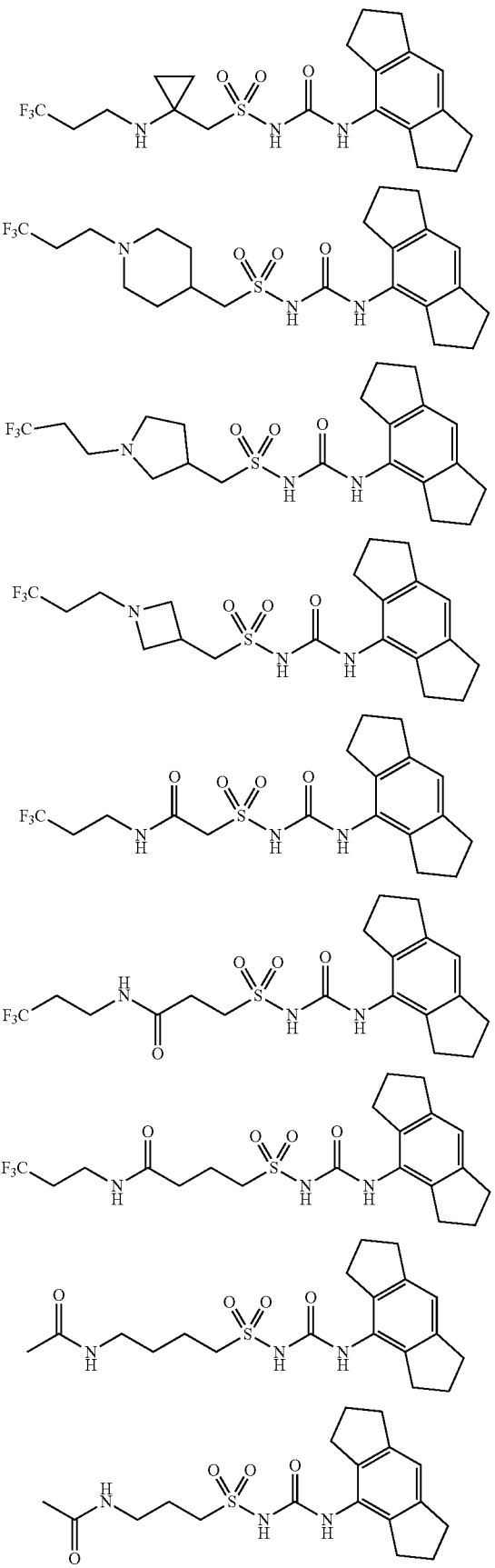

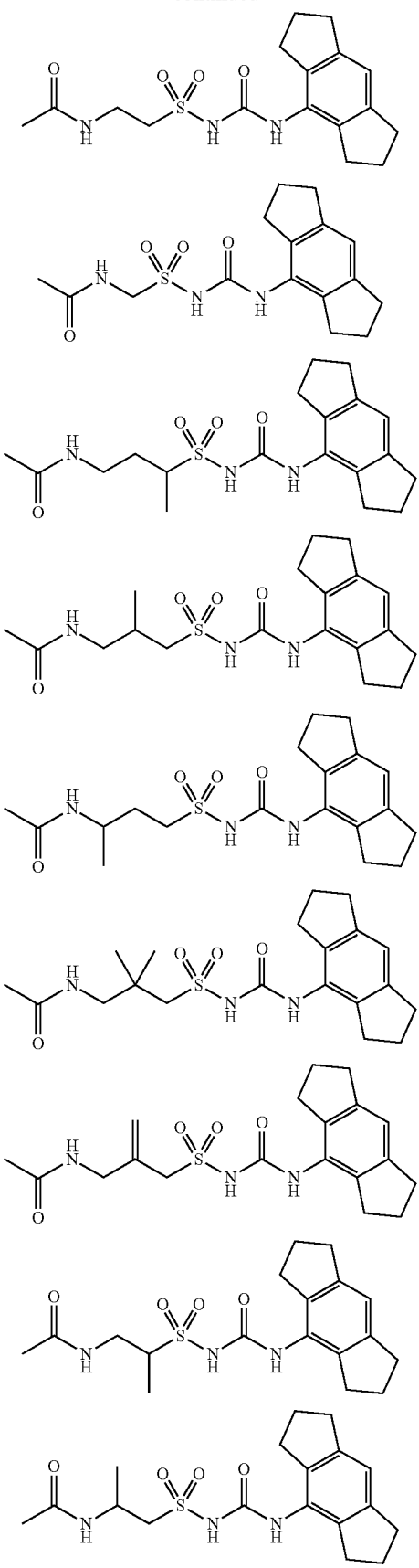
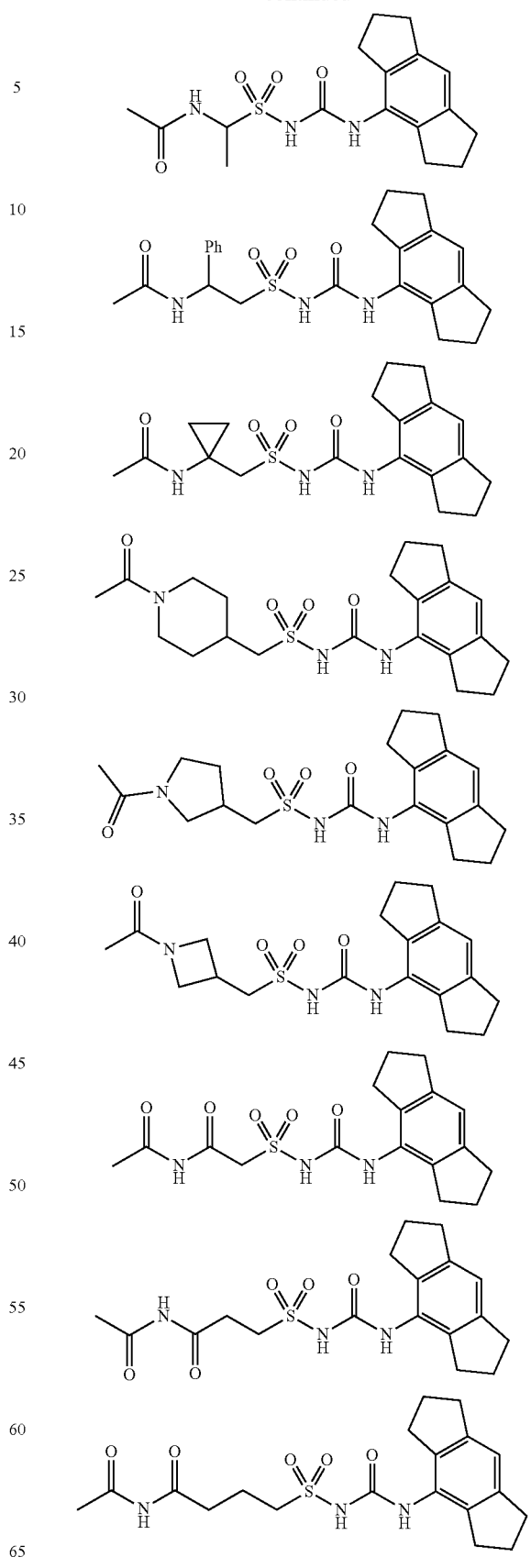

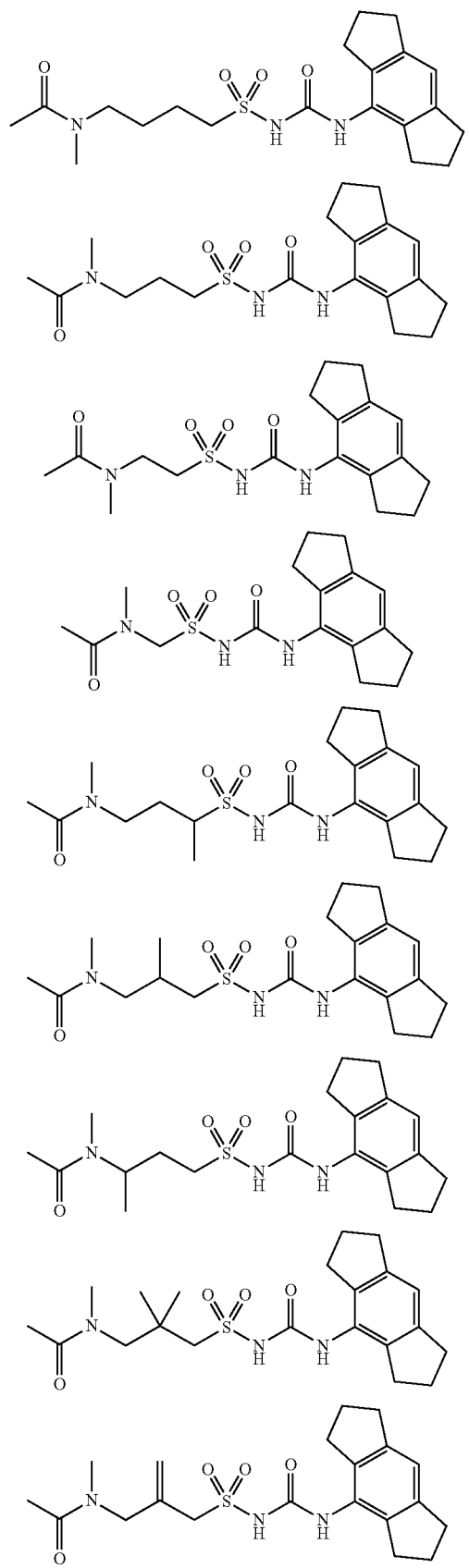
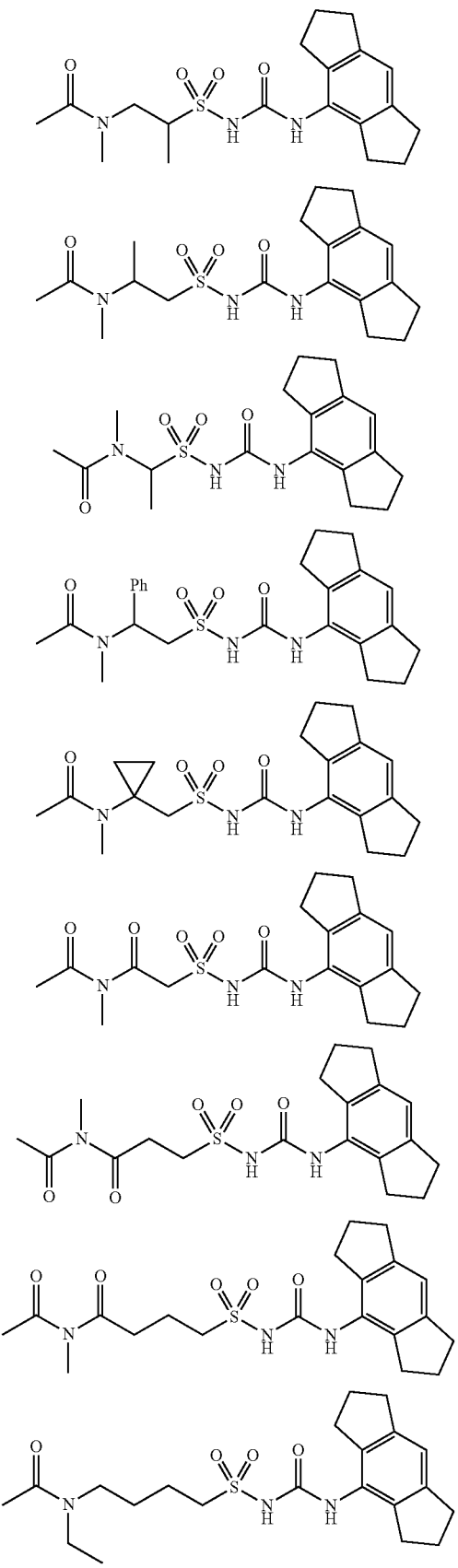

115
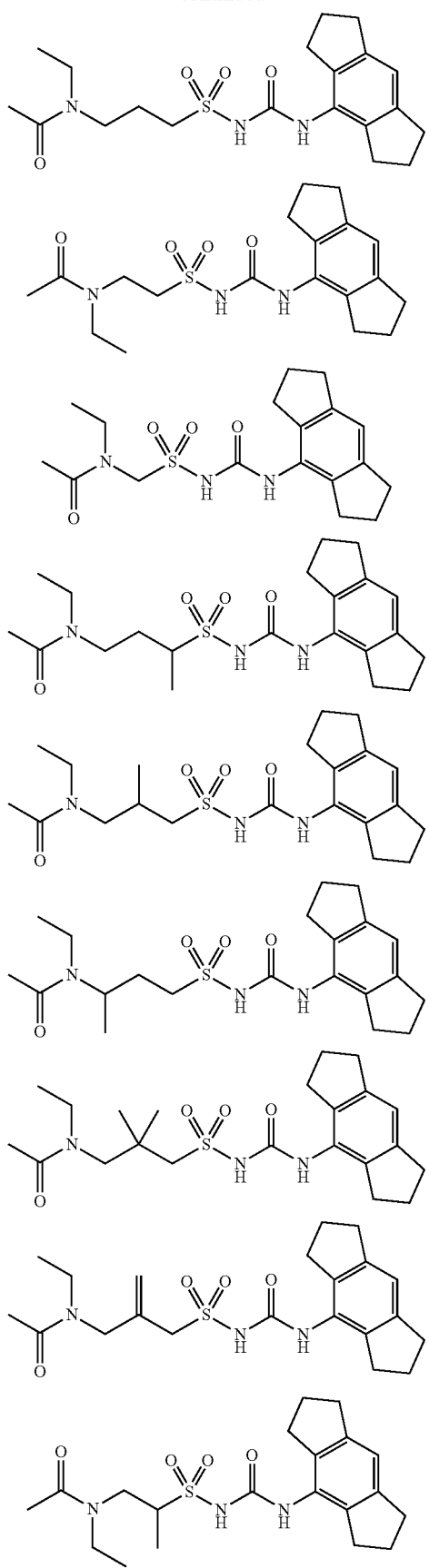
116
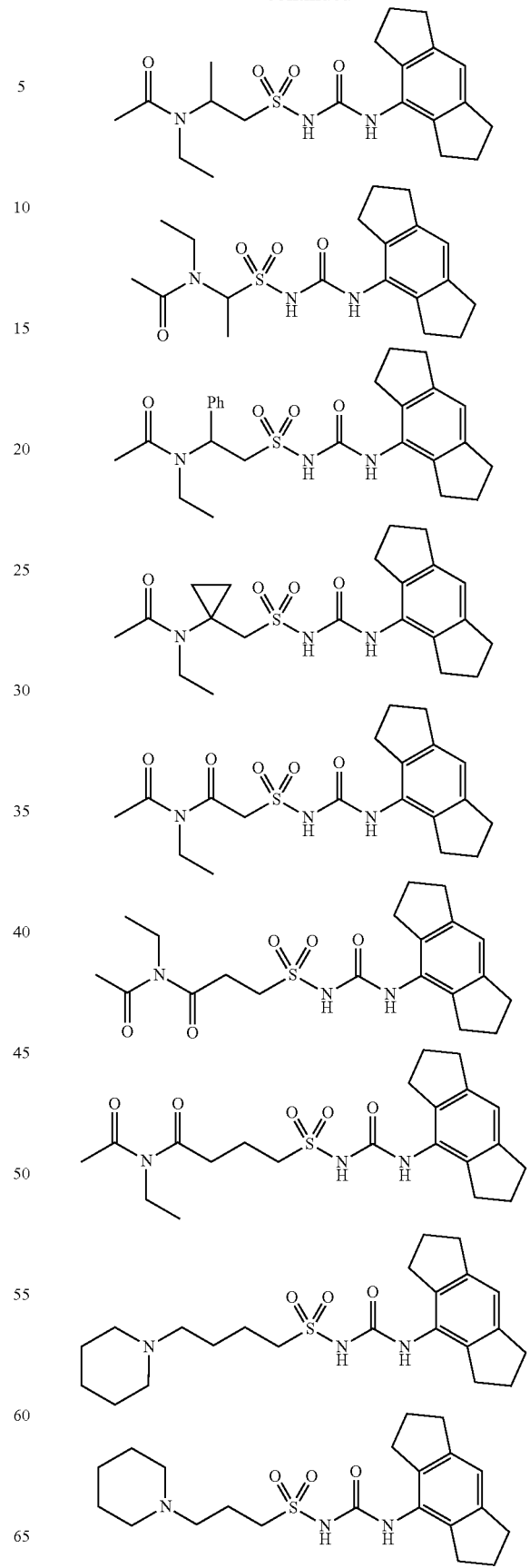

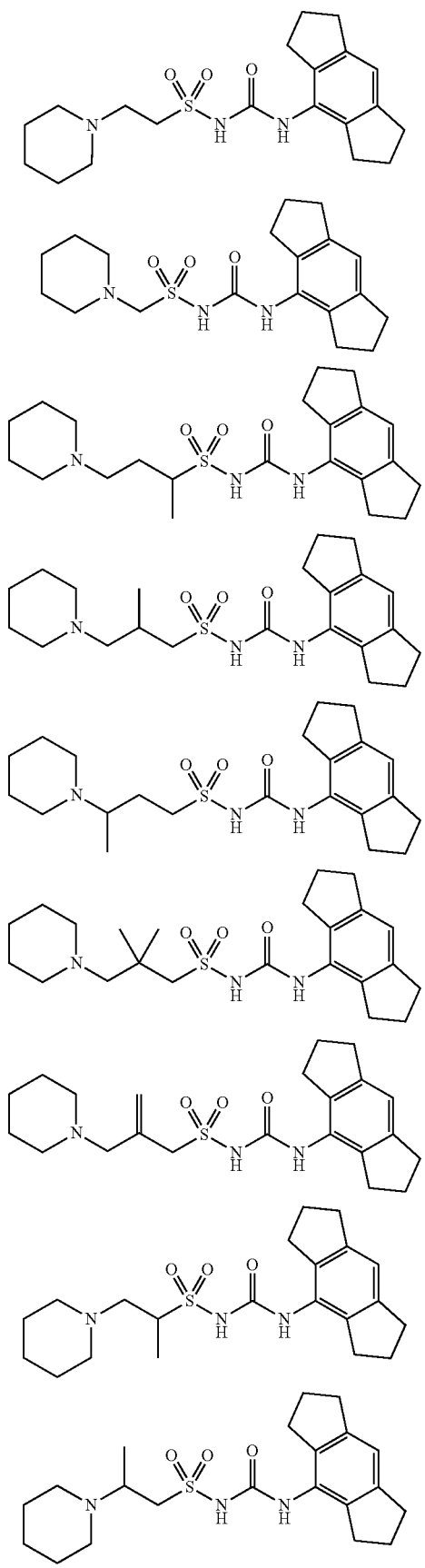
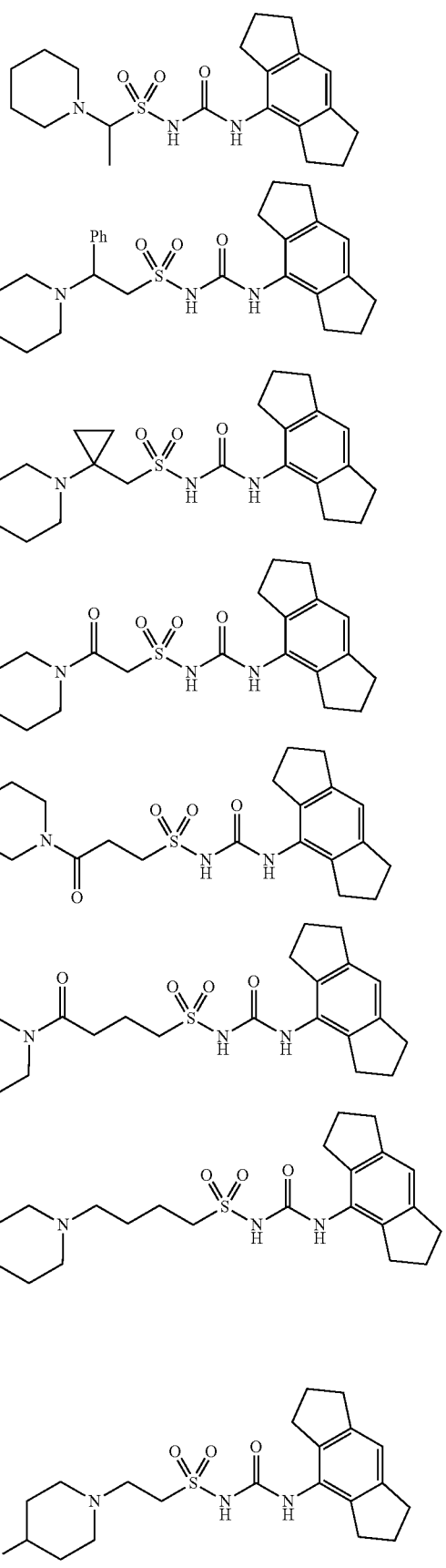

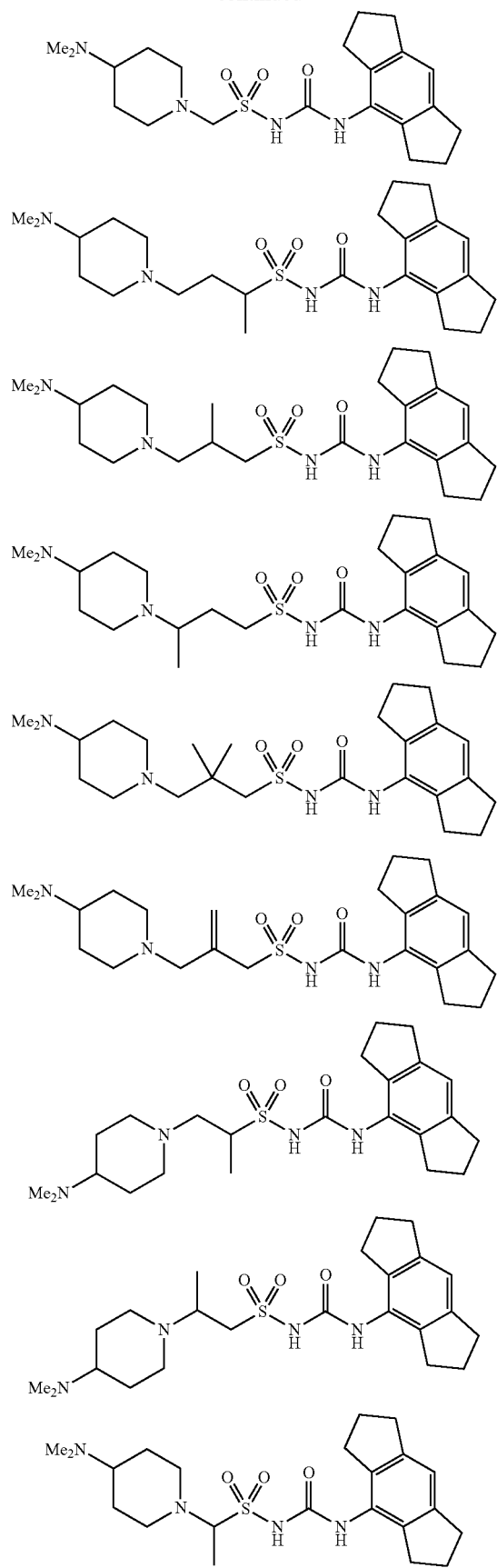
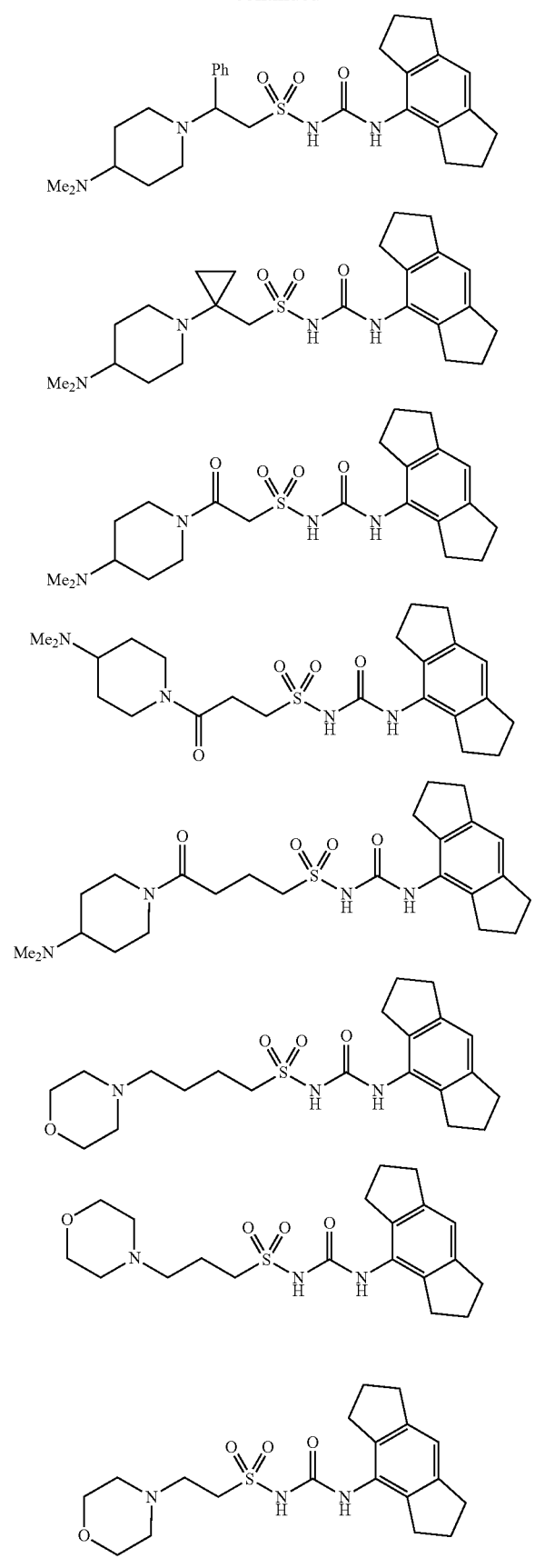

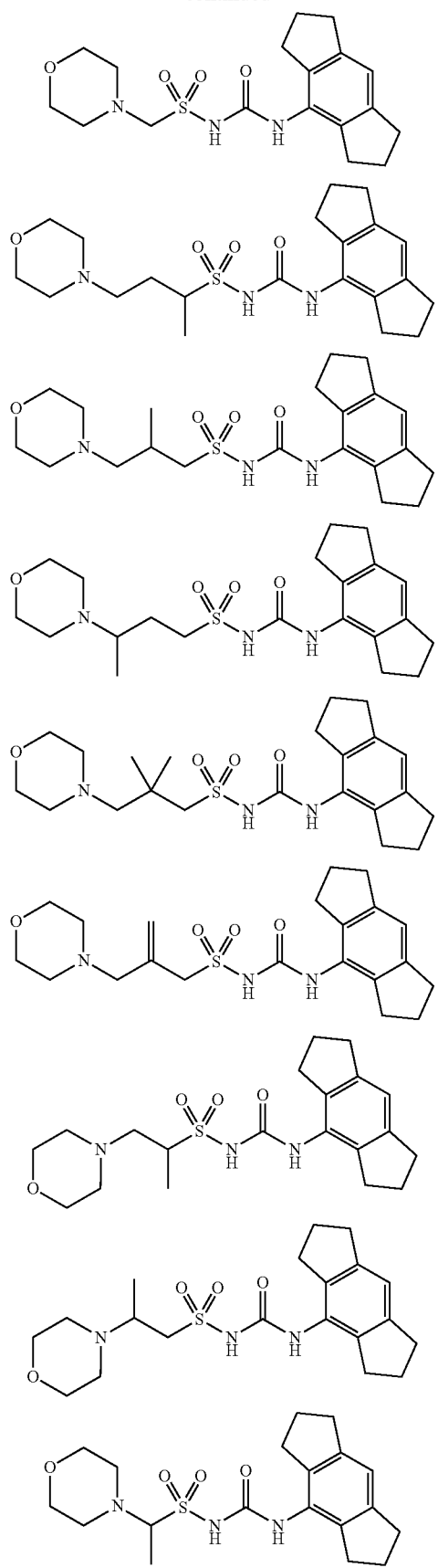
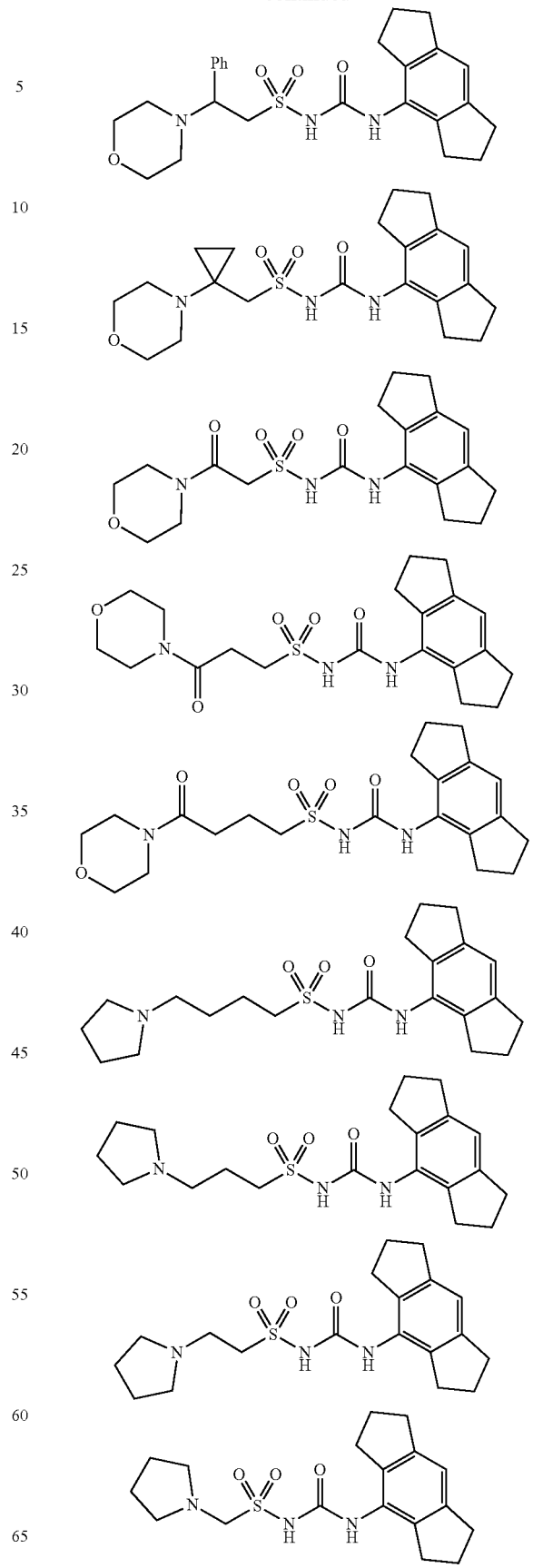

123
-continued
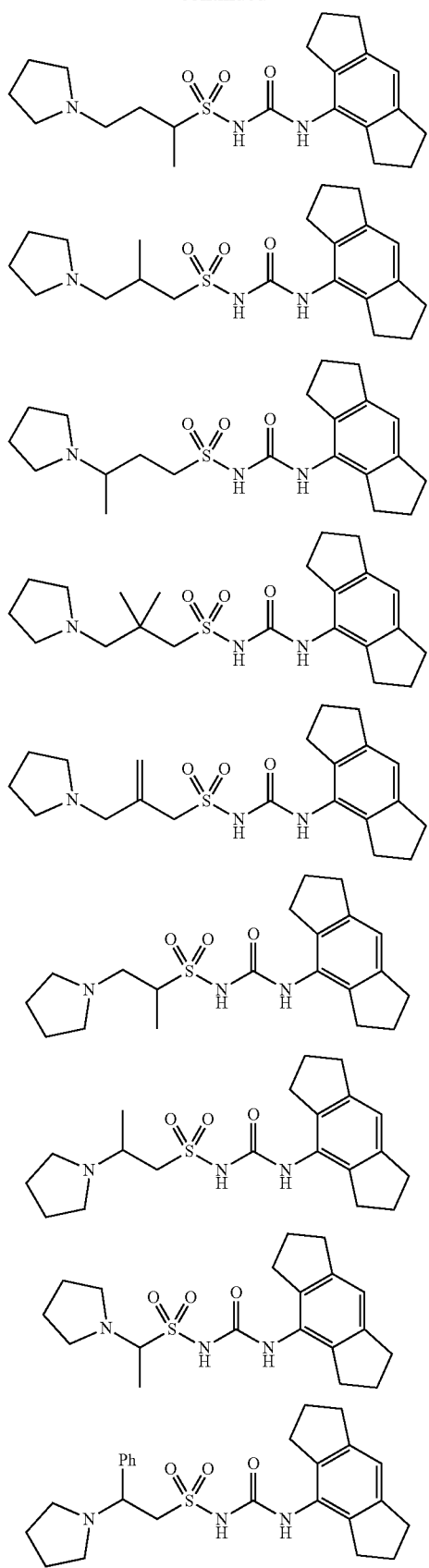
124
-continued
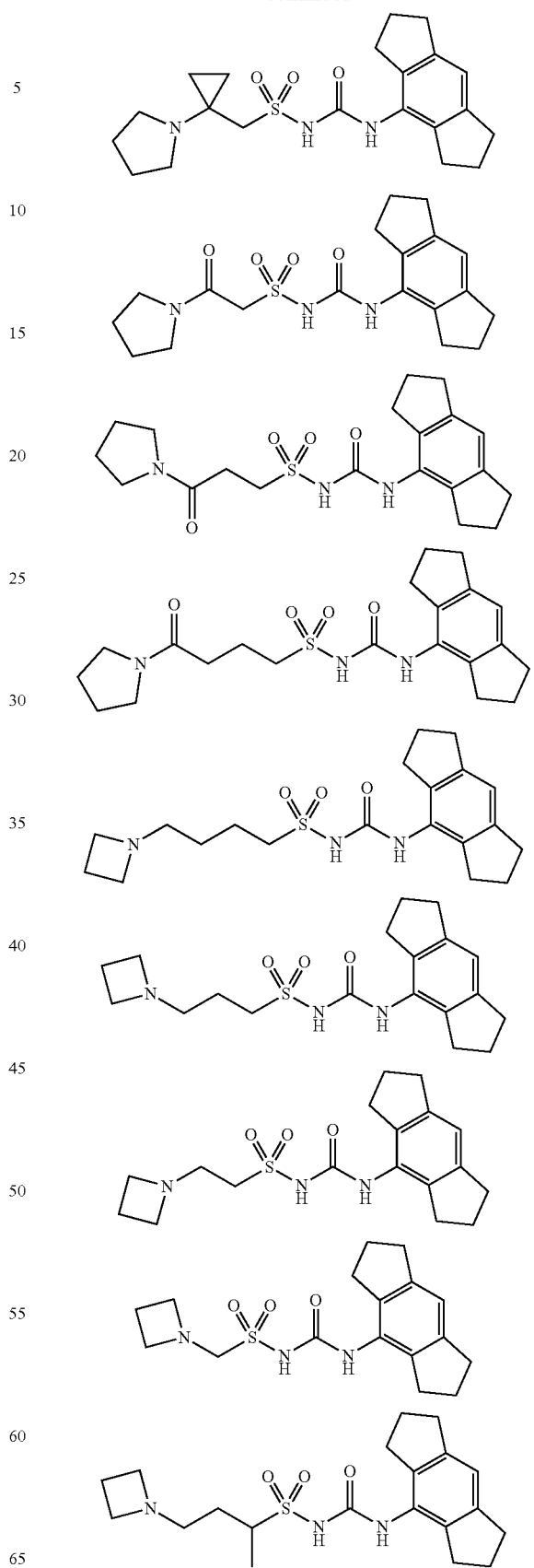

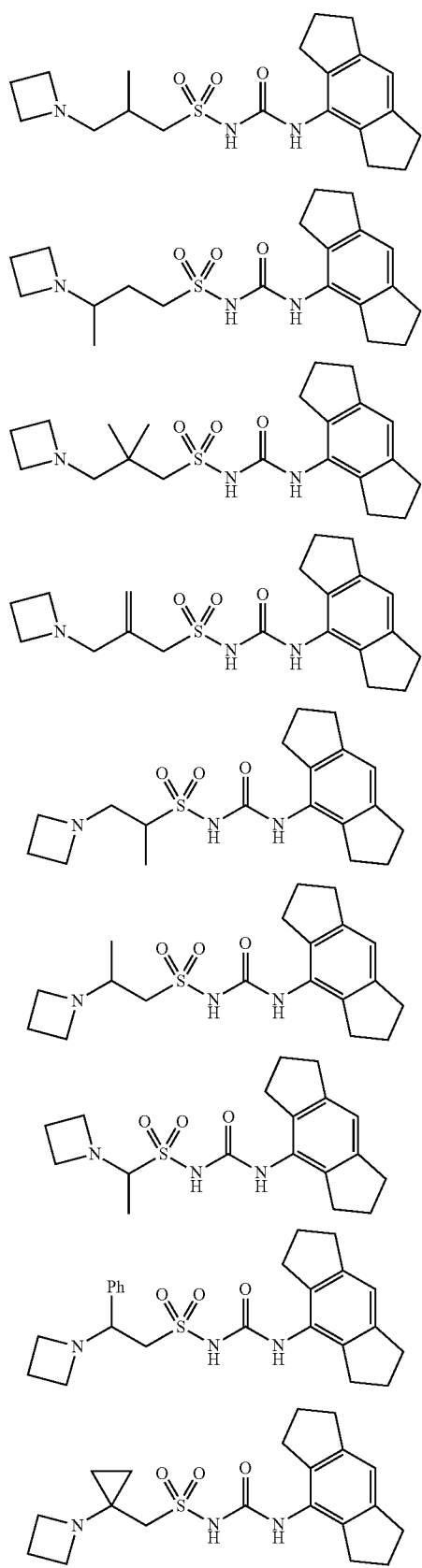
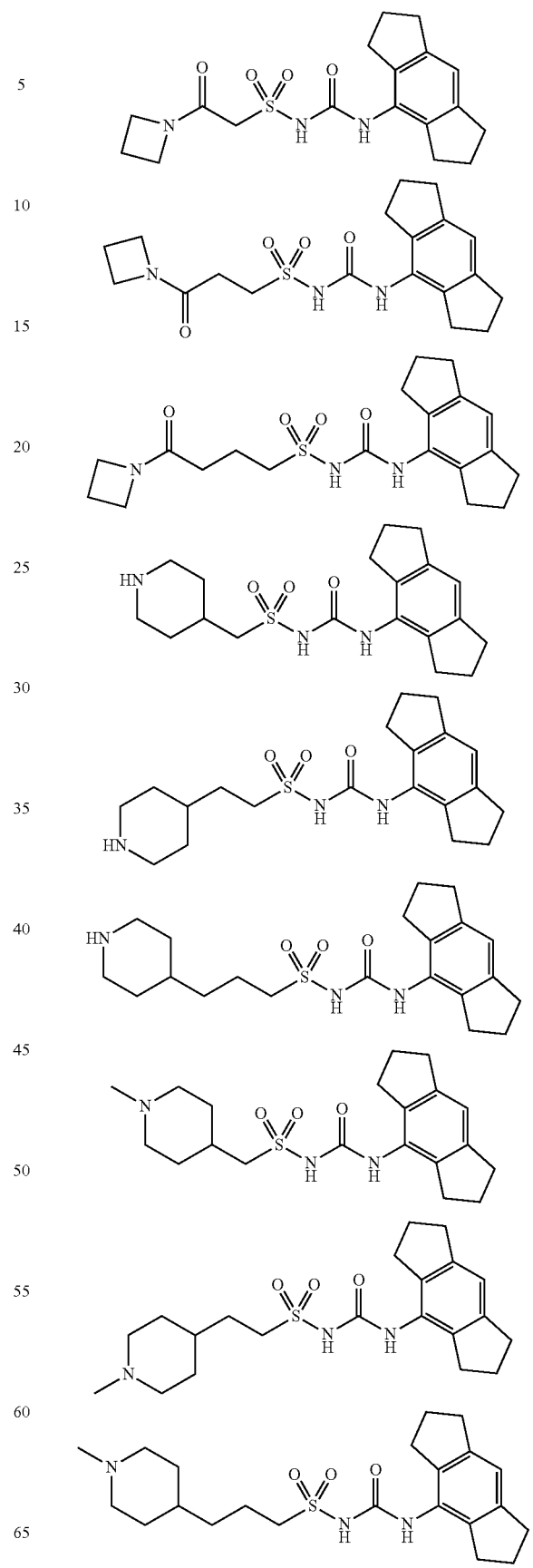

127
-continued
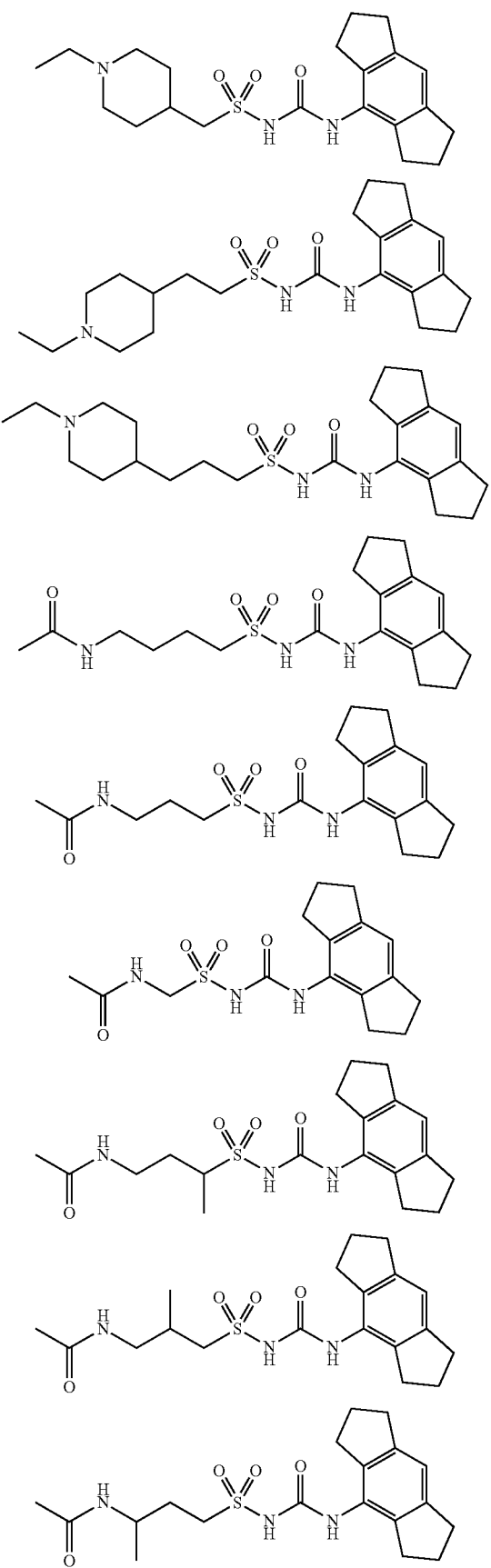
128
-continued
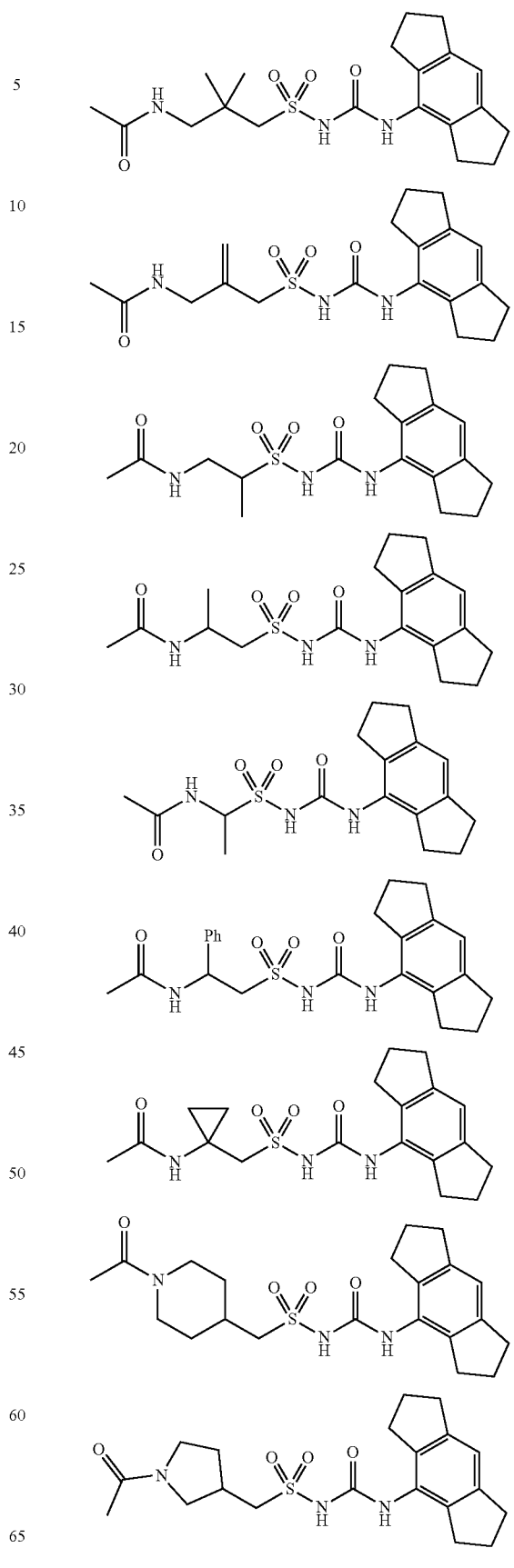

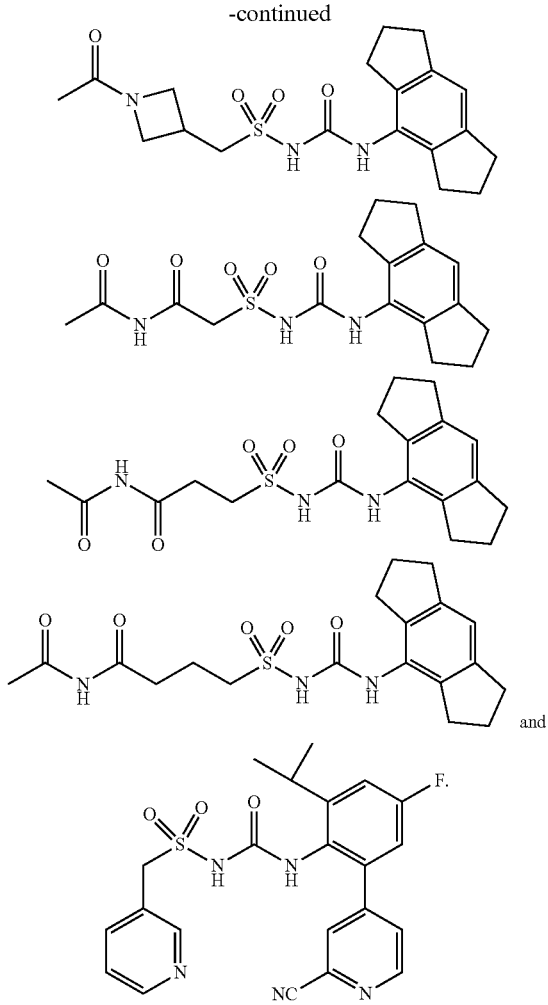

and

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, $4^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the present invention, the disease, disorder or condition is responsive to NLRP3 inhibition.

As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198 (3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149(4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): eo122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13:1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:
- (i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;
- (ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;
- (iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;
- (iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or *Trypanosomes*), helminth infections (e.g. from *Schistosoma*, roundworms, tapeworms or flukes) and prion infections;
(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;
(vi) metabolic diseases such as type 2 diabetes (T2D), atherosclerosis, obesity, gout, and pseudo-gout;
(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;
(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;
(ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);
(x) renal diseases including chronic kidney disease, oxalate nephropathy, nephrocalcinosis, glomerulonephritis, and diabetic nephropathy;
(xi) ocular diseases including those of the ocular epithelium, age-related macular degeneration (AMD) (dry and wet), uveitis, corneal infection, diabetic retinopathy, optic nerve damage, dry eye, and glaucoma;
(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;
(xiii) lymphatic conditions such as lymphangitis and Castleman's disease;
(xiv) psychological disorders such as depression and psychological stress;
(xv) graft versus host disease;
(xvi) allodynia including mechanical allodynia; and (xvii) any disease where an individual has been determined to carry a germline or somatic non-silent mutation in NLRP3.
In one embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.
More typically, the disease, disorder or condition is selected from:
(i) cancer;
(ii) an infection;
(iii) a central nervous system disease; or
(iv) a cardiovascular disease.
In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.
In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis*, *Mycobacterium avium intracellulare*, *Pneumocystis carinii* pneumonia, orchitis/epidydimitis, *Legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure; and/or (xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

In one embodiment of the fifth, sixth, seventh, eighth, ninth or tenth aspect of the present invention, the disease, disorder or condition is not a disease or disorder mediated by NFκB. In one embodiment of the fifth, sixth, seventh, eighth, ninth or tenth aspect of the present invention, the disease, disorder or condition is not rheumatoid arthritis, osteoarthritis, an autoimmune disease, psoriasis, asthma, a cardiovascular disease, an acute coronary syndrome, atherosclerosis, myocardial infarction, unstable angina, congestive heart failure, Alzheimer's disease, multiple sclerosis, cancer, type II diabetes, metabolic syndrome X, inflammatory bowel disease, systemic lupus erythematosus, Grave's disease, myasthenia gravis, insulin resistance, autoimmune hemolytic anemia, scleroderma with anticollagen antibodies, pernicious anemia, or diabetes mellitus. In one embodiment of the fifth, sixth, seventh, eighth, ninth or tenth aspect of the present invention, the disease, disorder or condition is not inflammatory bowel disease.

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a *Vinca* alkaloid, a podophyllotoxin and/or a taxane. In some embodiments, the one or more *Vinca* alkaloids may be derived from the Madagascar periwinkle, *Catharanthus roseus* (formerly known as *Vinca rosea*), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —N$_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES—COMPOUND SYNTHESIS

All solvents, reagents and compounds were purchased and used without further purification unless stated otherwise.

Abbreviations

2-MeTHF 2-methyltetrahydrofuran
Ac$_2$O acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMA dimethylacetamide
DMAP 4-dimethylaminopyridine, also called N,N-dimethylpyridin-4-amine
DME dimethoxyethane
DMF N,N-dimethylformamide
DMSO dimethyl sulfoxide
eq or equiv equivalent
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaO$^t$Bu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
Pd(dba)$_3$ tris(dibenzylideneacetone) dipalladium(0)
Pd(dppf)Cl$_2$ [1,1'-bis(diphenylphosphino)ferrocene]dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight Experimental Methods Analytical Methods NMR spectra were recorded at 300, 400 or 500 MHz (unless stated otherwise) with chemical shifts reported in parts per million. Spectra were measured at 298 K, unless indicated otherwise, and were referenced relative to the solvent resonance. Spectra were recorded using one of the following machines:
- An Agilent VNMRS 300 instrument fitted with a 7.05 Tesla magnet from Oxford instruments, indirect detection probe and direct drive console including PFG module.
- An Agilent MercuryPlus 300 instrument fitted with a 7.05 Tesla magnet from Oxford instruments, 4 nuclei auto-switchable probe and Mercury plus console.
- A Bruker 400 MHz spectrometer using ICON-NMR, under TopSpin program control.
- A Bruker Avance III spectrometer at 400 MHz fitted with a BBO 5 mm liquid probe.
- A Bruker Avance III HD spectrometer at 500 MHz, equipped with a Bruker 5 mm SmartProbe™.

LC-MS Methods: Using SHIMADZU LCMS-2020, Agilent 1200 LC/G1956A MSD and Agilent 1200\G6110A, Agilent 1200 LC & Agilent 6110 MSD. Mobile Phase: A: 0.025% $NH_3 \cdot H_2O$ in water (v/v); B: acetonitrile. Column: Kinetex EVO C18 2.1×30 mm, 5 μm.

Reversed Phase HPLC Conditions for the LCMS Analytical Methods:

Methods 1a and 1b:
Waters Xselect CSH C18 XP column, 2.5 m (4.6×30 mm) at 40° C.; flow rate 2.5-4.5 mL min$^{-1}$ eluted with a water-acetonitrile gradient containing either 0.1% v/v formic acid (Method 1a) or 10 mM ammonium bicarbonate in water (Method 1b) over 4 minutes employing UV detection at 254 nm. Gradient information: 0-3.00 min, ramped from 95% water-5% acetonitrile to 5% water-95% acetonitrile; 3.00-3.01 min, held at 5% water-95% acetonitrile, flow rate increased to 4.5 mL min$^{-1}$; 3.01-3.50 min, held at 5% water-95% acetonitrile; 3.50-3.60 min, returned to 95% water-5% acetonitrile, flow rate reduced to 3.50 mL min$^{-1}$; 3.60-3.90 min, held at 95% water-5% acetonitrile; 3.90-4.00 min, held at 95% water-5% acetonitrile, flow rate reduced to 2.5 mL min$^{-1}$.

HPLC and LC-MS were recorded on an Agilent 1290 series with UV detector and HP 6130 MSD mass detector. Mobile phase A: ammonium acetate (10 mM); water/MeOH/acetonitrile (900:60:40); mobile phase B: ammonium acetate (10 mM); water/MeOH/acetonitrile (100:540:360); column, Waters XBridge BEH C18 XP (2.1×50 mm, 2.5 μm).
Pump flow: 0.6 mL/min UV detection: 215, 238 nm
Injection volume: 0.2 μL Run time: 4.0 min
Column temperature: 35° C. Mass detection: API-ES +ve and −ve Pump Program:

| Gradient Time (min) | % A | % B |
|---|---|---|
| 0.0 | 80 | 20 |
| 0.5 | 80 | 20 |
| 2.0 | 0 | 100 |

Reversed Phase HPLC Conditions for the UPLC Analytical Methods:

Methods 2a and 2b:
Waters BEH C18 (2.1×30 mm, 1.7 μm) at 40° C.; flow rate 0.77 mL min$^{-1}$ eluted with a $H_2O$-MeCN gradient containing either 0.1% v/v formic acid (Method 2a) or 10 mM $NH_4HCO_3$ in water (Method 2b) over 3 min employing UV detection at 254 nm. Gradient information: 0-0.11 min, held at 95% water-5% acetonitrile, flow rate 0.77 mL min$^{-1}$; 0.11-2.15 min, ramped from 95% water-5% acetonitrile to 5% water-95% acetonitrile; 2.15-2.49 min, held at 5% water-95% acetonitrile, flow rate 0.77 mL min$^{-1}$; 2.49-2.56 min, returned to 95% water-5% acetonitrile; 2.56-3.00 min, held at 95% water-5% acetonitrile, flow rate reduced to 0.77 mL min$^{-1}$.

Purification Methods

Method 1 (Acidic Preparation):
Waters X-Select CSH column C18, 5 μm (19×50 mm), flow rate 28 mL/min eluting with a water-acetonitrile gradient containing 0.1% v/v formic acid over 6.5 minutes using UV detection at 254 nm. Gradient information: 0.0-0.2 minutes, 20% acetonitrile; 0.2-5.5 minutes, ramped from 20% acetonitrile to 40% acetonitrile; 5.5-5.6 minutes, ramped from 40% acetonitrile to 95% acetonitrile; 5.6-6.5 minutes, held at 95% acetonitrile.

Method 2 (Basic Preparation):
Waters X-Bridge Prep column C18.5 μm (19×50 mm), flow rate 28 mL/min eluting with a 10 mM ammonium bicarbonate-acetonitrile gradient over 6.5 minutes using UV detection at 254 nm. Gradient information: 0.0-0.2 minutes, 10% acetonitrile; 0.2-5.5 minutes, ramped from 10% acetonitrile to 40% acetonitrile; 5.5-5.6 minutes, ramped from 40% acetonitrile to 95% acetonitrile; 5.6-6.5 minutes, held at 95% acetonitrile.

Method 3:
Phenomenex Gemini column, 10 μm (150×25 mm), flow rate=25 mL/min eluting with a water-acetonitrile gradient containing 0.04% $NH_3$ at pH 10 over 9 minutes using UV detection at 220 and 254 nm. Gradient information: 0-9 minutes, ramped from 8% to 35% acetonitrile; 9-9.2 minutes, ramped from 35% to 100% acetonitrile; 9.2-15.2 minutes, held at 100% acetonitrile.

Method 4:
Buchi Sepracore® X50 system driven by a C-605 pump module, C-620 Sepracore control package, C-640 UV photometer detection unit and C-660 fraction collector.
Revelis C18 reversed-phase 12 g cartridge

| | |
|---|---|
| Carbon loading | 18% |
| Surface area | 568 m$^2$/g |
| Pore diameter | 65 Angstrom |
| pH (5% slurry) | 5.1 |
| Average particle size | 40 μm |

The column was conditioned before use with MeOH (5 min) then brought to $H_2O$ (in 5 min) and kept 5 min at $H_2O$. Flow rate=30 mL/min.

Separation Runs:

| Time (min) | A: water (%) | B: MeOH (%) |
|---|---|---|
| 0 | 100 | 0 |
| 5 | 100 | 0 |
| 30 | 30 | 70 |
| 30.1 | 0 | 100 |
| 35 | 0 | 100 |

Detection wavelength: 215, 235, 254 and 280 nm. Before each new run, the cartridge was cleaned using the conditioning method.

Synthesis of Intermediates

Intermediate A1: 4-Isocyanato-1,2,3,5,6,7-hexahydro-s-indacene

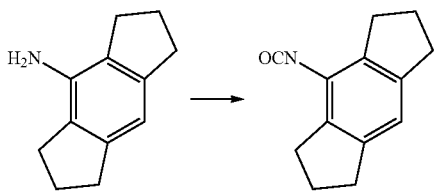

To a solution of phosgene (4.45 mL, 20% weight in toluene, 8.4 mmol) in ethyl acetate (90 mL) was added dropwise a solution of 1,2,3,5,6,7-hexahydro-s-indacen-4-amine (589 mg, 3.4 mmol) in ethyl acetate (45 mL) at ambient temperature. The resulting reaction mixture was then heated to reflux for 3 hours and upon cooling was filtered and concentrated in vacuo to afford the title compound as a brown oil (756 mg, 100% yield). The crude product was used directly in the next step without further purification.

$^1$H NMR (CDCl$_3$) δ 6.8 (s, 1H), 2.89 (m, 8H) and 2.09 (m, 4H).

Intermediate A2: 4-(7-Fluoro-4-isocyanato-2,3-dihydro-H-inden-5-yl)pyridine

Step A: 7-Fluoro-4-nitro-2,3-dihydro-1H-inden-1-one

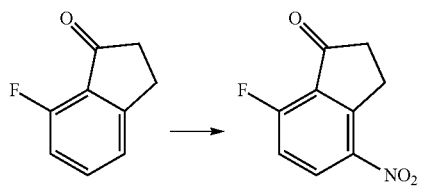 [SMILES: O=C1CCc2cccc(F)c21 ; O=C1CCc2c([N+](=O)[O-])ccc(F)c21]

To a mixture of 7-fluoro-2,3-dihydro-1H-inden-1-one 9.5 g, 3.27 mmol, 1 eq) in concentrated H$_2$SO$_4$ (100 mL) was added dropwise a solution of HNO$_3$ (5.37 mL, 82.25 mmol, 69 wt % in water, 1.3 eq) in concentrated H$_2$SO$_4$ (20 mL) at −15° C. Then the reaction mixture was stirred at 0° C. for 0.5 hour. The mixture was quenched with water (500 mL) at 0° C., and then extracted with EtOAc (3×300 mL). The combined organic phases were dried over anhydrous Na$_2$SO$_4$, filtered and concentrated in vacuo. The residue was purified by silica gel column chromatography (SiO$_2$, petroleum ether:ethyl acetate, 10:1 to 3:1) to give the title compound (11.4 g, 92%) as a yellow solid.

$^1$H NMR (CDCl$_3$) δ 8.51 (dd, 1H), 7.22 (t, 1H), 3.69-3.65 (m, 2H) and 2.88-2.82 (m, 2H).

Step B: 7-Fluoro-4-nitro-2,3-dihydro-H-inden-1-ol

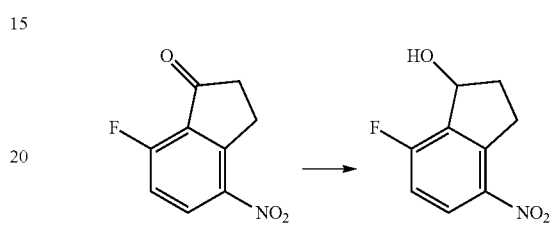

To a mixture of 7-fluoro-4-nitro-2,3-dihydro-1H-inden-1-one (30 g, 153.73 mmol, 1 eq) in EtOH (450 mL) was added NaBH$_4$ (11.63 g, 307-46 mmol, 2 eq) in portions. The reaction mixture was stirred at 15° C. for 1 hour. Then the mixture was poured into water (500 mL) and extracted with DCM (2×200 mL). The combined organic phases were washed with brine (200 mL), dried over anhydrous Na$_2$SO$_4$, filtered and concentrated in vacuo to give the title compound (30 g, crude) as brown oil.

$^1$H NMR (CDCl$_3$) δ 8.21 (dd, 1H), 7.08 (t, 1H), 5.59-5.56 (m, 1H), 3.66-3.59 (m, 1H), 3.44-3.39 (m, 1H), 2.56-2.51 (m, 1H) and 2.22-2.17 (m, 2H).

Step C: 4-Fluoro-7-nitro-2,3-dihydro-1H-indene

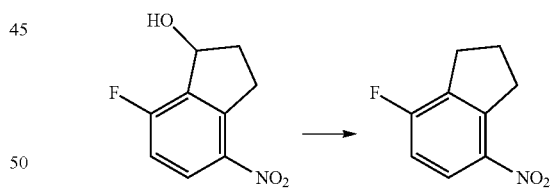

To a mixture of 7-fluoro-4-nitro-2,3-dihydro-1H-inden-1-ol (4.5 g, 22.82 mmol, 1 eq) in TFA (20 mL) was added Et$_3$SiH (7.96 g, 68.47 mmol, 3 eq) in one portion. The reaction mixture was stirred at 25° C. for 12 hours. Then the mixture was quenched with water (100 mL) and extracted with EtOAc (3×100 mL). The combined organic layers were washed with saturated aqueous NaHCO$_3$ solution (2×100 mL), dried over anhydrous Na$_2$SO$_4$, filtered and concentrated in vacuo to give the title compound (5 g, crude) as brown oil.

$^1$H NMR (CDCl$_3$) δ 8.06 (dd, 1H), 7.01 (t, 1H), 3.46 (t, 2H), 3.04 (t, 2H) and 2.25-2.20 (m, 2H).

Step D: 7-Fluoro-2,3-dihydro-1H-inden-4-amine

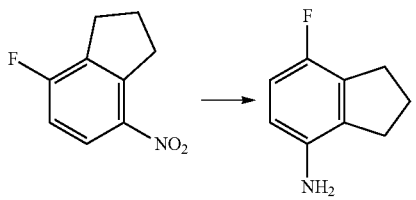 [SMILES: O=[N+]([O-])c1ccc(F)c2c1CCC2 ; Nc1ccc(F)c2c1CCC2]

To a mixture of 4-fluoro-7-nitro-2,3-dihydro-1H-indene (5 g, 27.60 mmol, 1 eq) in MeOH (50 mL) was added Pd/C (0.5 g, 10 wt % loading on activated carbon) at 25° C. under a nitrogen atmosphere. Then the reaction mixture was stirred at 25° C. for 12 hours under hydrogen (15 psi). The mixture was filtered and the filtrate was concentrated in vacuo. The residue was purified by silica gel column chromatography (SiO$_2$, petroleum ether:ethyl acetate, 50:1 to 10:1) to give the title compound (1.8 g, 43%) as a brown solid.

$^1$H NMR (CDCl$_3$) δ 6.69 (t, 1H), 6.44 (dd, 1H), 0.47 (br s, 2H), 2.95 (t, 2H), 2.75 (t, 2H), 2.75 (t, 2 H) and 2.19-2.11 (m, 2H).

Step E: 5-Bromo-7-fluoro-2,3-dihydro-1H-inden-4-amine

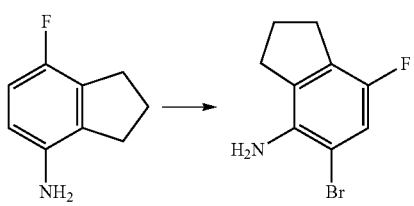 [SMILES: Nc1ccc(F)c2c1CCC2 ; Nc1c(Br)cc(F)c2c1CCC2]

To a solution of 7-fluoro-2,3-dihydro-1H-inden-4-amine (8.3 g, 54.90 mmol, 1 eq) in toluene (100 mL) was added NBS (10.26 g, 57.65 mmol, 1.05 eq) in one portion at 25° C. The reaction mixture turned dark brown immediately and then the mixture was stirred at 25° C. for 30 minutes. The reaction mixture was quenched with saturated aqueous Na$_2$SO$_3$ solution (200 mL) and extracted with EtOAc (2×100 mL). The combined organic phases were washed with brine (100 mL), dried over anhydrous Na$_2$SO$_4$, filtered and concentrated in vacuo. The residue was purified by silica gel column chromatography (SiO$_2$, petroleum ether:ethyl acetate, 1:0 to 20:1) to give the title compound (8.51 g, 67%) as a brown solid.

$^1$H NMR (CDCl$_3$) δ 6.99 (d, 1H), 3.81 (br s, 2H), 2.92 (t, 2H), 2.78 (t, 2H) and 2.21-2.13 (m, 2H).

Step F: 7-Fluoro-5-(pyridin-4-yl)-2,3-dihydro-1H-inden-4-amine

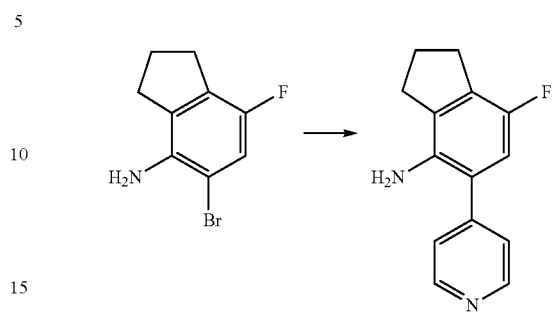

To a mixture of 5-bromo-7-fluoro-2,3-dihydro-1H-inden-4-amine (3.5 g, 15.21 mmol, 1 eq) and pyridin-4-ylboronic acid (1.96 g, 15.97 mmol, 1.05 eq) in dioxane (50 mL) and H$_2$O (5 mL) was added K$_2$CO$_3$ (6.31 g, 45.64 mmol, 3 eq) and Pd(dppf)Cl$_2$ (1.11 g, 1.52 mmol, 0.1 eq) in one portion under a nitrogen atmosphere. Then the reaction mixture was heated to 80° C. for 12 hours. The reaction mixture was filtered. The filtrate was diluted with water (50 mL) and extracted with EtOAc (3×100 mL). The combined organic phases were washed with brine (100 mL), dried over anhydrous Na$_2$SO$_4$, filtered and concentrated in vacuo. The residue was purified by silica gel column chromatography (SiO$_2$, petroleum ether:ethyl acetate, 10:1 to 2:1) to give the title compound (1.7 g, 4% yield, 90.98% purity on HPLC) as a brown solid.

$^1$H NMR (CDCl$_3$) δ 8.68 (dd, 2H), 7.40 (dd, 2H), 6.72 (d, 1H), 3.76 (br s, 2H), 3.01 (t, 2H), 2.80 (t, 2H) and 2.26-2.18 (m, 2H).

Step G: 4-(7-Fluoro-4-isocyanato-2,3-dihydro-1H-inden-5-yl)pyridine

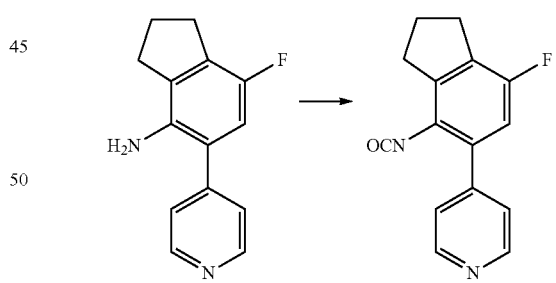

To a solution of 7-fluoro-5-(pyridin-4-yl)-2,3-dihydro-1H-inden-4-amine (400 mg, 1.75 mmol, 1 eq) and TEA (355 mg, 3.50 mmol, 2 eq) in THF (30 mL) was added bis(trichloromethyl) carbonate (208 mg, 700.94 μmol, 0.4 eq) at 0° C. The reaction mixture was stirred at 70° C. for 30 minutes. Then the reaction mixture was filtered through a pad of silica gel and the filter cake was washed with THF (20 mL). The filtrate was concentrated in vacuo to reduce to 10 mL, which was used directly in the next step.

Intermediate A3: 4-(5-Fluoro-2-isocyanato-3-isopropylphenyl)picolinonitrile

Step A: 4-Fluoro-2-(prop-1-en-2-yl)aniline

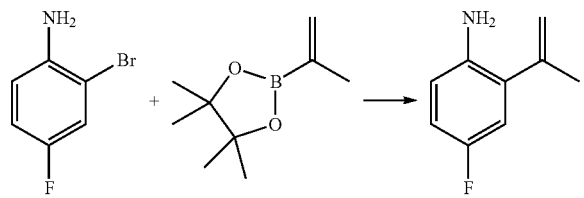

To a mixture of 2-bromo-4-fluoroaniline (39 g, 205.25 mmol, 1 eq), 4,4,5,5-tetramethyl-2-(prop-1-en-2-yl)-1,3,2-dioxaborolane (36.21 g, 215.51 mmol, 1.05 eq) and $K_2CO_3$ (70.92 g, 513.12 mmol, 2.5 eq) in dioxane (200 mL) and $H_2O$ (40 mL) was added Pd(dppf)Cl$_2$ (7.51 g, 10.26 mmol, 0.05 eq) under a nitrogen atmosphere. Then the reaction mixture was stirred at 80° C. for 5 hours. The reaction mixture was quenched by addition of $H_2O$ (600 mL) and extracted with EtOAc (2×500 mL). The combined organic layers were washed with brine (2×600 mL), dried over anhydrous $Na_2SO_4$, filtered and concentrated under reduced pressure. The residue was purified by silica gel column chromatography (SiO$_2$, petroleum ether:ethyl acetate 1:0 to 100:1) to give the title compound (27 g, 77% yield, 89% purity on LCMS) as a yellow oil.

$^1$H NMR (CDCl$_3$) δ 6.81-6.76 (m, 2H), 6.66-6.62 (m, 1H), 5.38 (s, 1H), 5.08 (s, 1H), 3.69 (br s, 2H) and 1.25 (s, 3H).

LCMS: m/z 152.2 (M+H)$^+$ (ES$^+$).

Step B: 4-Fluoro-2-isopropylaniline

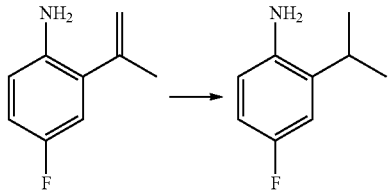

To a solution of 4-fluoro-2-(prop-1-en-2-yl)aniline (21 g, 138.91 mmol, 1 eq) in MeOH (300 mL) was added Pd/C (2.1 g, 178.59 mmol, 10 wt % loading on activated carbon) under a nitrogen atmosphere. The reaction mixture was degassed in vacuo and purged with hydrogen several times. The reaction mixture was stirred at 25° C. for 12 hours under hydrogen (50 psi). The reaction mixture was filtered and the filtrate was concentrated in vacuo to give the title compound (20 g, crude) as a yellow oil.

$^1$H NMR (CDCl$_3$) δ 6.86 (dd, 1H), 6.75-6.72 (m, 1H), 6.63-6.61 (m, 1H), 3.50 (br s, 2H), 2.95-2.84 (m, 1H) and 1.25 (d, 6H).

LCMS: m/z 154.2 (M+H)$^+$ (ES$^+$).

Step C: 2-Bromo-4-fluoro-6-isopropylaniline

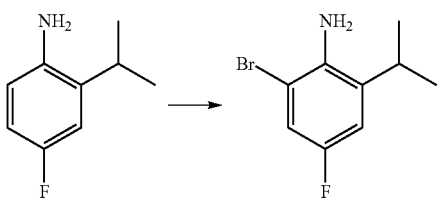

To a solution of 4-fluoro-2-isopropylaniline (20 g, 130.55 mmol, 1 eq) in toluene (250 mL) was added NBS (23.24 g, 130.55 mmol, 1 eq) at 25° C. The reaction mixture was stirred at 25° C. for 10 minutes. The reaction mixture was poured into $H_2O$ (300 mL) and extracted with EtOAc (2×250 mL). The combined organic phases were washed with brine (2×400 mL), dried over anhydrous $Na_2SO_4$, filtered and concentrated in vacuo. The residue was purified by silica gel column chromatography (SiO$_2$, eluting only by using petroleum ether) to give the title compound (30 g, 99%) as a black brown oil.

$^1$H NMR (CDCl$_3$) δ 6.99 (dd, 1H), 6.78 (dd, 1H), 3.91 (br s, 2H), 2.88-2.71 (m, 1H) and 1.17 (d, 6H).

LCMS: m/z 232.1 (M+H)$^+$ (ES$^+$).

Step D: 4-(2-Amino-5-fluoro-3-isopropylphenyl)picolinonitrile

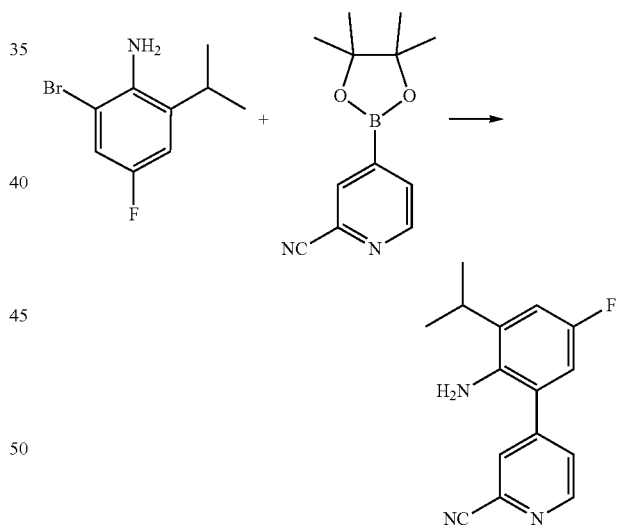

To a solution of 2-bromo-4-fluoro-6-isopropylaniline (3.6 g, 15.51 mmol, 1 eq) and 4-(4,4,5,5-tetramethyl-1,3,2-dioxaborolan-2-yl)picolinonitrile (3.60 g, 15.67 mmol, 1.01 eq) in dioxane (90 mL) and $H_2O$ (9 mL) was added $Na_2CO_3$ (4.11 g, 38.78 mmol, 2.5 eq). Then Pd(dppf)Cl$_2$ (1.13 g, 1.55 mmol, 0.1 eq) was added to the mixture under a nitrogen atmosphere. The resulting mixture was stirred at 80° C. for 2 hours under nitrogen. Then the mixture was concentrated in vacuo. The residue was purified by silica gel column chromatography (SiO$_2$, petroleum ether:ethyl acetate, 20:1 to 5:1) and then triturated with petroleum ether (10 mL) to give the title compound (2.65 g, 65% yield, 97% purity on LCMS) as a yellow solid.

$^1$HNMR (CDCl$_3$) δ 8.79 (d, 1H), 7.86 (d, 1H), 7.65 (dd, 1H), 6.99 (dd, 1H), 6.70 (dd, 1H), 3.63 (br s, 2H), 2.98-2.87 (m, 1H) and 1.30 (d, 6H).

LCMS: m/z 256.2 (M+H)$^+$ (ES$^+$).

Step E: 4-(5-Fluoro-2-isocyanato-3-isopropylphenyl)picolinonitrile

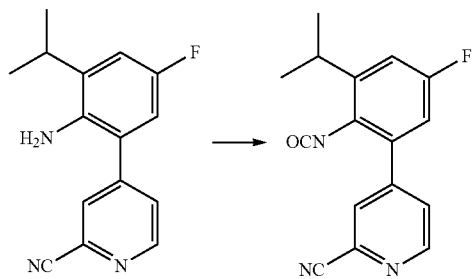

To a solution of 4-(2-amino-5-fluoro-3-isopropylphenyl)picolinonitrile (1 g, 3.92 mmol, 1 eq) in THF (40 mL) was added TEA (793 mg, 7.83 mmol, 2 eq). To the above mixture was added triphosgene (465 mg, 1.57 mmol, 0.4 eq) in portions at 5'C. Then the mixture was stirred at 70° C. for 1 hour. The mixture was diluted with EtOAc (200 mL) and then filtered through silica gel. The filtrate was concentrated in vacuo to give the title compound (1.2 g, crude) as a yellow solid, which was used directly in the next step.

Intermediate A4: 4-(5-Fluoro-2-isocyanato-3-isopropylphenyl)-2-methoxypyridine

Step A: 4-Fluoro-2-isopropyl-6-(2-methoxypyridin-4-yl)aniline

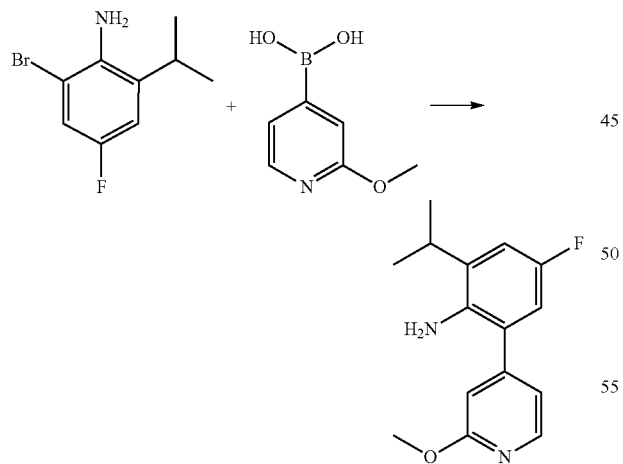

To a solution of 2-bromo-4-fluoro-6-isopropylaniline 12 g, 51.70 mmol, 1 eq in dioxane (240 mL) and H$_2$O (48 mL) was added (2-methoxypyridin-4-yl)boronic acid (9.49 g, 62.04 mmol, 1.2 eq) and Na$_2$CO$_3$ (13.70 g, 129.26 mmol, 2.5 eq). The reaction mixture was purged with nitrogen three times. Then Pd(dppf)Cl$_2$ (3.78 g, 5.17 mmol, 0.1 eq) was added to the mixture under a nitrogen atmosphere. The resulting mixture was heated at 80° C. for 2 hours. The reaction mixture was quenched with H$_2$O (800 mL) and extracted with EtOAc (2×600 mL). The combined organic layers were washed with brine (2×800 mL), dried over anhydrous Na$_2$SO$_4$, filtered and concentrated under reduced pressure. The residue was purified by silica gel column chromatography (SiO$_2$, petroleum ether:ethyl acetate, 70:1 to 10:1) and then triturated with hexane (100 mL) to give the title compound (10.05 g, 72% yield, 96% purity on LCMS).

$^1$H NMR (CDCl$_3$) δ 8.24 (d, 1H), 6.97 (d, 1H), 6.93 (d, 1H), 6.83 (s, 1H), 6.73-6.70 (m, 1H), 3.99 (s, 3H), 3.66 (br s, 2H), 2.97-2.89 (m, 1H) and 1.29 (dd, 6H).

LCMS: m/z 261.1 (M+H)$^+$ (ES$^+$).

Step B: 4-(5-Fluoro-2-isocyanato-3-isopropylphenyl)-2-methoxypyridine

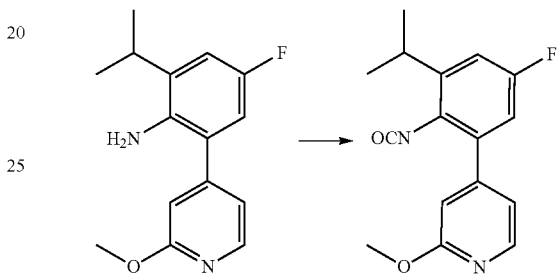

To a solution of 4-fluoro-2-isopropyl-6-(2-methoxypyridin-4-yl)aniline (1 g, 3.84 mmol, 1 eq) in THF (40 mL) was added TEA (777 mg, 7.68 mmol, 2 eq). Then triphosgene (456 mg, 1.54 mmol, 0.4 eq) was added in portions at 5'C. The mixture was stirred at 70° C. for 1 hour. The mixture was diluted with EtOAc (200 mL) and filtered through silica gel. The filtrate was concentrated in vacuo to give the title compound (1.1 g, crude) as a yellow oil, which was used directly in the next step.

Intermediate A5: 4-(4-Isocyanato-2,3-dihydro-1H-inden-5-yl)-2-methoxypyridine

Step A: 4-Nitro-2,3-dihydro-1H-indene

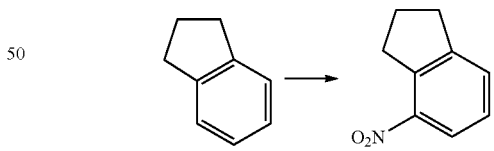

To a mixture of 2,3-dihydro-1H-indene (60 g, 507.72 mmol, 62.50 mL, 1 eq) in concentrated H$_2$SO$_4$ (30 mL) was added a mixture of HNO$_3$ (50 mL, 69 wt % in water) and concentrated H$_2$SO$_4$ (50 mL) dropwise at 0° C. over a period of 3.5 hours. The reaction mixture was stirred at 0° C. for 0.5 hour. Then the reaction mixture was poured into ice water (600 mL) and extracted with ethyl acetate (2×400 mL). The combined organic layers were washed with water (500 mL), saturated aqueous NaHCO$_3$ solution (500 mL) and brine (2×500 mL). The organic layer was dried over anhydrous Na$_2$SO$_4$, filtered and concentrated in vacuo. The residue was purified by silica gel column chromatography (SiO$_2$, petroleum ether:ethyl acetate, 1:0 to 100:1) to give the title compound (55 g, 66%) as a colourless oil.

$^1$H NMR (CDCl$_3$): δ 7.98 (d, 1H), 7.51 (d, 1H), 7.30 (t, 1H), 3.41 (t, 2H), 302 (t, 2H) and 2.22-2.20 (m, 2H).

Step B: 2,3-Dihydro-H-inden-4-amine

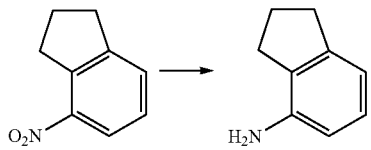 [SMILES: O=[N+]([O-])c1cccc2c1CCC2 ; Nc1cccc2c1CCC2]

To a solution of 4-nitro-2,3-dihydro-1H-indene (55 g, contained another regio-isomer) in MeOH (500 mL) was added Pd/C (5 g, 10 wt % loading on activated carbon) under N$_2$ atmosphere. The suspension was degassed under vacuum and purged with H$_2$ several times. The reaction mixture was stirred under H$_2$ (50 psi) at 20° C. for 12 hours. The reaction mixture was filtered and the filtrate was concentrated in vacuo. The residue was purified by silica gel column chromatography (SiO$_2$, petroleum ether:ethyl acetate, 1:0 to 100:4) to give the title compound (19.82 g, 43% yield, 96.39% purity on LCMS) as a brown oil.

$^1$H NMR (CDCl$_3$): δ 7.01 (t, 1H), 6.71 (d, 1H), 6.51 (d, 1H), 3.57 (br s, 2H), 2.93 (t, 2H), 2.75 (t, 2H) and 2.16-2.08 (m, 2H).

LCMS: m/z 134.2 (M+H)$^+$ (ES$^+$).

Step C: N-(2,3-Dihydro-H-inden-4-yl)acetamide

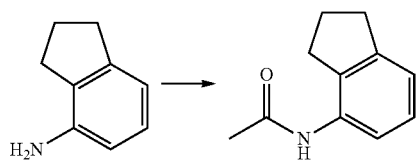

To a solution of 2,3-dihydro-1H-inden-4-amine (19.8 g, 148.66 mmol, 1 eq) and TEA (19.56 g, 193.26 mmol, 1.3 eq) in DCM (300 mL) was added dropwise Ac$_2$O (17.45 g, 170.96 mmol, 1.15 eq) over 6 minutes at 0° C. Then the reaction mixture was warmed to 16° C. and stirred for 1.4 hours. The mixture was poured into water (500 mL) and extracted with DCM (2×300 mL). The combined organic phases were washed with brine (2×500 mL), dried over anhydrous Na$_2$SO$_4$, filtered and concentrated in vacuo to give the title compound (25.74 g, 96% yield, 96.69% purity on LCMS) as a white solid.

$^1$H NMR (CDCl$_3$): δ 7.70 (d, 1H), 7.15 (t, 1H), 7.02 (d, 1H), 2.95 (t, 2H), 2.81 (t, 2H), 2.18 (s, 3H) and 2.15-2.08 (m, 2H).

LCMS: m/z 176.2 (M+H)$^+$ (ES$^+$)

Step D: N-(5-Bromo-2,3-dihydro-H-inden-4-yl)acetamide

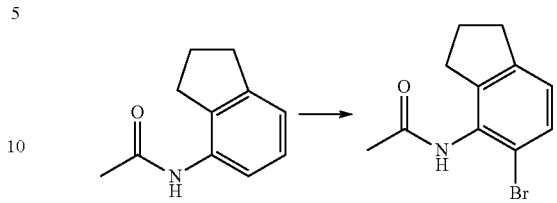

N-(2,3-dihydro-1H-inden-4-yl)acetamide (34.6 g, 197.46 mmol, 1 eq), p-toluenesulfonic acid (18.70 g, 108.60 mmol, 0.55 eq) and Pd(OAc)$_2$ (2.22 g, 9.87 mmol, 0.05 eq) were suspended in toluene (400 mL) and stirred at 20° C. for 0.5 hour under air atmosphere. NBS (38.66 g, 217.20 mmol, 1.1 eq) was added. Then the reaction mixture was stirred at 20° C. for 2 hours. The reaction mixture was poured into water (500 mL) and extracted with ethyl acetate (2×500 mL). The combined organic phases were washed with brine (2×500 mL), dried over anhydrous Na$_2$SO$_4$, filtered and concentrated in vacuo. The residue was purified by silica gel column chromatography (SiO$_2$, petroleum ether:ethyl acetate, 10:1 to 2:1) to give the title compound (13.9 g, 27% yield, 98.1% purity on LCMS) as a white solid.

$^1$H NMR (CDCl$_3$): δ 7.33 (d, 1H), 7.16 (s, 1H), 6.98 (d, 1H), 2.92-2.83 (m, 4H), 2.21 (s, 3H) and 2.10-2.02 (m, 2H).

LCMS: m/z 254.1 (M+H)$^+$ (ES$^+$).

Step E: 5-Bromo-2,3-dihydro-1H-inden-4-amine

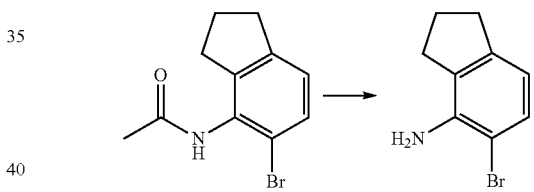

A mixture of N-(5-bromo-2,3-dihydro-1H-inden-4-yl)acetamide (45.68 g, 179.76 mmol, 1 eq) in EtOH (200 mL) and concentrated HCl (300 mL, 36 wt % in water) was stirred at 80° C. for 36 hours. The reaction mixture was cooled to 0° C. in an ice bath and some solid precipitated. The suspension was filtered. The filter cake was washed with ice water (50 mL) and dried in vacuo to give the title compound (34.1 g, 72% yield, 94.08% purity on LCMS, HCl salt) as a grey solid.

$^1$H NMR (DMSO-d$_6$): δ 7.67 (br s, 2H), 7.24 (d, 1H), 6.69 (d, 1H), 2.85 (t, 2H), 2.79 (t, 2H) and 2.04-1.96 (m, 2H).

LCMS: m/z 212.0 (M+H)$^+$ (ES$^+$).

Step F: 5-(2-Methoxypyridin-4-yl)-2,3-dihydro-1H-inden-4-amine

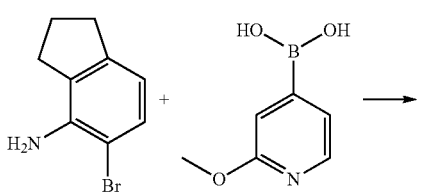

161

-continued

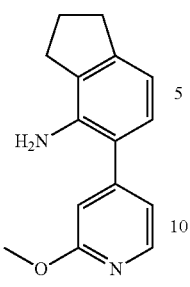

A solution of (2-methoxypyridin-4-yl)boronic acid (25.11 g, 164.15 mmol, 1.2 eq), 5-bromo-2,3-dihydro-1H-inden-4-amine (34 g, 136.80 mmol, 1 eq, HCl salt) and K$_2$CO$_3$ (60.50 g, 437.74 mmol, 3.2 eq) in dioxane (500 mL) and H$_2$O (100 mL) was degassed with nitrogen for 15 minutes before Pd(dppf)Cl$_2$·CH$_2$Cl$_2$ (6 g, 7.35 mmol, 0.053 eq) was added. The reaction mixture was heated to 80° C. for 12 hours. The mixture was poured into water (500 mL) and extracted with ethyl acetate (2×500 mL). The combined organic phases were washed with brine (2×700 mL), dried over anhydrous Na$_2$SO$_4$, filtered and concentrated in vacuo. The residue was purified by silica gel column chromatography (SiO$_2$, petroleum ether:ethyl acetate, 1:0 to 10:1) to give the title compound (27.4 g, 79% yield, 95% purity on LCMS) as a white solid.

$^1$H NMR (CDCl$_3$): δ 8.22 (d, 1H), 7.03-7.00 (m, 1H), 6.99 (d, 1H), 6.87 (s, 1H), 6.77 (d, 1H), 3.99 (s, 3H), 3.77 (br s, 2H), 2.97 (t, 2H), 2.77 (t, 2H) and 2.21-2.13 (m, 2H).

LCMS: m/z 241.2 (M+H)$^+$ (ES$^+$).

Step G: 4-(4-Isocyanato-2,3-dihydro-H-inden-5-yl)-2-methoxypyridine

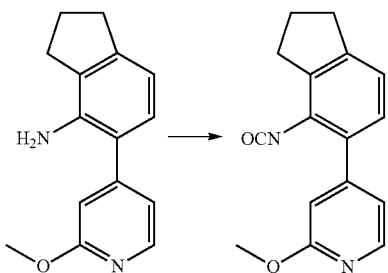

To a solution of 5-(2-methoxypyridin-4-yl)-2,3-dihydro-1H-inden-4-amine (11 g, 45.78 mmol, 1 eq) and TEA (5.10 g, 50-35 mmol, 1.1 eq) in THF (275 mL) was added bis(trichloromethyl) carbonate (4.93 g, 16.61 mmol, 0.36 eq) in portions at 0° C. Then the reaction mixture was stirred at 16° C. for 0.5 hour. The reaction mixture was filtered and the filter cake was washed with THF (2 L). The filtrate was concentrated in vacuo to give the title compound (9.04 g, 74%) as a light yellow solid.

$^1$H NMR (CDCl$_3$): δ 8.28 (d, 1H), 7.20-7.16 (m, 3H), 7.02 (s, 1H), 4.16 (s, 3H), 3.04-2.99 (m, 4H) and 2.23-2.15 (m, 2H).

162

Intermediate A6: 3-(5-Fluoro-2-isocyanato-3-isopropylphenyl)pyridine

Step A: 4-Fluoro-2-isopropyl-6-(pyridin-3-yl)aniline

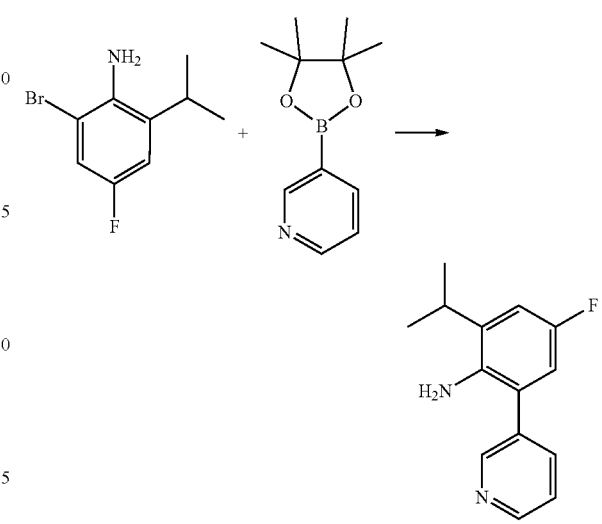

To a solution of 2-bromo-4-fluoro-6-isopropylaniline (21 g, 90.48 mmol, 1 eq) in dioxane (450 mL) and H$_2$O (90 mL) was added 3-(4,4,5,5-tetramethyl-1,3,2-dioxaborolan-2-yl) pyridine (22.26 g, 108.58 mmol, 1.2 eq) and Na$_2$CO$_3$ (23.98 g, 226.20 mmol, 2.5 eq). The reaction mixture was purged with N$_2$ three times. Then Pd(dppf)Cl$_2$ (5.10 g, 6.97 mmol, 0.077 eq) was added under N$_2$ atmosphere. The resulting mixture was heated to 80° C. and stirred for 2 hours. The reaction mixture was quenched by addition of H$_2$O (800 mL) and extracted with EtOAc (2×600 mL). The combined organic layers were washed with brine (2×800 mL), dried over anhydrous Na$_2$SO$_4$, filtered and concentrated under reduced pressure. The residue was purified by silica gel column chromatography (SiO$_2$, petroleum ether:ethyl acetate, 50:1 to 1:1) and then triturated with hexane (40 mL) to give the title compound (17 g, 82%) as a grey solid.

$^1$H NMR (CDCl$_3$): δ 8.70 (d, 1H), 8.63 (dd, 1H), 7.79 (dd, 1H), 7.41-7.38 (m, 1H), 6.94 (dd, 1H), 6.71 (dd, 1H), 3.57 (s, 2H), 2.97-2.88 (m, 1H) and 1.30 (d, 6H). LCMS: m/z 231.2 (M+H)$^+$ (ES$^+$).

Step B: 3-(5-Fluoro-2-isocyanato-3-isopropylphenyl)pyridine

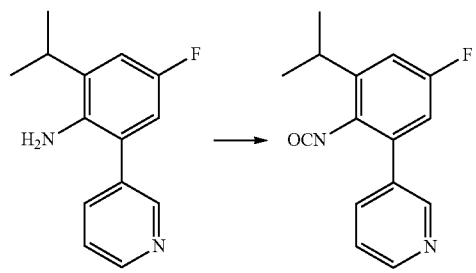

To a solution of 4-fluoro-2-isopropyl-6-(pyridin-3-yl)aniline (0.5 g, 2.17 mmol, 1 eq) and TEA (439 mg, 4.34 mmol, 2 eq) in THF (10 mL) was added triphosgene (257 mg, 868.51 μmol, 0.4 eq) in portions at 5° C. Then the reaction mixture was heated to 70° C. and stirred for 1 hour. The reaction mixture was concentrated in vacuo. The residue was treated with EtOAc (100 mL) and filtered. The filtrate was concentrated in vacuo to give the title compound (0.2 g, crude) as a yellow oil, which was used directly in the next step.

Intermediate A7: 4-(4-Isocyanato-2,3-dihydro-H-inden-5-yl)-2-methoxypyridine

Step A: N-(5-Bromo-2,3-dihydro-H-inden-4-yl)pivalamide

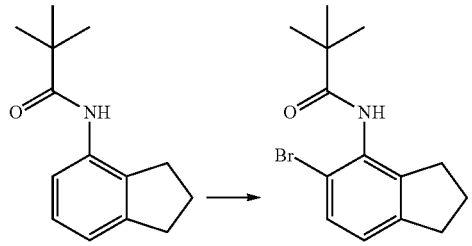 [SMILES: CC(C)(C)C(=O)Nc1cccc2c1CCC2 ; CC(C)(C)C(=O)Nc1c(Br)ccc2c1CCC2]

N-(2,3-Dihydro-1H-inden-4-yl)pivalamide (1 g, 4.60 mmol), p-toluenesulfonic acid monohydrate (0.45 g, 2.366 mmol), Pd(OAc)$_2$ (0.05 g, 0.223 mmol), and NBS (0.9 g, 5.06 mmol) were suspended in toluene (20 mL) and stirred under air for 16 hours. The dark green mixture was diluted with EtOAc (20 mL), and then washed with saturated aq. NaHCO$_3$ (2×10 mL), water (2×10 mL) and brine (10 mL). The organic phase was dried (Na$_2$SO$_4$), filtered and concentrated in vacuo to give a dark green amorphous solid. The crude product was purified by chromatography on silica gel (40 g column, 0-30% EtOAc/isohexane) to afford the title compound (1.662 g, 100%) as a colourless crystalline solid that was contaminated with a small amount of reaction byproducts.

LCMS m/z 296.3/298.3 (M+H)$^+$ (ES$^+$).

Step B: 5-Bromo-2,3-dihydro-1H-inden-4-amine

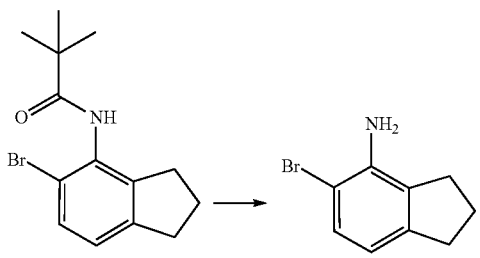 [SMILES: CC(C)(C)C(=O)Nc1c(Br)ccc2c1CCC2 ; Nc1c(Br)ccc2c1CCC2]

N-(5-Bromo-2,3-dihydro-1H-inden-4-yl)pivalamide (0.632 g, 2.134 mmol) was dissolved in ethanol (5 mL) and stirred at room temperature. H$_2$SO$_4$ (95% aq.) (5 ml, 89 mmol) was slowly added to water (5 mL) and this mixture was then added to the reaction mixture. The slurry was heated to 100° C. (bath temperature) at which point the mixture became homogeneous and it was stirred at this temperature over the weekend. The mixture was cooled to room temperature and then basified with 2M aq. NaOH. The mixture was extracted with dichloromethane (3×20 mL). The organic phase was dried by passing through a hydrophobic frit, and then concentrated in vacuo. The crude product was purified by chromatography on silica gel (40 g column, 0-50% EtOAc/isohexane) to afford the title compound (0.138 g, 29%).

$^1$H NMR (CDCl$_3$) δ 7.23 (d, J=7.9 Hz, 1H), 6.57 (d, J=8.0 Hz, 1H), 3.92 (s, 2H), 2.89 (t, J=7.6 Hz, 2H), 2.77 (t, J=7.4 Hz, 2H), 2.15 (p, J=7.5 Hz, 2H).

Step C: 5-(2-Methoxypyridin-4-yl)-2,3-dihydro-1H-inden-4-amine

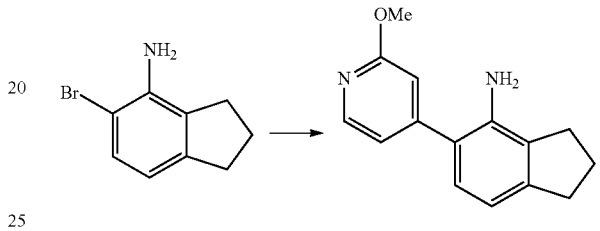

5-Bromo-2,3-dihydro-1H-inden-4-amine (280 mg, 1.320 mmol) was dissolved in dioxane (5 mL). A solution of potassium carbonate (600 mg, 4.34 mmol) in water (1 mL) and (2-methoxypyridin-4-yl)boronic acid (250 mg, 1.635 mmol) were added. The mixture was degassed with nitrogen for 15 minutes before Pd(dppf)Cl$_2$.CH$_2$Cl$_2$ (60 mg, 0.073 mmol) was added. The reaction mixture was heated to 80° C. (bath temperature) for 2 hours. The mixture was cooled to room temperature and partitioned between dichloromethane (30 mL) and water (20 mL). The organic phase was dried by passing through a hydrophobic frit and concentrated in vacuo to give a brown oil. The crude product was purified by chromatography on silica gel (12 g column, 0-50% EtOAc/isohexane) to afford the title compound (0.289 g, 87%) as a pale yellow crystalline solid.

$^1$H NMR (CDCl$_3$) δ 8.26 (d, J=5.4 Hz, 1H), 7.11 (d, J=5.0 Hz, 1H), 7.01 (d, J=7.7 Hz, 1H), 6.97 (s, 1H), 6.80 (d, J=7.6 Hz, 1H), 4.06 (s, 3H), 2.98 (t, J=7.6 Hz, 2H), 2.80 (t, J=7.4 Hz, 2H), 2.19 (p, J=7.5 Hz, 2H), NH$_2$ not observed.

LCMS m/z 241.3 (M+H)$^+$ (ES$^+$).

Step D: 4-(4-Isocyanato-2,3-dihydro-H-inden-5-yl)-2-methoxypyridine

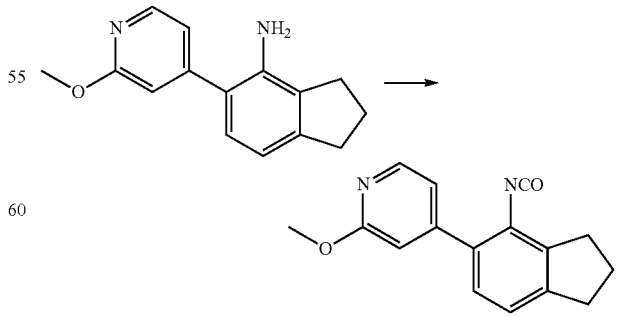

5-(2-Methoxypyridin-4-yl)-2,3-dihydro-1H-inden-4-amine (500 mg, 2.081 mmol) was dissolved in DCM (10 mL) and sat aq NaHCO₃ (5 mL) was added. A solution of triphosgene (250 mg, 0.842 mmol) in DCM (5 mL) was added and the mixture stirred at room temperature for 1 hour. The organic phase was separated, dried by passing through a hydrophobic frit and concentrated in vacuo to afford the title compound (523 mg, 94%) as a pale yellow oil that was used without further purification.

$^1$H NMR (CDCl₃) δ 8.25 (d, J=5.2 Hz, 1H), 7.18-7.13 (m, 2H), 7.01 (dd, J=5.3, 1.5 Hz, 1H), 6.86 (s, 1H), 4.03 (s, 3H), 3.04 (t, J=7.5 Hz, 4H), 2.21 (p, J=7.5 Hz, 2H).

Intermediate A8: 4-(4-Isocyanato-2,3-dihydrobenzofuran-5-yl)-2-methoxypyridine

Step A:
N-(5-Bromo-2,3-dihydrobenzofuran-4-yl)acetamide

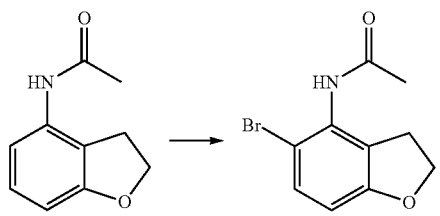

N-(2,3-dihydrobenzofuran-4-yl)acetamide (13.1 g, 73.9 mmol), 4-methylbenzenesulfonic acid hydrate (7.73 g, 40.7 mmol) and diacetoxypalladium (0.830 g, 3.70 mmol) were suspended in toluene (250 mL) and stirred for 20 minutes. NBS (14.47 g, 81 mmol) was added and the mixture was stirred for 30 minutes, diluted with EtOAc (150 mL), and washed with aq NaHCO₃ (100 mL) and aq Na₂S2O3 (10 wt %, 100 mL). The aqueous phases were further extracted with DCM (150 mL). The organic phases were combined, dried (MgSO₄), filtered and concentrated under reduced pressure to afford the title compound (22.27 g, quant., purity 85% by LCMS) which was used crude in the next step.

LCMS; m/z 255.9, 257.9 (M+H)⁺ (ES⁺).

Step B: 5-Bromo-2,3-dihydrobenzofuran-4-amine

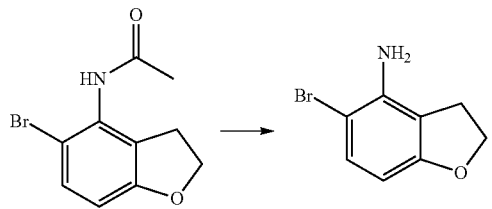

A solution of N-(5-bromo-2,3-dihydrobenzofuran-4-yl) acetamide (22.27 g, 73.9 mmol) in MeOH (400 mL) and conc H₂SO₄ (40 mL) was stirred at reflux for 18 hours. The volatiles were removed under reduced pressure, the residue taken up in DCM (300 mL) and basified with aq NaOH 1 M (100 mL). The organic phase was separated, dried (Na₂SO₄), filtered and concentrated under reduced pressure. The crude product was purified by chromatography on silica gel (220 g cartridge, 0-100% EtOAc/isohexane) to afford the title compound (9.17 g, 57%) as an off white solid.

$^1$H NMR (CDCl₃) δ 7.16 (dt, J=8.4, 0.9 Hz, 1H), 6.17 (d, J=8.4 Hz, 1H), 4.61 (t, J=8.7 Hz, 2H), 3.99 (br. s, 2H), 3.05 (t, J=8.7 Hz, 2H).

Step C: 5-(2-Methoxypyridin-4-yl)-2,3-dihydrobenzofuran-4-amine

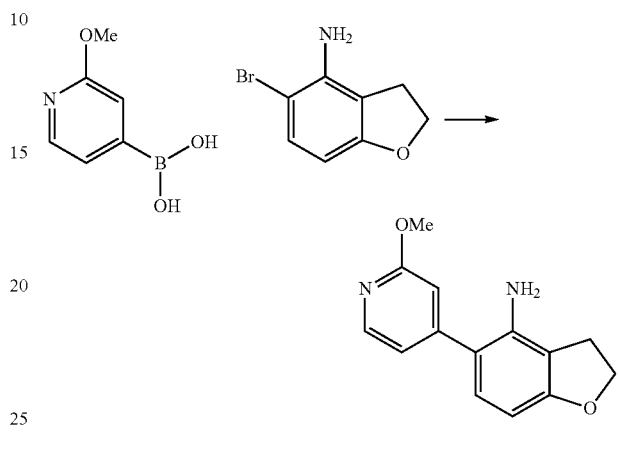

Prepared according to the general procedure of 5-(2-methoxypyridin-4-yl)-2,3-dihydro-1H-inden-4-amine (Intermediate A7, Step C) from 5-bromo-2,3-dihydrobenzofuran-4-amine and (2-methoxypyridin-4-yl)boronic acid to afford the title compound (2.25 g, 79%) as an off white solid.

$^1$H NMR (DMSO-d₆) δ 8.15 (d, J=5.2 Hz, 1H), 6.99 (dd, J=5.3, 1.5 Hz, 1H), 6.84 (d, J=8.2 Hz, 1H), 6.78 (s, 1H), 6.14 (d, J=8.1 Hz, 1H), 4.91 (s, 2H), 4.54 (t, J=8.7 Hz, 2H), 3.87 (s, 3H), 3.01 (t, J=8.7 Hz, 2H).

LCMS; m/z 243.1 (M+H)⁺ (ES⁺).

Step D: 4-(4-Isocyanato-2,3-dihydrobenzofuran-5-yl)-2-methoxypyridine

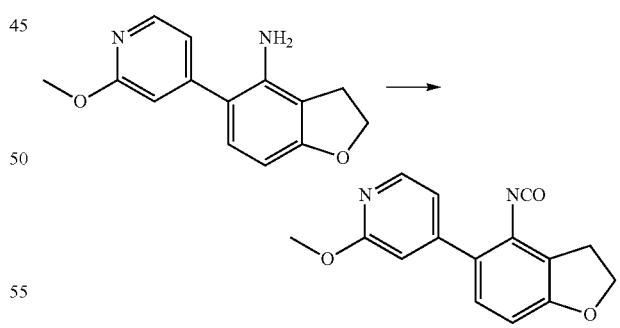

Prepared according to the general procedure of 4-(4-isocyanato-2,3-dihydro-H-inden-5-yl)-2-methoxypyridine (Intermediate A7, Step D) from 5-(2-methoxypyridin-4-yl)-2,3-dihydrobenzofuran-4-amine to afford the title compound (926 mg, 79%) as a pale yellow solid.

$^1$H NMR (CDCl₃) δ 8.23 (d, J=5.3 Hz, 1H), 7.13 (d, J=8.3 Hz, 1H), 6.98 (dd, J=5.3, 1.4 Hz, 1H), 6.83 (s, 1H), 6.74 (d, J=8.3 Hz, 1H), 4.72 (t, J=8.7 Hz, 2H), 4.02 (s, 3H), 3.33 (t, J=8.7 Hz, 2H).

Intermediate A9:
5-Chloro-2-isocyanato-1,3-diisopropylbenzene

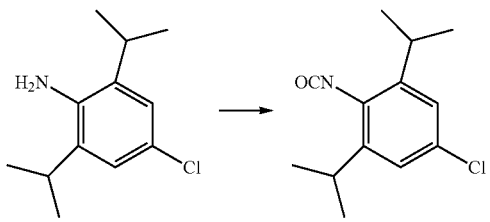

To a solution of 4-chloro-2,6-diisopropylaniline (0.105 g, 0.496 mmol) in toluene (1 mL) was added a phosgene solution (0.65 mL, 20 wt % in toluene, 1.22 mmol) and the reaction mixture was refluxed for 1 hour. Upon cooling, the mixture was concentrated in vacuo to afford the title compound as an orange oil (0.111 g, 94%).

$^1$H NMR (CDCl$_3$) δ 7.07 (d, 2H), 3.17 (h, 2H), 1.24 (d, 12H).

Intermediate A10:
5-Fluoro-2-isocyanato-1,3-diisopropylbenzene

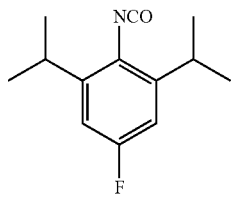

4-Fluoro-2,6-diisopropylaniline (1 g, 5.12 mmol) and triethylamine (0.785 mL, 5.63 mmol) were dissolved in THF (10 mL) and cooled to 0° C. Triphosgene (0.760 g, 2.56 mmol) was added to the mixture portionwise and the reaction mixture was stirred for 16 hours at room temperature. The mixture was concentrated in vacuo. Isohexane (50 mL) was added and the suspension filtered through silica (3 g). The filtrate was dried under reduced pressure to afford the title compound (900 mg, 75%) as a colourless oil.

$^1$H NMR (DMSO-d6) δ 6.80 (d, J=9.4 Hz, 2H), 3.27-3.12 (m, 2H), 1.23 (d, J=6.8 Hz, 12H).

Intermediate P1:
(1-Ethylpiperidin-4-yl)methanesulfonamide

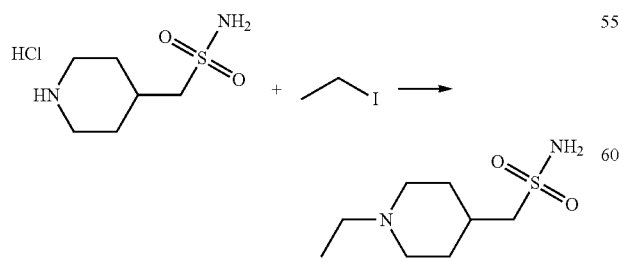

To a suspension of piperidin-4-yl-methanesulfonamide hydrochloric acid (200 mg, 0.93 mmol) and potassium carbonate (514 mg, 3.7 mmol, 4.0 equiv.) in acetonitrile (10 mL) was added iodoethane (74 μL, 0.93 mmol, 1.0 equiv.). The reaction mixture was stirred at room temperature overnight and then filtered. The residue was washed with methanol and the filtrates were combined and concentrated in vacuo. The crude was dissolved in methanol, coated on hydromatrix and then submitted for normal phase flash chromatography on silica gel using dichloromethane and a mixture of 3.5 M ammonia in methanol to afford the title compound (176 mg, 91%).

$^1$H NMR (CD$_3$OD) δ 3.34 (m, 2H), 3.09 (d, 2H), 2.93 (q, 2H), 2.64 (t, 2H), 2.19 (m, 3H), 1.58 (q, 2H) and 1.23 (t, 3H).

Intermediate P2: 3-(4-(Dimethylamino)piperidin-1-yl)propane-1-sulfonamide

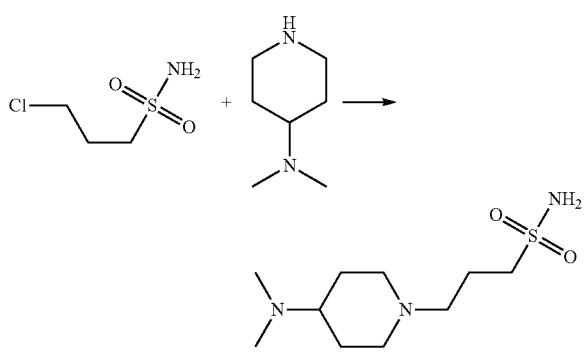

To a solution of 3-chloropropane-1-sulfonamide (213 mg, 1.35 mmol) in acetonitrile (10 mL) was added triethylamine (225 μL, 1.62 mmol, 1.2 equiv.), N,N-dimethylpiperidin-4-amine (208 mg, 1.62 mmol, 1.2 equiv.) and potassium iodide (45 mg, 0.27 mmol). The reaction mixture was irradiated in the microwave at 100° C. for 90 minutes and heated for another 2 hours conventionally at 100° C. The mixture was allowed to cool to room temperature and concentrated in vacuo to afford the crude title compound (>100% yield); the material still contained salts and impurities but was used without further purification.

$^1$H NMR (CD$_3$OD) δ 3-3 (m, 2H), 3.21 (m, 2H), 3.03 (m, 2H), 2.75 (m, 2H), 2.5 (m, 1H), 2.33 (s, 6H), 1.95 (m, 2H) and 1.72-1.42 (m, 4H).

Intermediate P3:
3-(Diethylamino)propane-1-sulfonamide

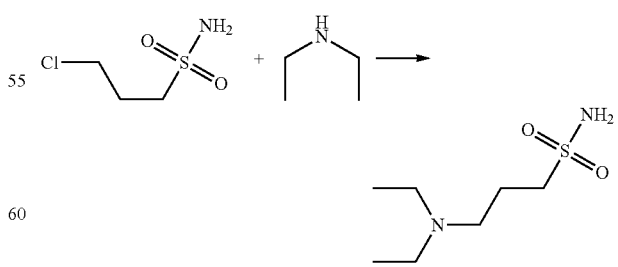

To a solution of 3-chloropropane-1-sulfonamide (203 mg, 1.29 mmol) in acetonitrile (10 mL) was added triethylamine (214 μL, 1.55 mmol, 1.2 equiv.), N,N-diethylamine (159 μL, 1.55 mmol, 1.2 equiv.) and potassium iodide (43 mg, 0.26 mmol) and the reaction mixture was irradiated in the microwave at 100° C. for 90 minutes. Additional potassium iodide (150 mg) was added and the resulting mixture was heated conventionally for another 2 hours at 100° C. Upon cooling to room temperature the mixture was concentrated in vacuo to afford the crude title compound (>100% yield); the material still contained salts and impurities but was used without further purification.

$^1$H NMR (CD$_3$OD) δ 2.86 (m, 6H), 2.47 (m, 2H), 2.23 (m, 2H) and 1.18 (t, 6H).

LCMS: m/z 195.1 (M+H)$^+$ (ES$^+$).

Intermediate P4:
3-(Dimethylamino)propane-1-sulfonamide

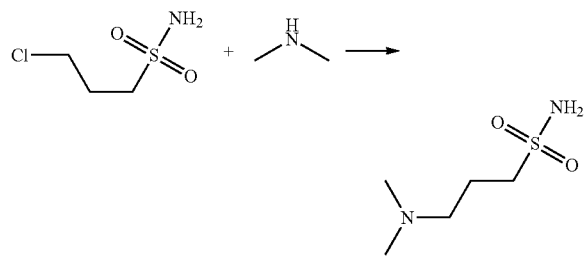

To a solution of 3-chloropropane-1-sulfonamide (203 mg, 1.29 mmol) in 2M dimethylamine in THF (7 mL) was added triethylamine (0.18 mL, 1.29 mmol) and potassium iodide (214 mg, 1.29 mmol). The mixture was heated in the microwave at 80° C. for 90 minutes. The solvents were evaporated and the residue was purified over silica, using dichloromethane and a mixture of 3.5 M ammonia in methanol as the eluent to afford the title compound (51 mg, 24%), as a white solid.

$^1$H NMR (CD$_3$OD) δ 3.20 (t, 2H), 2.44 (t, 2H), 2.24 (s, 6H), 2.04 (m, 2H).

Intermediate P5:
4-Morpholinobutane-1-sulfonamide

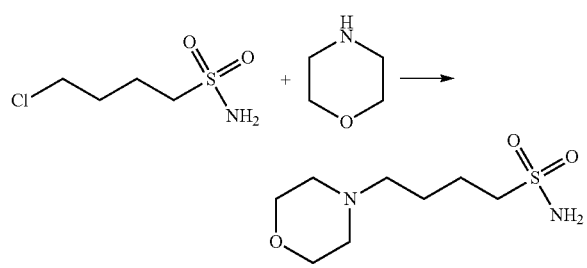

To a solution of 4-chlorobutane-1-sulfonamide (250 mg, 1.46 mmol) in acetonitrile (5 mL) was added potassium carbonate (200 mg, 1.46 mmol), potassium iodide (40 mg, 0.24 mmol) and morpholine (140 mg, 1.6 mmol). The mixture was refluxed under nitrogen for 18 hours. The solvents were evaporated and the residue was purified by chromatography on silicagel using dichloromethane and a mixture of 3.5 M ammonia in methanol as the eluent to afford the title compound (56 mg, 17%) as a white solid.

$^1$H NMR (Chloroform-d) δ 4.70 (s, 2H), 3.82-3.58 (m, 4H), 3.34-3.04 (m, 2H), 2.64-2.24 (m, 6H), 1.93 (m, 2H), 1.79-1.52 (m, 2H).

Intermediate P6:
4-(Diethylamino)butane-1-sulfonamide

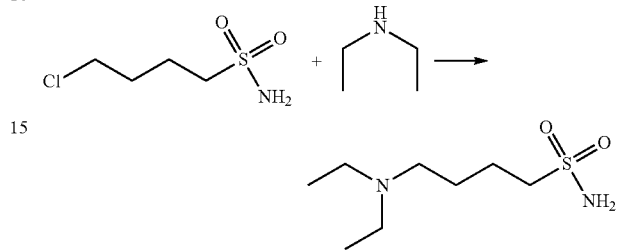

To a solution of 4-chlorobutane-1-sulfonamide (250 mg, 1.46 mmol) in acetonitrile (5 mL) was added potassium carbonate (200 mg, 1.46 mmol), potassium iodide (60 mg, 0.36 mmol) and diethylamine (0.3 mL, 2.9 mmol). The mixture was refluxed under nitrogen for 18 hours. The solvents were evaporated and the residue was purified by chromatography on silicagel using dichloromethane and a mixture of 3.5 M ammonia in methanol as the eluent to afford the title compound (60 mg, 20%) as a colourless oil.

$^1$H NMR (Chloroform-d) δ 3.35-2.86 (m, 2H), 2.72-2.33 (m, 6H), 1.91 (m, 2H), 1.78-1.48 (m, 2H), 1.03 (t, 6H).

Intermediate P7:
2-(Benzyl(ethyl)amino)ethane-1-sulfonamide

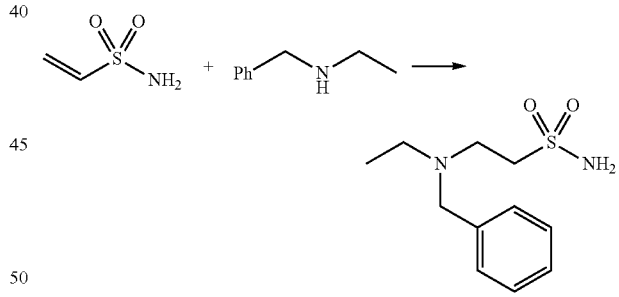

Ethene sulfonamide (250 mg, 2.33 mmol) was dissolved in THF (12.5 mL) and N-ethylbenzylamine (0.36 mL, 331 mg, 2.45 mmol) was added and the solution stirred for 15 minutes at ambient temperature. Triethylamine (0.98 mL, 0.71 g, 7.0 mmol) was added and the mixture stirred for 24 hours at room temperature. The now slightly turbid mixture was evaporated in vacuo. The residue was dissolved in a few mL of DCM/MeOH (1/1) and applied to automated column chromatography (40 g SiO$_2$, 5-30% MeOH/3.5N ammonia in DCM). This afforded the title compound (420 mg, 1.73 mmol, 74%) in 99.3% purity (ELSD-HPLC) after evaporation of the selected fractions.

$^1$H NMR (CDCl3) δ 7.30 (m, 5H), 3.64 (s, 2H), 3.17 (dd, 2H), 3.04 (dd, 2H), 2.59 (q, 2H), 1.10 (t, 3H).

Intermediate P8:
2-Morpholinoethane-1-sulfonamide

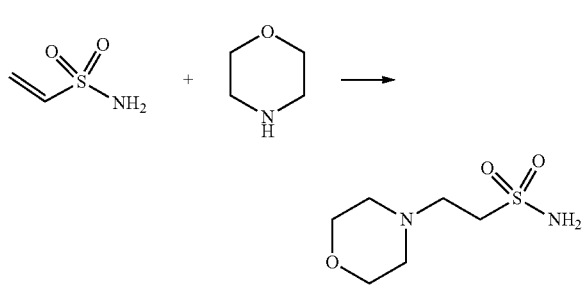

Prepared according to 2-(benzyl(ethyl)amino)ethane-1-sulfonamide (Intermediate P7) using ethene sulfonamide (375 mg, 3.5 mmol) and morpholine (0.35 mL, 351 mg, 4.03 mmol) to yield the title compound (520 mg, 61%) after column chromatography.

HPLC-MS: 100% (ELSD), M 194+1 (ACPI pos.)

$^1$H NMR (DMSO-d6) δ 6.75 (s, 2H), 3.56 (dd, J=4.8, 4.4 Hz, 4H), 3.32 (s, 2H), 3.15 (dd, J=8.7, 6.4 Hz, 2H), 2.69 (dd, J=9.7, 8.0 Hz, 2H), 2.39 (dd, J=5.3, 4.4 Hz, 2H).

Intermediate P9:
4-(Benzyl(ethyl)amino)butane-1-sulfonamide

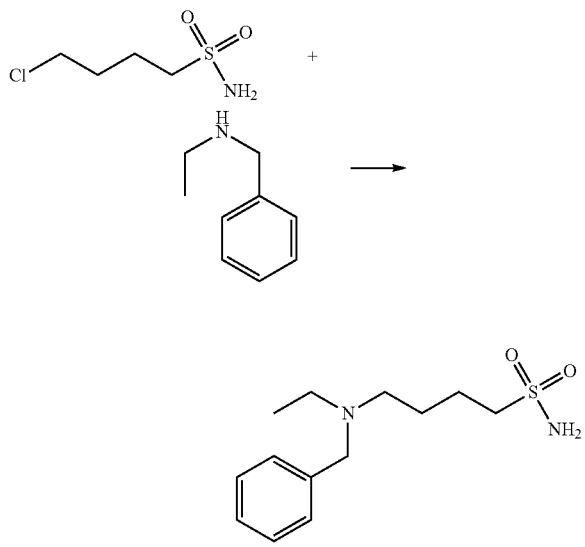

To a solution of 4-chlorobutane-1-sulfonamide (200 mg, 1.17 mmol) in acetonitrile (5 mL) was added and ethylbenzylamine (2 mL, 13.5 mmol). The mixture was refluxed under nitrogen for 18 hours. The solvents were evaporated and the residue was triturated with heptane. The resulting solids were filtered and dried to afford the title compound as a white solid (300 mg, 95%).

$^1$H NMR (Chloroform-d) δ 7.80-6.71 (m, 5H), 4.58 (s, 2H), 3.56 (s, 2H), 3.12 (t, 2H), 2.47 (m, 4H), 1.97 (m, 2H), 1.60 (m, 2H), 1.11 (t, 3H).

Intermediate P10:
3-Morpholinopropane-1-sulfonamide

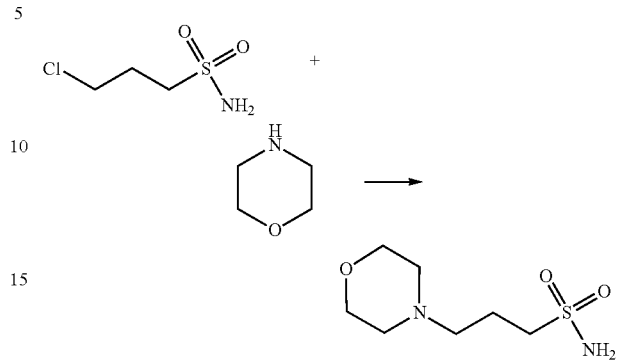

To a solution of 3-chloropropane-1-sulfonamide (200 mg, 1.17 mmol) in acetonitrile (5 mL) was added morpholine (0.44 g, 5 mmol). The mixture was refluxed under nitrogen for 18 hours. The solvents were evaporated and the residue was triturated with t-butylmethyl ether. The resulting oil was decanted and triturated with heptane. The heptane was decanted to afford the title compound as a colourless oil (90 mg, 34%).

$^1$H NMR (Chloroform-d) δ 3.71 (m, 4H), 3.24 (t, 2H), 2.62-2.40 (m, 6H), 2.08 (m, 2H).

Intermediate P11:
3-(Piperidin-1-yl)propane-1-sulfonamide

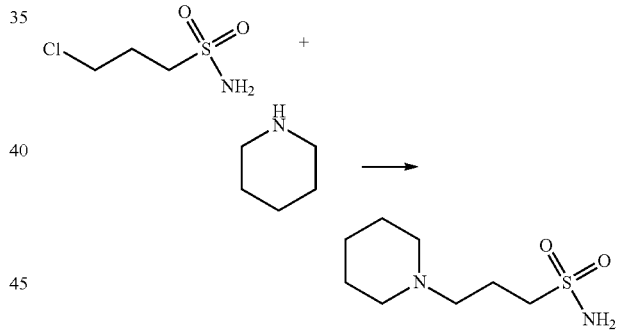

To a solution of 3-chloropropane-1-sulfonamide (200 mg, 1.27 mmol) in acetonitrile (5 mL) was added piperidine (0.44 g, 5 mmol). The mixture was refluxed under nitrogen for 18 hours. The solvents were evaporated and the residue was triturated with t-butylmethyl ether. The solids were filtered and triturated in THF. The solids were filtered and the mother liquor was evaporated to afford the title compound as an oil that solidified upon standing (100 mg, 38%).

$^1$H NMR (Chloroform-d) δ 3.23 (t, J=6.6 Hz, 2H), 2.64-2.33 (m, 6H), 2.09 (m, 2H), 1.60 (m, 4H), 1.47 (dd, 2H).

Intermediate P12:
2-(Diethylamino)ethane-1-sulfonamide

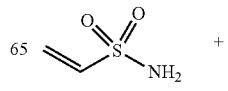

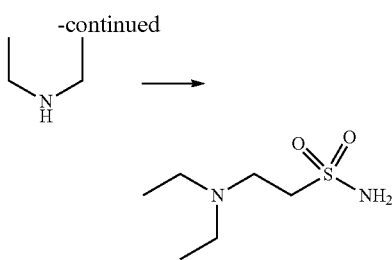

Prepared according to 2-(benzyl(ethyl)amino)ethane-1-sulfonamide (Intermediate P7) using ethene sulfonamide (ca. 60% content, 500 mg, 2.8 mmol) and diethylamine (0.43 mL, 307 mg, 4.2 mmol) to yield the title compound (186 mg, 36%) after column chromatography.

HPLC-MS: 84% purity by ELSD, M 180+1 (ACPI pos.)

$^1$H NMR (DMSO-d6) δ 6.74 (s, 2H), 3.13-3.01 (m, 2H), 2.88-2.76 (m, 2H), 2.52-2.38 (m, 4H overlapping with d-DMSO), 0.96 (t, J=7.1 Hz, 6H).

Intermediate P13:
2-(Ethylamino)ethane-1-sulfonamide

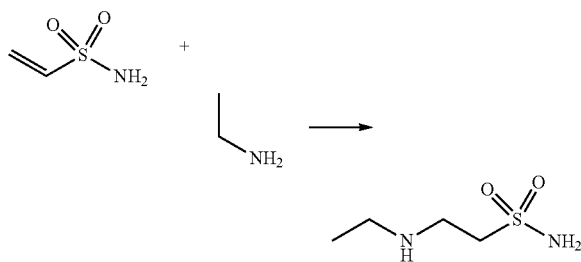

Prepared according to 2-(benzyl(ethyl)amino)ethane-1-sulfonamide (Intermediate P7) using ethene sulfonamide (ca. 60% content, 500 mg, 2.8 mmol) and ethylamine (2M in THF, 2.1 mL, 4.2 mmol) to yield the title compound (131 mg, 30%) after column chromatography.

HPLC-MS: 98% (ELSD), M 152+1 (ACPI pos.)

$^1$H NMR (DMSO-d6) δ 6.74 (s, 2H), 3.09 (t, J=7.0 Hz, 2H), 2.87 (t, J=7.0 Hz, 2H), 2.54 (m, 2H, overlapping with d-DMSO), 0.96 (t, J=7.2 Hz, 3H).

Intermediate P14:
(1-Ethylazetidin-3-yl)methanesulfonamide

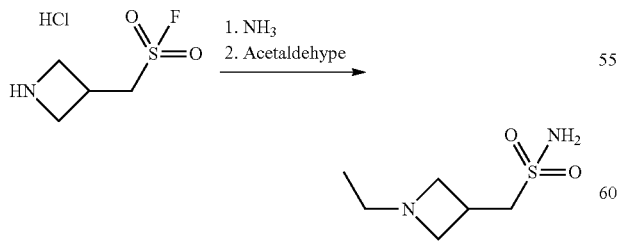

To a solution of 7 M ammonia in methanol (2 mL, 14 mmol) was added (azetidin-3-yl)methanesulfonyl fluoride hydrochloride (250 mg, 1.3 mmol). The reaction mixture was stirred for one hour and then concentrated in vacuo. The solid material was suspended in acetonitrile (10 mL) and then acetaldehyde (109 µL, 1.95 mmol) was added followed by sodium triacetoxyborohydride (413 mg, 1.95 mmol). The reaction mixture was stirred overnight at room temperature. The solution was concentrated in vacuo. The crude material was suspended in methanol, coated on Agilient hydromatrix (a high purity, inert diatomaceous earth sorbent) and then submitted to normal phase flash chromatography using dichloromethane and ammonia (3.5 M) in methanol to afford the title compound (17 mg, 7%), which was used without further purification.

$^1$H NMR (CD$_3$OD) δ 3.90 (m, 2H), 3.55 (m, 2H), 3.38 (m, 2H), 3.20 (m, 1H), 2.88 (q, 2H), 1.08 (t, 3H).

Intermediate P15:
(1-Methylpiperidin-4-yl)methanesulfonamide

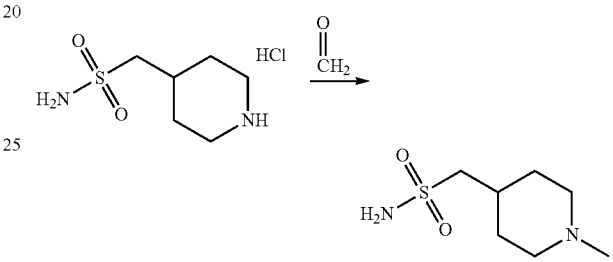

To a suspension of piperidin-4-yl-methanesulfonamide hydrochloric acid (200 mg, 0.93 mmol, 1.0 equiv.), triethylamine (0.16 mL, 1.16 mmol, 1.2 equiv.), formaldehyde (37% in water, stabilized with methanol; 80 µL, 0.98 mmol, 1.05 equiv.) in acetonitrile (10 mL) and sodium triacetoxyborohydride (246 mg, 1.16 mmol, 1.25 equiv.) was added. The reaction mixture was stirred overnight and then concentrated in vacuo. The crude material was suspended in methanol, coated on Agilient hydromatrix (a high purity, inert diatomaceous earth sorbent) and then submitted to normal phase flash chromatography using dichloromethane and ammonia (3.5 M) in methanol to afford the title compound (82 mg, 43%), which was used without further purification.

$^1$H NMR (DMSO-d6) δ 6.76 (s, 2H), 2.88 (d, 2H), 2.69 (m, 2H), 2.10 (s, 3H), 1.78 (m, 5H), 1.25 (m, 2H).

Intermediate P16:
(1-Methylpyrrolidin-3-yl)methanesulfonamide

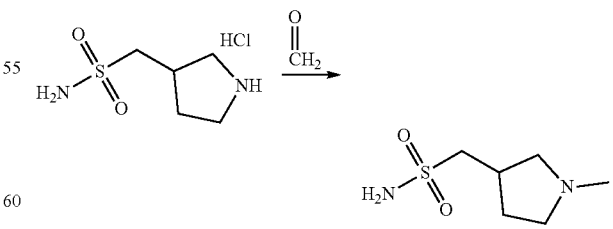

Prepared as described for (1-methylpiperidin-4-yl)methanesulfonamide (Intermediate P15) from (pyrrolidin-3-yl)methanesulfonamide hydrochloride and formaldehyde. The title compound (95 mg, 53%) was used without further purification.

$^1$H NMR (DMSO-d6) δ 6.75 (s, 2H), 3.00 (dd, 2H), 2.67 (m, 1H), 2.37 (m, 2H), 2.24 (m, 5H), 2.00 (m, 1H), 1.49 (m, 1H).

Intermediate P17:
(1-Ethylpyrrolidin-3-yl)methanesulfonamide

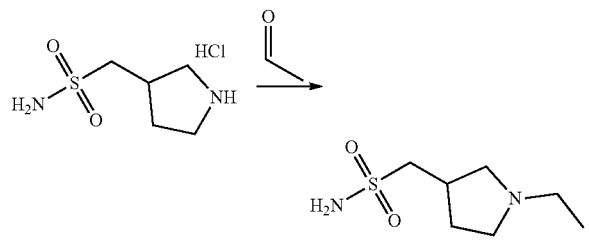

Prepared as described for (1-methylpiperidin-4-yl)methanesulfonamide (Intermediate P15) from (pyrrolidin-3-yl)methanesulfonamide hydrochloride and acetaldehyde. The title compound (86 mg, 44%) was used without further purification.
$^1$H NMR (DMSO-d6) δ 6.76 (s, 2H), 3.01 (m, 2H), 2.71 (m, 1H), 2.37 (m, 4H), 2.23 (m, 2H), 1.99 (m, 1H), 1.48 (m, 1H), 0.98 (t, 3H).

Intermediate P18:
(1-Isopropylpyrrolidin-3-yl)methanesulfonamide

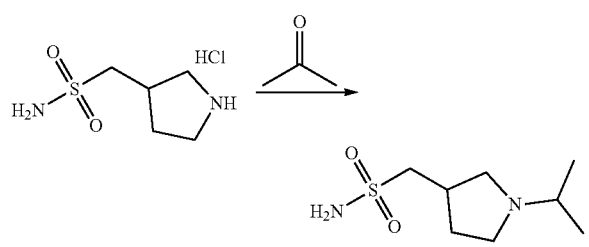

Prepared as described for (1-methylpiperidin-4-yl)methanesulfonamide (Intermediate P15) from (pyrrolidin-3-yl)methanesulfonamide hydrochloride and acetone. The title compound (167 mg, 81%) was used without further purification.
$^1$H NMR (DMSO-d6) δ 6.75 (s, 2H), 3.01 (m, 2H), 2.79 (dd, 1H), 2.55 (m, 1H), 2.41 (m, 1H), 2.27 (m, 3H), 1.97 (m, 1H), 1.47 (m, 1H), 0.98 (dd, 6H).

Intermediate P19:
1-(Dimethylamino)propane-2-sulfonamide

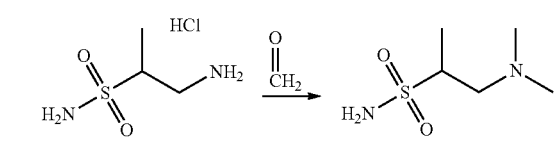

Prepared as described for (1-methylpiperidin-4-yl)methanesulfonamide (Intermediate P15) from 1-aminopropane-2-sulfonamide hydrochloride, except that 2 equivalents of formaldehyde and sodium triacetoxyborohydride were used instead of one. The title compound (16 mg, 13%) was used without further purification.
$^1$H NMR (CD3OD) δ 3.50 (m, 1H), 3.21 (m, 1H), 3.01 (dd, 1H), 2.71 (s, 6H), 1.40 (d, 3H).

Intermediate P20:
2-(Piperidin-1-yl)ethane-1-sulfonamide

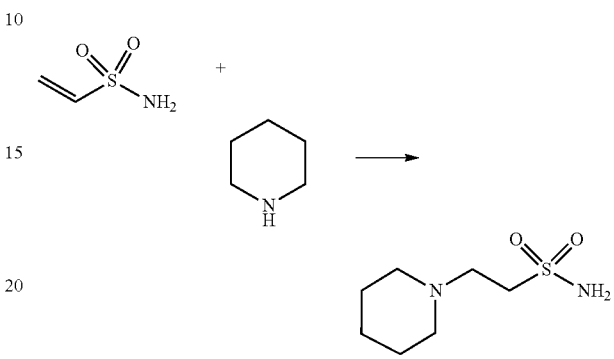

Prepared according to 2-(benzyl(ethyl)amino)ethane-1-sulfonamide (Intermediate P7) using ethene sulfonamide (375 mg, 3.15 mmol) and piperidine (0.36 mL, 308 mg, 3.62 mmol) to yield the title compound (206 mg, 34%) after column chromatography.
HPLC-MS: 100% (ELSD), M 192+1 (ACPI pos.)
$^1$H NMR (Chloroform-d) δ 3.20 (dd, J=7.4, 6.5 Hz, 2H), 2.87 (dd, J=5.5, 4.6 Hz, 2H), 2.48 (t, J=5.2 Hz, 3H), 1.63-149 (m, 5H), 1.49-1.42 (m, 2H).

Intermediate P21:
2-(Azetidin-1-yl)ethane-1-sulfonamide

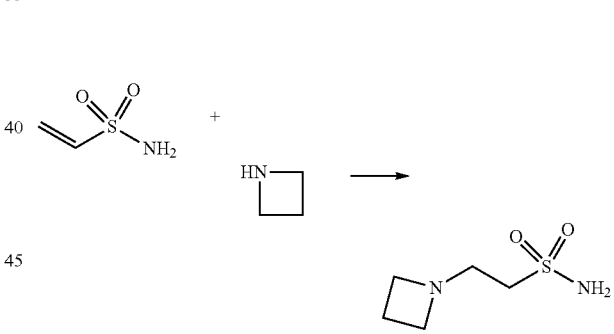

Prepared according to 2-(benzyl(ethyl)amino)ethane-1-sulfonamide (Intermediate P7) using ethene sulfonamide (375 mg, 3.15 mmol) and azetidine hydrochloride (339 mg, 3.62 mmol) to yield the title compound (396 mg, 76%) after column chromatography.
HPLC-MS: 68% (ELSD), M 164+1 (ACPI pos.)
$^1$H NMR (Chloroform-d) δ 3.96-3.76 (m, 2H), 3.37-3.16 (m, 2H), 2.43 (m, 4H), 1.18 (dq, J=9.4, 5.7, 4.5 Hz, 2H).

Intermediate P22:
3-(Ethyl(methyl)amino)propane-1-sulfonamide

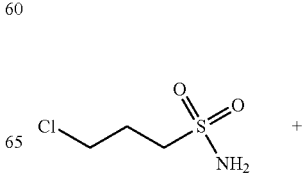

-continued

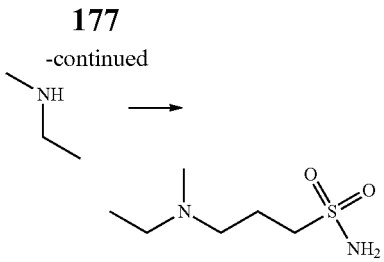

To a solution of 3-chloropropane-1-sulfonamide (200 mg, 1.27 mmol) in acetonitrile (4 mL) was added N-methylethanamine (300 mg, 5.08 mmol). The mixture was heated in the microwave at 80° C. for 30 minutes. The solvents were evaporated and the residue was triturated with TBME. The resulting solids were isolated by decantation of the solution and THF (5 mL) was added to the remaining solids followed by 200 mg triethylamine. After 3 hours the mixture was filtered and the filtrate concentrated to afford the title compound as a white solid (70 mg, 31%).

$^1$H NMR (Chloroform-d) δ 3.18-3.04 (m, 2H), 2.64-2.41 (m, 4H), 2.29 (s, 3H), 2.12-1.92 (m, 2H), 1.11 (t, 3H).

Intermediate P23: (4-Cyanophenyl)methanesulfonamide

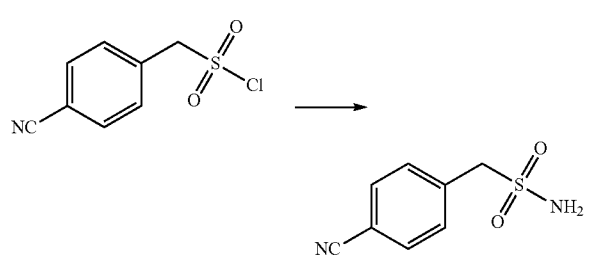

To a solution of saturated ammonia in THF (3 mL) was added dropwise a solution of (4-cyanophenyl)methanesulfonyl chloride (100 mg, 646 µmol, 1 eq) in THF (1 mL). The mixture was stirred at 20° C. for 1 hour and then concentrated under reduced pressure. The residue was diluted with water (3 mL) and then the mixture was extracted into ethyl acetate (2×3 mL). The combined organic layers were washed with brine (3 mL), dried (anhydrous Na$_2$SO$_4$), filtered and concentrated in vacuo to give the title compound (110 mg, >100%) as a white solid.

$^1$H NMR (400 MHz, CDCl$_3$) δ 7.85 (d, 2H), 7.56 (d, 2H), 6.93 (br s, 2H) and 4.40 (s, 2H).

Intermediate P24: 2-Ethyl-2-azaspiro[3.3]heptane-6-sulfonamide

Step A: tert-Butyl 6-((methylsulfonyl)oxy)-2-azaspiro[3.3]heptane-2-carboxylate

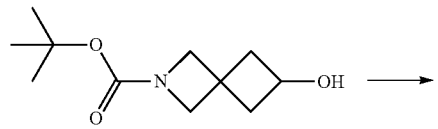

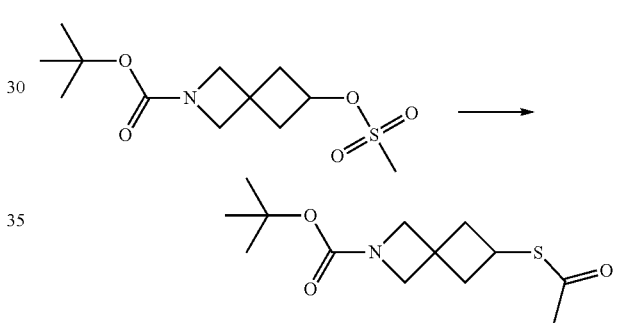

To a solution of tert-butyl 6-hydroxy-2-azaspiro[3.3]heptane-2-carboxylate (2 g, 9.4 mmol) in dichloromethane (25 mL) was added triethylamine (2.6 mL, 18.8 mmol). The solution was cooled to 0° C. and a solution of methanesulfonylchloride (0.8 mL, 10.3 mmol) in dichloromethane (5 mL) was added dropwise. The mixture was stirred for 18 hours at room temperature and then washed with water and brine, dried (sodium sulfate), filtered and evaporated to afford the title compound (2.7 g, yield 100%) as a white solid.

$^1$H NMR (CDCl$_3$): δ=4.89 (m, 1H), 3.94 (s, 4H), 2.99 (s, 3H), 2.70 (m, 2H), 2.48 (m, 2H) and 1.44 (s, 9H).

Step B: tert-Butyl 6-(acetylthio)-2-azaspiro[3.3]heptane-2-carboxylate

To a solution of tert-butyl 6-((methylsulfonyl)oxy)-2-azaspiro[3.3]heptane-2-carboxylate (1 g, 3.4 mmol) in acetonitrile (10 mL) and dimethylformamide (40 mL) was added potassium thioacetate (1.57 g, 13.7 mmol). The reaction was heated to reflux for 18 hours and upon cooling was poured into water (200 mL) and ethyl acetate (100 mL). The mixture was separated and the water layer was extracted with ethyl acetate. The combined organic layers were washed with water (4×) and brine, before being dried (sodium sulfate), filtered and evaporated in vacuo to afford the title compound (1 g, yield 100%) as a brown oil.

$^1$H NMR (CDCl$_3$): δ=3.96 (s, 2H), 3.90 (m, 1H), 3.86 (s, 2H), 2.65 (m, 2H), 2.27 (s, 3H), 2.18 (m, 2H) and 1.42 (s, 9H).

Step C: tert-Butyl 6-sulfamoyl-2-azaspiro[3.3]heptane-2-carboxylate

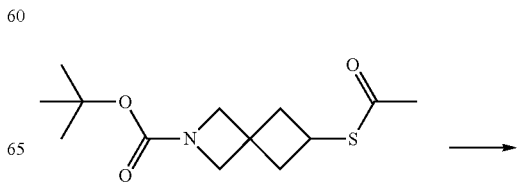

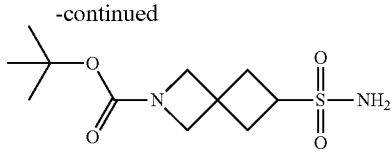

A mixture of tert-butyl 6-(acetylthio)-2-azaspiro[3.3]heptane-2-carboxylate (650 mg, 2.4 mmol), acetic acid (5 mL) and water (1 mL) was cooled in ice/water. N-chloro succinimide (960 mg, 7.8 mmol) was added in portions over a 10 minute period. Then the reaction mixture was stirred at room temperature for 1 hour, before being poured into cold aqueous ammonium hydroxide (50 mL, 25%). The mixture was allowed to stir for 18 hours at room temperature, before the solvents were evaporated in vacuo and the residue was triturated in tetrahydrofuran and decanted. The combined tetrahydrofuran layers were evaporated and the residue was purified over silica, using dichloromethane/methanol (9:1) as the eluent. The title compound was obtained as a white foam (240 mg, yield 36%).

$^1$H NMR (CDCl$_3$): δ=4.87 (br s, 2H), 3.96 (s, 4H), 3.72 (m, 1H), 2.62 (m, 4H) and 1.44 (s, 9H).

Step D: 2-Azaspiro[3.3]heptane-6-sulfonamide, trifluoroacetic acid salt

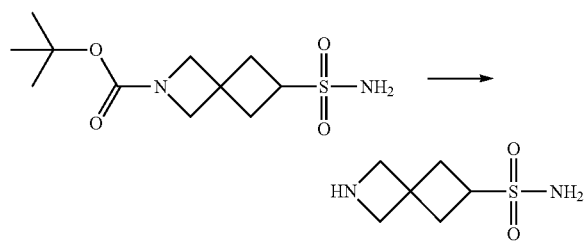

To a solution of tert-butyl 6-sulfamoyl-2-azaspiro[3.3]heptane-2-carboxylate (240 mg, 0.87 mmol) in dichloromethane (10 mL) was added trifluoroacetic acid (0.26 mL, 3.5 mmol). The reaction was stirred for 48 hours and the solvents were evaporated. The residue was dissolved in methanol and purified over Amberlite 410 ion exchange resin, to afford the title compound (100 mg, yield 67%) as a pale yellow oil.

$^1$H NMR (CD$_3$OD): δ=3.93 (s, 4H), 3.66 (m, 1H) and 2.64 (m, 4H).

Step E: 2-Ethyl-2-azaspiro[3.3]heptane-6-sulfonamide

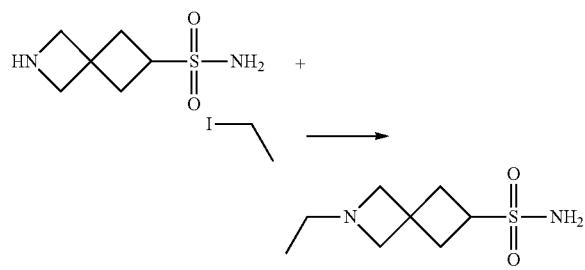

To a mixture of 2-azaspiro[3.3]heptane-6-sulfonamide trifluoroacetic acid salt (75 mg, 0.43 mmol), triethylamine (160 mg, 1.6 mmol) and acetonitrile (5 mL) was added ethyliodide (66 mg, 0.43 mmol). After stirring overnight at room temperature, the reaction mixture was concentrated in vacuo. The crude material was purified by normal phase flash chromatography using ethyl acetate and methanol (9:1) as eluent to afford the product as a mixture with triethylamine salts. The crude product was dissolved in methanol and filtered over Amberlite 410. The solvent was evaporated to afford the title compound (8 mg, yield 15%).

$^1$H NMR (CD$_3$OD): δ=3.67 (m, 1H), 3.24 (d, 4H), 2.50 (d, 4H), 2.43 (q, 2H) and 0.95 (t, 3H).

Intermediate P25: 2-Isopropyl-2-azaspiro[3.3]heptane-6-sulfonamide

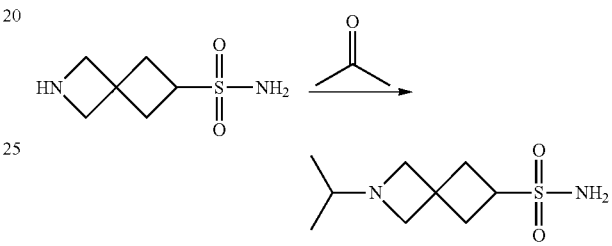

To a solution of 2-azaspiro[3.3]heptane-6-sulfonamide (50 mg, 0.28 mmol) and acetone (25 mg, 0.43 mmol, 1.5 equiv.) in acetonitrile (5 mL) was added sodium triacetoxyborohydride (89 mg, 0.43 mmol, 1.5 equiv.). The reaction mixture was stirred for 18 hours at room temperature and then concentrated in vacuo. The crude material was dissolved in methanol and treated with Amberlite 410 ion exchange resin. The mixture was filtered and the methanol was evaporated. The residue was triturated in THF. The mixture was filtered and the THF was evaporated to afford the title compound (40 mg, yield 65%) which was used as such.

$^1$H NMR (CD3OD): δ=3.71 (m, 1H), 3.25 (m, 4H), 2.53 (m, 4H), 2.33 (m, 1H), 0.93 (d, 6H).

Intermediate P26: 2-Methyl-2-azaspiro[3.3]heptane-6-sulfonamide

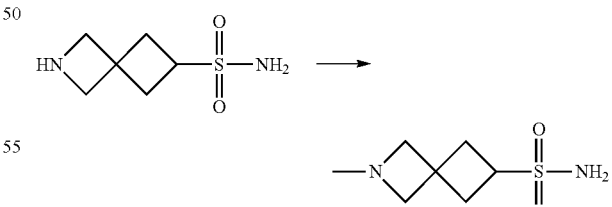

To a solution of 2-azaspiro[3.3]heptane-6-sulfonamide (50 mg, 0.28 mmol) and formaldehyde (32 μL, 37% in water, 0.43 mmol, 1.5 equiv.) in acetonitrile (5 mL) was added sodium triacetoxyborohydride (90 mg, 0.43 mmol, 1.5 equiv.). The reaction mixture was stirred for 18 hours at room temperature and then concentrated in vacuo. The crude material was dissolved in methanol and treated with Amberlite 410 ion exchange resin. The mixture was filtered and the methanol was evaporated. The residue was triturated in THF. The mixture was filtered and the THF was evaporated to afford the title compound (40 mg, yield 74%) which was used as such.

$^1$H NMR (CD$_3$OD): δ=3.71 (m, 1H), 3.37-3.21 (m, 4H), 2.52 (m, 4H), 2.29 (s, 3H).

Intermediate P27: 3-(Benzyl(ethyl)amino)propane-1-sulfonamide

Step A: 3-(Benzyl(ethyl)amino)propane-1-sulfonic acid

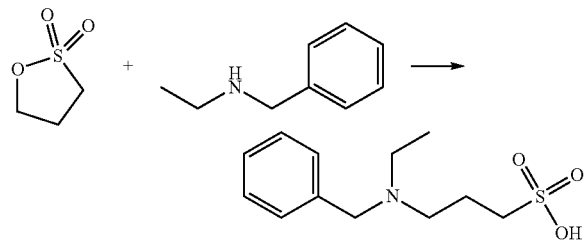

To a solution of 1,2-oxathiolane 2,2-dioxide (1 g, 8.19 mmol, 719.42 µL, 1 eq) in DCM (5 mL) was added N-benzylethanamine (3.94 g, 29.15 mmol, 3.56 eq) at 0° C. Then the resulting mixture was stirred at 25° C. for 2.5 hours. The mixture was concentrated in vacuo. The residue was triturated with EtOAc (40 mL) to give the title compound (2.4 g, crude) as a white solid.

$^1$H NMR (DMSO-d$_6$): δ 7.37-7.23 (m, 5H), 4.08 (s, 2H), 2.91 (q, 2H), 2.50-2.40 (m, 4H), 1.81-173 (m, 2H) and 0.98 (t, 3H).

LCMS: m/z 258.1 (M+H)$^+$ (ES$^+$).

Step B: 3-(Benzyl(ethyl)amino)propane-1-sulfonyl chloride

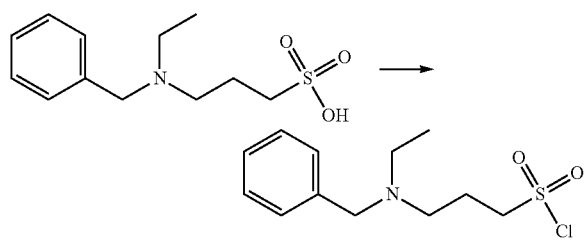

A solution of 3-(benzyl(ethyl)amino)propane-1-sulfonic acid (2.1 g, 8.16 mmol, 1 eq) in SOCl$_2$ (17.22 g, 144.74 mmol, 17.74 eq) was stirred at 80° C. for 6 hours. The mixture was concentrated in vacuo to give the title compound (2 g, crude) as a yellow oil, which was used directly in the next step.

Step C: 3-(Benzyl(ethyl)amino)propane-1-sulfonamide

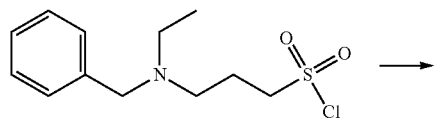

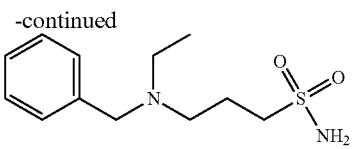

To a solution of 3-(benzyl(ethyl)amino)propane-1-sulfonyl chloride (2 g, crude) in THF (3 mL) was added to a saturated solution of NH$_3$ in THF (100 mL) at 0° C. Then the mixture was stirred at 20° C. for 14 hours. The mixture was filtered and the filtrate was concentrated in vacuo. The residue was purified by reversed phase flash chromatography (0.1% NH$_3$·H$_2$O-MeCN) to give the title compound (1.15 g, 62% yield, 100% purity on LCMS) as a white solid.

$^1$H NMR (CDCl$_3$): δ 7.37-7.28 (m, 5H), 4.98 (br s, 2H), 3.57 (s, 2H), 3.15 (t, 2H), 2.61-2.52 (m, 4H), 2.06-2.00 (m, 2H) and 1.07 (t, 3H).

Intermediate P28: 3-Methoxypropane-1-sulfonamide

Step A: Sodium 3-methoxypropane-1-sulfonate

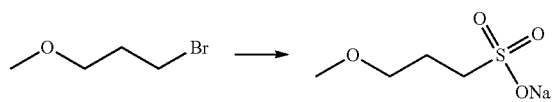

A mixture of 1-bromo-3-methoxypropane (2 g, 13.07 mmol, 1 eq) and Na$_2$SO$_3$ (1.65 g, 13.07 mmol, 1 eq) in H$_2$O (20 mL) was heated to 100° C. and stirred for 16 hours. Then the reaction mixture was cooled and lyophilized to give the title compound (2.25 g, 97%, Na salt) as a white solid.

$^1$H NMR (D$_2$O): δ 3.56 (t, 2H), 3.34 (s, 3H), 2.95-2.92 (m, 2H) and 2.02-1.94 (m, 2H).

LCMS: m/z 155.1 (M−Na+H)$^+$ (ES$^+$).

Step B: 3-Methoxypropane-1-sulfonyl chloride

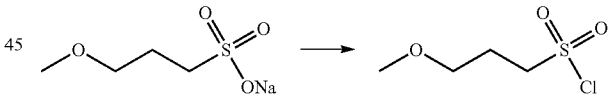

A solution of sodium 3-methoxypropane-1-sylfonate (0.7 g, 4.54 mmol, 1 eq) in POCl$_3$ (8.25 g, 53.80 mmol, 11.85 eq) was stirred at 80° C. for 5 hours. Then the mixture was stirred at 100° C. for 2 hours. The mixture was diluted with DCM (80 mL) and filtered. The filtrate was concentrated in vacuo to give the title compound (600 mg, crude) as a yellow oil, which was used directly in the next step.

Step C: 3-Methoxypropane-1-sulfonamide

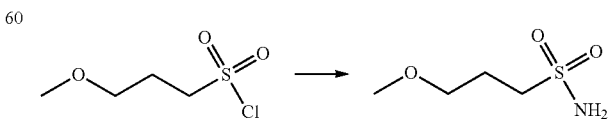

NH$_3$ (15 psi) was bubbled into THF (20 mL) at 0° C. for 5 minutes. A solution of 3-methoxypropane-1-sulfonyl chloride (600 mg, crude) in THF (2 mL) was added to the NH₃/THF solution (20 mL). Then the mixture was stirred at 20° C. for 14 hours. The reaction mixture was filtered and the filtrate was concentrated in vacuo to give the crude compound (300 mg, crude) as a yellow oil.

¹H NMR (CDCl₃): δ 4.94 (br s, 2H), 3.53 (t, 2H), 3.35 (s, 3H), 3.25 (t, 2H) and 2.17-2.10 (m, 2H).

Intermediate P20:
3-(Dimethylamino)-2-methylpropane-1-sulfonamide

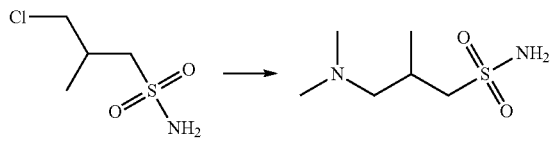

3-Chloro-2-methylpropane-1-sulfonamide (50 mg, 0.3 mmol) was dissolved in dimethylamine (5 mL, 2M in THF). The mixture was heated for 30 minutes at 180° C. in a microwave. The solvents were evaporated. The residue was triturated in THF (20 mL) and triethylamine (100 mg, 1 mmol). The solids were filtered off and the solvent was evaporated to afford the title compound (14 mg, 11%) as a white solid.

¹H NMR (Methanol-d₄) δ 3.30 (m, 2H), 2.93 (m, 2H), 2.38 (s, 6H), 1.40 (m, 1H), 1.16 (d, 3H).

Intermediate P30: 3-Azidopropane-1-sulfonamide

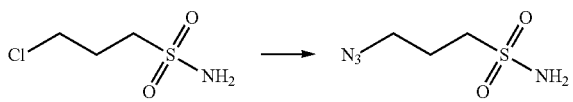 [SMILES: NS(=O)(=O)CCCCl ; [N-]=[N+]=NCCCS(N)(=O)=O]

To a solution of 3-chloropropane-1-sulfonamide (200 mg, 1.3 mmol) in acetone (10 mL) was added sodium azide (200 mg, 3 mmol) in water (1 mL). The mixture was refluxed for 36 hours. The solvents were evaporated. The residue was triturated with THF. The THF layer was filtered and evaporated to afford the title compound as a yellow oil (200 mg, 96%).

¹H NMR (CD₃OD) δ 3.51 (t, 2H), 3.17 (t, 2H), 2.07 (m, 2H).

Intermediate P31:
(1-(Oxetan-3-yl)pyrrolidin-3-yl)methanesulfonamide

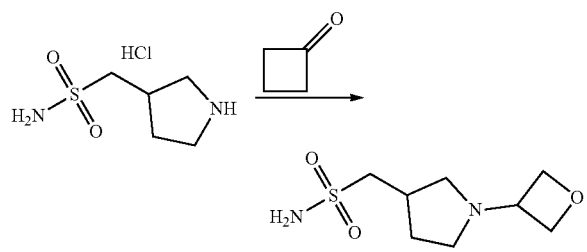

To a suspension of (pyrrolidin-3-yl)methanesulfonamide hydrochloride (100 mg, 0.50 mmol, 0.5 equiv.), triethylamine (83 μL, 0.6 mmol, 1.2 equiv.) and 3-oxetanone (35 μL, 0.55 mmol, 1.1 equiv.) in acetonitrile (10 mL) was added sodium triacetoxyborohydride (132 mg, 0.625 mmol, 1.25 equiv.). The reaction mixture was stirred overnight at room temperature and then concentrated in vacuo. The crude material was suspended in methanol, coated on Agilent hydromatrix (a high purity, inert diatomaceous earth sorbent) and then submitted to normal phase flash chromatography using dichloromethane and ammonia in methanol (3.5 M) to afford the title compound (37 mg, 33%), which was used without further purification.

¹H NMR (DMSO-d₆) δ 6.77 (s, 2H), 4.53 (td, 2H), 4.40 (td, 2H), 3.60-3.45 (m, 1H), 3.03 (d, 2H), 2.72 (dd, 1H), 2.57-2.52 (m, 1H), 2.44-2.32 (m, 2H), 2.20 (dd, 1H), 2.08-1.93 (m, 1H), 1.58-1.43 (m, 1H).

Intermediate P32:
N,N,N-Trimethyl-3-sulfamoylpropan-1-aminium

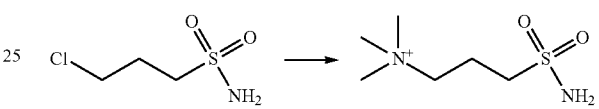

To trimethylamine (4.2 M in ethanol, 4 mL, 16.8 mmol) was added 3-chloropropane-1-sulfonamide (159 mg, 1 mol). The mixture was heated for 30 minutes at 100° C. in a microwave. The solids were collected by filtration to afford the title compound (100 mg, 55%).

¹H NMR (dmso-D₆) δ 3.45 (m, 2H), 3.10 (s, 9H), 3.07 (m, 2H), 2.17 (m, 2H).

Intermediate P33:
3-(Benzyl(methyl)amino)propane-1-sulfonamide

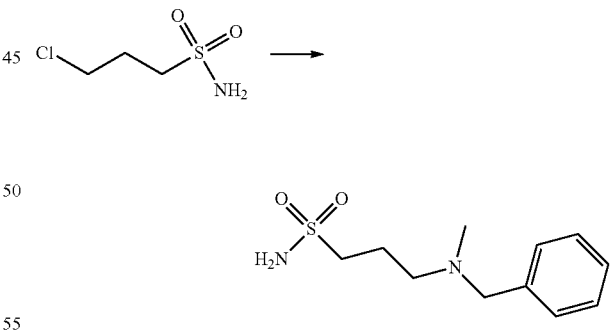

To 3-chloropropane sulfonamide (200 mg, 1.3 mmol) in acetonitrile (5 mL) was added N-methylbenzylamine (1 g, 5.1 mmol). The reaction was refluxed for 18 hours. The solvents were evaporated and the residue was triturated in TBME. The solids were filtered off and the solvent was evaporated. The residue was triturated in heptane. The solids were collected by filtration to afford the title compound (214 mg, 70%) as a white solid.

¹H NMR (CDCl₃) δ 7.30 (m, 5H), 3.54 (s, 2H), 3.22 (t, 2H), 2.53 (m, 2H), 2.25 (s, 3H), 2.09 (t, 2H).

Intermediate P34: 2-(3-Methyl-3H-diazirin-3-yl)ethane-1-sulfonamide

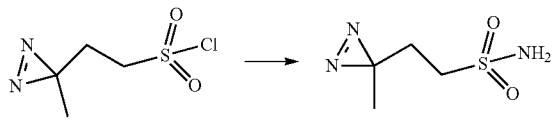

A solution of NH₃ in water (25%, 5 mL) was cooled to 4° C. 2-(3-Methyl-3H-diazirin-3-yl)ethane-1-sulfonyl chloride (150 mg, 0.82 mmol) in THF (3 mL) was added. The mixture was stirred for 18 hours at room temperature. The organic layer was separated, dried (on sodium sulphate), filtered and evaporated to afford the title compound (75 mg, 50%) as a colourless oil, which solidified upon standing.

¹H NMR (CD₃OD) δ 3.15 (t, 2H), 1.78 (t, 2H), 1.05 (s, 3H).

Intermediate P35: 3-(Methoxy(methyl)amino)propane-1-sulfonamide

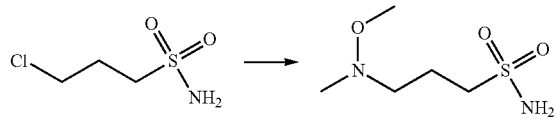

To 3-chloropropane sulfonamide (200 mg, 1.3 mmol) in acetonitrile (5 mL) was added N,O-dimethylhydroxylamine (310 mg, 5 mmol) and triethylamine (1.4 g, 14 mmol). The mixture was refluxed for 18 hours. The solvents were evaporated and the residue was purified over silica, using dichloromethane and a mixture of 3.5 M ammonia in methanol as the eluent, to afford the title compound as a colourless oil (100 mg, 43%).

¹H NMR (CD₃OD) δ 8.20 (m, 2H), 7.62 (d, 1H), 7.53 (d, 1H), 5.26 (d, 2H), 4.08-3.66 (m, 4H), 3.00 (m, 6H), 2.12 (m, 2H).

Intermediate P36: ((1S,E)-2-(Hydroxyimino)-7,7-dimethylbicyclo[2.2.1]heptan-1-yl)methanesulfonamide

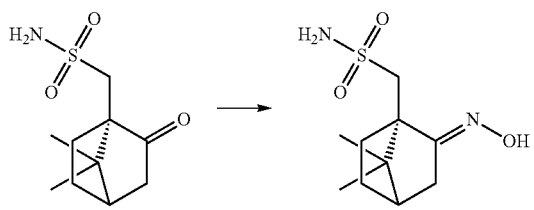 [SMILES: CC1(C)C2CC[C@@]1(CS(N)(=O)=O)C(=O)C2 ; CC1(C)C2CC[C@@]1(CS(N)(=O)=O)/C(=N/O)C2]

To a suspension of (1S)-10-camphorsulfonamide (505 mg, 2.18 mmol) in ethanol (7 mL) and demineralized water (3.5 mL) was added sodium acetate (360 mg, 4.37 mmol), followed by hydroxylamine hydrochloride (303 mg, 4.37 mmol). The mixture was stirred at reflux overnight and then concentrated in vacuo to remove the ethanol. The residual water phase was extracted with dichloromethane and the organic phase was collected, dried with anhydrous sodium sulfate, filtered, and concentrated to afford the title compound (448 mg, 83%) as a white solid.

¹H NMR (Chloroform-d) δ 6.95 (d, J=25.2 Hz, 1H), 5.62 (s, 2H), 3.51 (d, J=15.0 Hz, 1H), 3.23 (d, J=15.0 Hz, 1H), 2.62 (dt, J=18.2, 4.0 Hz, 1H), 2.25-1.83 (m, 5H), 1.36 (ddd, J=12.8, 8.6, 4.7 Hz, 1H), 0.96 (s, 3H), 0.86 (s, 3H).

Intermediate P37: 3-(Azetidin-1-yl)propane-1-sulfonamide

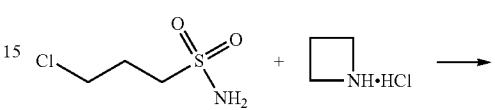

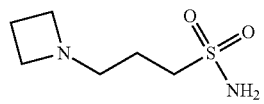

To a solution of azetidine HCl (267 mg, 2.8 mmol) in methanol (4 mL) was added a solution of sodium hydroxide (114 mg, 2.8 mmol) in water (1 mL) and 3-chloropropane-1-sulfonamide (200 mg, 1.3 mmol). The mixture was heated for 30 minutes at 100° C. in a microwave. The solvents were evaporated and the residue was purified over silica, using dichloromethane and a mixture of 3.5 M ammonia in methanol as the eluent, to afford the title compound as a colourless oil (10 mg, 4%).

¹H NMR (CD₃OD) δ 4.19 (m, 4H), 3.37 (m, 2H), 3.19 (t, 2H), 2.52 (m, 2H), 2.17 (m, 2H).

Intermediate P38: 3-(Methyl(prop-2-yn-1-yl)amino)propane-1-sulfonamide

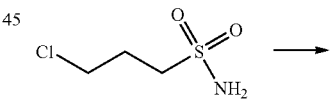

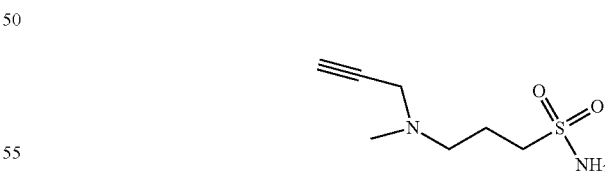

To 3-chloropropane sulfonamide (200 mg, 1.3 mmol) in acetonitrile (20 mL) was added 3-methylamino-1-propyne (340 mg, 5.1 mmol) and potassium iodide (60 mg, 0.36 mmol). The reaction was refluxed for 18 hours. The solvents were evaporated and the residue was triturated in THF. The THF layer was decanted and evaporated to afford the title compound (175 mg, 73%) as a white solid.

¹H NMR (CDCl₃) δ 3.37 (s, 2H), 3.23 (t, 2H), 2.63 (t, 2H), 2.33 (s, 3H), 2.26 (s, 1H), 2.05 (m, 2H).

Intermediate P39: (4-Methylmorpholin-2-yl)methanesulfonamide

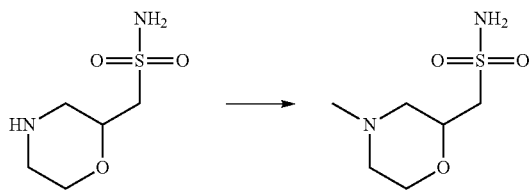

To a suspension of morpholin-2-ylmethanesulfonamide hydrochloride (40 mg, 0.18 mmol), triethylamine (19 mg, 0.18 mmol, 1.0 equiv.) and formaldehyde (37% in water stabilized with methanol; 18 mg, 0.22 mmol, 1.2 equiv.) in acetonitrile (5 mL) was added sodium triacetoxyborohydride (47 mg, 0.22 mmol, 1.2 equiv.). The reaction mixture was stirred at room temperature overnight. Methanol was added and the mixture was concentrated to afford the crude title compound (~0.1 g), which was used without further purification.

Intermediate P40: (4-Ethylmorpholin-2-yl)methanesulfonamide

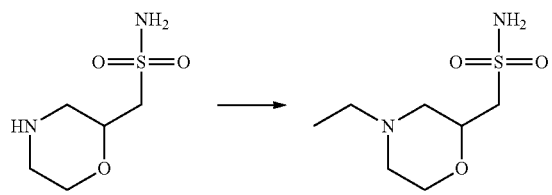

To a suspension of morpholin-2-ylmethanesulfonamide hydrochloride (32 mg, 0.15 mmol), triethylamine (15 mg, 0.15 mmol, 1.0 equiv.) and acetaldehyde (8 mg, 0.18 mmol, 1.2 equiv.) in acetonitrile (5 mL) was added sodium triacetoxyborohydride (38 mg, 0.18 mmol, 1.2 equiv.). The reaction mixture was stirred overnight. Methanol was added and the mixture was concentrated to afford the crude title compound (~90 mg), which was used without further purification.

Intermediate P41: (4-Isopropylmorpholin-2-yl)methanesulfonamide

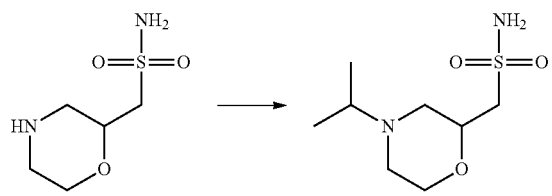

To a suspension of morpholin-2-ylmethanesulfonamide hydrochloride (31 mg, 0.14 mmol), triethylamine (14 mg, 0.14 mmol, 1.0 equiv.) and acetone (10 mg, 0.17 mmol, 1.2 equiv.) in acetonitrile (5 mL) was added sodium triacetoxyborohydride (36 mg, 0.17 mmol, 1.2 equiv.). The reaction mixture was stirred overnight. Methanol was added and the mixture was concentrated to afford the crude title compound (~90 mg), which was used without further purification.

Intermediate P42: (2-Isopropyl-6-oxa-2-azaspiro[3.4]octan-7-yl) methanesulfonamide

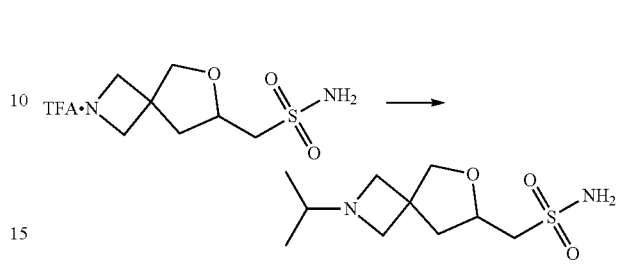

Prepared as described for (2-methyl-6-oxa-2-azaspiro[34]octan-7-yl)methanesulfonamide (Intermediate P45) from (6-oxa-2-azaspiro[3.4]octan-7-yl) methanesulfonamide TFA salt and acetone to afford the title compound as an oil (10 mg, 33%).

$^1$H NMR (CD$_3$OD) δ 4.31 (m, 1H), 3.99 (d, 1H), 3.86 (d, 1H), 3.28 (m, 6H), 2.54 (m, 1H), 2.44 (m, 1H), 1.96 (m, 1H), 0.97 (d, 6H).

Intermediate P43: 3-(Dimethylamino)butane-1-sulfonamide

Step A: 3-Azidobutane-1-sulfonamide

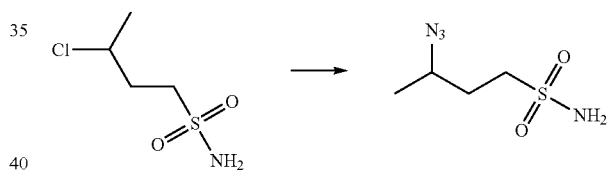

To 3-chlorobutane-1-sulfonamide chloride (50 mg, 0.3 mmol) in DMF (3 mL) was added NaN$_3$ (25 mg, 0.4 mmol). The reaction was heated for 18 hours at 100° C. The solvents were evaporated and the residue was triturated in chloroform. The chloroform layer was filtered and evaporated to afford the title compound as a brown oil (25 mg, 47%).

$^1$H NMR (CDCl$_3$) δ 3.15 (m, 2H), 2.96 (d, 3H), 2.01 (m, 2H), 1.36 (d, 3H).

Step B: 3-Aminobutane-1-sulfonamide

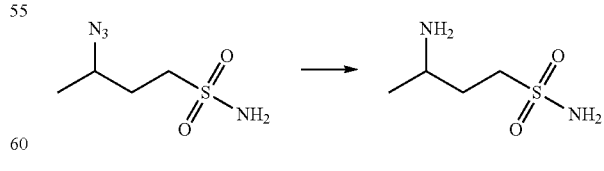

To 3-azidobutane-1-sulfonamide (130 mg, 0.73 mmol) in THF (5 mL) was added Pd—C (20 mg, 10% Pd). The mixture was stirred for 18 hours under hydrogen atmosphere. The mixture was filtered over Celite® and evaporated to afford the title compound as a brown oil (120 mg, 100%).

$^1$H NMR (CDCl$_3$) δ 3.17 (m, 2H), 3.12 (m, 2H), 2.01 (m, 2H), 1.36 (d, 3H).

Step C: 3-(Dimethylamino)butane-1-sulfonamide

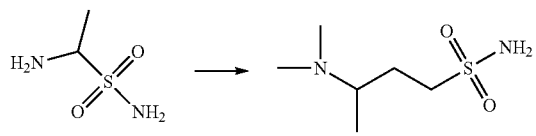

To 3-aminobutane-1-sulfonamide (110 mg, 0.72 mmol) in acetonitrile (5 mL) was added paraformaldehyde (86 mg, 3 mmol). Then sodium triacetoxyborohydride (612 mg, 3 mmol) was added and the mixture was stirred for 18 hours at room temperature. Methanol (10 mL) was added and the solvents were evaporated (2×). The residue was triturated in THF (20 mL) containing triethylamine (0.7 g, 7 mmol). The solids were filtered and the solvent was evaporated. The residue was purified over silica, using dichloromethane and a mixture of 3.5 M ammonia in methanol as the eluent, to afford the title compound as a colourless oil (14 mg, 11%).

$^1$H NMR (CD$_3$OD) δ 3.18 (t, 2H), 2.63 (m, 1H), 2.60 (s, 6H), 2.2 (m, 2H), 1.24 (d, 3H).

Intermediate P44: (2-Ethyl-6-oxa-2-azaspiro[3.4]octan-7-yl) methanesulfonamide

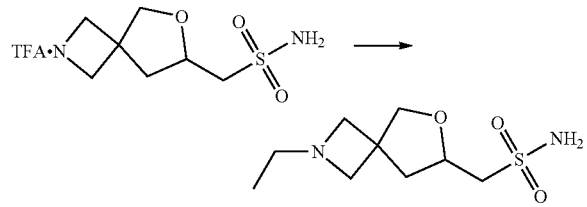

Prepared as described for (2-methyl-6-oxa-2-azaspiro[3.4]octan-7-yl)methanesulfonamide (Intermediate P45) from (6-oxa-2-azaspiro[3.4]octan-7-yl) methanesulfonamide TFA salt and ethanal to afford the title compound as an oil (15 mg, 13%).

$^1$H NMR (CD$_3$OD) δ 4.33 (m, 1H), 4.02 (d, 1H), 3.88 (d, 1H), 3.35 (m, 6H), 2.62 (q, 2H), 2.45 (m, 1H) 2.03 (m, 1H), 1.00 (t, 3H).

Intermediate P45: (2-Methyl-6-oxa-2-azaspiro[3.4]octan-7-yl) methanesulfonamide

Step A: (6-Oxa-2-azaspiro[3.4]octan-7-yl)methanesulfonamide, TFA Salt

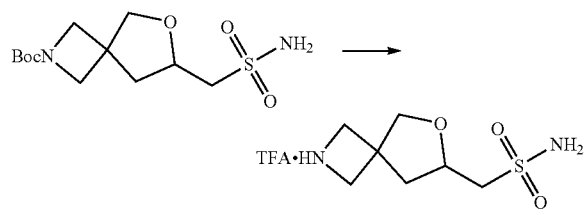

To a solution of N-Boc-(6-oxa-2-azaspiro[3.4]octan-7-yl) methanesulfonamide (330 mg, 1 mmol) in dichloromethane (10 ml) was added trifluoroacetic acid (2 mL). After stirring for 18 hours at room temperature under nitrogen, the solvents were evaporated to afford the title compound as a pale yellow oil (330 mg, 100%).

$^1$H NMR (CD$_3$OD) δ 4.30 (m, 1H), 4.10 (m, 5H), 3.91 (m, 1H), 3.35 (m, 2H), 2.59 (m, 1H), 2.16 (m, 1H).

Step B: (2-Methyl-6-oxa-2-azaspiro[3.4]octan-7-yl) methanesulfonamide

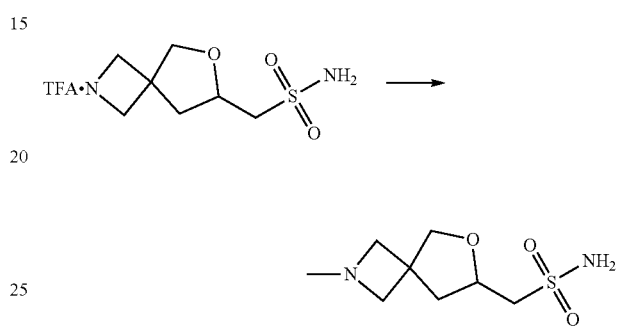

To the TFA salt of (6-oxa-2-azaspiro[3.4]octan-7-yl) methanesulfonamide (150 mg, 0.48 mmol) in acetonitrile (10 mL), was added triethylamine (100 mg, 0.99 mmol), paraformaldehyde (30 mg, 0.97 mmol), followed by sodium triacetoxyborohydride (205 mg, 0.97 mmol). After 18 hours stirring at room temperature under nitrogen, methanol (10 mL) was added and the mixture was evaporated (2×). The residue was purified over silica, using dichloromethane and a mixture of 3.5 M ammonia in methanol as the eluent, to afford the title compound as an oil (17 mg, 17%).

$^1$H NMR (CD$_3$OD) δ 4.33 (m, 1H), 4.02 (d, 1H), 3.88 (d, 1H), 3.60 (m, 4H), 3.32 (m, 2H), 2.53 (s, 3H), 2.45 (m, 1H) 2.03 (m, 1H).

Intermediate P46: 3-(Dimethylamino)-2,2-dimethylpropane-1-sulfonamide

Step A:
3-Azido-2,2-dimethylpropane-1-sulfonamide

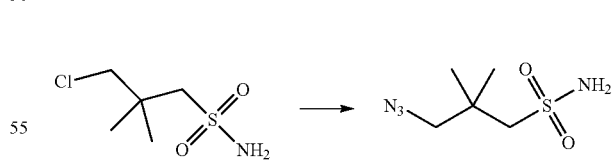

To 3-Chloro-2,2-dimethylpropane-1-sulfonamide (130 mg, 0.7 mmol) in DMF (3 mL) was added NaN$_3$ (91 mg, 1.4 mmol). The reaction was heated for 48 hours at 120° C. The solvents were evaporated and the residue was triturated in THF. The solids were filtered and the THF was evaporated to afford the crude title compound (220 mg, 61%) as a brown oil.

$^1$H NMR (CDCl$_3$) δ 2.95 (s, 2H), 2.87 (s, 2H), 1.27 (s, 6H).

Step B:
3-Amino-2,2-dimethylpropane-1-sulfonamide

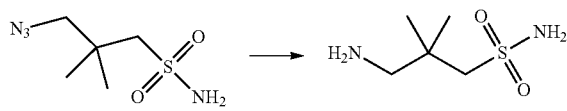

To 3-azido-2,2-dimethylpropane-1-sulfonamide (130 mg, 0.67 mmol) In THF (5 mL) was added Pd—C (20 mg, 10% Pd). The mixture was stirred for 64 hours under a hydrogen atmosphere. The mixture was filtered over Celite® and evaporated to afford the title compound (0 mg, 80%) as an oil.

$^1$H NMR (CDCl$_3$) δ 2.95 (s, 2H), 2.87 (s, 2H), 1.27 (s, 6H).

Step C:
3-(Dimethylamino)-2,2-dimethylpropane-1-sulfonic acid triethylamine salt

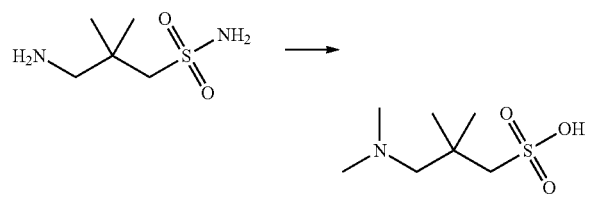

To 3-amino-2,2-dimethylpropane-1-sulfonamide (160 mg, 0.6 mmol) in water (1 mL) and formic acid (1 mL, 6.6 mmol) was added formaldehyde (1 mL, 37% aqueous solution, 2.5 mmol). The mixture was refluxed for 6 hours. The solvents were evaporated. The residue was triturated in THF (10 mL) containing triethylamine (250 mg, 2.5 mmol). The solids were filtered to afford the title compound (80 mg, 45%) as a white solid.

$^1$H NMR (CD$_3$OD) δ 3.06 (s, 2H), 2.96 (s, 6H), 2.89 (s, 2H), 1.27 (s, 6H).

Step D: 3-(Dimethylamino)-2,2-dimethylpropane-1-sulfonamide

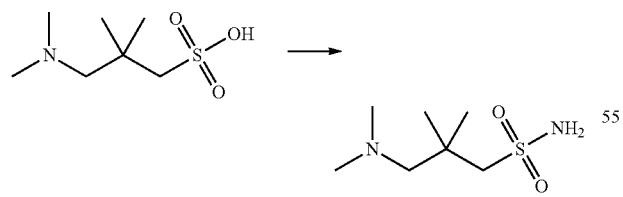

To 3-(dimethylamino)-2,2-dimethylpropane-1-sulfonic acid triethylamine salt (70 mg, 0.24 mmol) in dichloromethane (10 mL) was added DMF (2 drops). The mixture was cooled to 0° C. Then thionyl chloride (0.1 mL, 1.4 mmol) was added. The reaction was stirred for 18 hours at room temperature. The solvents were evaporated. The residue was triturated in THF. The THF layer was separated and added dropwise to a solution of ammonia in methanol (7 N). The mixture was stirred for 18 hours. The solvents were evaporated. The residue was triturated in THF. The solids were filtered. The THF was evaporated to afford the title compound (24 mg, 52%) as an off-white solid.

$^1$H NMR (CDCl$_3$) δ 3.51 (s, 2H), 3.29 (s, 2H), 2.37 (s, 6H), 1.19 (s, 6H).

Intermediate P47:
4-(Dimethylamino)butane-1-sulfonamide

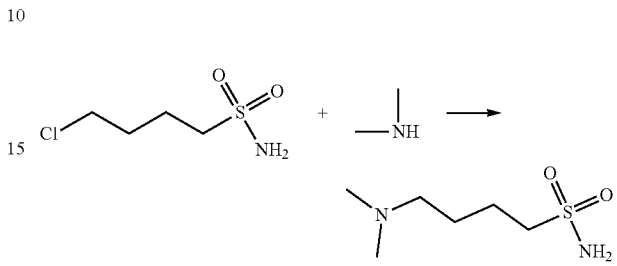

To 4-chlorobutane-1-sulfonamide (200 mg, 1.2 mmol) in acetonitrile (4 mL) was added dimethylamine in THF (2.3 mL 2M, 4.6 mmol). The mixture was heated for 30 minutes at 100° C. in a microwave. The solvents were evaporated and the residue was purified over silica, using dichloromethane and a mixture of 3.5 M ammonia in methanol as the eluent, to afford the title compound as a colourless oil (32 mg, 15%).

$^1$H NMR (CD$_3$OD) δ 4.19 (m, 4H), 3.37 (m, 4H), 2.49 (m, 2H), 1.90 (m, 2H), 1.75 (m, 2H).

Intermediate P48:
(1-Methylpiperidin-3-yl)methanesulfonamide

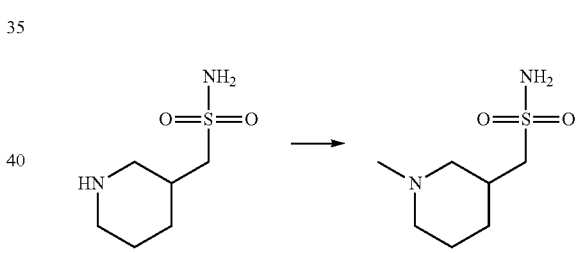

To a suspension of piperidin-3-ylmethanesulfonamide (80 mg, 0.45 mmol) and formaldehyde (37% in water stabilized with methanol; 44 mg, 0.54 mmol, 1.2 equiv.) in acetonitrile (10 mL) was added sodium triacetoxyborohydride (114 mg, 0.54 mmol, 1.2 equiv.). The reaction mixture was stirred overnight. Methanol was added and the mixture was concentrated to afford the crude title compound (~300 mg), which was used without further purification.

Intermediate P49:
(1-Ethylpiperidin-3-yl)methanesulfonamide

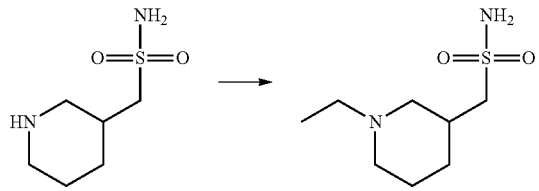

To a suspension of piperidin-3-ylmethanesulfonamide (70 mg, 0.39 mmol) and acetaldehyde (21 mg, 0.47 mmol, 1.2 equiv.) in acetonitrile (10 mL) was added sodium triacetoxyborohydride (100 mg, 0.47 mmol, 1.2 equiv.). The reaction mixture was stirred overnight. Methanol was added and the mixture was concentrated to afford the crude title compound (~300 mg), which was used without further purification.

Intermediate P50: tert-Butyl ((S)-1-((N-((1,2,3,5,6,7-hexahydro-s-indacen-4-yl)carbamoyl)sulfamoyl)methyl)-7,7-dimethylbicyclo[2.2.1]heptan-2-yl) carbamate, Potassium Salt Step A: ((1S)-2-Amino-7,7-dimethylbicyclo[2.2.1]heptan-1-yl)methanesulfonamide

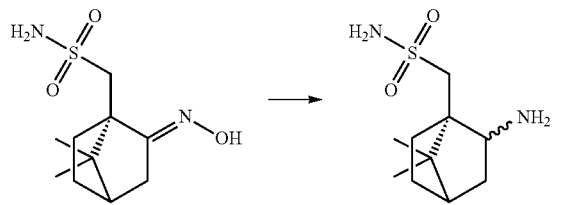 [SMILES: CC1(C)C2CC[C@@]1(CS(N)(=O)=O)/C(=N/O)C2 ; CC1(C)C2CC[C@@]1(CS(N)(=O)=O)C(N)C2]

A mixture of ((1S,E)-2-(hydroxyimino)-7,7-dimethylbicyclo[2.2.1] heptan-1-yl)methanesulfonamide (Intermediate P36) (365 mg, 1.48 mmol) and Raney-Ni (~50 mg) in ethanol (7 mL) and 25% ammonia (1 mL) was equipped with a H₂ balloon and stirred overnight at room temperature, followed by another 4 hours at 50° C. The reaction mixture was allowed to cool to room temperature, filtered through Celite® and concentrated to afford the title compound (300 mg, 87%) as a white solid.

$^1$H NMR (Chloroform-d) δ 3.72 (q, J=6.9 Hz, 1H), 3.46 (d, J=19.5 Hz, 1H), 3.26-3.15 (m, 1H), 2.97 (d, J=13.3 Hz, 1H), 2.86-2.64 (m, 1H), 2.41-1.10 (m, 9H), 1.01-0.76 (m, 6H).

Step B: tert-Butyl((1S)-7,7-dimethyl-1-(sulfamoylmethyl)bicyclo[2.2.1]heptan-2-yl) carbamate

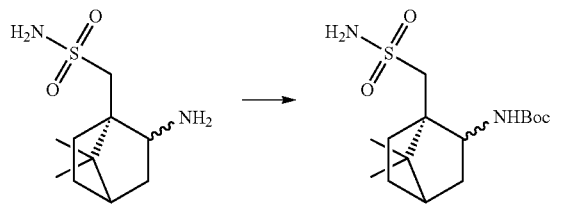 [SMILES: CC1(C)C2CC[C@@]1(CS(N)(=O)=O)C(N)C2 ; CC(C)(C)OC(=O)NC1CC2CC[C@]1(CS(N)(=O)=O)C2(C)C]

A solution of ((1S)-2-amino-7,7-dimethylbicyclo[2.2.1]heptan-1-yl)methanesulfonamide (180 mg, 0.77 mmol) in THF (5 mL) was treated with Et₃N (0.11 mL, 0.77 mmol) and Boc₂O (170 mg, 0.77 mmol) and stirred over the weekend. The mixture was concentrated and partitioned between DCM and water. The organic phase was separated and dried (Na₂SO₄), filtered and concentrated to afford the crude title compound (~300 mg), which was used as such for the next step.

$^1$H NMR (Chloroform-d) δ 3.17 (d, J=13.2 Hz, 1H), 2.96 (d, J=13.3 Hz, 1H), 2.86-2.67 (m, 1H), 2.50-1.67 (m, 10H), 1.52 (s, 9H), 1.16-0.80 (m, 6H).

Step C: tert-Butyl((1S)-1-((N-((1,2,3,5,6,7-hexahydro-s-indacen-4-yl)carbamoyl) sulfamoyl)methyl)-7,7-dimethylbicyclo[2.2.1]heptan-2-yl)carbamate, Potassium Salt

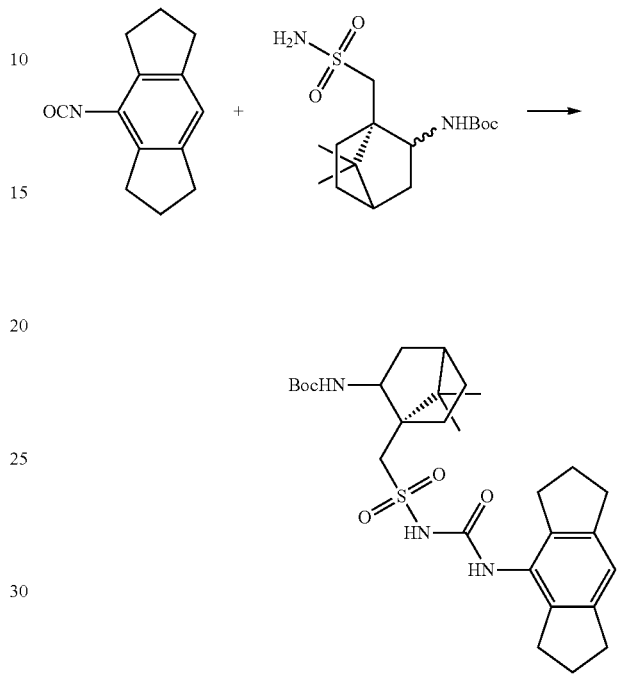

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and tert-butyl ((1S)-7,7-dimethyl-1-(sulfamoylmethyl)bicyclo[2.2.1]heptan-2-yl)carbamate to afford the title compound. The reaction mixture was concentrated to afford the crude product (~200 mg) which was used as such.

LCMS: m/z 530 (M−H)⁻ (ES⁻).

Intermediate P51: 4-(Azetidin-1-yl)butane-1-sulfonamide

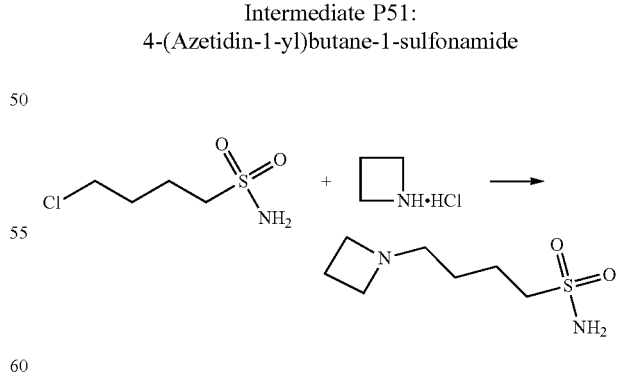

Prepared as described for 3-(azetidin-1-yl)propane-1-sulfonamide (Intermediate P37) using 4-chlorobutane-1-sulfonamide to afford the title compound a colourless oil (6 mg, 3%).

$^1$H NMR (CD₃OD) δ 4.19 (m, 4H), 3.37 (m, 4H), 2.49 (m, 2H), 1.90 (m, 2H), 1.75 (m, 2H).

Intermediate P52: 1-(Azetidin-1-ylmethyl)cyclopropane-1-sulfonamide

Step A: 1-(Azetidin-1-ylmethyl)-N-(tert-butyl)cyclopropane-1-sulfonamide

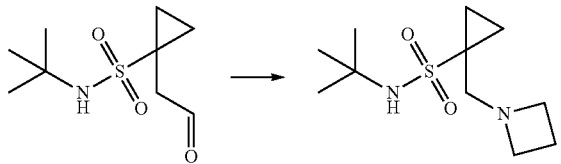 [SMILES: CC(C)(C)NS(=O)(=O)C1(CC=O)CC1 ; CC(C)(C)NS(=O)(=O)C1(CN2CCC2)CC1]

To a suspension of cyclobutylamine (68 mg, 0.73 mmol) in THF (5 mL) was added triethylamine (120 mg, 1.2 mmol) and N-(tert-butyl)-1-(2-oxoethyl)cyclopropane-1-sulfonamide (100 mg, 0.49 mmol). Sodium cyanoborohydride (50 mg, 0.79 mmol) was added and the mixture was stirred for 18 hours at room temperature under nitrogen. Dichloromethane was added and the mixture was washed with water and brine. The organic layer was dried (on sodium sulfate), filtered and evaporated. The residue was purified over silica, using dichloromethane and a mixture of 3.5 M ammonia in methanol as the eluent, to afford the title compound as a colourless oil (50 mg, 42%).

$^1$H NMR (CD$_3$OD) δ 3.30 (m, 4H), 2.80 (s, 2H), 2.10 (m, 2H), 1.35 (s, 9H), 1.24 (m, 2H), 0.89 (m, 2H).

Step B: 1-(Azetidin-1-ylmethyl)cyclopropane-1-sulfonamide

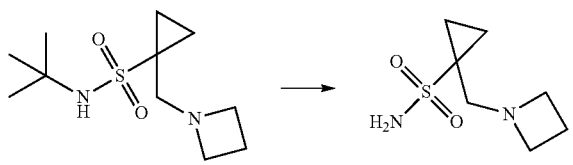 [SMILES: CC(C)(C)NS(=O)(=O)C1(CN2CCC2)CC1 ; NS(=O)(=O)C1(CN2CCC2)CC1]

A solution of 1-(azetidin-1-ylmethyl)-N-(tert-butyl)cyclopropane-1-sulfonamide (50 mg, 0.2 mmol) in TFA (10 mL) was stirred for 64 hours at room temperature under nitrogen. Then the solvents were evaporated and the residue was purified over silica, using dichloromethane and a mixture of 3.5 M ammonia in methanol as the eluent, to afford the title compound as a white solid (20 mg, 51%).

$^1$H NMR (CD$_3$OD) δ 3.36 (m, 4H), 2.87 (s, 2H), 2.12 (m, 2H), 1.26 (m, 2H), 0.89 (m, 2H).

Intermediate P53: 2-(Pyrrolidin-1-yl)ethane-1-sulfonamide

Step A: N,N-Bis(4-methoxybenzyl)-2-(pyrrolidin-1-yl)ethane-1-sulfonamide

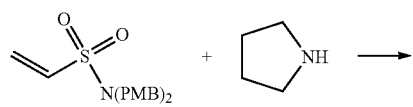

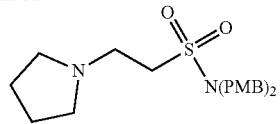

Prepared as described for N,N-bis(4-methoxybenzyl)-2-(2-methylazetidin-1-yl)ethane-1-sulfonamide (Intermediate P54, Step A) from N,N-bis(4-methoxybenzyl)ethenesulfonamide and pyrrolidine to afford the title compound as an oil (361 mg, 100%).

$^1$H NMR (CDCl$_3$) δ 7.20 (d, 4H), 6.86 (d, 4H), 4.25 (s, 4H), 3.79 (s, 6H), 3.09 (m, 2H), 2.87 (m, 2H), 2.44 (m, 4H), 1.75 (m, 4H).

Step B: 2-(Pyrrolidin-1-yl)ethane-1-sulfonamide

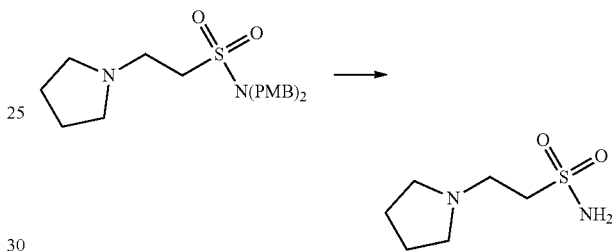

Prepared as described for 2-(azetidin-1-yl)propane-1-sulfonamide (Intermediate P56, Step B) from N,N-bis(4-methoxybenzyl)-2-(pyrrolidin-1-yl)ethane-1-sulfonamide. The solvents were evaporated and the residue was purified over silica, using dichloromethane and a mixture of 3.5 M ammonia in methanol as the eluent, to afford the title compound as a white solid (110 mg, 74%).

$^1$H NMR (CDCl$_3$) δ 3.32 (m, 2H), 2.96 (t, 2H), 2.61 (m, 4H), 1.84 (m, 4H).

Intermediate P54: 2-(2-Methylazetidin-1-yl)ethane-1-sulfonamide

Step A: N,N-Bis(4-methoxybenzyl)-2-(2-methylazetidin-1-yl)ethane-1-sulfonamide

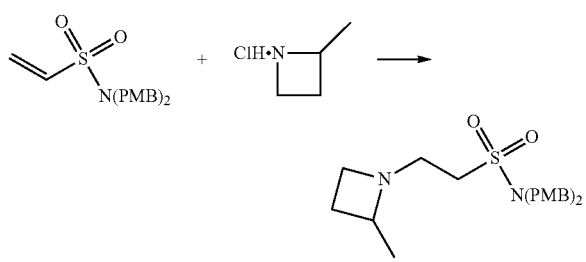

To methyl-azetidine HCl (55 mg, 0.52 mmol) in methanol (3 mL) was added N,N-bis(4-methoxybenzyl)prop-1-ene-1-sulfonamide (150 mg, 0.43 mmol) and triethylamine (0.7 g, 7 mmol). The mixture was stirred for 18 hours at room temperature under nitrogen. The solvents were evaporated and the residue was triturated in THF. The mixture was filtered and the solvent was evaporated to afford the title compound (170 mg, 94%) as a colourless oil.

¹H NMR (CD₃OD) δ 3.40 (m, 2H), 3.16 (m, 2H), 2.99 (m, 2H), 2.82 (m, 1H), 2.15 (m, 1H), 1.83 (m, 1H), 1.24 (d, 3H).

Step B:
2-(2-Methylazetidin-1-yl)ethane-1-sulfonamide

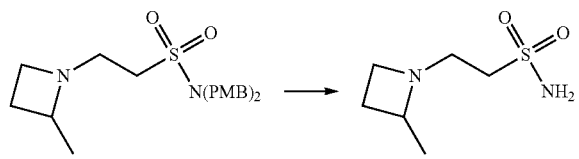

Prepared as described for 2-(azetidin-1-yl)-propane-1-sulfonamide (Intermediate P56, Step B) from N,N-bis(4-methoxybenzyl)-2-(2-methylazetidin-1-yl)ethane-1-sulfonamide. The solvents were evaporated and the residue was purified over silica, using dichloromethane and a mixture of 3.5 M ammonia in methanol as the eluent, to afford the title compound as a colourless oil (41 mg, 54%).

¹H NMR (CD₃OD) δ 3.40 (m, 2H), 3.16 (m, 2H), 2.99 (m, 2H), 2.82 (m, 1H), 2.15 (m, 1H), 1.83 (m, 1H), 1.24 (d, 3H).

Intermediate P55:
2-(3-Fluoroazetidin-1-yl)ethane-1-sulfonamide

Step A: 2-(3-Fluoroazetidin-1-yl)-N,N-bis(4-methoxybenzyl)ethane-1-sulfonamide

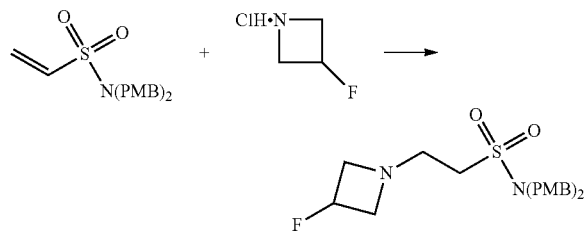

To 3-fluoroazetidine HCl (60 mg, 0.52 mmol) in methanol (3 mL) was added potassium hydroxide (29 mg, 0.42 mmol) and N,N-bis(4-methoxybenzyl)ethenesulfonamide (150 mg, 0.43 mmol). The mixture was stirred for 30 minutes at 100° C. in a microwave. The solvents were evaporated to afford the crude title compound (250 mg, 100%) as an oil.

¹H NMR (CDCl₃) δ 7.23 (d, 4H), 6.91 (d, 4H), 5.08 (m, 1H), 4.27 (s, 4H), 3.83 (s, 6H), 3.61 (m, 4H), 3.18 (m, 2H), 3.08 (m, 2H).

Step B:
2-(3-Fluoroazetidin-1-yl)ethane-1-sulfonamide

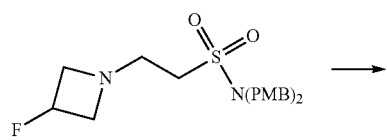

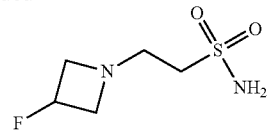

Prepared as described for 2-(azetidin-1-yl)propane-1-sulfonamide (Intermediate P56, Step B) from 2-(3-fluoroazetidin-1-yl)-N,N-bis(4-methoxybenzyl)ethane-1-sulfonamide. The solvents were evaporated and the residue was purified over silica, using dichloromethane and a mixture of 3.5 M ammonia in methanol as the eluent, to afford the title compound as a colourless oil (125 mg, 69%).

¹H NMR (CD₃OD) δ 5.14 (m, 1H), 3.75 (m, 4H), 3.34 (m, 2H), 3.14 (m, 2H), 3.04 (m, 2H).

Intermediate P56:
2-(Azetidin-1-yl)propane-1-sulfonamide

Step A: 2-(Azetidin-1-yl)-N,N-bis(4-methoxybenzyl)propane-1-sulfonamide

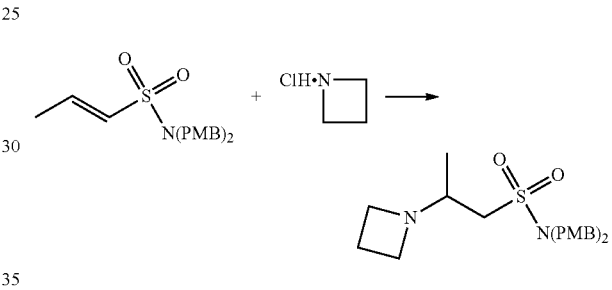

To azetidine HCl (46 mg, 0.36 mmol) in methanol (3 mL) was added N,N-bis(4-methoxybenzyl)prop-1-ene-1-sulfonamide (150 mg, 0.41 mmol) and triethylamine (200 mg, 1.98 mmol). The mixture was stirred for 30 minutes at 100° C. in a microwave. The solvents were evaporated and the residue was purified over silica, using dichloromethane and a mixture of 3.5 M ammonia in methanol as the eluent, to afford the title compound as a colourless oil (100 mg, 58%).

¹H NMR (CD₃OD) δ 7.23 (m, 4H), 6.88 (m, 4H), 4.24 (s, 4H), 3.80 (s, 6H), 3.13 (m, 4H), 2.76 (m, 2H), 2.53 (m, 1H), 2.00 (m, 2H), 1.16 (d, 3H).

Step B: 2-(Azetidin-1-yl)propane-1-sulfonamide

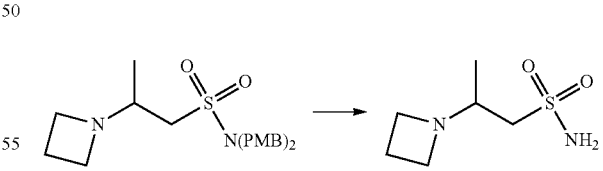

A solution of 2-(azetidin-1-yl)-N,N-bis(4-methoxybenzyl)propane-1-sulfonamide (100 mg, 0.58 mmol) in trifluoroacetic acid (3 mL) was stirred for 18 hours at 21° C. The solvents were evaporated and the residue was triturated in methanol and filtered over Celite®. The methanol layer was treated with Dowex® strongly basic ion exchange resin. The mixture was filtered and the methanol was evaporated to afford the title compound as a colourless oil (50 mg, 50%).

¹H NMR (CD₃OD) δ 3.29 (m, 4H), 3.15 (m, 1H), 2.84 (m, 2H), 2.04 (m, 2H), 1.16 (d, 3H).

Intermediate P57: Methyl 3-sulfamoylpropanoate

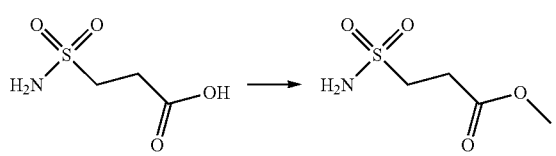

To 3-sulfamoylpropanoic acid (200 mg, 1.3 mmol) in methanol (20 mL) was added sulfuric acid (30 mg, 0.3 mmol). The mixture was stirred for 18 hours at room temperature. The mixture was filtered through Celite® and the solvent was evaporated to afford the title compound (225 mg, 100%) as a colourless oil, which crystallized upon standing.

$^1$H NMR (CD$_3$OD) δ 3.70 (s, 3H), 3.35 (m, 2H), 2.84 (m, 2H).

Intermediate P58: (1-Isopropylpiperidin-3-yl)methanesulfonamide

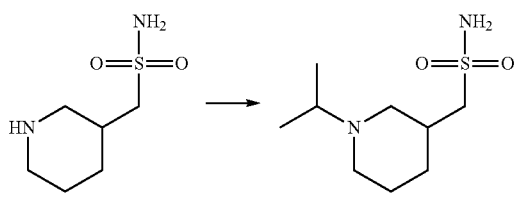

To a suspension of piperidin-3-ylmethanesulfonamide (70 mg, 0.39 mmol, 1.0 equiv.) and acetone (28 mg, 0.47 mmol, 1.2 equiv.) in acetonitrile (10 mL) was added sodium triacetoxyborohydride (100 mg, 0.47 mmol, 1.2 equiv.). The reaction mixture was stirred overnight. Methanol was added and the mixture was concentrated to afford the crude title compound (~200 mg), which was used without further purification.

Intermediate P59: 3-Methoxy-N-methyl-N-(3-sulfamoylpropyl)propanamide

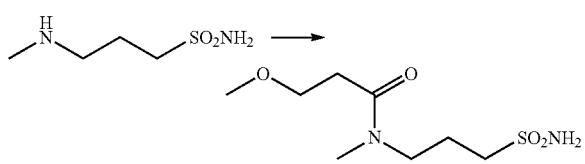

Prepared as described for methyl methyl(3-sulfamoylpropyl)carbamate (Intermediate P64) from 3-(methylamino)propane-1-sulfonamide and 3-methoxypropionyl chloride. The title compound was obtained as a colourless oil (54 mg, 69%).

$^1$H NMR (CD$_3$OD) δ 3.66 (m, 2H), 3.54 (m, 2H), 3.30 (s, 3H), 3.05 (m, 2H), 3.05 (s, 3H), 2.51 (m, 2H), 2.05 (m, 2H).

Intermediate P60: N-Methyl-N-(3-sulfamoylpropyl)isobutyramide

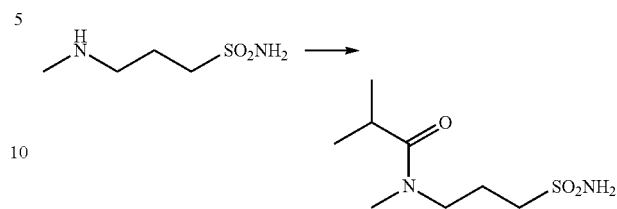

Prepared as described for methyl methyl(3-sulfamoylpropyl)carbamate (Intermediate P64) from 3-(methylamino)propane-1-sulfonamide and isobutyryl chloride. The title compound was obtained as a colourless oil (64 mg, 88%).

$^1$H NMR (CD$_3$OD) δ 3.50 (m, 2H), 3.16 (m, 2H), 3.05 (s, 3H), 2.40 (m, 1H), 2.16 (m, 2H), 0.92 (m, 6H).

Intermediate P61: N-Methyl-N-(3-sulfamoylpropyl)formamide

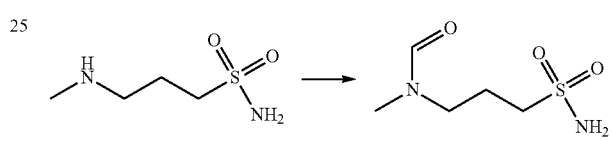

Prepared as described for methyl methyl(3-sulfamoylpropyl)carbamate (Intermediate P64) from 3-(methylamino)propane-1-sulfonamide and acetic formic anhydride. The title compound was obtained as a colourless oil (100 mg, 100%).

$^1$H NMR (CD$_3$OD) δ 3.19 (m, 4H), 2.70 (s, 3H), 2.19 (m, 2H).

Intermediate P62: N,N-Dimethyl-3-sulfamoylpropanamide

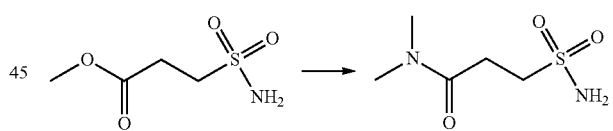

Methyl 3-sulfamoylpropanoate (160 mg, 0.96 mmol) was added to dimethylamine in methanol (2 M, 5 mL, 10 mmol). The mixture was stirred for 1 hour at 120° C. in a microwave. The solvents were evaporated and the residue was purified over silica, using dichloromethane and methanol as the eluent, to afford the title compound as a white solid (28 mg, 16%).

$^1$H NMR (CD$_3$OD) δ 3.35 (m, 2H), 3.08 (s, 3H), 2.96 (s, 3H), 2.90 (t, 2H).

Intermediate P63: 3-(Benzyl(isopropyl)amino)propane-1-sulfonamide

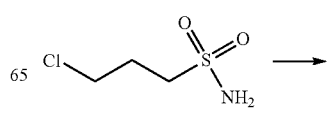

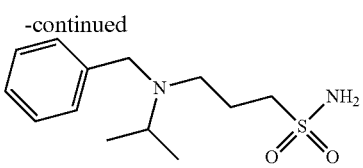

To 3-chloropropane sulfonamide (250 mg, 1.6 mmol) in acetonitrile (5 mL) was added N-benzylpropan-2-amine (0.95 g, 6.34 mmol) and potassium iodide (50 mg, 0.3 mmol). The reaction was heated for 1 hour at 160° C. The solvents were evaporated and the residue was triturated in TBME. The organic layer was decanted and the residue was triturated in heptane. The organic layer was decanted to afford the title compound (190 mg, 44%) as a pale yellow oil.

$^1$H NMR (CDCl$_3$) δ 7.31 (m, 5H), 3.50 (s, 2H), 3.08 (m, 2H), 2.98 (m, 1H), 2.57 (m, 2H), 1.90 (m, 2H), 1.04 (d, 6H).

Intermediate P64: Methyl methyl(3-sulfamoylpropyl)carbamate

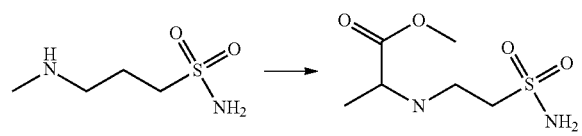

To 3-(methylamino)propane-1-sulfonamide (60 mg, 0.39 mmol) in dichloromethane (10 mL) was added triethylamine (60 mg, 0.6 mmol). The mixture was cooled to 0° C. A solution of methyl chloroformate (41 mg, 0.43 mmol) in dichloromethane (5 mL) was added dropwise. The mixture was stirred for 18 hours at room temperature. The solvents were evaporated and the residue was purified over silica, using dichloromethane/methanol as the eluent, to afford the title compound as a white solid (15 mg, 18%).

$^1$H NMR (CD$_3$OD) δ 3.70 (s, 3H), 3.69 (m, 2H), 3.55 (m, 2H), 3.07 (s, 3H), 2.54 (m, 3H).

Intermediate P65: 3-(Dimethylamino)propane-1-sulfonamide

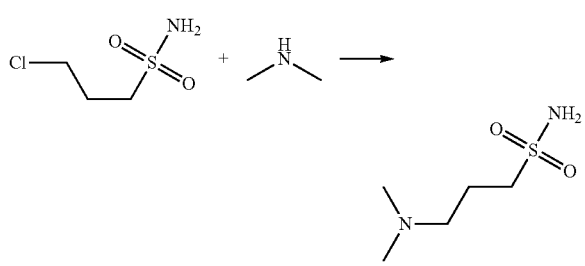

To a solution of 3-chloropropane-1-sulfonamide (203 mg, 1.29 mmol) in 2M dimethylamine in THF (7 mL) was added triethylamine (0.18 mL, 1.29 mmol) and potassium iodide (214 mg, 1.29 mmol). The mixture was heated in a microwave at 80° C. for 90 minutes. The solvents were evaporated and the residue was purified over silica, using dichloromethane and a mixture of 3.5 M ammonia in methanol as the eluent, to afford the title compound (51 mg, 24%) as a white solid.

$^1$H NMR (CD$_3$OD) δ 3.20 (t, 2H), 2.44 (t, 2H), 2.24 (s, 6H), 2.04 (m, 2H).

Intermediate P66: 2-(2,2-Dimethylazetidin-1-yl)ethane-1-sulfonamide, TFA salt

Step A: 2-(2,2-Dimethylazetidin-1-yl)-N,N-bis(4-methoxybenzyl)ethane-1-sulfonamide

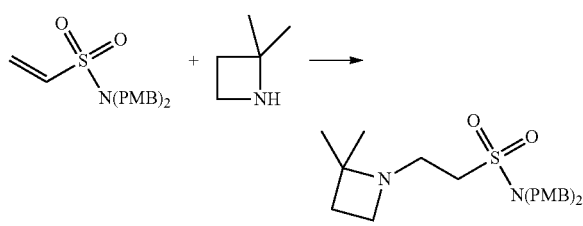

Prepared as described for 2-(azetidin-1-yl)-N,N-bis(4-methoxybenzyl)propane-1-sulfonamide (Intermediate P56, Step A) from N,N-bis(4-methoxybenzyl)ethenesulfonamide and 2,2-dimethylazetidine to afford the title compound as an oil (125 mg, 100%).

$^1$H NMR (CDCl$_3$) δ 7.17 (d, 4H), 6.87 (d, 4H), 4.22 (s, 4H), 3.77 (s, 6H), 3.00 (m, 2H), 2.84 (m, 2H), 2.73 (m, 2H), 1.82 (m, 2H), 1.10 (s, 6H).

Step B: 2-(2,2-Dimethylazetidin-1-yl)ethane-1-sulfonamide, TFA salt

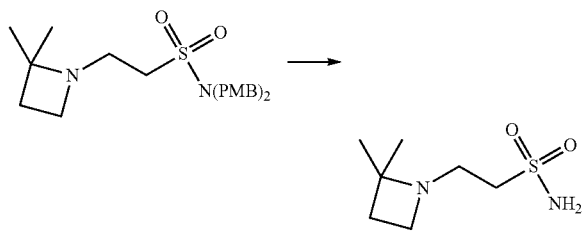

Prepared as described for 2-(azetidin-1-yl)propane-1-sulfonamide (Intermediate P56, Step B) from 2-(2,2-dimethyllazetidin-1-yl)-N,N-bis(4-methoxybenzyl)ethane-1-sulfonamide to afford the title compound as colourless oil (83 mg, 92%).

$^1$H NMR (CD$_3$OD) δ 4.05 (m, 2H), 3.47 (m, 6H), 2.38 (m, 2H), 1.66 (d, 6H).

Intermediate P67: 2-(2,4-Dimethylazetidin-1-yl)ethane-1-sulfonamide, TFA salt

Step A: 2-(2,4-Dimethylazetidin-1-yl)-N,N-bis(4-methoxybenzyl)ethane-1-sulfonamide

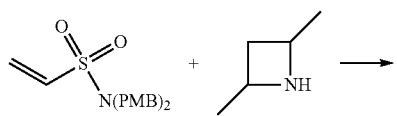

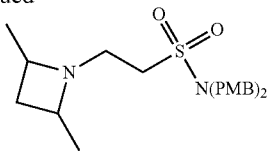

Prepared as described for 2-(azetidin-1-yl)-N,N-bis(4-methoxybenzyl)propane-1-sulfonamide (Intermediate P56, Step A) from N,N-bis(4-methoxybenzyl)ethenesulfonamide and 2,4-dimethylazetidine HCl salt to afford the title compound as a colourless oil (125 mg, 100%).

$^1$H NMR (CDCl$_3$) δ 7.19 (d, 4H), 6.84 (d, 4H), 4.24 (s, 4H), 3.78 (s, 6H), 3.33 (m, 6H), 2.92 (m, 2H), 2.25 (m, 1H), 1.55 (d, 6H).

Step B:
2-(2,4-Dimethylazetidin-1-yl)ethane-1-sulfonamide, TFA salt

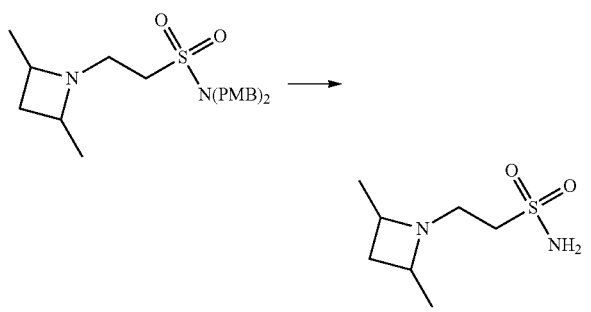

Prepared as described for 2-(azetidin-1-yl)propane-1-sulfonamide (Intermediate P56, Step B) from 2-(2,4-dimethylazetidin-1-yl)-N,N-bis(4-methoxybenzyl)ethane-1-sulfonamide. The solvents were evaporated and the residue was triturated in water. The water layer was filtered and lyophilized to afford the title compound as a white solid (120 mg, 133%) which was used as such.

$^1$H NMR (CD$_3$OD) δ 3.50 (m, 6H), 2.74 (m, 1H), 2.01 (m, 1H), 1.56 (d, 6H).

Intermediate P68: 2-(2-Isopropylazetidin-1-yl)ethane-1-sulfonamide, TFA Salt

Step A: 2-(2-Isopropylazetidin-1-yl)-N,N-bis(4-methoxybenzyl)ethane-1-sulfonamide

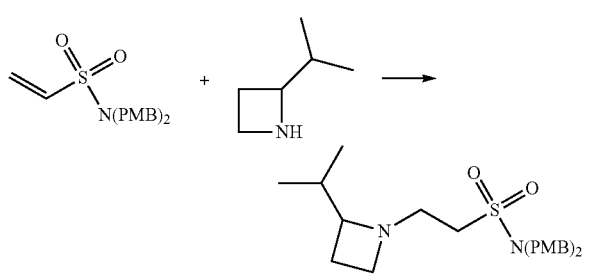

Prepared as described for 2-(azetidin-1-yl)-N,N-bis(4-methoxybenzyl)propane-1-sulfonamide (Intermediate P56, Step A) from N,N-bis(4-methoxybenzyl)ethenesulfonamide and 2-isopropylazetidine HCl salt to afford the title compound a colourless an oil (129 mg, 100%).

$^1$H NMR (CDCl$_3$) δ 7.19 (d, 4H), 6.87 (d, 4H), 4.25 (s, 4H), 3.78 (s, 6H), 3.76 (m, 2H), 3.32 (m, 2H), 3.09 (m, 2H), 2.28 (m, 2H), 1.55 (m, 1H), 0.92 (d, 6H).

Step B:
2-(2-Isopropylazetidin-1-yl)ethane-1-sulfonamide, TFA Salt

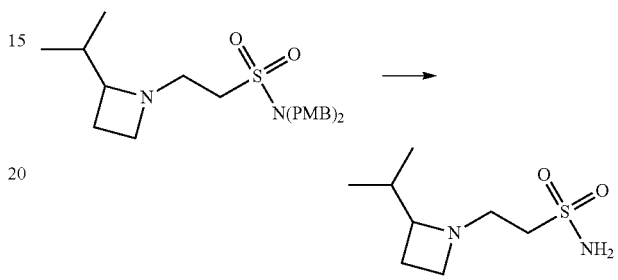

Prepared as described for 2-(azetidin-1-yl)propane-1-sulfonamide (Intermediate P56, Step B) from 2-(2-isopropylazetidin-1-yl)-N,N-bis(4-methoxybenzyl)ethane-1-sulfonamide to afford the title compound as colourless oil (120 mg, 136%).

$^1$H NMR (CD$_3$OD) δ 4.06 (m, 3H), 3.67 (m, 2H), 3.40 (m, 2H), 2.36 (m, 3H), 1.0 (d, 6H).

Intermediate P69: (1-Methylpyrrolidin-2-yl)methanesulfonamide

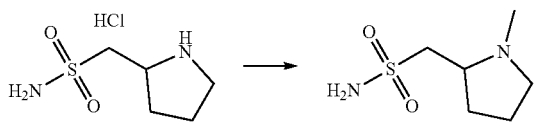

Prepared as described for 1-(oxetan-3-yl)pyrrolidin-3-yl)methanesulfonamide (Intermediate P31) from formaldehyde (37% in water stabilized with methanol) and pyrrolidin-2-ylmethanesulfonamide hydrochloride. The title compound (25 mg, 18%) was used without further purification.

$^1$H NMR (CD$_3$OD) δ 3.49 (dd, 1H), 3.25-3.16 (m, 1H), 3.09 (dd, 1H), 2.95-2.81 (m, 1H), 2.52-2.38 (m, 4H), 2.38-2.24 (m, 1H), 1.98-1.75 (m, 3H).

Intermediate P70: (1-Ethylpyrrolidin-2-yl)methanesulfonamide

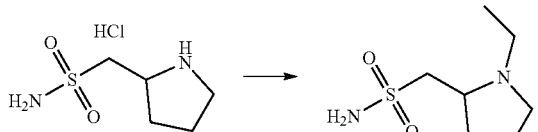

Prepared as described for (1-(oxetan-3-yl)pyrrolidin-3-yl)methanesulfonamide (Intermediate P31) from acetaldehyde and pyrrolidin-2-ylmethanesulfonamide hydrochloride. The title compound (34 mg, 22%) was used without further purification.

¹H NMR (CD₃OD) δ 3.54-3.40 (m, 1H), 3.29-3.24 (m, 1H), 3.23-2.99 (m, 2H), 2.60-2.41 (m, 2H), 2.38-2.22 (m, 1H), 1.96-1.77 (m, 4H), 1.19 (t, 3H).

Intermediate P71:
(1-Isopropylpyrrolidin-2-yl)methanesulfonamide

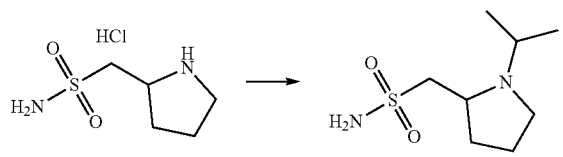

Prepared as described for (1-(oxetan-3-yl)pyrrolidin-3-yl)methanesulfonamide (Intermediate P31) from acetone and pyrrolidin-2-ylmethanesulfonamide hydrochloride. The title compound (98 mg, 60%) was used without further purification.

¹H NMR (CD₃OD) δ 3.53-3.32 (m, 2H), 3.25-3.04 (m, 2H), 2.99 (dt, 1H), 2.79-2.66 (m, 1H), 2.14 (dq, 1H), 2.03-1.76 (m, 3H), 1.21 (d, 3H), 1.13 (d, 3H).

Intermediate P72:
(1-Isopropylpiperidin-2-yl)methanesulfonamide

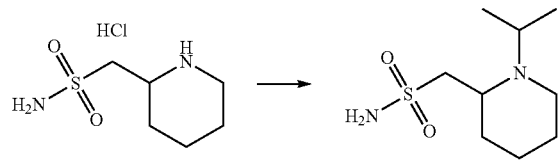

Prepared as described for (1-(oxetan-3-yl)pyrrolidin-3-yl)methanesulfonamide (Intermediate P31) from acetone and piperidin-2-ylmethanesulfonamide hydrochloride. The title compound (33 mg, 19%) was used without further purification.

¹H NMR (CD₃OD) δ 3.27-3.05 (m, 4H), 2.82-2.67 (m, 2H), 1.83 (d, 2H), 1.74-1.56 (m, 1H), 1.55-1.41 (m, 2H), 1.41-1.25 (m, 1H), 1.15 (dd, 6H).

Intermediate P73:
(1-Ethylpiperidin-2-yl)methanesulfonamide

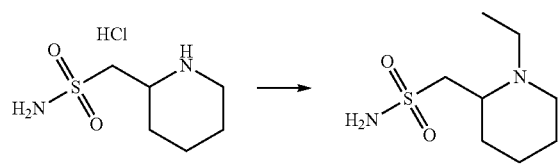

Prepared as described for (1-(oxetan-3-yl)pyrrolidin-3-yl)methanesulfonamide (Intermediate P31) from acetaldehyde and piperidin-2-ylmethanesulfonamide hydrochloride. The title compound (9 mg, 5%) was used without further purification.

¹H NMR (CD₃OD) δ 3.25-3.04 (m, 4H), 2.73 (td, 1H), 2.53 (dd, 2H), 1.87-1.73 (m, 2H), 1.74-1.58 (m, 1H), 1.48 (m, 2H), 1.39-1.24 (m, 1H), 1.11 (t, 3H).

Intermediate P74:
(1-Isopropyl-1H-pyrazol-3-yl)methanesulfonamide

Step A: Methyl 1-isopropyl-1H-pyrazole-3-carboxylate and methyl 1-isopropyl-1H-pyrazole-5-carboxylate

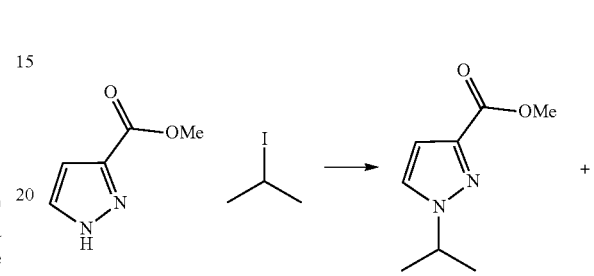

A mixture of methyl 1H-pyrazole-3-carboxylate (2 g, 15.86 mmol), 2-iodopropane (1.8 mL, 18.03 mmol) and K₂CO₃ (4.38 g, 31.7 mmol) in DMF (20 mL) was stirred at 60° C. for 3 days. The reaction was quenched with water (30 mL) and extracted with EtOAc (3×60 mL). The combined organic extracts were washed with brine (50 mL), passed through a phase separator and the solvent was removed in vacuo. The residue was purified by chromatography on silica gel (40 g column, 0-100% EtOAc/iso-hexane) to afford methyl 1-isopropyl-1H-pyrazole-3-carboxylate (1379 g, 51%) as a clear colourless oil and methyl 1-isopropyl-1H-pyrazole-5-carboxylate (951 mg, 35%) as a clear colourless oil.

Methyl 1-isopropyl-1H-pyrazole-3-carboxylate

¹H NMR (DMSO-d6) δ 7.90 (d, J=2.3 Hz, 1H), 6.73 (d, J=2.3 Hz, 1H), 4.59 (sept, J=6.7 Hz, 1H), 3.78 (s, 3H), 1.42 (d, J=6.7 Hz, 6H).

LCMS; m/z 169.5 (M+H)⁺ (ES⁺).

Methyl 1-isopropyl-1H-pyrazole-5-carboxylate

¹H NMR (DMSO-d6) δ 7.57 (d, J=2.0 Hz, 1H), 6.85 (d, J=2.0 Hz, 1H), 5.41 (sept, J=6.6 Hz, 1H), 3.82 (s, 3H), 1.40 (d, J=6.6 Hz, 6H).

LCMS; m/z 169.2 (M+H)⁺ (ES⁺).

Step B: (1-Isopropyl-H-pyrazol-3-yl)methanol

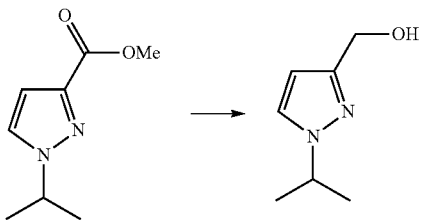

To a solution of methyl 1-isopropyl-1H-pyrazole-3-carboxylate (1.37 g, 7.98 mmol) in THF (20 mL) at 0° C. was slowly added LiAlH$_4$ (2 M in THF, 6 mL, 12.0 mmol). The resulting mixture was stirred at 0° C. for 30 minutes and then at room temperature overnight. The reaction was sequentially quenched with water (0.3 mL), 2 M NaOH (0.75 mL) and water (2 mL). Na$_2$SO$_4$ was added, the mixture was stirred for 30 minutes and then filtered over a plug of Celite® rinsing with EtOAc. The solvent was evaporated and the residue was purified by chromatography on silica gel (24 g column, 0-10% MeOH/DCM) to afford the title compound (779 mg, 70%) as a clear colourless oil.

$^1$H NMR (DMSO-d6) δ 7.63 (d, J=2.2 Hz, 1H), 6.14 (d, J=2.2 Hz, 1H), 4.92 (t, J=5.8 Hz, 1H), 4.42 (sept, J=6.7 Hz, 1H), 4.38 (d, J=5.8 Hz, 2H), 1.38 (d, J=6.7 Hz, 6H).

LCMS; m/z 141.1 (M+H)$^+$ (ES$^+$).

Step C: 3-(Bromomethyl)-1-isopropyl-H-pyrazole

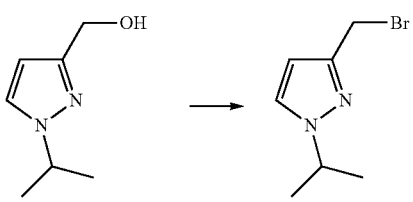

To a solution of (1-isopropyl-1H-pyrazol-3-yl)methanol (779 mg, 5.56 mmol) in DCM (50 mL) at 0° C. was slowly added tribromophosphine (0.55 mL, 5.85 mmol) in DCM (10 mL). The resulting mixture was warmed to room temperature and stirred overnight. The mixture was poured onto ice (~50 g) and stirred until all ice was dissolved. Sat aq NaHCO$_3$ (20 mL) was added. The layers were separated and the aqueous layer was extracted with DCM (2×50 mL). The combined organic extracts were passed through a phase separator and the solvent was removed in vacuo. The residue was purified by chromatography on silica gel (24 g column, 0-50% EtOAc/isohexane) to afford the title compound (865 mg, 73%) as a clear colourless oil.

$^1$H NMR (DMSO-d6) δ 7.71 (d, J=2.3 Hz, 1H), 6.28 (d, J=2.3 Hz, 1H), 4.60 (s, 2H), 4.46 (sept, J=6.7 Hz, 1H), 1.39 (d, J=6.7 Hz, 6H).

LCMS; m/z 203.1/205.1 (M+H)$^+$ (ES$^+$).

Step D: (1-Isopropyl-H-pyrazol-3-yl)methanesulfonamide

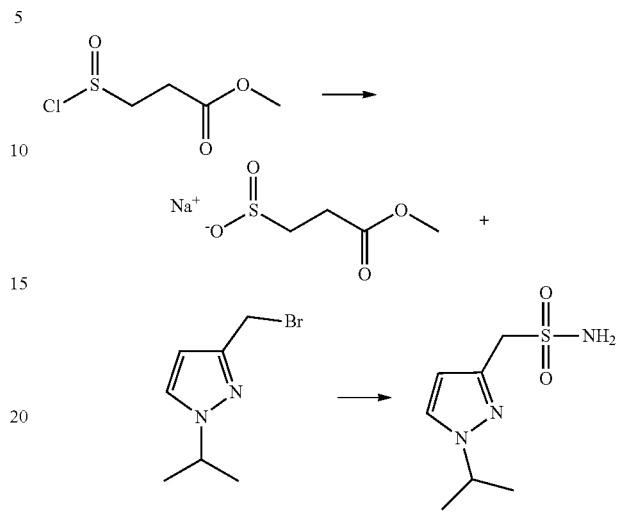

A mixture of methyl 3-(chlorosulfonyl)propanoate (1.0 g, 5.36 mmol), sodium sulfite (1.4 g, 11.11 mmol) and sodium bicarbonate (0.94 g, 11.19 mmol) in water (6 mL) was stirred at 80° C. overnight. The solvent was evaporated to give a white solid. Ethanol (30 mL) was added and the mixture was heated to 60° C. for 1 hour and subsequently filtered while being warm. The filtrate was evaporated to afford sodium 3-methoxy-3-oxopropane-1-sulfinate (588 mg, 50% purity by NMR) as a white solid which was used directly.

To a solution of sodium 3-methoxy-3-oxopropane-1-sulfinate (588 mg, 1.688 mmol) in DMSO (2.5 mL) was added 3-(bromomethyl)-1-isopropyl-1H-pyrazole (280 mg, 1.310 mmol) and the mixture was stirred at room temperature for 45 minutes. The mixture was diluted with water (5 mL) and extracted with EtOAC (4×30 mL). The combined organic extracts were washed with brine (25 mL), passed through a phase separator and the solvent was removed in vacuo. The residue was dissolved in THF (5 mL) and MeOH (1.2 mL) and NaOMe (5.4 M in MeOH, 0.35 mL, 1.89 mmol) was added. The mixture was stirred at room temperature for 15 minutes. The solvent was removed in vacuo and the residue was dissolved in water (0.8 mL). (Aminooxy)sulfonic acid (1.2 g, 10.61 mmol) and sodium acetate (360 mg, 4.39 mmol) were added and the mixture was stirred at room temperature for 2 days. The mixture was diluted with sat aq NaHCO$_3$ (30 mL) and extracted with EtOAc (2×40 mL). The combined organic extracts were washed with brine (30 mL), passed through a phase separator and the solvent was removed in vacuo. The residue was purified by chromatography on silica gel (12 g column, 0-10% MeOH/DCM) and then further purified by preparative HPLC (Teledyne EZ Prep, basic (0.1% ammonium bicarbonate), basic, Waters X-Bridge Prep-C18, 5 μm, 19×50 mm column, 5-10% MeCN in water) to afford the title compound (31 mg, 11%) as a white solid.

$^1$H NMR (DMSO-d6) δ 7.72 (d, J=2.3 Hz, 1H), 6.79 (s, 2H), 6.26 (d, J=2.3 Hz, 1H), 4.46 (sept, J=6.7 Hz, 1H), 4.23 (s, 2H), 1.40 (d, J=6.7 Hz, 6H).

LCMS; m/z 204.5 (M+H)$^+$ (ES$^+$).

Intermediate P75: N-Methyl-N-(3-sulfamoylpropyl)acetamide

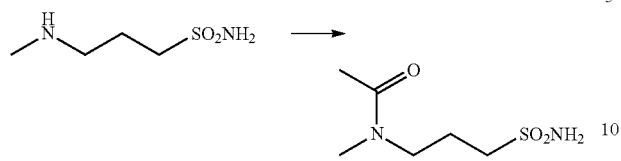

Prepared as described for methyl methyl(3-sulfamoylpropyl)carbamate (Intermediate P64) from 3-(methylamino)propane-1-sulfonamide and acetic anhydride. The solvents were evaporated and the residue was triturated in THF. The THF was filtered (over Celite®) and evaporated to afford the title compound as a colourless oil (100 mg, quant.) which was used without further purification.

$^1$H NMR (Methanol-$d_4$) δ 3.54 (t, 2H), 3.16 (t, 2H), 3.05 (s, 3H), 2.16 (m, 2H), 2.13 (s, 3H).

Preparation of Examples

Example 1: 1-(1-Ethylpiperidin-4-yl)-N-((1,2,3,5,6,7-hexahydro-s-indacen-4-yl)carbamoyl)methanesulfonamide, potassium salt

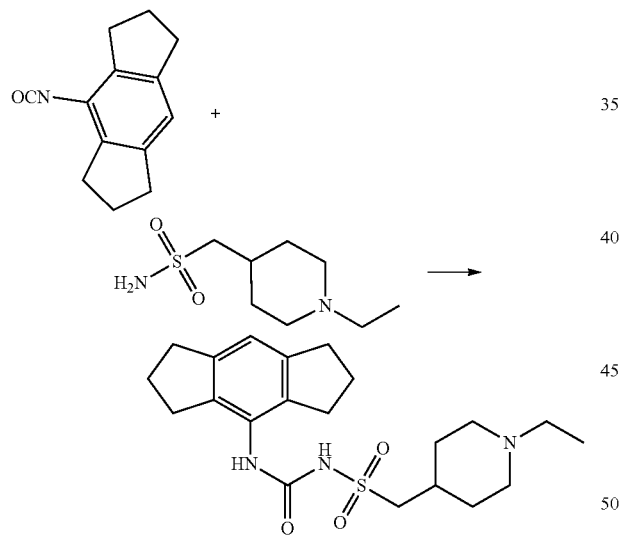

To a cooled (0 °C.) solution of (1-ethylpiperidin-4-yl)methanesulfonamide (Intermediate P1; 76 mg, 0.37 mmol) in THF (2.5 mL) was added potassium tert-butoxide (41 mg, 0.37 mmol). The ice bath was removed and the reaction mixture was stirred whilst being allowed to warm to room temperature over 40 minutes. A solution of 4-isocyanato-1,2,3,5,6,7-hexahydro-s-indacene (Intermediate A1; 73 mg, 0.37 mmol) in THF (1 mL) was added and the mixture was stirred overnight at room temperature. The reaction mixture was concentrated in vacuo and DMSO (1 mL) was added. The suspension was filtered over cotton wool and subsequently submitted for purification by reversed phase column chromatography (see "Experimental Methods") to afford the title compound (28 mg, 19%) as a white solid.

$^1$H NMR (CD$_3$OD) δ 6.86 (s, 1H), 3.18 (m, 2H), 3.07 (m, 2H), 2.82 (m, 8H), 2.57 (m, 2H), 2.24 (m, 2H), 2.04 (m, 7H), 1.44 (m, 2H) and 1.16 (t, 3H).

LCMS: m/z 406 (M+H)$^+$ (ES$^+$); 404 (M−H)$^−$ (ES$^−$).

Example 2: 3-(4-(Dimethylamino)piperidin-1-yl)-N-((1,2,3,5,6,7-hexahydro-s-indacen-4-yl)carbamoyl)propane-1-sulfonamide, potassium salt

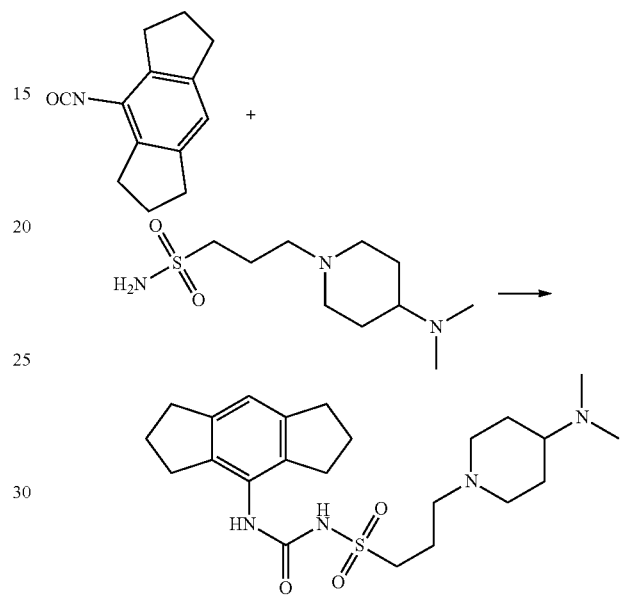

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-(4-(dimethylamino)piperidin-1-yl)propane-1-sulfonamide (Intermediate P2) to afford the title compound (13%) as a light yellow solid.

$^1$H NMR (CD$_3$OD) δ 6.86 (s, 1H), 3.23 (m, 1H), 3.08 (m, 4H), 2.82 (m, 8H), 2.46 (m, 2H), 2.34 (s, 6H), 2.02 (m, 10H) and 1.58 (m, 2H).

LCMS: m/z 449 (M+H)$^+$ (ES$^+$); 447 (M−H)$^−$ (ES$^−$).

Example 3: 3-(Diethylamino)-N-((1,2,3,5,6,7-hexahydro-s-indacen-4-yl)carbamoyl)propane-1-sulfonamide, potassium salt

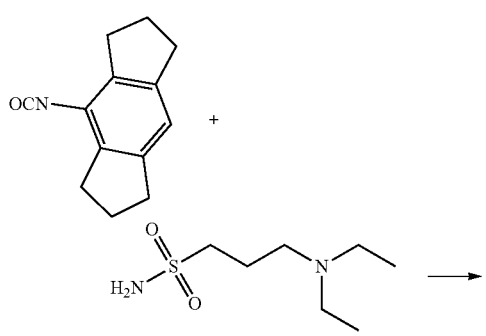

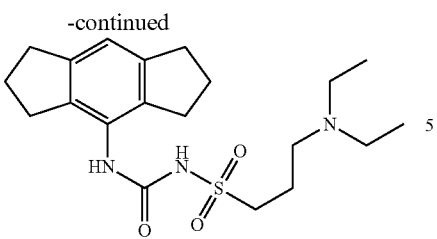

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-(diethylamino)propane-1-sulfonamide (Intermediate P3) to afford the title compound (11%) as a light yellow solid.

¹H NMR (CD₃OD) δ 6.86 (s, 1H), 3.28 (m, 4H), 2.95 (m, 2H), 2.82 (m, 10H), 2.02 (m, 6H) and 1.18 (t, 6H).

LCMS: m/z 394 (M+H)⁺ (ES⁺).

Example 4: 1-((1S)-7,7-Dimethyl-2-oxobicyclo[2.2.1]heptan-1-yl)-N-((1,2,3,5,6,7-hexahydro-s-indacen-4-yl)carbamoyl)methanesulfonamide, Potassium Salt

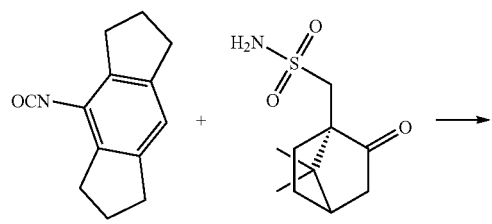

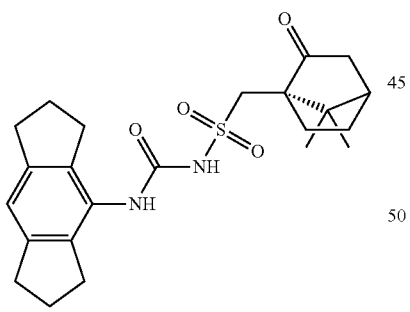

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1S)-10-camphorsulfonamide to afford the title compound (63%) as a white solid.

¹H NMR (CD₃OD) δ 6.86 (s, 1H), 3.63 (d, 1H), 3.23 (d, 1H), 2.82 (m, 8H), 2.62 (m, 1H), 2.37 (m, 1H), 2.02 (m, 6H), 1.88 (d, 1H), 1.7 (m, 1H), 1.42 (m, 1H), 1.1 (s, 3H) and 0.85 (s, 3H).

LCMS: m/z 431 (M+H)⁺ (ES⁺); 429 (M−H)⁻ (ES⁻).

Example 5: 2-(Dimethylamino)-N-((1,2,3,5,6,7-hexahydro-s-indacen-4-yl)carbamoyl)ethane-1-sulfonamide, potassium salt

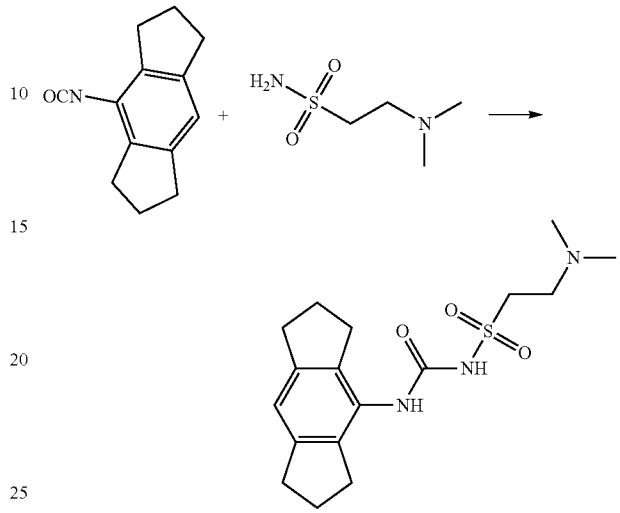

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(dimethylamino)ethane-1-sulfonamide to afford the title compound (52%) as a white solid.

¹H NMR (CD₃OD) δ 6.86 (s, 1H), 3.42 (m, 2H), 2.88 (m, 2H), 2.82 (m, 8H), 2.33 (s, 6H) and 2.02 (m, 4H).

LCMS: m/z 352 (M+H)⁺ (ES⁺); 350 (M−H)⁻ (ES⁻).

Example 6: N-(2-(N-((1,2,3,5,6,7-Hexahydro-s-indacen-4-yl)carbamoyl) sulfamoyl)ethyl)acetamide, Potassium Salt Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and N-(2-sulfamoylethyl)acetamide to afford the title compound (67%) as a white solid.

$^1$H NMR (CD$_3$OD) δ 6.86 (s, 1H), 3.61 (m, 2H), 3.37 (m, 2H), 2.82 (m, 8H), 2.02 (m, 4H) and 1.93 (s, 3H).

LCMS: m/z 366 (M+H)$^+$ (ES$^+$); 364 (M-H)$^-$ (ES$^-$).

Example 7: 1-(1-(Dimethylamino)cyclopropyl)-N-((1,2,3,5,6,7-hexahydro-s-indacen-4-yl)carbamoyl) methanesulfonamide, potassium salt

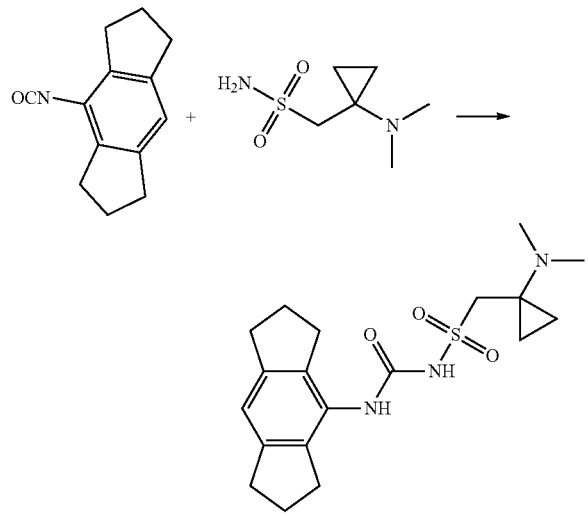

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-(dimethylamino)cyclopropyl)methanesulfonamide to afford the title compound (57%) as a white solid.

$^1$H NMR (CD$_3$OD) δ 6.86 (s, 1H), 3.58 (s, 2H), 2.82 (m, 8H), 2.38 (s, 6H), 2.02 (m, 4H), 1.17 (m, 2H) and 1.66 (m, 2H).

LCMS: m/z 378 (M+H)$^+$ (ES$^+$); 376 (M-H)$^-$ (ES$^-$).

Example 8: 3-(Dimethylamino)-N-((1,2,3,5,6,7-hexahydro-s-indacen-4-yl)carbamoyl)propane-1-sulfonamide, potassium salt

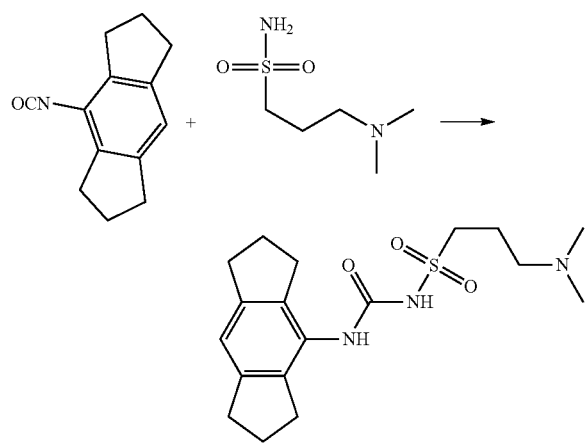

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-(dimethylamino)propane-1-sulfonamide (Intermediate P4) to afford the title compound (52%) as a white solid.

$^1$H NMR (CD3OD) δ 6.87 (s, 1H), 3.24 (dd, 2H), 2.83 (m, 10H), 2.59 (t, 2H), 2.35 (s, 6H), 2.02 (m, 4H).

LCMS: m/z 366 (M+H)$^+$ (ES$^+$); 364 (M-H)$^-$ (ES$^-$).

Example 9: N-((1,2,3,5,6,7-Hexahydro-s-indacen-4-yl)carbamoyl)-4-morpholinobutane-1-sulfonamide, Potassium Salt

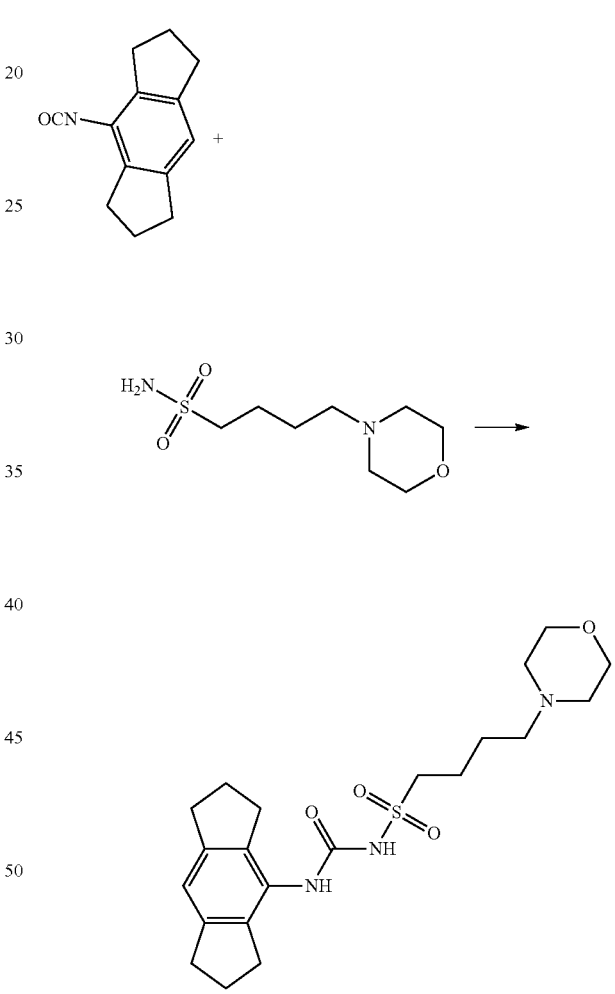

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 4-morpholinobutane-1-sulfonamide (Intermediate P5) to afford the title compound (55%) as a white solid.

$^1$H NMR (CD3OD) δ 6.87 (s, 1H), 3.73-3.62 (m, 4H), 3.28-3.18 (m, 2H), 2.82 (m, 8H), 2.46 (t, 4H), 2.44-2.32 (m, 2H), 2.03 (m, 4H), 1.93-1.74 (m, 2H), 1.66 (t, 2H).

LCMS: m/z 422 (M+H)+(ES+); 420 (M-H)- (ES-).

Example 10: 4-(Diethylamino)-N-((1,2,3,5,6,7-hexahydro-s-indacen-4-yl)carbamoyl)butane-1-sulfonamide, potassium salt

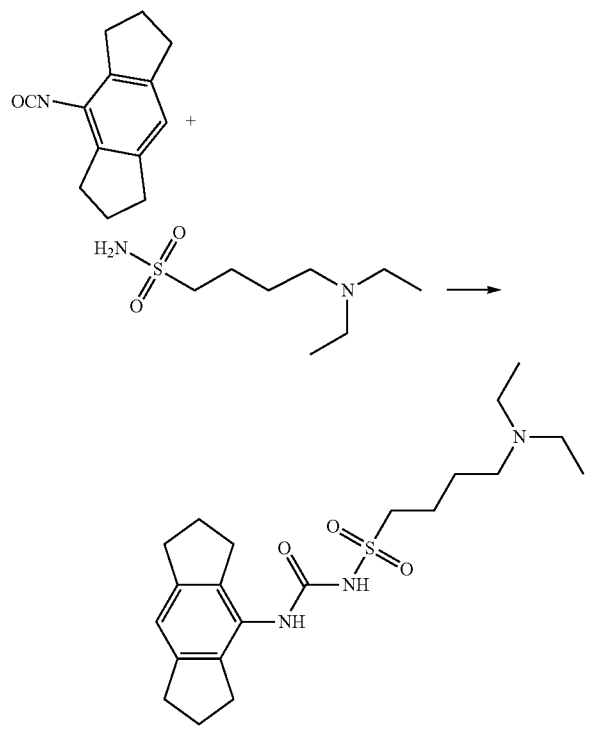

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 4-(diethylamino)butane-1-sulfonamide (Intermediate P6) to afford the title compound (61%) as a white solid.

$^1$H NMR (CD3OD) δ 6.88 (s, 1H), 3.26 (dd, 2H), 3.04 (m, 6H), 2.83 (m, 9H), 2.13-1.92 (m, 4H), 1.91-1.73 (m, 3H), 1.22 (t, 6H).

LCMS: m/z 408 (M+H)+(ES+); 406 (M−H)− (ES−).

Example 11: 2-(Benzyl(ethyl)amino)-N-((1,2,3,5,6,7-hexahydro-s-indacen-4-yl)carbamoyl)ethane-1-sulfonamide, potassium salt

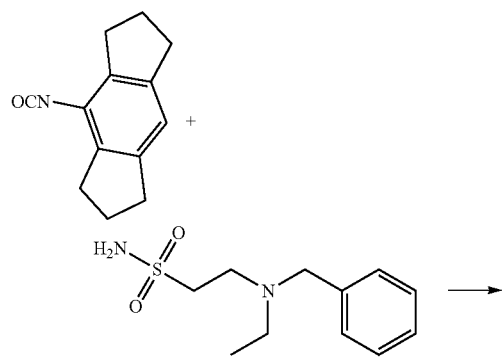

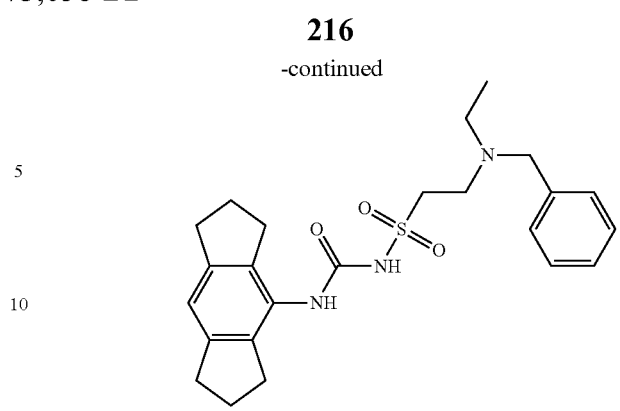

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(benzyl(ethyl)amino)ethane-1-sulfonamide (Intermediate P7) to afford the title compound (24%) as a white solid.

$^1$H NMR (CD3OD) δ 7.42-7.11 (m, 5H), 6.86 (s, 1H), 3.63 (s, 2H), 3.51-3.40 (m, 2H), 3.11-2.95 (m, 2H), 2.81 (m, 8H), 2.55 (q, 2H), 2.02 (m, 4H), 1.16-0.99 (m, 3H).

LCMS: m/z 442 (M+H)+(ES+); 440 (M−H)− (ES−).

Example 12: N-((1,2,3,5,6,7-Hexahydro-s-indacen-4-yl)carbamoyl)-2-morpholinoethane-1-sulfonamide, Potassium Salt

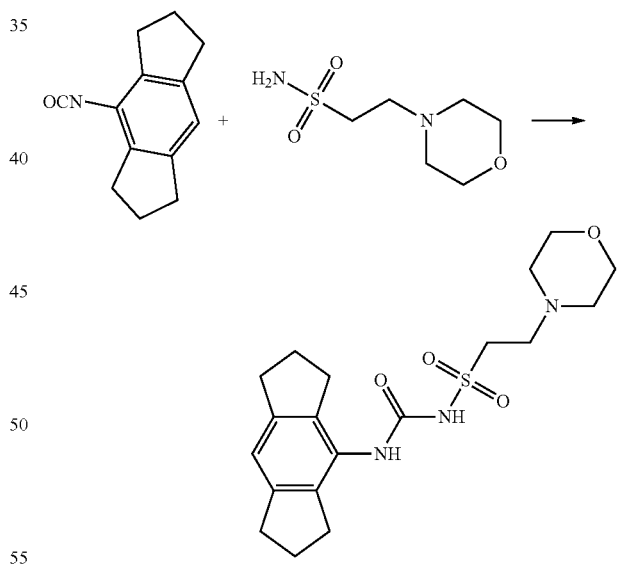

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-morpholinoethane-1-sulfonamide (Intermediate P8) to afford the title compound (87%) as a white solid.

$^1$H NMR (CD$_3$OD) δ 6.87 (s, 1H), 3.68 (m, 4H), 3.53-3.38 (m, 2H), 2.96-2.74 (m, 10H), 2.51 (dd, 4H), 2.02 (m, 4H).

LCMS: m/z 394 (M+H)+(ES+); 392 (M−H)− (ES−).

Example 13: 4-(Benzyl(ethyl)amino)-N-((1,2,3,5,6,7-hexahydro-s-indacen-4-yl)carbamoyl)butane-1-sulfonamide, potassium salt

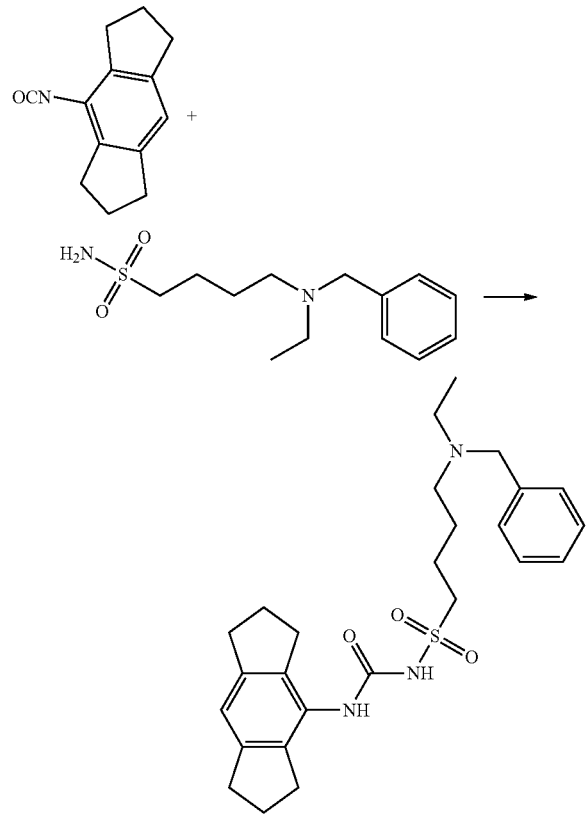

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 4-(benzyl(ethyl)amino)butane-1-sulfonamide (Intermediate P9) to afford the title compound (22%) as a white solid.

$^1$H NMR (CD3OD) δ 7.52-7.20 (m, 5H), 6.87 (s, 1H), 3.86 (s, 2H), 3.24 (t, 2H), 2.90-2.62 (m, 12H), 2.16-1.89 (m, 8H), 1.23-1.06 (m, 3H).

LCMS: m/z 470 (M+H)+(ES+); 468 (M−H)− (ES−).

Example 14: N-((1,2,3,5,6,7-Hexahydro-s-indacen-4-yl)carbamoyl)-3-methoxypropane-1-sulfonamide, Potassium Salt

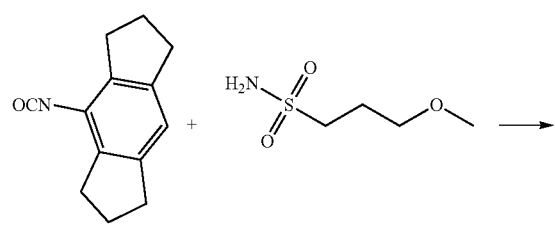

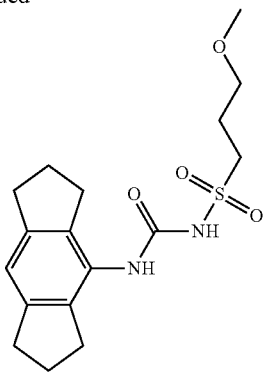

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-methoxypropane-1-sulfonamide to afford the title compound (51%) as a white solid.

$^1$H NMR (CD3OD) δ 6.87 (s, 1H), 3.50 (t, 2H), 3.33 (s, 3H), 3.30-3.16 (m, 2H), 2.82 (m, 8H), 2.17-1.91 (m, 6H).

LCMS: m/z 353 (M+H)+(ES+); 351 (M−H)− (ES−).

Example 15: N-((1,2,3,5,6,7-Hexahydro-s-indacen-4-yl)carbamoyl)-3-morpholinopropane-1-sulfonamide, Potassium Salt

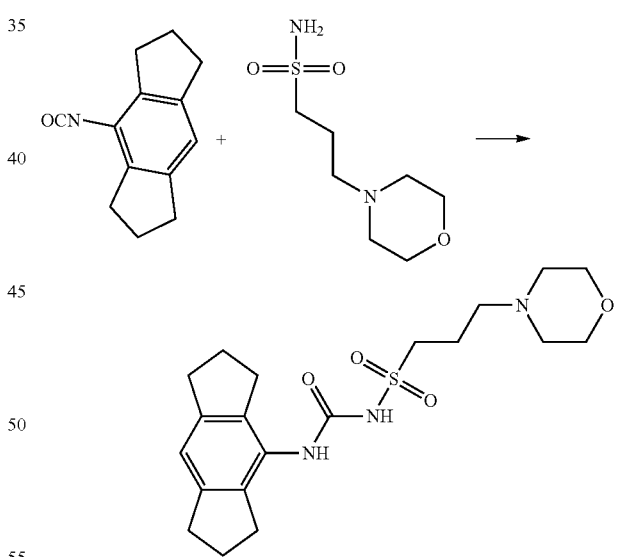

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-morpholinopropane-1-sulfonamide (Intermediate P10) to afford the title compound (62%) as a white solid.

$^1$H NMR (CD3OD) δ 6.87 (s, 1H), 3.79-3.59 (m, 4H), 3.28-3.18 (m, 2H), 2.82 (m, 8H), 2.58-2.41 (m, 6H), 2.02 (m, 6H).

LCMS: m/z 408 (M+H)+(ES+); 406 (M−H)− (ES−).

Example 16: N-((1,2,3,5,6,7-Hexahydro-s-indacen-4-yl)carbamoyl)-3-(piperidin-1-yl)propane-1-sulfonamide, Potassium Salt

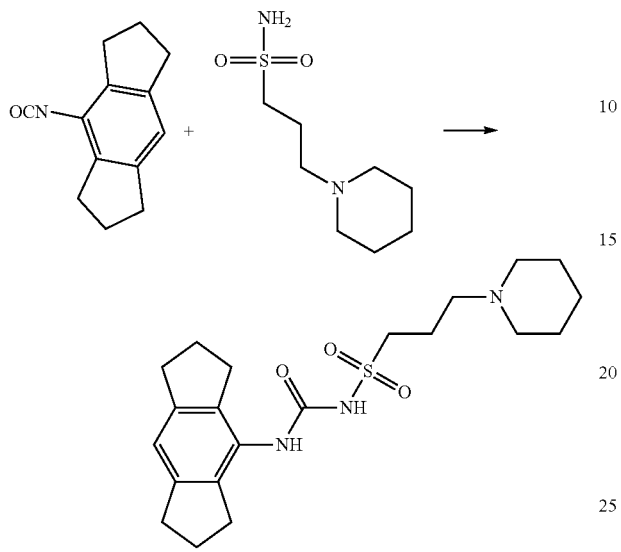

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-(piperidin-1-yl)propane-1-sulfonamide (Intermediate P11) to afford the title compound (28%) as a white solid.

$^1$H NMR (CD3OD) δ 6.88 (s, 1H), 3.26 (t, 2H), 2.83 (m, 10H), 2.50 (t, 2H), 2.12 (q, 2H), 2.02 (m, 6H), 1.68 (q, 3H), 1.64-1.38 (m, 3H).

LCMS: m/z 406 (M+H)+(ES+); 404 (M−H)− (ES−).

Example 17: 1-(1-Ethylazetidin-3-yl)-N-((1,2,3,5,6,7-hexahydro-s-indacen-4-yl)carbamoyl)methanesulfonamide, potassium salt

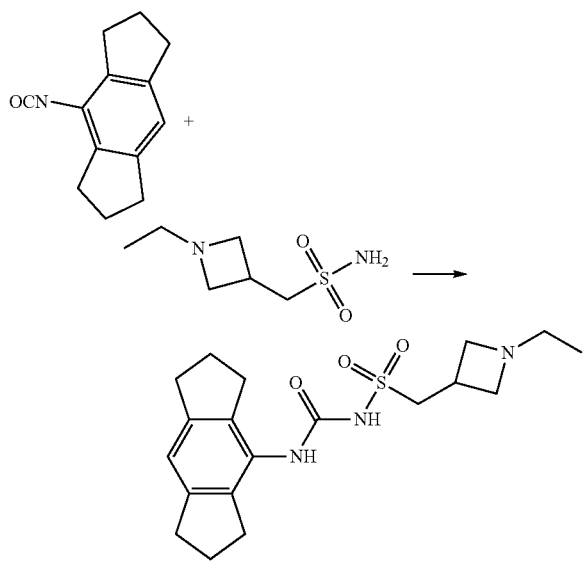

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-ethylazetidin-3-yl)methanesulfonamide (Intermediate P14) to afford the title compound (11%) as a white solid.

$^1$H NMR (CD3OD) δ 6.89 (s, 1H), 4.05 (t, 1H), 3.87 (t, 2H), 3.59 (m, 1H), 3.55-3.39 (m, 3H), 3.24-3.05 (m, 1H), 2.95-2.70 (m, 9H), 2.04 (m, 4H), 1.05 (t, 3H).

LCMS: m/z 378 (M+H)+(ES+); 376 (M−H)− (ES−).

Example 18: 2-(Diethylamino)-N-((1,2,3,5,6,7-hexahydro-s-indacen-4-yl)carbamoyl)ethane-1-sulfonamide, potassium salt

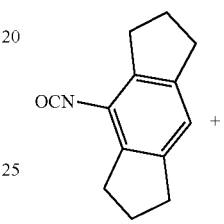

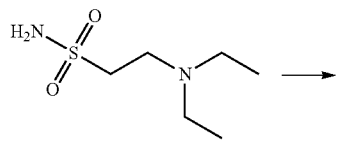

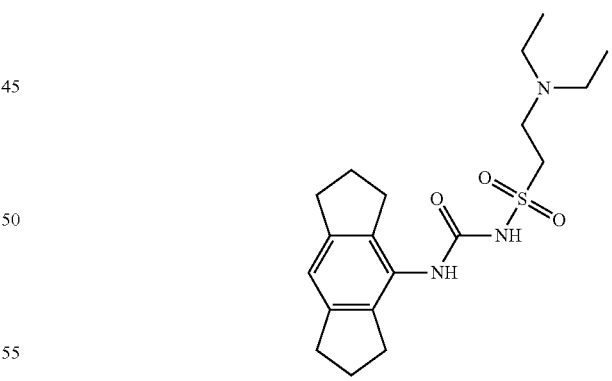

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(diethylamino)ethane-1-sulfonamide (Intermediate P12) to afford the title compound (33%) as a white solid.

$^1$H NMR (CD3OD) δ 6.88 (s, 1H), 3.48 (t, 2H), 2.83 (m, 14H), 2.02 (m, 4H), 1.19 (t, 6H).

LCMS: m/z 380 (M+H)+(ES+); 378 (M−H)− (ES−).

Example 19: 2-(Ethylamino)-N-((1,2,3,5,6,7-hexahydro-s-indacen-4-yl)carbamoyl)ethane-1-sulfonamide, potassium salt

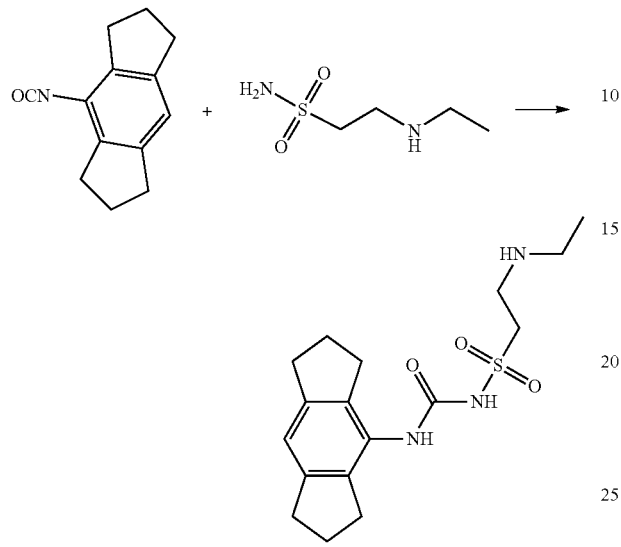

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(ethylamino)ethane-1-sulfonamide (Intermediate P13) to afford the title compound (8%) as a white solid.

$^1$H NMR (CD3OD) δ 6.90 (s, 1H), 3.45 (t, 2H), 3.22 (t, 2H), 2.86 (t, 10H), 2.81 (s, 1H), 2.04 (m, 4H), 1.21 (t, 3H).
LCMS: m/z 352 (M+H)+(ES+); 350 (M−H)− (ES−).

Example 20: N-((1,2,3,5,6,7-Hexahydro-s-indacen-4-yl)carbamoyl)-1-(pyridin-3-yl)methanesulfonamide, potassium salt

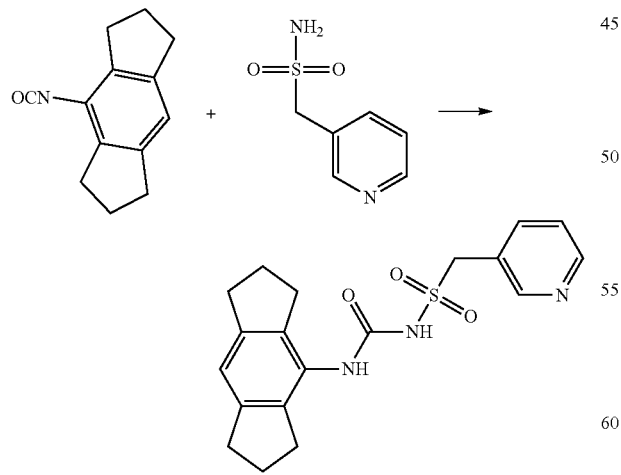

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and pyridin-3-ylmethanesulfonamide to afford the title compound (66%) as a white solid.

$^1$H NMR (CD3OD) δ 8.61 (d, 1H), 8.46 (dd, 1H), 7.94 (d, 1H), 7.42 (dd, 1H), 6.90 (s, 1H), 4.54 (s, 2H), 2.85 (m, 8H), 2.06 (m, 4H).
LCMS: m/z 372 (M+H)+(ES+); 370 (M−H)− (ES−).

Example 21: N-((1,2,3,5,6,7-Hexahydro-s-indacen-4-yl)carbamoyl)-1-(pyridin-2-yl)methanesulfonamide, potassium salt

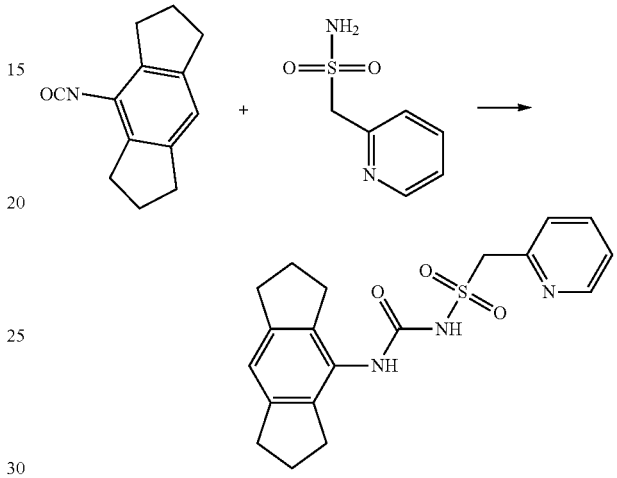

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and pyridin-2-ylmethanesulfonamide to afford the title compound (67%) as a white solid.

$^1$H NMR (CD3OD) δ 8.54-8.42 (m, 1H), 7.79 (td, 1H), 7.61 (d, 1H), 7.33 (ddd, 1H), 6.88 (s, 1H), 4.66 (s, 2H), 2.84 (m, 8H), 2.04 (m, 4H).
LCMS: m/z 372 (M+H)$^+$ (ES$^+$); 370 (M−H)$^−$ (ES$^−$).

Example 22: N-((1,2,3,5,6,7-Hexahydro-s-indacen-4-yl)carbamoyl)-1-(1-methylpiperidin-4-yl)methanesulfonamide, Potassium Salt

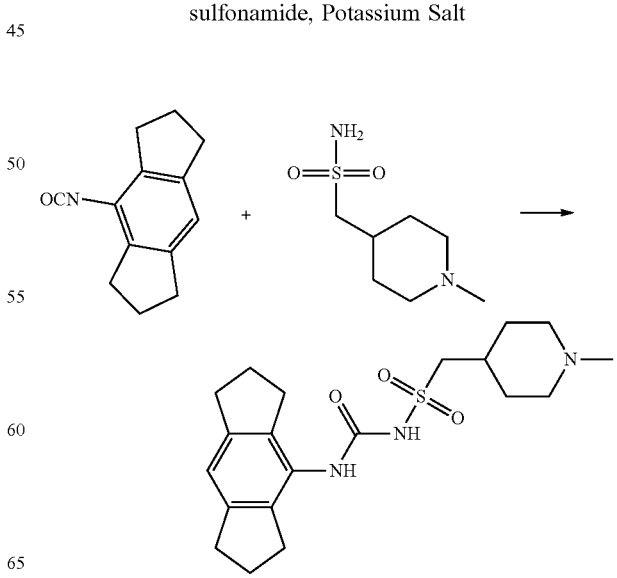

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-methylpiperidin-4-yl)methanesulfonamide (Intermediate P15) to afford the title compound (27%) as a white solid.

$^1$H NMR (CD3OD) δ 7.01 (s, 1H), 3.42 (m, 2H), 3.17 (m, 2H), 2.93 (m, 2H), 2.77-2.67 (m, 11H), 2.13-1.95 (m, 9H).

LCMS: m/z 392 (M+H)+(ES+); 390 (M−H)− (ES−).

Example 23: N-((1,2,3,5,6,7-Hexahydro-s-indacen-4-yl)carbamoyl)-1-(1-methylpyrrolidin-3-yl)methanesulfonamide, Potassium Salt

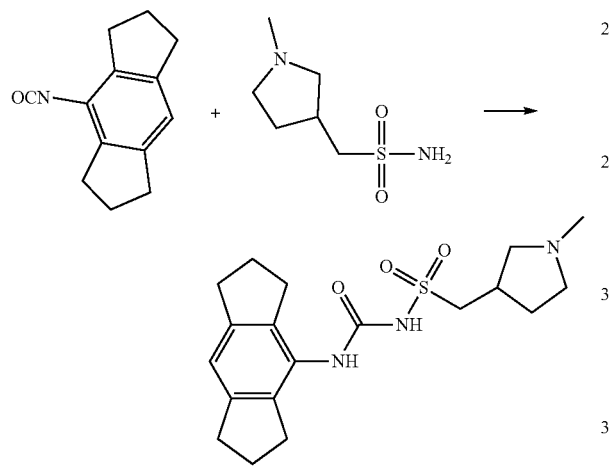

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-methylpyrrolidin-3-yl)methanesulfonamide (Intermediate P16) to afford the title compound (70%) as a white solid.

$^1$H NMR (CD$_3$OD) δ 6.92 (s, 1H), 3.53-339 (m, 2H), 3.05 (dt, 2H), 2.86 (m, 10H), 2.70 (d, 4H), 2.30 (m, 1H), 2.06 (m, 4H), 1.95-1.74 (m, 1H).

LCMS: m/z 378 (M+H)$^+$ (ES$^+$); 376 (M−H)$^-$ (ES$^-$).

Example 24: 1-(1-Ethylpyrrolidin-3-yl)-N-((1,2,3,5,6,7-hexahydro-s-indacen-4-yl)carbamoyl)methanesulfonamide, potassium salt

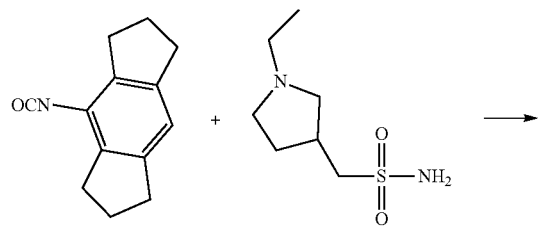

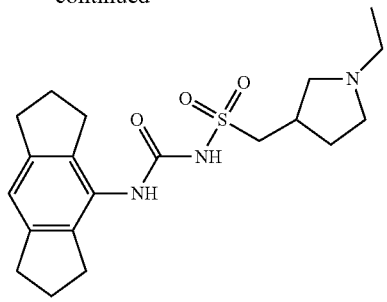

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-ethylpyrrolidin-3-yl)methanesulfonamide (Intermediate P17) to afford the title compound (53%) as a white solid.

$^1$H NMR (CD$_3$OD) δ 6.90 (s, 1H), 3.54 (dd, 1H), 3.46-3.34 (m, 1H), 3.24-3.09 (m, 3H), 3.04 (q, 2H), 2.83 (m, 10H), 2.39-2.19 (m, 1H), 2.03 (m, 4H), 1.92-1.72 (m, 1H), 1.24 (t, 3H).

LCMS: m/z 392 (M+H)$^+$ (ES$^+$); 390 (M−H)$^-$ (ES$^-$).

Example 25: N-((1,2,3,5,6,7-Hexahydro-s-indacen-4-yl)carbamoyl)-1-(1-isopropylpyrrolidin-3-yl)methanesulfonamide, Potassium Salt

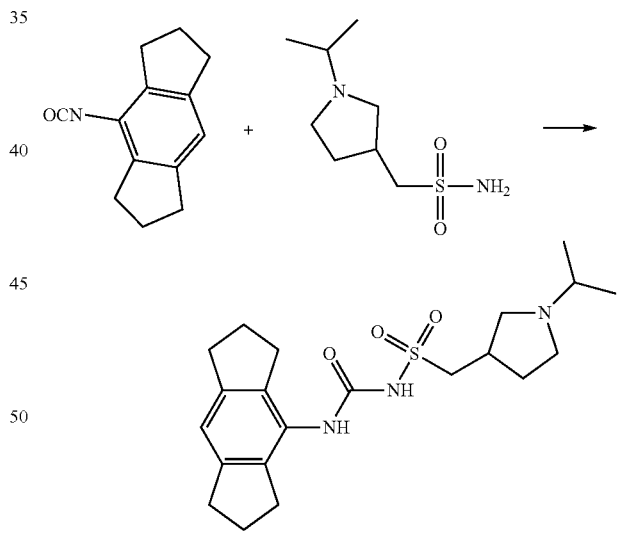

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and (1-isopropylpyrrolidin-3-yl)methanesulfonamide (Intermediate P18) to afford the title compound (44%) as a white solid.

$^1$H NMR (CD$_3$OD) δ 6.89 (s, 1H), 3.57 (dd, 1H), 3.49-3.34 (m, 1H), 3.26-3.12 (m, 3H), 3.06 (dd, 1H), 2.83 (m, 10H), 2.40-2.21 (m, 1H), 2.03 (m, 4H), 1.81 (dq, 1H), 1.28 (dd, 6H).

Example 26: 1-(Dimethylamino)-N-((1,2,3,5,6,7-hexahydro-s-indacen-4-yl)carbamoyl)propane-2-sulfonamide, potassium salt

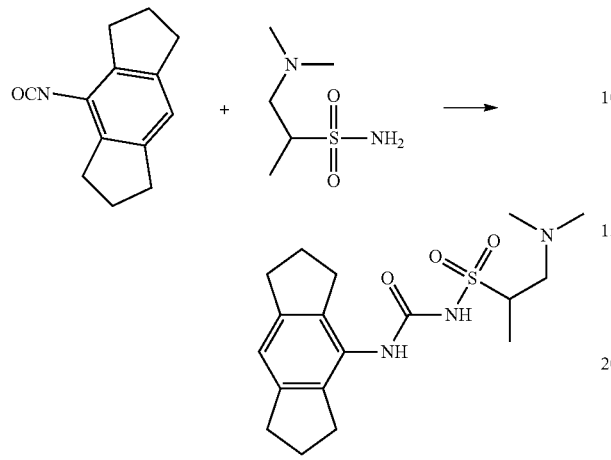

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 1-(dimethylamino)propane-2-sulfonamide (Intermediate P19) to afford the title compound (17%) as a white solid.

$^1$H NMR (CD$_3$OD) δ 6.88 (s, 1H), 3.71 (d, 1H), 2.94 (s, 1H), 2.83 (m, 8H), 2.69 (d, 1H), 2.39 (s, 6H), 2.03 (m, 4H), 1.38 (d, 3H).

LCMS: m/z 366 (M+H)+(ES+); 364 (M−H)− (ES−).

Example 27: 3-(Ethyl(methyl)amino)-N-((1,2,3,5,6,7-hexahydro-s-indacen-4-yl)carbamoyl)propane-1-sulfonamide, potassium salt

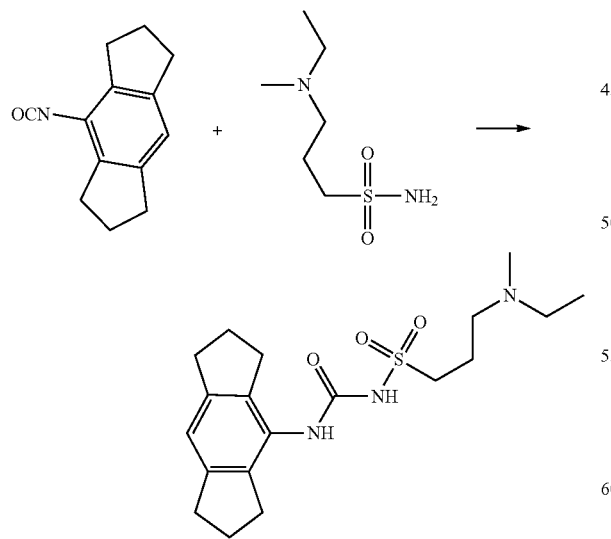

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 3-(ethyl(methyl)amino)propane-1-sulfonamide (Intermediate P22) to afford the title compound (44%) as a white solid.

$^1$H NMR (CD$_3$OD) δ 6.88 (s, 1H), 3.26 (t, 2H), 3.00-2.89 (m, 2H), 2.89-2.73 (m, 10H), 2.53 (s, 3H), 2.06 (m, 6H), 1.19 (t, 3H).

LCMS: m/z 380 (M+H)+ (ES+); 378 (M−H)− (ES−).

Example 28: N-((1,2,3,5,6,7-Hexahydro-s-indacen-4-yl)carbamoyl)-2-(piperidin-1-yl)ethane-1-sulfonamide, Potassium Salt

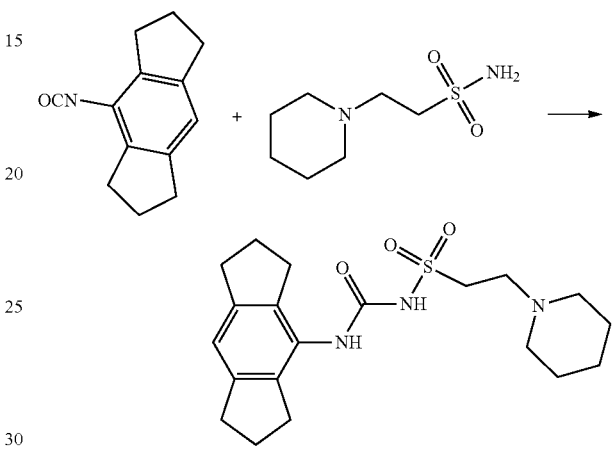

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(piperidin-1-yl)ethane-1-sulfonamide (Intermediate P20) to afford the title compound (37%) as a white solid.

$^1$H NMR (CD3OD) δ 6.87 (s, 1H), 3.55-3.40 (m, 2H), 3.03-2.92 (m, 2H), 2.83 (m, 8H), 2.60 (d, 4H), 2.02 (m, 4H), 1.64 (dq, 4H), 1.50 (t, 2H).

LCMS: m/z 392 (M+H)+(ES+); 390 (M−H)− (ES−).

Example 20: 2-(Azetidin-1-yl)-N-((1,2,3,5,6,7-hexahydro-s-indacen-4-yl)carbamoyl)ethane-1-sulfonamide, Potassium Salt

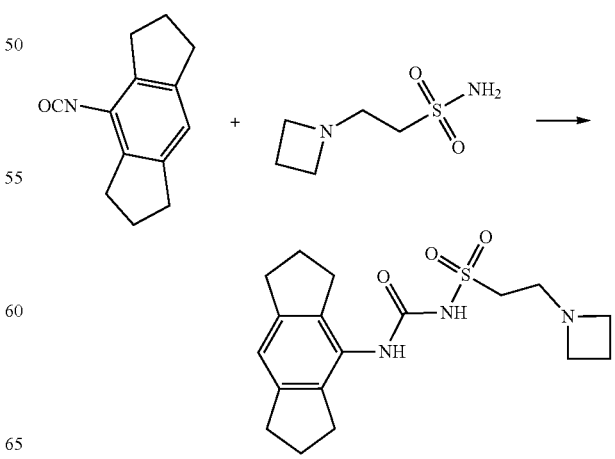

Prepared as described for 1-(1-ethylpiperidin-4-yl)-N-((1,2,3,5,6,7-hexahydro-s-indacen-4-yl)carbamoyl)methanesulfonamide, potassium salt (Example 1) using 4-isocyanato-1,2,3,5,6,7-hexahydro-s-indacene (Intermediate A1) and 2-(azetidin-1-yl)ethane-1-sulfonamide (Intermediate P21) to afford the title compound (1%) as a white solid.

LCMS: m/z 364 (M+H)+(ES+); 362 (M−H)− (ES−).

Example 30: 1-(4-Cyanophenyl)-N-((1,2,3,5,6,7-hexahydro-s-indacen-4-yl) carbamoyl)methanesulfonamide, sodium salt

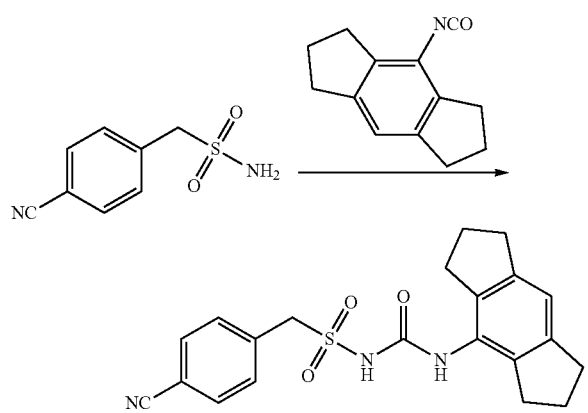

To a solution of (4-cyanophenyl)methanesulfonamide (Intermediate P23) (110 mg, 560.58 µmol, 1 eq) in THF (5 mL) was added sodium methoxide (30.28 mg, 560.58 µmol, 1 eq) at 20° C. After stirring for 15 minutes, 4-isocyanato-1,2,3,5,6,7-hexahydro-s-indacene (Intermediate A1) (111.69 mg, 560.58 µmol, 1 eq) was added to the mixture. The mixture was stirred at 20° C. for 15 hours and then filtered. The collected solid was triturated with ethyl acetate (3×5 mL) and the combined layers were concentrated in vacuo to give the title compound (99 mg, 40%) as a white solid.

$^1$H NMR (400 MHz, DMSO-$d_6$) δ 7.72 (d, 2H), 7.47 (d, 2H), 7.24 (br s, 1H), 6.78 (s, 1H), 4.34 (s, 2H), 2.77-2.69 (m, 8H) and 1.95-1.91 (m, 4H).

LCMS: m/z 396 (M+H)+ (ES+).

Example 31: Methyl 4-((N-((1,2,3,5,6,7-hexahydro-s-indacen-4-yl) carbamoyl)sulfamoyl)methyl)benzoate, sodium salt

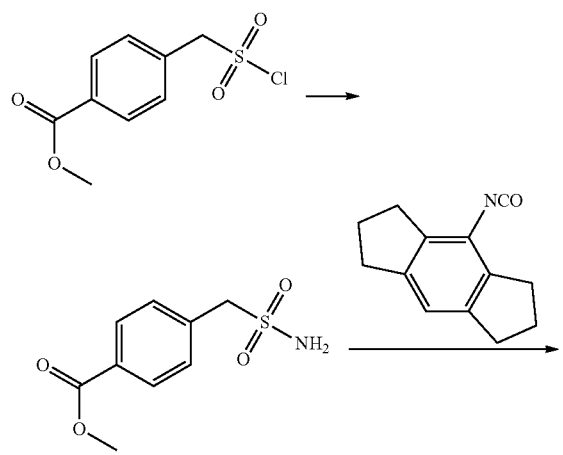

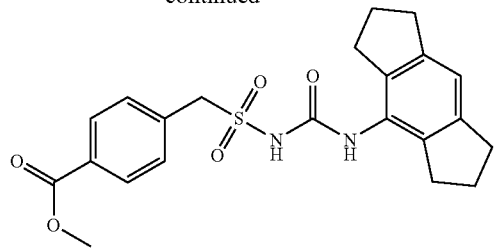

Prepared as described for 1-(4-cyanophenyl)-N-((1,2,3,5,6,7-hexahydro-s-indacen-4-yl)carbamoyl)methanesulfonamide, sodium salt (Example 30) to afford the title compound (125 mg, 72%) as a white solid.

$^1$H NMR (400 MHz, DMSO-$d_6$) δ 7.84 (d, 2H), 7.44 (d, 2H), 7.26 (br s, 1H), 6.79 (s, 1H), 4.32 (s, 2H), 3.84 (s, 3H), 2.79-2.70 (m, 8H) and 1.95-1.91 (m, 4H).

LCMS: m/z 429 (M+H)+ (ES+).

Example 32: N-((1,2,3,5,6,7-Hexahydro-s-indacen-4-yl)carbamoyl)-1-(3-methoxyphenyl)methanesulfonamide, Sodium Salt

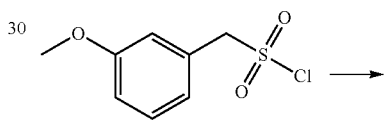

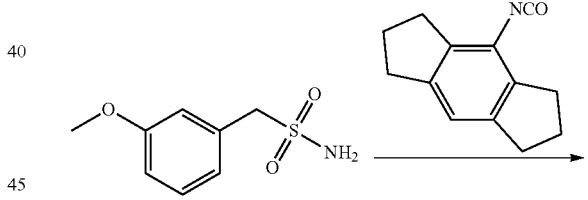

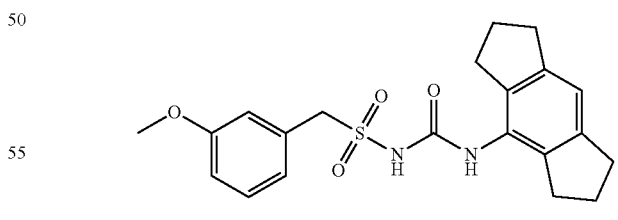

Prepared as described for 1-(4-cyanophenyl)-N-((1,2,3,5,6,7-hexahydro-s-indacen-4-yl)carbamoyl)methanesulfonamide, sodium salt (Example 30) to afford the title compound (172 mg, 31%) as a white solid.

$^1$H NMR (400 MHz, DMSO-$d_6$) δ 7.30-7.29 (m, 4H), 7.25 (br s, 1H), 6.78 (s, 1H), 4.21 (s, 2H), 3.33 (s, 3H), 2.77-2.72 (m, 8H) and 1.95-1.91 (m, 4H).

LCMS: m/z 401 (M+H)+ (ES+).

Example 33: Methyl 2-((N-((1,2,3,5,6,7-hexahydro-s-indacen-4-yl) carbamoyl)sulfamoyl)methyl)benzoate

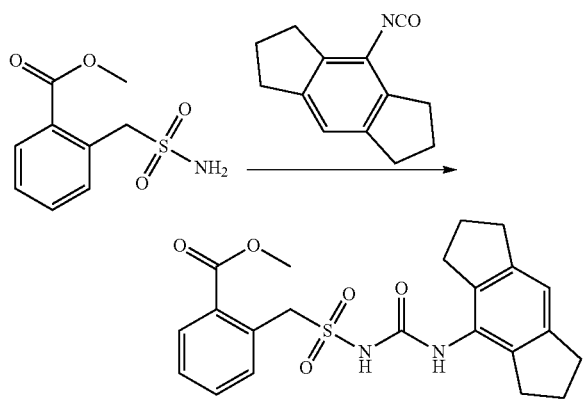

To a solution of methyl 2-(sulfamoylmethyl)benzoate (100 mg, 436.20 µmol) in THF (4 mL) was added sodium methoxide (23.56 mg, 436.20 µmol). The mixture was stirred at 20° C. for 30 minutes before 4-isocyanato-1,2,3,5,6,7-hexahydro-s-indacene (Intermediate A1) (104.29 mg, 523.44 µmol, 1.2 eq) was added. The reaction mixture was stirred at 20° C. for 16 hours and then concentrated in vacuo. The crude product was purified by prep-HPLC (column: Phenomenex Gemini 150 mm*25 mm*10 µm; mobile phase: [water (0.04% NH$_3$H$_2$O+10 mM NH$_4$HCO$_3$)-acetonitrile]; B %: 20%-50%, 12 min) to give the title compound (46 mg, 25%) as a white solid.

$^1$H NMR (400 MHz, DMSO-d$_6$) δ 10.17 (br s, 1H), 7.88-7.86 (m, 2H), 7.63-7.61 (m, 1H), 7.57-7.55 (m, 1H), 7.42-7.40 (m, 1H), 6.98 (s, 1H), 5.19 (s, 2H), 3.79 (s, 3H), 2.85-2.81 (m, 4H), 2.74-2.72 (m, 4H) and 2.05-1.99 (m, 4H).

LCMS: m/z 451 (M+Na)$^+$ (ES$^+$).

Example 34: 3-Azido-N-((1,2,3,5,6,7-hexahydro-s-indacen-4-yl)carbamoyl) propane-1-sulfonamide, Potassium Salt

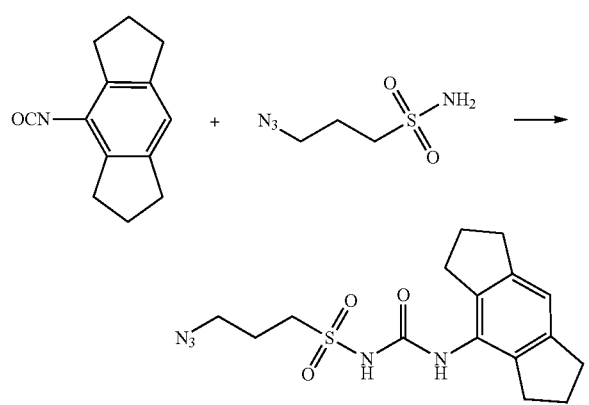

To a solution of 3-azidopropane-1-sulfonamide (Intermediate P30) (200 mg, 2.1 mmol) in THF (15 mL) was added potassium tert-butoxide (236 mg, 2.1 mmol). The mixture was stirred at room temperature for 45 minutes. 4-Isocyanato-1,2,3,5,6,7-hexahydro-s-indacene (Intermediate A1) (419 mg, 2.1 mmol) was added and the mixture was stirred for 2 hours at room temperature. Then the reaction mixture was concentrated in vacuo and a part of the mixture was dissolved in DMSO (1 mL) and submitted for purification by reversed phase column chromatography (see "Experimental Methods", "Purification Method") to afford an initial amount of title compound (55 mg) as a white solid. The remainder of the batch was stored.

LCMS: m/z 364 (M+H)$^+$ (ES$^+$); 362 (M–H)$^-$ (ES$^-$).

Example 35: N-((1,2,3,5,6,7-Hexahydro-s-indacen-4-yl)carbamoyl)-1-(1-methyl-1H-pyrazol-4-yl)methanesulfonamide

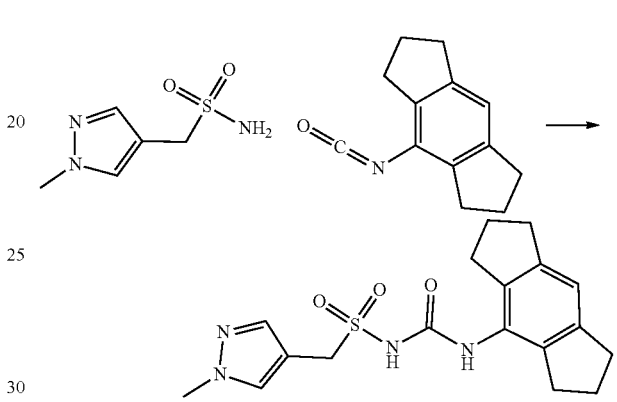

NaO$^t$Bu (2 M in THF, 0.17 mL, 0.34 mmol) was added to a solution of (1-methyl-1H-pyrazol-4-yl)methanesulfonamide (60 mg, 0.325 mmol) in a mixture of THF (3.5 mL) and DMF (0.5 mL) at room temperature. The mixture was stirred for 1 hour, before 4-isocyanato-1,2,3,5,6,7-hexahydro-s-indacene (Intermediate A1) (71 mg, 0.358 mmol) was added in a single portion and the reaction mixture was stirred for 21 hours at room temperature. EtOAc (10 mL) was added, followed by aq 2 M NaOH (~0.2 mL) and water (3 mL). The phases were separated and the organic phase was washed with water (3 mL). The combined aqueous phases were filtered and purified by chromatography on RP Flash C18 (12 g column, 5-100% MeCN/10 mM ammonium bicarbonate) to afford the title compound (0.10 g, 81%) as a white solid.

$^1$H NMR (DMSO-d6) δ 7.58 (s, 1H), 7.53 (br s, 1H), 7.30 (s, 1H), 6.86 (s, 1H), 4.31-4.23 (m, 2H), 3.80 (s, 3H), 2.79 (t, J=7.4 Hz, 4H), 2.72 (t, J=7.3 Hz, 4H), 1.96 (p, J=7.5 Hz, 4H). NH not observed.

LCMS; m/z 397.3 (M+Na)+(ES+).

Example 36: 3-(Dimethylamino)-N-((1,2,3,5,6,7-hexahydro-s-indacen-4-yl)carbamoyl)-2-methylpropane-1-sulfonamide, potassium salt

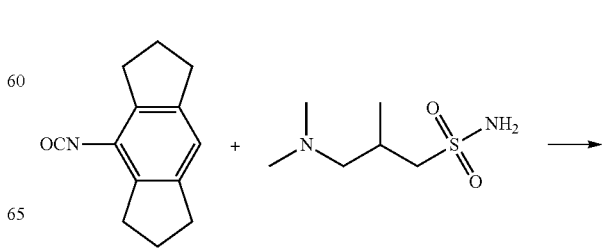

231

-continued

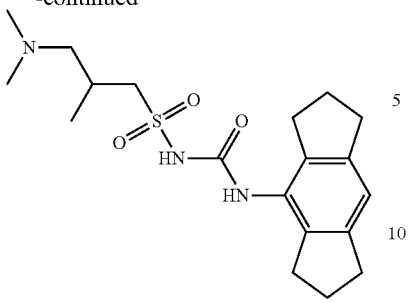

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(dimethylamino)-2-methylpropane-1-sulfonamide (Intermediate P29) to afford the title compound (2 mg, 3%) as a white solid.

$^1$H NMR (Methanol-d$_4$) δ 6.88 (s, 1H), 3.29-3.06 (m, 2H), 2.83 (m, 9H), 2.77-2.59 (m, 1H), 2.46 (s, 6H), 2.45 (m, 1H), 2.02 (m, 4H), 1.15 (d, 3H).

LCMS: m/z 380 (M+H)$^+$ (ES$^+$); 378 (M–H)$^-$ (ES$^-$).

Example 37: 3-(Diethylamino)-N-((4-fluoro-2-isopropyl-6-(pyridin-3-yl) phenyl)carbamoyl)propane-1-sulfonamide

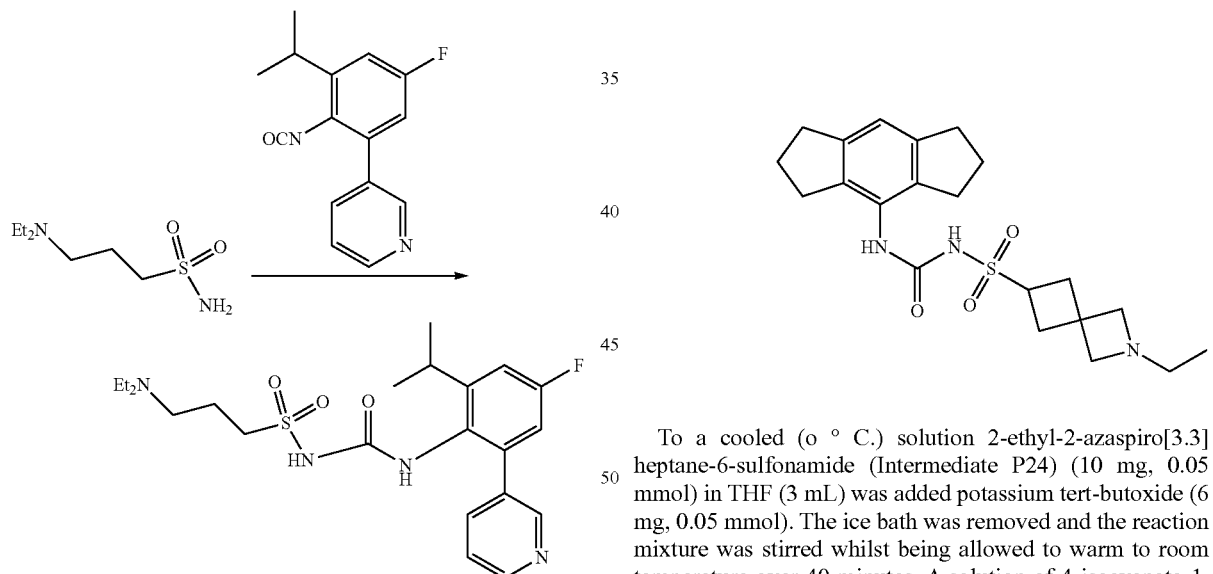

To a solution of 3-(diethylamino)propane-1-sulfonamide (Intermediate P3) (200 mg, 1.03 mmol, 1 eq) in THF (5 mL) was added NaOMe (56 mg, 1.03 mmol, 1 eq) and 3-(5-fluoro-2-isocyanato-3-isopropylphenyl)pyridine (Intermediate A6) (263.80 mg, 1.03 mmol, 1 eq). The reaction mixture was stirred at 70° C. for 30 minutes. The reaction mixture was filtered and the filtrate was concentrated in vacuo. The residue was purified by prep-HPLC (column: Phenomenex Gemini, 250 mm*25 mm*5 μm; mobile phase: [A: water (0.04% ammonium hydroxide v/v); B: MeCN]; B %: 18%-39%, 10 min) to give the title compound (58.2 mg, 11% yield, 100% purity on LCMS) as a brown solid.

232

$^1$H NMR (DMSO-d$_6$): δ 8.59 (br s, 1H), 8.50 (dd, 1H), 7.83-7.81 (m, 1H), 7.38 (dd 2H), 7.12 (dd, 1H), 6.97 (d, 1H), 3.29-3.25 (m, 1H), 2.75-2.73 (m, 2H), 2.49-2.43 (m, 6H), 1.64-1.60 (m, 2H), 1.16 (d, 6H) and 0.97 (t, 6H).

LCMS: m/z 451.2 (M+H)$^+$ (ES$^+$).

Example 38: 2-Ethyl-N-((1,2,3,5,6,7-hexahydro-s-indacen-4-yl)carbamoyl)-2-azaspiro[3.3]heptane-6-sulfonamide, potassium salt To a cooled (0° C.) solution 2-ethyl-2-azaspiro[3.3]heptane-6-sulfonamide (Intermediate P24) (10 mg, 0.05 mmol) in THF (3 mL) was added potassium tert-butoxide (6 mg, 0.05 mmol). The ice bath was removed and the reaction mixture was stirred whilst being allowed to warm to room temperature over 40 minutes. A solution of 4-isocyanato-1,2,3,5,6,7-hexahydro-s-indacene (Intermediate A1) (10 mg, 0.05 mmol) in THF (1 mL) was added and the mixture was stirred overnight at room temperature. The reaction mixture was concentrated in vacuo and DMSO (1 mL) was added. The suspension was filtered over cotton wool and subsequently submitted for purification by reversed phase column chromatography (see "Experimental Methods") to afford the title compound (7 mg, 35%) as a white solid.

$^1$H NMR (CD$_3$OD) δ 6.86 (s, 1H), 4.05 (m, 1H), 3.61 (m, 4H), 2.82 (m, 8H), 2.73 (m, 2H), 2.64 (m, 2H), 2.53 (m, 2H), 2.02 (m, 4H) and 1.03 (t, 3H).

LCMS: m/z 404 (M+H)$^+$ (ES$^+$); 402 (M–H)$^-$ (ES$^-$).

Example 39: N-((1,2,3,5,6,7-Hexahydro-s-indacen-4-yl)carbamoyl)-2-isopropyl-2-azaspiro[3.3]heptane-6-sulfonamide, potassium salt

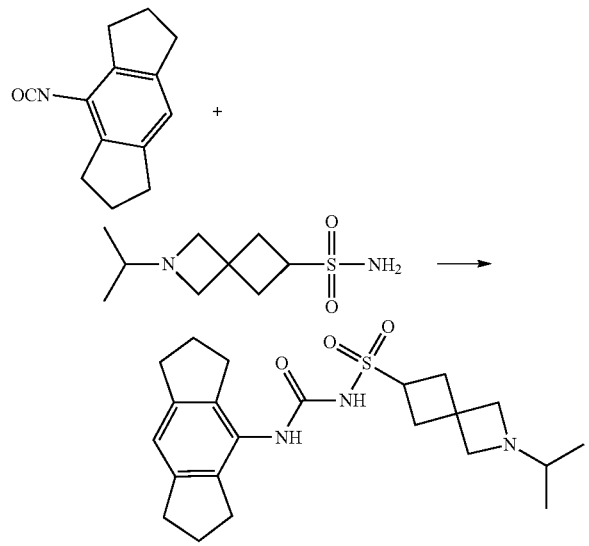

Prepared as described for 2-ethyl-N-((1,2,3,5,6,7-hexahydro-s-indacen-4-yl)carbamoyl)-2-azaspiro[33]heptane-6-sulfonamide, potassium salt (Example 38) using 4-isocyanato-1,2,3,5,6,7-hexahydro-s-indacene (Intermediate A1) and 2-isopropyl-2-azaspiro[3.3]heptane-6-sulfonamide (Intermediate P25) to afford the title compound (41%) as a white solid.

$^1$H NMR (CD$_3$OD) δ 6.89 (s, 1H), 4.28-3.80 (m, 5H), 3.26-3.12 (m, 1H), 2.81 (dt, 8H), 2.73-2.55 (m, 4H), 2.04 (q, 4H), 1.14 (d, 6H).

LCMS: m/z 418 (M+H)+(ES+); 416 (M−H)− (ES−).

Example 40: N-((1,2,3,5,6,7-Hexahydro-s-indacen-4-yl)carbamoyl)-2-methyl-2-azaspiro[3.3]heptane-6-sulfonamide, potassium salt

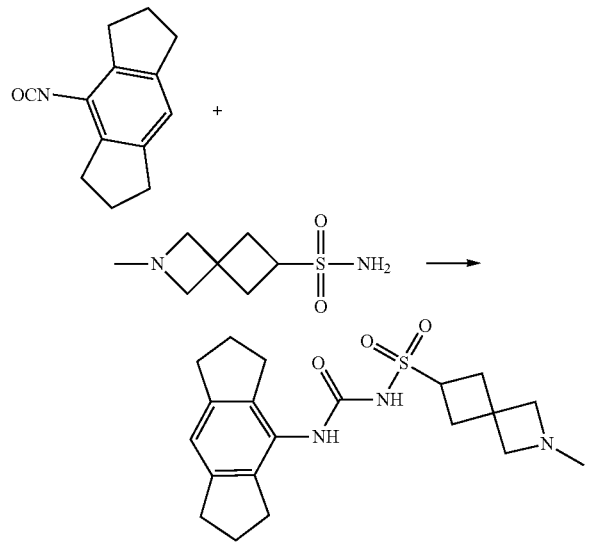

Prepared as described for 2-ethyl-N-((1,2,3,5,6,7-hexahydro-s-indacen-4-yl)carbamoyl)-2-azaspiro[3.3]heptane-6-sulfonamide, potassium salt (Example 38) using 4-isocyanato-1,2,3,5,6,7-hexahydro-s-indacene (Intermediate A1) and 2-methyl-2-azaspiro[3.3]heptane-6-sulfonamide (Intermediate P26) to afford the title compound (14%) as a white solid.

$^1$H NMR (CD$_3$OD) δ 6.88 (s, 1H), 4.04 (m, 5H), 2.96-2.72 (m, 11H), 2.72-2.55 (m, 4H), 2.02 (m, 4H).

LCMS: m/z 390 (M+H)+(ES+); 388 (M−H)− (ES−).

Example 41: N-((2-(2-Cyanopyridin-4-yl)-4-fluoro-6-isopropylphenyl) carbamoyl)-3-(diethylamino)propane-1-sulfonamide

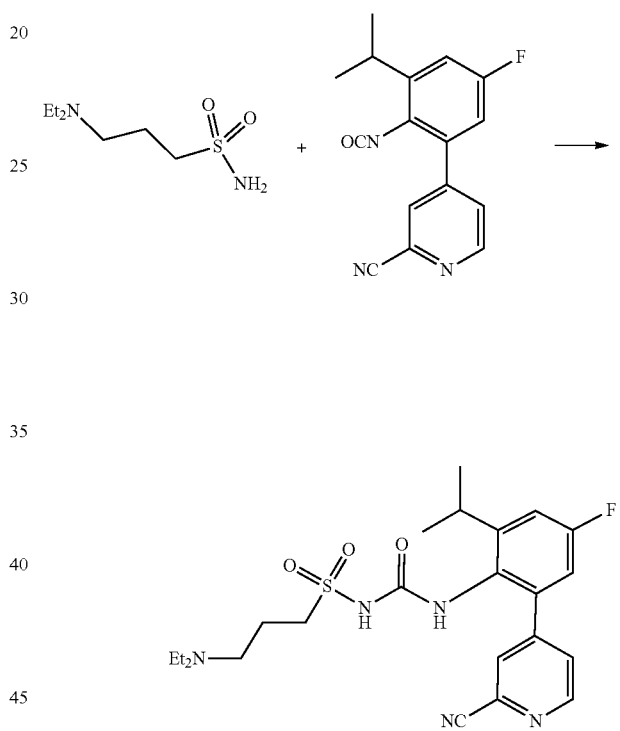

To a solution of 3-(diethylamino)propane-1-sulfonamide (Intermediate P3) (80 mg, 411.75 μmol, 1 eq) in THF (1 mL) was added t-BuONa (40 mg, 411.75 μmol, 1 eq) and the mixture was stirred at 25° C. for 10 minutes. Then 4-(5-fluoro-2-isocyanato-3-isopropylphenyl)picolinonitrile (Intermediate A3) (116 mg, 411.75 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 12%-42%, 11.5 min) to give the title compound (105.29 mg, 55% yield, 100% purity on LCMS) as a white solid.

$^1$H NMR (DMSO-d$_6$): δ 8.75 (d, 1H), 8.08 (s, 1H), 7.79-7.73 (m, 2H), 7.23 (d, 1H), 7.13 (d, 1H), 3.09-3.06 (m, 1H), 3.03-2.88 (m, 8H), 1.75-1.72 (m, 2H), 1.16 (d, 6H) and 1.09 (t, 6H).

LCMS: m/z 476.3 (M+H)$^+$ (ES$^+$).

235

Example 42: 3-(Diethylamino)-N-((4-fluoro-2-isopropyl-6-(2-methoxypyridin-4-yl)phenyl)carbamoyl)propane-1-sulfonamide

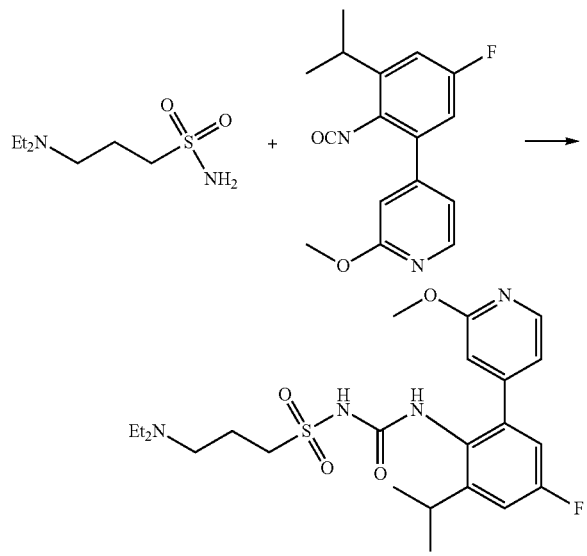

To a solution of 3-(diethylamino)propane-1-sulfonamide (Intermediate P3) (80 mg, 411.75 μmol, 1 eq) in THF (1 mL) was added t-BuONa (40 mg, 411.75 μmol, 1 eq) and the mixture was stirred at 25° C. for 10 minutes. Then 4-(5-fluoro-2-isocyanato-3-isopropylphenyl)-2-methoxypyridine (Intermediate A4) (118 mg, 411.75 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 18%-48%, 11.5 min) to give the title compound (59.65 mg, 30% yield, 100% purity on LCMS) as a white solid.

$^1$H NMR (DMSO-d$_6$): δ 8.15 (d, 1H), 7.64 (s, 1H), 7.19 (d, 1H), 7.09-6.95 (m, 2H), 6.85 (s, 1H), 3.87 (s, 3H), 3.23-3.20 (m, 1H), 3.04-2.75 (m, 8H), 1.77-1.72 (m, 2H), 1.16 (d, 6H) and 1.09-1.04 (m, 6H).

LCMS: m/z 481.3 (M+H)$^+$ (ES$^+$).

Example 43: 3-(Diethylamino)-N-((5-(2-methoxypyridin-4-yl)-2,3-dihydro-1H-inden-4-yl)carbamoyl)propane-1-sulfonamide

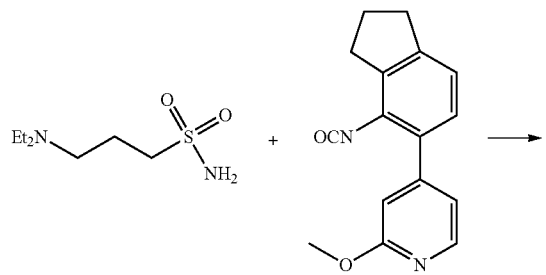

236

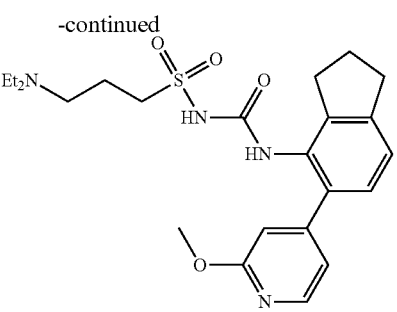

To a solution of 3-(diethylamino)propane-1-sulfonamide (Intermediate P3) (80 mg, 411.75 μmol, 1 eq) in THF (1 mL) was added t-BuONa (40 mg, 411.75 μmol, 1 eq) and the mixture was stirred at 25° C. for 10 minutes. Then 4-(4-isocyanato-2,3-dihydro-1H-inden-5-yl)-2-methoxypyridine (Intermediate A5) (171 mg, 411.75 μmol, purity: 64% on LCMS, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 15%-45%, 11.5 min) to give the title compound (53.15 mg, 28% yield, 100% purity on LCMS) as a pink solid.

$^1$H NMR (DMSO-d$_6$): δ 8.13 (d, 1H), 7.64 (br s, 1H), 7.15 (d, 1H), 7.09 (d, 1H), 6.97 (dd, 1H), 6.78 (s, 1H), 3.86 (s, 3H), 3.08 (t, 2H), 2.91 (t, 2H), 2.85-2.76 (m, 8H), 2.03-2.00 (m, 2H), 1.82-1.78 (m, 2H) and 1.05 (t, 6H).

LCMS: m/z 461.3 (M+H)$^+$ (ES$^+$).

Example 44: 3-(Diethylamino)-N-((7-fluoro-5-(pyridin-4-yl)-2,3-dihydro-1H-inden-4-yl)carbamoyl)propane-1-sulfonamide

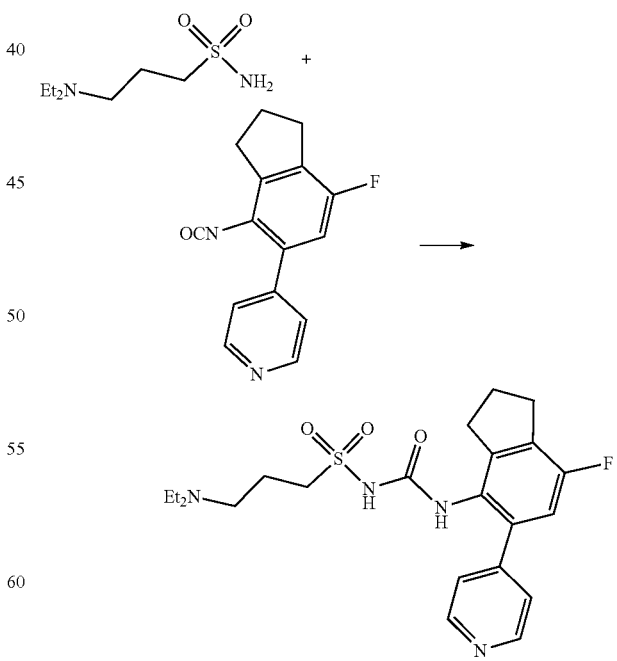

A mixture of 3-(diethylamino)propane-1-sulfonamide (Intermediate P3) (60 mg, 308.81 μmol, 1 eq) and t-BuONa (30 mg, 308.81 μmol, 1 eq) in THF (2 mL) was stirred at 25°

Example 45: 3-(Benzyl(ethyl)amino)-N-((4-fluoro-2-isopropyl-6-(2-methoxypyridin-4-yl)phenyl)carbamoyl)propane-1-sulfonamide

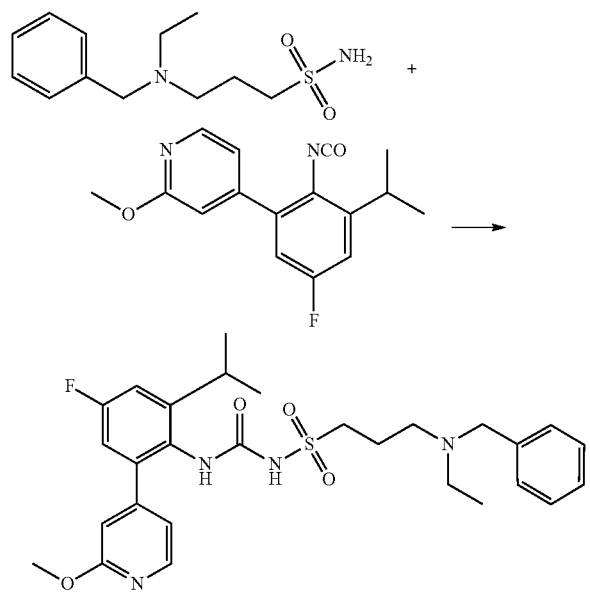

To a solution of 3-(benzyl(ethyl)amino)propane-1-sulfonamide (Intermediate P27) (90 mg, 351.06 μmol, 1 eq) in THF (1 mL) was added t-BuONa (34 mg, 351.06 μmol, 1 eq) and the mixture was stirred at 25° C. for 10 minutes. Then 4-(5-fluoro-2-isocyanato-3-isopropylphenyl)-2-methoxypyridine (Intermediate A4) (101 mg, 351.06 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 20%-50%, 11.5 min) to give the title compound (66.21 mg, 35% yield, 100% purity on LCMS) as a white solid.

$^1$H NMR (DMSO-d$_6$): δ 8.13 (d, 1H), 7.72 (s, 1H), 7.32-7.20 (m, 6H), 7.06-7.01 (m, 2H), 6.83 (s, 1H), 3.85 (s, 3H), 3.53 (s, 2H), 3.19-315 (m, 1H), 3.04-3.01 (m, 2H), 2.44-2.40 (m, 4H), 1.68-1.64 (m, 2H), 1.15 (d, 6H) and 0.96 (t, 3H).

LCMS: m/z 543.4 (M+H)$^+$ (ES$^+$).

C. for 10 minutes. Then 4-(7-fluoro-4-isocyanato-2,3-dihydro-1H-inden-5-yl)pyridine (Intermediate A2) (78 mg, 308.81 μmol, 1 eq) was added. The resulting mixture was stirred at 25° C. for 10 minutes. The reaction mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 10%-40%, 10 minutes) to give the title compound (18.1 mg, 13% yield, 100% purity on LCMS) as a white solid.

$^1$H NMR (DMSO-d$_6$): δ 8.58-8.56 (m, 2H), 7.61 (br s, 1H), 7.41 (d, 2H), 6.99 (d, 1H), 3.03 (t, 2H), 2.96 (t, 2H), 2.90-2.78 (m, 8H), 2.11-2.04 (m, 2H), 1.82-1.75 (m, 2H) and 1.07 (t, 6H).

LCMS: m/z 449.2 (M+H)$^+$ (ES$^+$).

Example 46: 3-(Benzyl(ethyl)amino)-N-((2-(2-cyanopyridin-4-yl)-4-fluoro-6-isopropylphenyl)carbamoyl)propane-1-sulfonamide

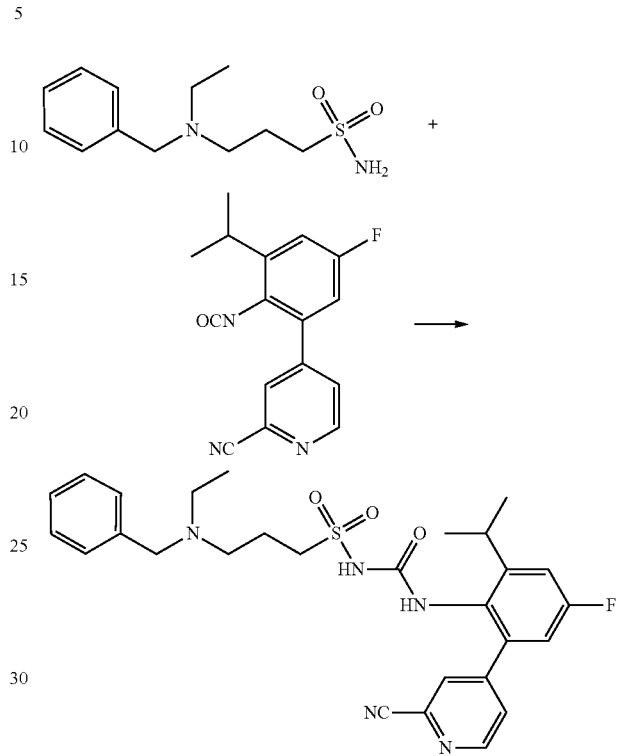

To a solution of 3-(benzyl(ethyl)amino)propane-1-sulfonamide (Intermediate P27) (100 mg, 390.07 μmol, 1 eq) in THF (1 mL) was added t-BuONa (37 mg, 390.07 μmol, 1 eq) and the mixture was stirred at 25° C. for 10 minutes. Then 4-(5-fluoro-2-isocyanato-3-isopropylphenyl)picolinonitrile (Intermediate A3) (no mg, 390.07 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 28%-58%, 11.5 min) to give the title compound (37.69 mg, 18% yield, 100% purity on LCMS) as a white solid.

$^1$H NMR (DMSO-d$_6$): δ 10.49 (br s, 1H), 8.76 (d, 1H), 8.14 (s, 1H), 8.09 (s, 1H), 7.76 (dd, 1H), 7.34-7.20 (m, 7H), 3.74 (s, 2H), 3.18-3.09 (m, 3H), 2.47-2.42 (m, 4H), 1.65-1.62 (m, 2H), 1.17 (d, 6H) and 0.96 (t, 3H).

LCMS: m/z 538.4 (M+H)$^+$ (ES$^+$).

Example 47: 3-(Benzyl(ethyl)amino)-N-((5-(2-methoxypyridin-4-yl)-2,3-dihydro-1H-inden-4-yl)carbamoyl)propane-1-sulfonamide

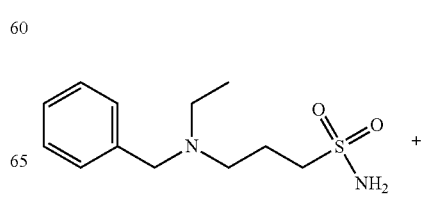

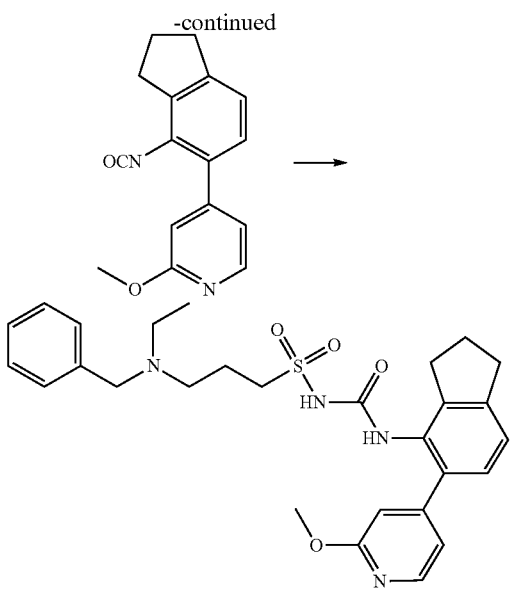

To a solution of 3-(benzyl(ethyl)amino)propane-1-sulfonamide (Intermediate P27) (100 mg, 390.07 μmol, 1 eq) in THF (1 mL) was added t-BuONa (37 mg, 390.07 μmol, 1 eq) and the mixture was stirred at 25° C. for 10 minutes. Then 4-(4-isocyanato-2,3-dihydro-1H-inden-5-yl)-2-methoxypyridine (Intermediate A5) (146 mg, 390.07 μmol, 1 eq) was added. The resulting mixture was stirred at 70° C. for 10 minutes. The mixture was concentrated in vacuo. The residue was purified by prep-HPLC (column: Waters Xbridge C18, 150 mm*50 mm*10 μm; mobile phase: [A: water (10 mM NH$_4$HCO$_3$); B: MeCN]; B %: 18%-48%, 11.5 min) to give the title compound (35.98 mg, 17% yield, 98% purity on LCMS) as a white solid.

$^1$H NMR (DMSO-d$_6$): δ 10.31 (br s, 1H), 8.16 (d, 1H), 8.00 (s, 1H), 7.32-7.26 (m, 4H), 7.24 (d, 2H), 7.14 (d, 1H), 6.93 (d, 1H), 6.75 (s, 1H), 3.86 (s, 3H), 3.56 (s, 2H), 3.26-3.22 (m, 2H), 2.93 (t, 2H), 2.79 (t, 2H), 2.47-2.40 (m, 4H), 2.02-1.97 (m, 2H), 1.81-1.76 (m, 2H) and 0.96 (t, 3H).

LCMS: m/z 523.3 (M+H)$^+$ (ES$^+$).

Example 48: 3-(Benzyl(ethyl)amino)-N-((7-fluoro-5-(pyridin-4-yl)-2,3-dihydro-1H-inden-4-yl)carbamoyl)propane-1-sulfonamide

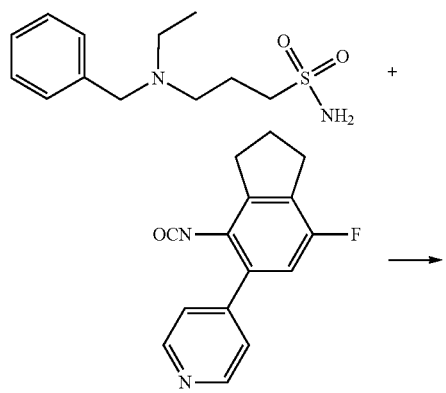

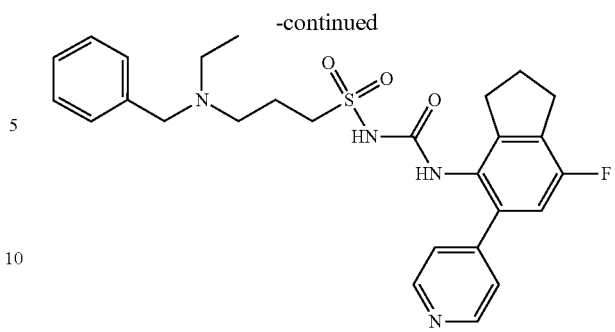

To a solution of 3-(benzyl(ethyl)amino)propane-1-sulfonamide (Intermediate P27) (101 mg, 393.30 μmol, 1 eq) in THF (1 mL) was added t-BuONa (38 mg, 393.30 μmol, 1 eq). The reaction mixture was stirred at 15° C. for 10 minutes. Then 4-(7-fluoro-4-isocyanato-2,3-dihydro-H-inden-5-yl)pyridine (Intermediate A2) (100 mg, 393.30 μmol, 1 eq) was added. The resulting mixture was stirred at 15° C. for 10 minutes. The reaction mixture was concentrated in vacuo. The residue was purified by prep-HPLC (column: Phenomenex Gemini C18, 150 mm*25 mm*10 μm, mobile phase: [A: water (0.05% ammonium hydroxide v/v); B: MeCN]; B %: 5%-35%, 10 min) to give the title compound (67.23 mg, 33% yield, 100% purity on LCMS) as a pink solid.

$^1$H NMR (DMSO-d$_6$): δ 8.57 (d, 2H), 7.86 (br s, 1H), 7.38 (d, 2H), 7.31 (d, 4H), 7.26-7.23 (m, 1H), 7.03 (d, 1H), 3.56 (s, 2H), 3.18-3.15 (m, 2H), 2.96 (t, 2H), 2.85 (t, 2H), 2.47-2.42 (m, 4H), 2.10-2.03 (m, 2H), 1.76-1.70 (m, 2H) and 0.96 (t, 3H).

LCMS: m/z 511.3 (M+H)$^+$ (ES$^+$).

Example 49: N-((2-(2-Cyanopyridin-4-yl)-4-fluoro-6-isopropylphenyl) carbamoyl)-3-methoxypropane-1-sulfonamide

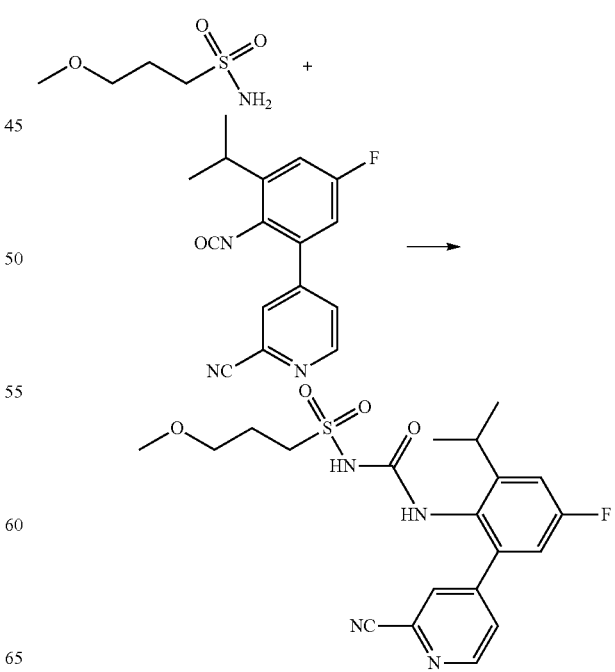

To a solution of 3-methoxypropane-1-sulfonamide (Intermediate P28) (65 mg, 426.62 μmol, 1.2 eq) in THF (1 mL) was added t-BuONa (34 mg, 355.51 μmol, 1 eq) and the mixture was stirred at 25° C. for 10 minutes. Then 4-(5-fluoro-2-isocyanato-3-isopropylphenyl)picolinonitrile (Intermediate A3) (100 mg, 355.51 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 5%-35%, 11.5 min) to give the title compound (113.93 mg, 74% yield, 100% purity on LCMS) as a white solid.

$^1$HNMR (DMSO-$d_6$): δ 8.71 (d, 1H), 8.06 (s, 1H), 7.77 (s, 1H), 7.58 (s, 1H), 7.23-7.18 (m, 1H), 7.10 (d, 1H), 3.29-3.24 (m, 3H), 3.21 (s, 3H), 2.76-2.73 (m, 2H), 1.60-1.57 (m, 2H) and 1.16 (d, 6H).

LCMS: m/z 435.2 (M+H)$^+$ (ES$^+$).

Example 50: N-((4-Fluoro-2-isopropyl-6-(2-methoxypyridin-4-yl) phenyl)carbamoyl)-3-methoxypropane-1-sulfonamide

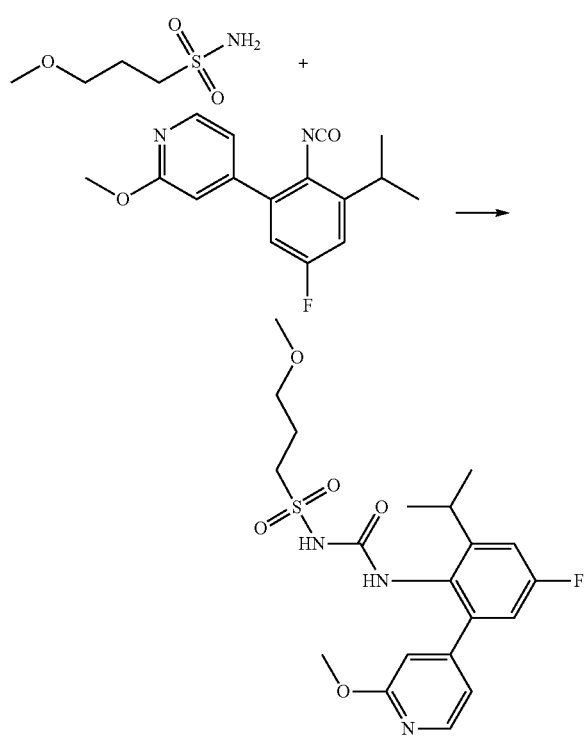

To a solution of 3-methoxypropane-1-sulfonamide (Intermediate P28) (64 mg, 419.14 μmol, 1.2 eq) in THF (1 mL) was added t-BuONa (34 mg, 349.28 μmol, 1 eq) and the mixture was stirred at 25° C. for 10 minutes. Then 4-(5-fluoro-2-isocyanato-3-isopropylphenyl)-2-methoxypyridine (Intermediate A4) (100 mg, 349.28 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 8%-38%, 11.5 min) to give the title compound (130.95 mg, 85% yield, 99.7% purity on LCMS) as a white solid.

$^1$H NMR (DMSO-$d_6$): δ 8.11 (d, 1H), 7.51 (s, 1H), 7.16 (d, 1H), 7.02-6.95 (m, 2H), 6.84 (s, 1H), 3.86 (s, 3H), 3.34-3.27 (m, 3H), 3.21 (s, 3H), 2.90-2.86 (m, 2H), 1.72-1.61 (m, 2H) and 1.15 (d, 6H).

LCMS: m/z 440.2 (M+H)$^+$ (ES$^+$).

Example 51: 3-Methoxy-N-((5-(2-methoxypyridin-4-yl)-2,3-dihydro-1H-inden-4-yl)carbamoyl)propane-1-sulfonamide

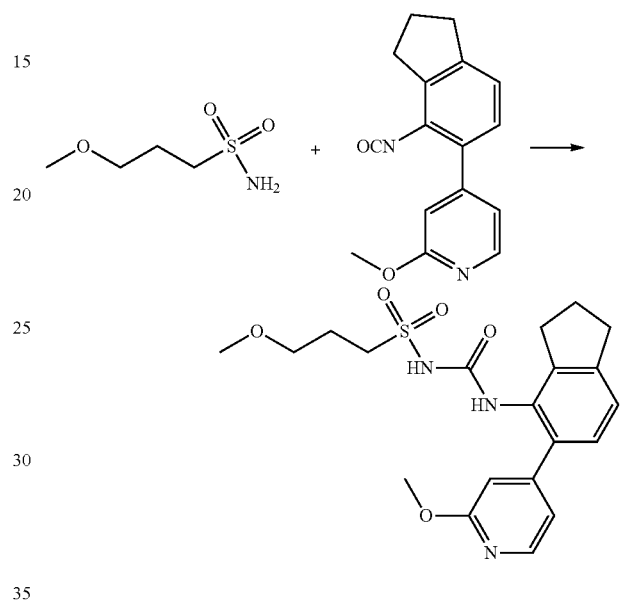

To a solution of 3-methoxypropane-1-sulfonamide (Intermediate P28) (72 mg, 469.98 μmol, 1.2 eq) in THF (1 mL) was added t-BuONa (38 mg, 391.65 μmol, 1 eq) and the mixture was stirred at 25° C. for 10 minutes. Then 4-(4-isocyanato-2,3-dihydro-1H-inden-5-yl)-2-methoxypyridine (Intermediate A5) (163 mg, 391.65 μmol, 1 eq) was added. The resulting mixture was stirred at 70° C. for 10 minutes. The mixture was concentrated in vacuo. The residue was purified by prep-HPLC (column: Waters Xbridge C18, 150 mm*25 mm*5 μm; mobile phase: [A: water (0.05% ammonium hydroxide v/v); B: MeCN]; B %: 5%-35%, 11.5 min) to give the title compound (15.13 mg, 9% yield, 100% purity on LCMS) as a white solid.

$^1$H NMR (DMSO-$d_6$): δ 10.34 (br s, 1H), 8.17 (d, 1H), 7.97 (br s, 1H), 7.24 (d, 1H), 7.14 (d, 1H), 6.94 (d, 1H), 6.76 (s, 1H), 3.88 (s, 3H), 3.37 (t, 2H), 3.26-3.20 (m, 5H), 2.95 (t, 2H), 2.81 (t, 2H), 2.06-2.02 (m, 2H) and 1.84-1.78 (m, 2H).

LCMS: m/z 420.2 (M+H)$^+$ (ES$^+$).

Example 52: N-((7-Fluoro-5-(pyridin-4-yl)-2,3-dihydro-H-inden-4-yl) carbamoyl)-3-methoxypropane-1-sulfonamide

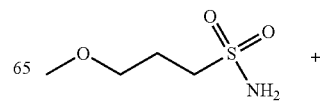

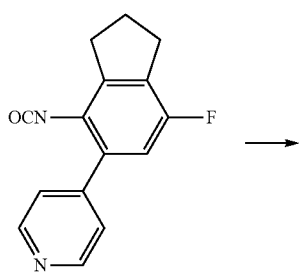

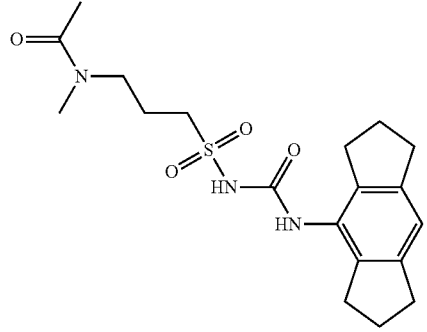

Prepared as described for N-ethyl-N-(4-(N-((1,2,3,5,6,7-hexahydro-s-indacen-4-yl)carbamoyl)sulfamoyl)cyclohexyl)acetamide, potassium salt (Example 63) using 4-isocyanato-1,2,3,5,6,7-hexahydro-s-indacene (Intermediate A1) and N-methyl-N-(3-sulfamoylpropyl)acetamide (Intermediate P75) to afford the title compound (60 mg, 37%) as a white solid.

$^1$H NMR (Methanol-d$_4$) δ 6.87 (s, 1H), 3.51 (q, 2H), 3.22 (m, 2H), 3.06 (s, 3H), 2.92 (s, 3H), 2.82 (m, 8H), 2.12-1.92 (m, 6H).

LCMS: m/z 394 (M+H)$^+$ (ES$^+$); 392 (M–H)$^-$ (ES$^-$).

Example 54: N-((4-Fluoro-2-isopropyl-6-(2-methoxypyridin-4-yl)phenyl) carbamoyl)-1-(pyridin-3-yl)methanesulfonamide To a solution of 3-methoxypropane-1-sulfonamide (Intermediate P28) (60 mg, 393.30 µmol, 1 eq) in THF (1 mL) was added t-BuONa (38 mg, 393.30 µmol, 1 eq). The reaction mixture was stirred at 15° C. for 10 minutes. Then 4-(7-fluoro-4-isocyanato-2,3-dihydro-1H-inden-5-yl)pyridine (Intermediate A2) (100 mg, 393.30 µmol, 1 eq) was added. The resulting mixture was stirred at 15° C. for 20 minutes. The reaction mixture was concentrated in vacuo. The residue was purified by prep-HPLC (column: Phenomenex Gemini C18, 150 mm*25 mm*10 µm; mobile phase: [A: water (0.05% ammonium hydroxide v/v); B: MeCN]; B %: 0%-30%, 10 min) to give the title compound (62.33 mg, 38% yield, 100% purity on LCMS) as a pink solid.

$^1$H NMR (DMSO-d$_6$): δ 8.57 (d, 2H), 7.63 (br s, 1H), 7.40 (d, 2H), 7.00 (d, 1H), 3.37-3.34 (m, 2H), 3.23 (s, 3H), 3.07-3.04 (m, 2H), 2.97 (t, H), 2.87 (t, 2H), 2.11-2.05 (m, 2H) and 1.79-1.72 (m, 2H).

LCMS: m/z 408.2 (M+H)$^+$ (ES$^+$).

Example 53: N-(3-(N-((1,2,3,5,6,7-Hexahydro-s-indacen-4-yl)carbamoyl) sulfamoyl)propyl)-N-methylacetamide, Potassium Salt

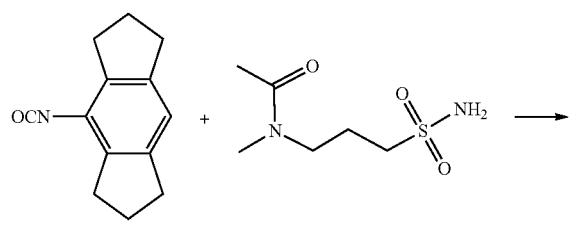

To a solution of pyridin-3-ylmethanesulfonamide (60 mg, 348.42 µmol, 1 eq) in THF (5 mL) was added t-BuONa (33 mg, 348.42 µmol, 1 eq) and 4-(5-fluoro-2-isocyanato-3- isopropylphenyl)-2-methoxypyridine (Intermediate A4) (100 mg, 348.42 µmol, 1 eq). The mixture was stirred at 25° C. for 30 minutes. The reaction mixture was concentrated under reduced pressure. The residue was purified by prep-HPLC (column: Phenomenex Gemini C18, 150 mm*25 mm*10 µm; mobile phase: [A: water (0.05% ammonium hydroxide v/v); B: MeCN]; B %: 8%-38%, 11.5 min) to give the title compound (70 mg, 44% yield, 100% purity on LCMS) as a white solid.

$^1$H NMR (DMSO-d$_6$): δ 8.50 (d, 1H), 8.41 (s, 1H), 8.16 (d, 1H), 7.61 (br s, 1H), 7.50 (d, 1H), 7.33-7.30 (m, 1H), 7.21 (d, 1H), 7.06-7.00 (m, 2H), 6.87 (s, 1H), 4.33 (s, 2H), 3.85 (s, 3H), 3.22-3.17 (t, 1H) and 1.20-1.04 (m, 6H).

LCMS: m/z 459.3 (M+H)$^+$ (ES$^+$).

Example 55: N-((5-(2-Methoxypyridin-4-yl)-2,3-dihydro-1H-inden-4-yl) carbamoyl)-1-(pyridin-3-yl)methanesulfonamide

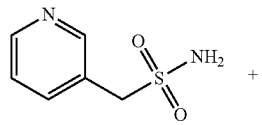

+

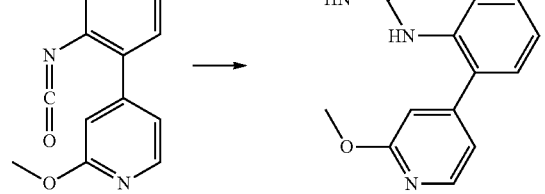

To a solution of pyridin-3-ylmethanesulfonamide (70 mg, 406.49 µmol, 1 eq) in THF (5 mL) was added t-BuONa (39 mg, 406.49 µmol, 1 eq) and 4-(4-isocyanato-2,3-dihydro-1H-inden-5-yl)-2-methoxypyridine (Intermediate A5) (108 mg, 406.49 µmol, 1 eq). The mixture was stirred at 25° C. for 30 minutes. The reaction mixture was concentrated under reduced pressure. The residue was purified by prep-HPLC (column: Phenomenex Gemini C18, 150 mm*25 mm*10 µm; mobile phase: [A: water (0.05% ammonium hydroxide v/v); B: MeCN]; B %: 5%-35%, 11.5 min) to give the title compound (65 mg, 36% yield, 100% purity on LCMS) as a white solid.

$^1$H NMR (DMSO-d$_6$): δ 8.52 (d, 1H), 8.46 (d, 1H), 8.16 (d, 1H), 7.61 (d, 1H), 7.37-734 (m, 1H), 7.17 (d, 1H), 7.10 (d, 1H), 6.97-6.95 (m, 1H), 6.78 (s, 1H), 4.45 (s, 2H), 3.86 (s, 3H), 2.93 (t, 2H), 2.83 (t, 2H) and 2.07-1.98 (m, 2H).

LCMS: m/z 439.3 (M+H)$^+$ (ES$^+$).

Example 56: N-((7-Fluoro-5-(pyridin-4-yl)-2,3-dihydro-1H-inden-4-yl) carbamoyl)-1-(pyridin-3-yl)methanesulfonamide

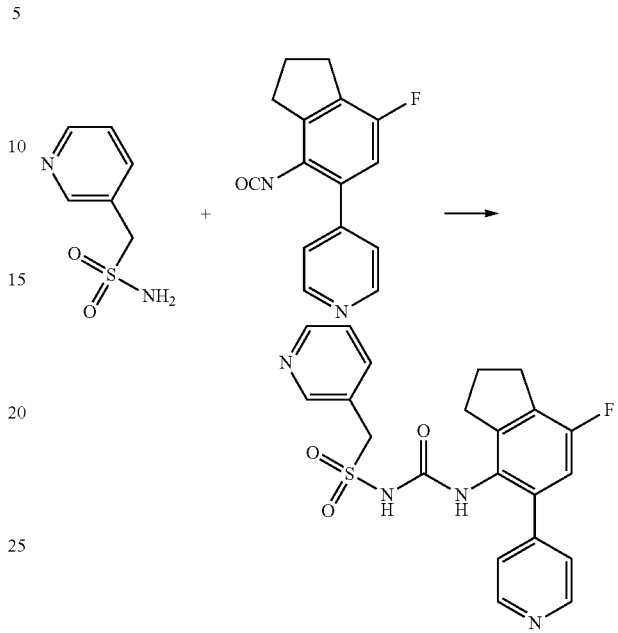

To a solution of pyridin-3-ylmethanesulfonamide (68 mg, 393.30 µmol, 1 eq) in THF (2 mL) was added t-BuONa (38 mg, 393.30 µmol, 1 eq). Then the reaction mixture was stirred at 25° C. for 10 minutes. A solution of 4-(7-fluoro-4-isocyanato-2,3-dihydro-H-inden-5-yl)pyridine (Intermediate A2) (100 mg, 393.30 µmol, 1 eq) in THF (2.5 mL) was added. The resulting mixture was stirred at 25° C. for 30 minutes. The reaction mixture was concentrated under reduced pressure. The residue was purified by prep-HPLC (column: Xtimate C18, 250 mm*50 mm*10 µm; mobile phase: [A: water (0.05% ammonium hydroxide v/v); B: MeCN]; B %: 1%-31%, 10 min) to give the title compound (22.34 mg, 13%) as a white solid.

$^1$H NMR (DMSO-d$_6$): δ 8.57 (d, 2H), 8.49-845 (m, 2H), 7.59 (d, 1H), 7.39 (d, 2H), 7.34-730 (m, 1H), 6.96 (d, 1H), 4.34 (s, 2H), 2.95 (t, 2H), 2.87 (t, 2H) and 210-2.05 (m, 2H).

LCMS: m/z 427.2 (M+H)$^+$ (ES$^+$).

Example 57: N-((2-(2-Cyanopyridin-4-yl)-4-fluoro-6-isopropylphenyl) carbamoyl)-1-(1-methylpyrrolidin-3-yl)methanesulfonamide

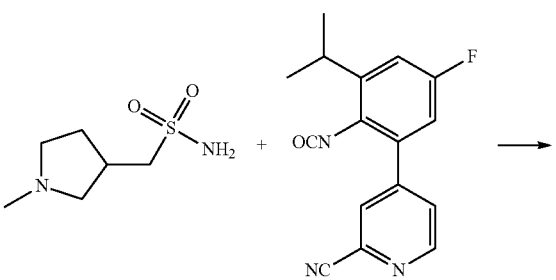

-continued

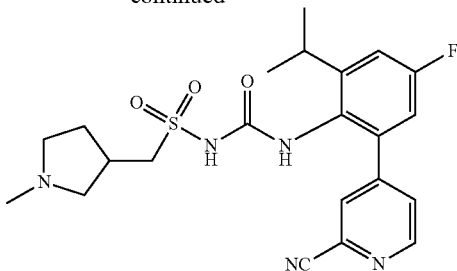

A solution of (1-methylpyrrolidin-3-yl)methanesulfonamide (Intermediate P16) (180 mg, crude) and t-BuONa (97 mg, 1.01 mmol, 1 eq) in THF (3 mL) was stirred at 25° C. for 10 minutes. Then 4-(5-fluoro-2-isocyanato-3-isopropylphenyl)picolinonitrile (Intermediate A3) (57 mg, 201.96 µmol, 0.2 eq) was added. The resulting mixture was stirred at 25° C. for 30 minutes. The reaction mixture was concentrated in vacuo. The residue was purified by prep-HPLC (column: Phenomenex Gemini C18, 150 mm*25 mm*5 µm, mobile phase: [A: water (0.05% ammonium hydroxide v/v); B: MeCN], B %: 10%-40%, 10.0 min) to give the title compound (17.51 mg, 4% yield, 100% purity on LCMS) as a white solid.

$^1$H NMR (DMSO-d$_6$+D$_2$O): δ 8.70 (d, 1H), 8.00 (s, 1H), 7.74 (s, 1H), 7.17 (dd, 1H), 7.06 (dd, 1H), 3.26-3.15 (m, 2H), 3.10-3.01 (m, 2H), 2.95-2.80 (m, 2H), 2.77-2.72 (m, 1H), 2.67 (s, 3H), 2.45-2.40 (m, 1H), 2.10-1.98 (m, 1H), 1.62-1.51 (m, 1H) and 1.13 (d, 6H).

LCMS: m/z 460.2 (M+H)$^+$ (ES$^+$).

Example 58: N-((4-Fluoro-2-isopropyl-6-(2-methoxypyridin-4-yl) phenyl)carbamoyl)-1-(1-methylpyrrolidin-3-yl)methanesulfonamide

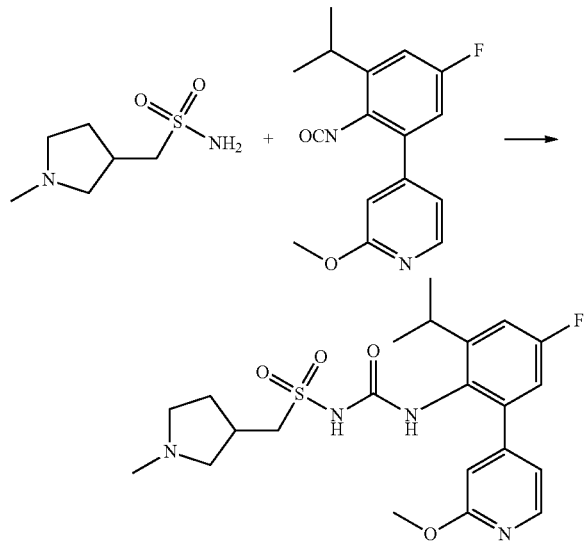

A solution of (1-methylpyrrolidin-3-yl)methanesulfonamide (Intermediate P16) (180 mg, crude) and t-BuONa (97 mg, 1.01 mmol, 1 eq) in THF (3 mL) was stirred at 25° C. for 10 minutes. Then 4-(5-fluoro-2-isocyanato-3-isopropylphenyl)-2-methoxypyridine (Intermediate A4) (58 mg, 201.96 µmol, 0.2 eq) was added. The resulting mixture was stirred at 25° C. for 30 minutes and then concentrated in vacuo. The residue was purified by prep-HPLC (column: Phenomenex Gemini C18, 150 mm*25 mm*5 µm, mobile phase: [A: water (0.05% ammonium hydroxide v/v); B: MeCN], B %: 12%-42%, 10.0 min) to give the title compound (4.92 mg, 1% yield, 100% purity on LCSM) as a white solid.

$^1$H NMR (DMSO-d$_6$+D$_2$O): δ 8.12 (d, 1H), 7.14-7.11 (m, 1H), 7.04-7.02 (m, 1H), 6.96-6.93 (m, 1H), 6.85-6.83 (m, 1H), 3.86 (s, 3H), 3.30-3.14 (m, 2H), 3.05-2.98 (m, 3H), 2.92-2.83 (m, 2H), 2.63 (s, 3H), 2.60-2.57 (m, 1H), 2.04-2.00 (m, 1H), 1.61-1.57 (m, 1H) and 1.14 (d, 6H).

LCMS: m/z 465.2 (M+H)$^+$ (ES$^+$).

Example 59: N-((5-(2-Methoxypyridin-4-yl)-2,3-dihydro-1H-inden-4-yl) carbamoyl)-1-(1-methylpyrrolidin-3-yl)methanesulfonamide

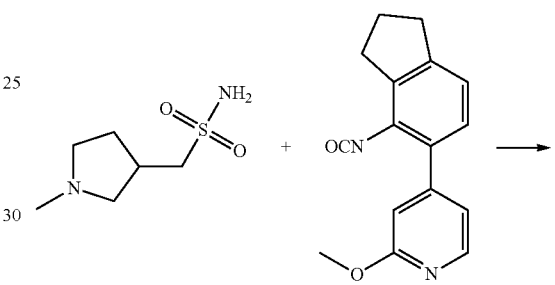

A solution of (1-methylpyrrolidin-3-yl)methanesulfonamide (Intermediate P16) (180 mg, crude) and t-BuONa (97 mg, 1.01 mmol, 1 eq) in THF (3 mL) was stirred at 25° C. for 10 minutes. Then 4-(4-isocyanato-2,3-dihydro-H-inden-5-yl)-2-methoxypyridine (Intermediate A5) (54 mg, 201.96 µmol, 0.2 eq) was added. The resulting mixture was stirred at 25° C. for 30 minutes and then concentrated in vacuo. The residue was purified by prep-HPLC (column: Phenomenex Gemini C18, 150 mm*25 mm*5 µm, mobile phase: [A: water (0.05% ammonium hydroxide v/v); B: MeCN], B %: 10%-40%, 10.0 min) to give the title compound (5-47 mg, 1% yield, 100% purity on LCMS) as a white solid.

$^1$H NMR (DMSO-d$_6$+D$_2$O): δ 8.09 (d, 1H), 7.11 (d, 1H), 7.04 (d, 1H), 6.98 (d, 1H), 6.78 (s, 1H), 3.84 (s, 3H), 3.28-3.21 (m, 1H), 3.15-3.01 (m, 3H), 2.95-2.90 (m, 1H), 2.89-2.86 (m, 3H), 2.84-2.78 (m, 2H), 2.64 (s, 3H), 2.61-255 (m, 1H), 2.11-1.96 (m, 3H) and 1.66-1.55 (m, 1H).

LCMS: m/z 445.2 (M+H)$^+$ (ES$^+$).

Example 60: N-((7-Fluoro-5-(pyridin-4-yl)-2,3-dihydro-1H-inden-4-yl) carbamoyl)-1-(1-methylpyrrolidin-3-yl)methanesulfonamide

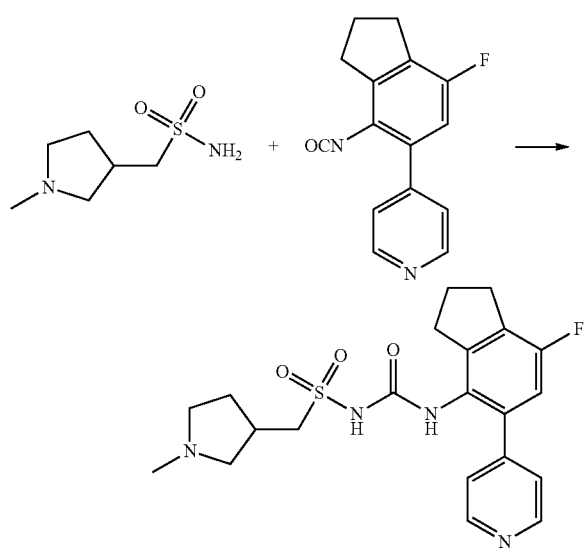

To a solution of (1-methylpyrrolidin-3-yl)methanesulfonamide (Intermediate P16) (180 mg, 1.01 mmol, 5 eq) in THF (2 mL) was added t-BuONa (97 mg, 1.01 mmol, 5 eq) and the mixture was stirred at 25° C. for 10 minutes. Then 4-(7-fluoro-4-isocyanato-2,3-dihydro-1H-inden-5-yl)pyridine (Intermediate A2) (51 mg, 201.96 μmol, 1 eq) in THF (1.5 mL) was added. The reaction mixture was stirred at 25° C. for 30 minutes. Most of the solvent was evaporated under reduced pressure. The residue was purified by prep-HPLC (Phenomenex Gemini C18, 150 mm*25 mm*5 μm, mobile phase: [A: water (0.05% ammonium hydroxide v/v); B: MeCN), B %: 8%-38%, 10 min) to give the title compound (5.52 mg, 6% yield, 100% purity on LCMS) as a white solid.

$^1$H NMR (DMSO-d$_6$): δ 8.55 (d, 2H), 7.41 (d, 2H), 7.40 (br s, 1H), 6.95 (d, 1H), 3.12-3.08 (m, 2H), 2.97-2.85 (m, 7H), 2.75-2.71 (m, 1H), 2.58 (s, 3H), 2.53-2.50 (m, 1H), 2.09-2.00 (m, 3H) and 1.59-1.57 (m, 1H).

LCMS: m/z 433.2 (M+H)$^+$ (ES$^+$).

Example 61: 2-Isopropoxy-N-((5-(2-methoxypyridin-4-yl)-2,3-dihydro-1H-inden-4-yl)carbamoyl)ethanesulfonamide, sodium salt

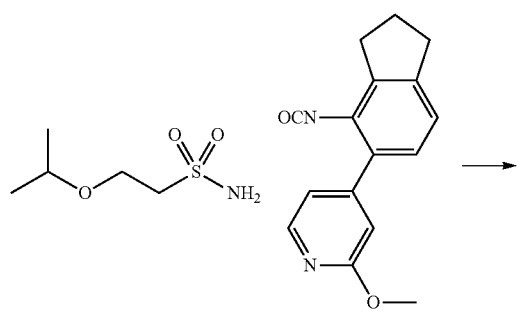

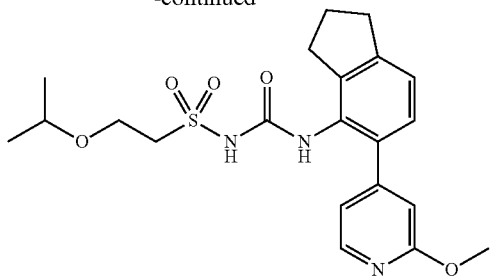

2-Isopropoxyethanesulfonamide (50 mg, 0.299 mmol) was dissolved in dry THF (2 mL). Sodium tert-butoxide (2M in THF) (160 μl, 0.320 mmol) was added and the mixture was stirred at room temperature for 30 minutes. A solution of 4-(4-isocyanato-2,3-dihydro-1H-inden-5-yl)-2-methoxypyridine (Intermediate A7) (80 mg, 0.299 mmol) in THF (1 mL) was added and the mixture was stirred for 2 hours at room temperature. The THF was removed in vacuo. The residue was dissolved in DMSO (2 mL) and then purified by basic prep-HPLC to afford to afford 2-isopropoxy-N-((5-(2-methoxypyridin-4-yl)-2,3-dihydro-1H-inden-4-yl)carbamoyl)ethanesulfonamide as a colourless solid. The solid was dissolved in aq NaOH (0.1 M, 0.74 mL, 1 eq) and the solution was freeze dried overnight to afford the title compound (30 mg, 22%) as a colourless solid.

$^1$H NMR (DMSO-d6) δ 8.10 (d, J=5.3 Hz, 1H), 7.13-7.02 (m, 3H), 7.00 (d, J=5.3 Hz, 1H), 6.81 (s, 1H), 3.86 (s, 3H), 3.57-3.48 (m, 3H), 3.14-3.06 (m, 2H), 2.90 (t, J=7.4 Hz, 2H), 2.85 (t, J=7.5 Hz, 2H), 1.99 (p, J=7.5 Hz, 2H), 1.07 (d, J=6.1 Hz, 6H).

LCMS; m/z 434.2 (M+H)$^+$ (ES$^+$); 432.1 (M–H)$^-$ (ES$^-$).

Example 62: 2-Isopropoxy-N-((5-(2-methoxypyridin-4-yl)-2,3-dihydro-benzofuran-4-yl)carbamoyl)ethanesulfonamide, sodium salt

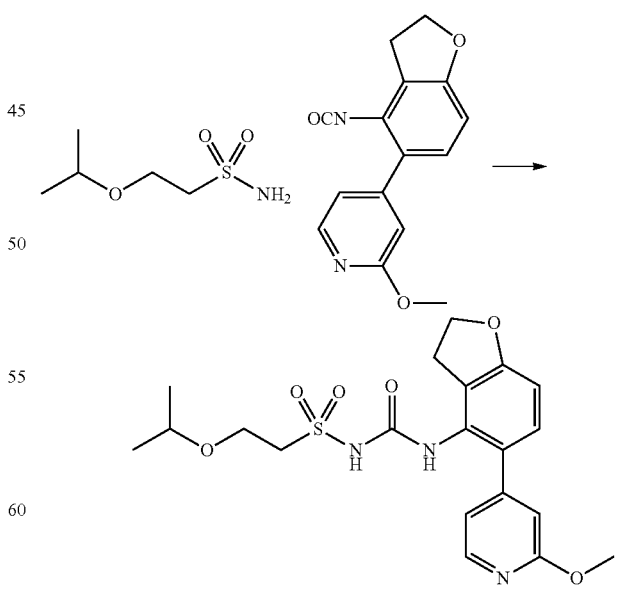

Prepared according to the general procedure 2-isopropoxy-N-((5-(2-methoxypyridin-4-yl)-2,3-dihydro-1H-inden-4-yl)carbamoyl)ethanesulfonamide, Sodium (Example 61) from 2-isopropoxyethanesulfonamide and 4-(4-isocyanato-2,3-dihydrobenzofuran-5-yl)-2-methoxypyridine (Intermediate A8) and 2-isopropoxyethanesulfonamide to afford the title compound (22 mg, 16%) as a white solid.

¹H NMR (DMSO-d6) δ 8.09 (d, J=5.3 Hz, 1H), 7.20 (s, 1H), 7.03 (d, J=8.2 Hz, 1H), 6.96 (dd, J=5.3, 1.4 Hz, 1H), 6.77 (d, J=1.3 Hz, 1H), 6.62 (d, J=8.2 Hz, 1H), 4.54 (t, J=8.7 Hz, 2H), 3.86 (s, 3H), 3.65-3.47 (m, 3H), 3.20-3.09 (m, 4H), 1.07 (d, J=6.1 Hz, 6H).

LCMS; m/z 436.1 (M+H)⁺ (ES⁺); 434.4 (M−H)⁻ (ES⁻).

Example 63: N-Ethyl-N-(4-(N-((1,2,3,5,6,7-hexahydro-s-indacen-4-yl) carbamoyl)sulfamoyl)cyclohexyl)acetamide, potassium salt

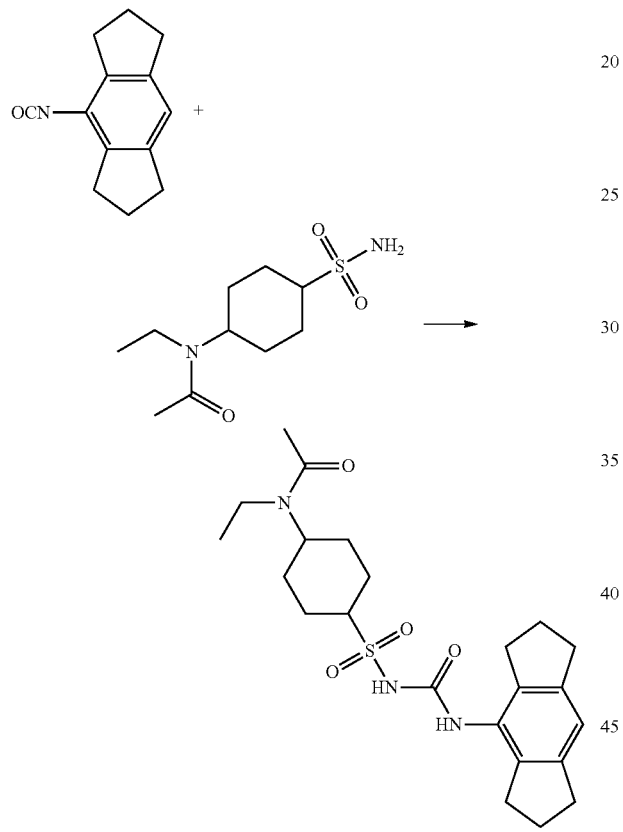

To a solution of N-ethyl-N-(4-sulfamoylcyclohexyl)acetamide (50 mg, 0.2 mmol) in THF (5 mL) was added potassium tert-butoxide (23 mg, 0.2 mmol). The mixture was stirred at room temperature for 45 minutes. 4-Isocyanato-1,2,3,5,6,7-hexahydro-s-indacene (Intermediate A1) (40 mg, 0.2 mmol) was added and the mixture was stirred for 2 hours at room temperature. Then the reaction mixture was concentrated in vacuo and DMSO (0.5-1 mL) was added. The mixture (filtered over cotton wool when solids were present) was submitted for purification by reversed phase column chromatography (see "Experimental Methods", "Purification Method") to afford the title compound (5 mg, 6%) as a white solid.

¹H NMR (Methanol-d₄) δ 6.87 (s, 1H), 4.22 (m, 1H), 3.65 (m, 1H), 2.82 (m, 10H), 2.29 (m, 2H), 2.12 (d, 2H), 2.12-1.88 (m, 6H), 1.72 (m, 5H), 1.20 (t, 3H).

LCMS: m/z 448 (M+H)⁺ (ES⁺); 446 (M−H)⁻ (ES⁻).

Example 64: N-((1,2,3,5,6,7-Hexahydro-s-indacen-4-yl)carbamoyl)-1-(1-(oxetan-3-yl)pyrrolidin-3-yl)methanesulfonamide, Potassium Salt

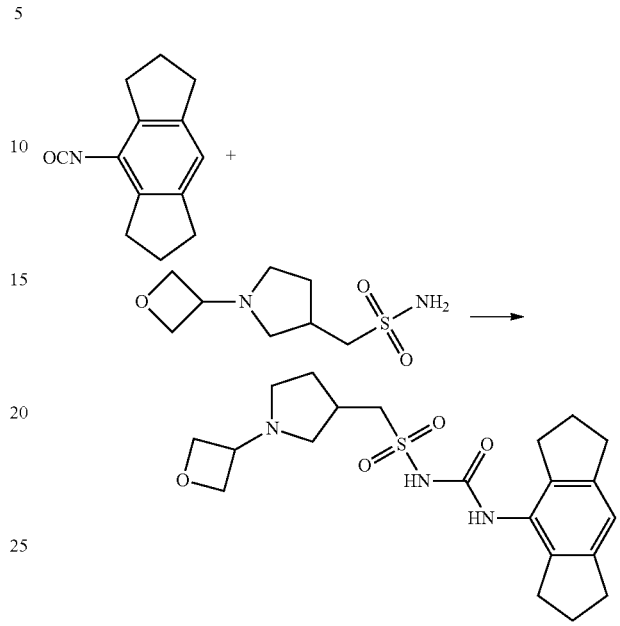

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A11 and (1-(oxetan-3-yl)pyrrolidin-3-yl)methanesulfonamide (Intermediate P31) to afford the title compound (25 mg, 36%) as a white solid.

¹H NMR (Deuterium Oxide) δ 6.95 (s, 1H), 4.73-4.58 (m, 2H), 4.56-4.37 (m, 2H), 3.80-3.57 (m, 1H), 3.21 (d, 2H), 3.01-2.82 (m, 1H), 2.68 (m, 9H), 2.46 (ddt, 2H), 2.16 (t, 1H), 2.07 (dd, 1H), 1.90 (m, 4H), 1.50 (dt, 1H).

LCMS: m/z 420 (M+H)⁺ (ES⁺); 418 (M−H)⁻ (ES⁻).

Example 65: 3-Amino-N-((1,2,3,5,6,7-hexahydro-s-indacen-4-yl)carbamoyl) propane-1-sulfonamide potassium salt

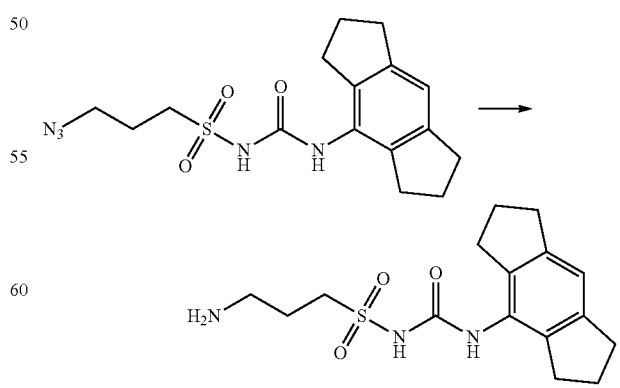

To 3-azido-N-((1,2,3,5,6,7-hexahydro-s-indacen-4-yl) carbamoyl)propane-1-sulfonamide, potassium salt (Example 34) (50 mg, 0.14 mmol) in methanol (5 mL) was added Pd—C (10%, 20 mg) in water (0.5 mL). The mixture was stirred for 18 hours under hydrogen atmosphere. Then the mixture was filtered through Celite® and evaporated. DMSO (0.5-1 mL) was added and the mixture was submitted for purification by reversed phase column chromatography (see "Experimental Methods", "Purification Method") to afford the title compound (50 mg, 100%) as a white solid.

$^1$H NMR (Methanol-$d_4$) δ 6.96 (s, 1H), 3.19 (t, 2H), 2.86 (t, 2H), 2.73 (m, 4H), 2.63 (m, 4H), 1.89 (m, 6H).

LCMS: m/z 338 (M+H)+(ES+); 336 (M−H)− (ES−).

Example 66: 3-(N-((1,2,3,5,6,7-Hexahydro-s-indacen-4-yl)carbamoyl) sulfamoyl)-N,N,N-trimethyl-propan-1-aminium, Potassium Salt

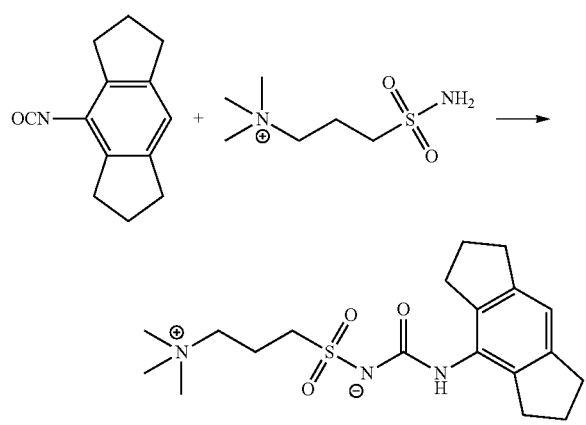

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and N,N,N-trimethyl-3-sulfamoylpropan-1-aminium (Intermediate P32) to afford the title compound (6 mg, 5%) as a white solid.

$^1$H NMR (Deuterium Oxide) δ 7.01 (s, 1H), 3.50-3.35 (m, 2H), 3.24 (t, 2H), 3.06 (s, 9H), 2.79-2.58 (m, 8H), 2.17 (p, 2H), 1.95 (p, 4H).

LCMS: m/z 380 (M+H)+ (ES+).

Example 67: 3-(Benzyl(methyl)amino)-N-((1,2,3,5,6,7-hexahydro-s-indacen-4-yl)carbamoyl)propane-1-sulfonamide, potassium salt

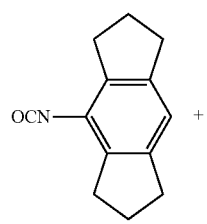

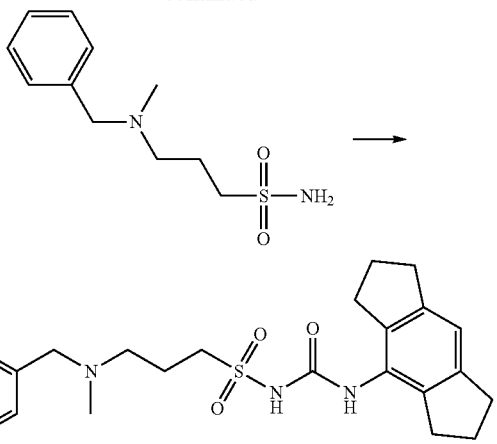

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(benzyl(methyl)amino)propane-1-sulfonamide (Intermediate P33) to afford the title compound (39 mg, 31%) as a white solid.

$^1$H NMR (Methanol-$d_4$) δ 7.48-7.23 (m, 5H), 6.88 (s, 1H), 3.80 (s, 2H), 3.34 (m, 2H), 2.82 (m, 10H), 2.37 (s, 3H), 2.13 (p, 2H), 2.01 (p, 4H).

LCMS: m/z 442 (M+H)+ (ES+); 440 (M−H)− (ES−).

Example 68: N-((1,2,3,5,6,7-Hexahydro-s-indacen-4-yl)carbamoyl)-2-(3-methyl-3H-diazirin-3-yl)ethane-1-sulfonamide, Potassium Salt

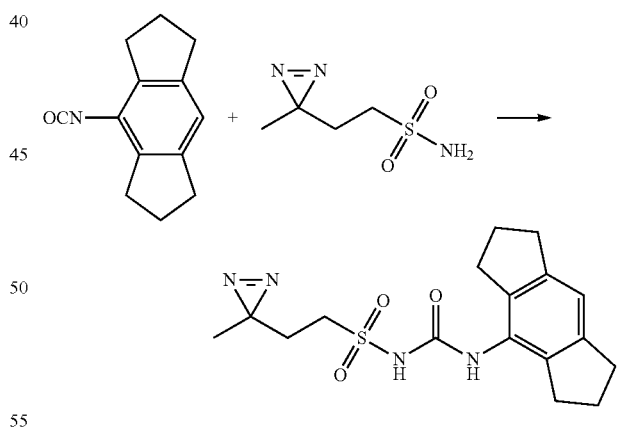

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(3-methyl-3H-diazirin-3-yl)ethane-1-sulfonamide (Intermediate P34) to afford the title compound (134 mg, 81%) as a white solid.

$^1$H NMR (Methanol-$d_4$) δ 6.87 (s, 1H), 3.22-3.02 (m, 2H), 2.82 (dt, 8H), 2.03 (p, 4H), 1.85-1.61 (m, 2H), 1.04 (s, 3H).

LCMS: m/z 363 (M+H)+ (ES+); 361 (M−H)− (ES−).

Example 69: N-((1,2,3,5,6,7-Hexahydro-s-indacen-4-yl)carbamoyl)-3-(methylamino)propane-1-sulfonamide, Potassium Salt

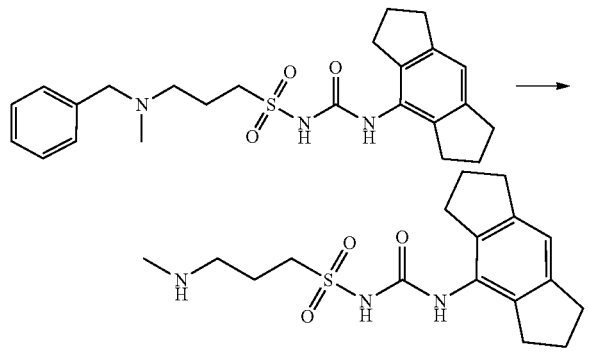

3-(Benzyl(methyl)amino)-N-((1,2,3,5,6,7-hexahydro-s-indacen-4-yl)carbamoyl)-propane-1-sulfonamide, potassium salt (Example 67) (32 mg, 0.072 mmol) was stirred in water (1 mL). 10% Pd/C (5 mg) was added and a hydrogen balloon was applied. The mixture was stirred overnight, filtered through Celite® and freeze-dried to afford the title compound (5 mg, 20%) as a white solid.

$^1$H NMR (Methanol-$d_4$) δ 6.87 (s, 1H), 2.83 (m, 12H), 2.47 (s, 3H), 2.04 (m, 6H).

LCMS: m/z 352 (M+H)$^+$ (ES$^+$); 350 (M−H)$^-$ (ES$^-$).

Example 70: N-((1,2,3,5,6,7-Hexahydro-s-indacen-4-yl)carbamoyl)-3-(methoxy(methyl)amino)propane-1-sulfonamide, Potassium Salt

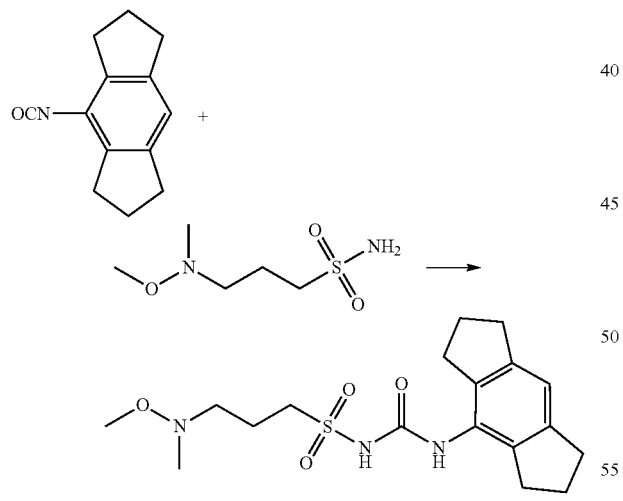

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(methoxy(methyl)amino)propane-1-sulfonamide (Intermediate P35) to afford the title compound (14 mg, 52%) as a white solid.

$^1$H NMR (Methanol-$d_4$) δ 6.87 (s, 1H), 3.49 (s, 3H), 2.83 (m, 10H), 2.80-2.67 (m, 2H), 2.54 (s, 3H), 2.03 (m, 6H).

LCMS: m/z 382 (M+H)$^+$ (ES$^+$); 380 (M−H)$^-$ (ES$^-$).

Example 71: N-((1,2,3,5,6,7-Hexahydro-s-indacen-4-yl)carbamoyl)-1-((1S,E)-2-(hydroxyimino)-7,7-dimethylbicyclo[2.2.1]heptan-1-yl)methane sulfonamide, Potassium Salt

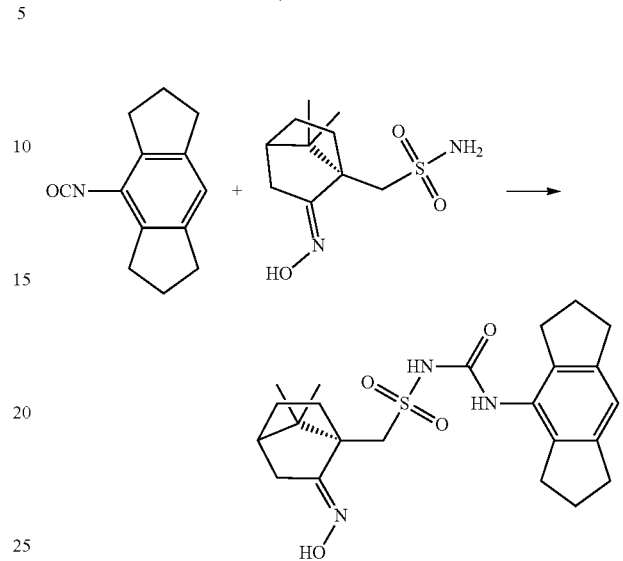

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1), ((1S,E)-2-(hydroxyimino)-7,7-dimethylbicyclo[2.2.1]heptan-1-yl)methanesulfonamide (Intermediate P36) and KOtBu (2 equiv.) to afford the title compound (35 mg, 23%) as a white solid.

$^1$H NMR (Methanol-$d_4$) δ 6.88 (s, 1H), 3.80 (d, 1H), 3.39 (d, 1H), 2.83 (m, 8H), 2.71-2.40 (m, 3H), 2.03 (p, 4H), 1.95-1.83 (m, 2H), 1.74 (m, 1H), 1.39-1.19 (m, 1H), 1.08 (s, 3H), 0.82 (s, 3H).

LCMS: m/z 446 (M+H)$^+$ (ES$^+$); 444 (M−H)$^-$ (ES$^-$).

Example 72: 3-(Azetidin-1-yl)-N-((1,2,3,5,6,7-hexahydro-s-indacen-4-yl) carbamoyl)propane-1-sulfonamide, Potassium Salt

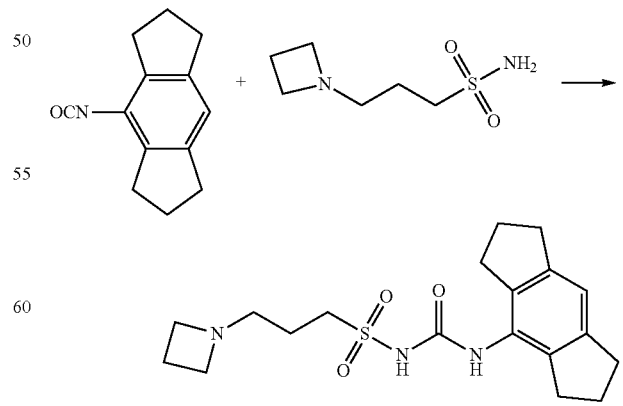

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(azetidin-1-yl)propane-1-sulfonamide (Intermediate P37) to afford the title compound (2 mg, 10%) as a white solid.

¹H NMR (Methanol-d₄) δ 6.89 (s, 1H), 3.55 (t, 4H), 3.25 (t, 2H), 2.84 (b, 10H), 2.30-2.13 (m, 2H), 2.04 (p, 4H), 1.99-1.82 (m, 2H).

LCMS: m/z 378 (M+H)⁺ (ES⁺); 376 (M–H)⁻ (ES⁻).

Example 73: N-((1,2,3,5,6,7-Hexahydro-s-indacen-4-yl)carbamoyl)propane-3-methyl(prop-2-yn-1-yl)amino)propane-1-sulfonamide, Potassium Salt

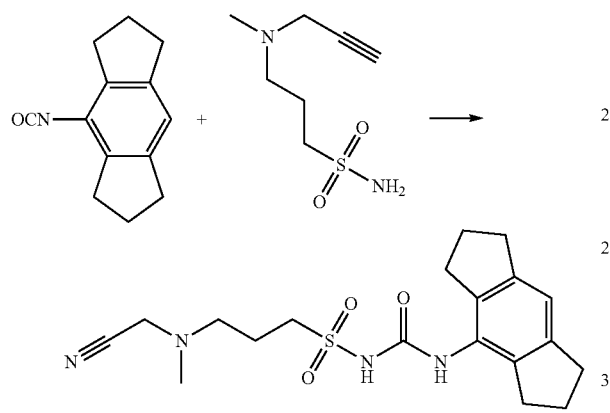

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(methyl(prop-2-yn-1-yl)amino)propane-1-sulfonamide (Intermediate P38) to afford the title compound (60 mg, 41%) as a white solid.

¹H NMR (Methanol-d₄) δ 6.88 (s, 1H), 3.43-3.29 (m, 3H), 3.29-3.15 (m, 2H), 2.83 (q, 8H), 2.70-2.50 (m, 2H), 2.32 (s, 3H), 2.01 (m, 6H).

LCMS: m/z 390 (M+H)⁺ (ES⁺); 388 (M–H)⁻ (ES⁻).

Example 74: N-((1,2,3,5,6,7-Hexahydro-s-indacen-4-yl)carbamoyl)-1-(4-methylmorpholin-2-yl)methanesulfonamide, Potassium Salt

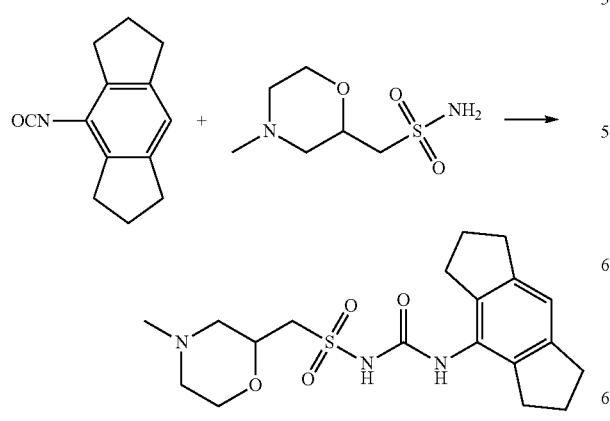

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (4-methylmorpholin-2-yl)methanesulfonamide (Intermediate P39) to afford the title compound (9 mg, 13%) as a white solid.

¹H NMR (Methanol-d₄) δ 6.87 (s, 1H), 4.05 (q, 1H), 3.94-3.77 (m, 1H), 3.65 (td, 1H), 3.40 (dd, 2H), 3.25-3.19 (m, 1H), 3.13 (d, 1H), 2.93-2.74 (m, 8H), 2.74-2.55 (m, 1H), 2.28 (d, 3H), 2.23-1.79 (m, 5H).

LCMS: m/z 394 (M+H)⁺ (ES⁺); 392 (M–H)⁻ (ES⁻).

Example 75: 1-(4-Ethylmorpholin-2-yl)-N-((1,2,3,5,6,7-hexahydro-s-indacen-4-yl)carbamoyl)methanesulfonamide, potassium salt

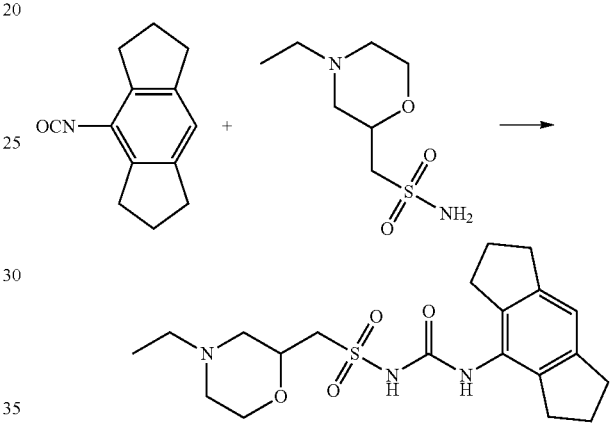

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (4-ethylmorpholin-2-yl)methanesulfonamide (Intermediate P40) to afford the title compound (7 mg, 11%) as a white solid.

¹H NMR (Methanol-d₄) δ 6.87 (s, 1H), 4.06 (s, 1H), 3.92-3.79 (m, 1H), 3.74-3.62 (m, 1H), 3.42 (dd, 2H), 3.22 (d, 2H), 2.83 (q, 9H), 2.46 (q, 2H), 2.21-1.86 (m, 5H), 1.11 (t, 3H).

LCMS: m/z 408 (M+H)⁺ (ES⁺); 406 (M–H)⁻ (ES⁻).

Example 76: N-((1,2,3,5,6,7-Hexahydro-s-indacen-4-yl)carbamoyl)-1-(4-isopropylmorpholin-2-yl)methanesulfonamide, Potassium Salt

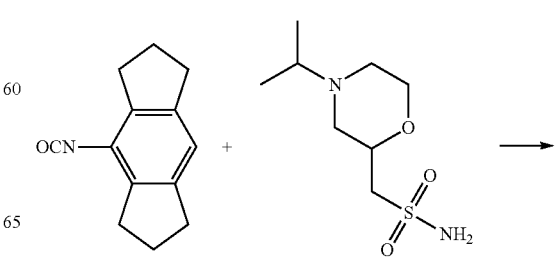

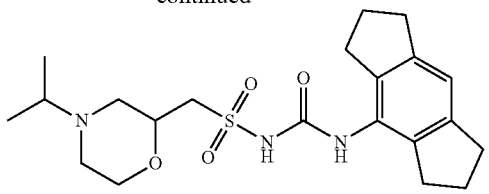

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (4-isopropylmorpholin-2-yl)methanesulfonamide (Intermediate P41) to afford the title compound (6 mg, 10%) as a white solid.

$^1$H NMR (Methanol-$d_4$) δ 6.88 (s, 1H), 4.06 (s, 1H), 3.89 (d, 1H), 3.79-3.59 (m, 1H), 3.44 (dd, 2H), 3.21 (d, 1H), 2.83 (m, 10H), 2.38 (m, 1H), 2.28-2.12 (m, 1H), 2.03 (p, 4H), 1.22-1.00 (m, 6H).

LCMS: m/z 422 (M+H)$^+$ (ES$^+$); 420 (M−H)$^-$ (ES$^-$).

Example 77: N-((1,2,3,5,6,7-Hexahydro-s-indacen-4-yl)carbamoyl)-1-(2-isopropyl-6-oxa-2-azaspiro[3.4]octan-7-yl)methanesulfonamide, Potassium Salt

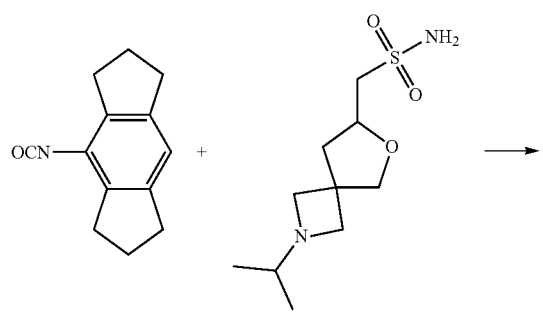

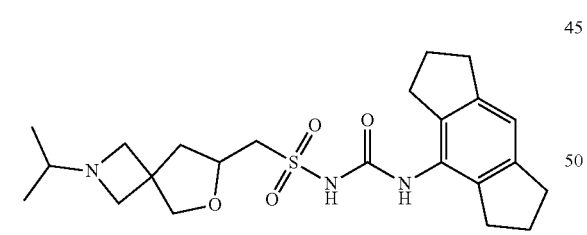

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (2-isopropyl-6-oxa-2-azaspiro[3.4]octan-7-yl)methanesulfonamide (Intermediate P42) to afford the title compound (10 mg, 56%) as a white solid.

$^1$H NMR (Methanol-$d_4$) δ 6.89 (s, 1H), 4.47-4.22 (m, 1H), 3.98 (d, 1H), 3.89-3.67 (m, 5H), 3.55 (dd, 1H), 3.49-3.37 (m, 1H), 2.95 (m, 1H), 2.83 (m, 8H), 2.46 (td, 1H), 2.15 (dd, 1H), 2.10-1.85 (m, 4H), 1.08-0.99 (m, 6H).

LCMS: m/z 448 (M+H)$^+$ (ES$^+$); 446 (M−H)$^-$ (ES$^-$).

Example 78: 3-(Dimethylamino)-N-((1,2,3,5,6,7-hexahydro-s-indacen-4-yl) carbamoyl)butane-1-sulfonamide, potassium salt

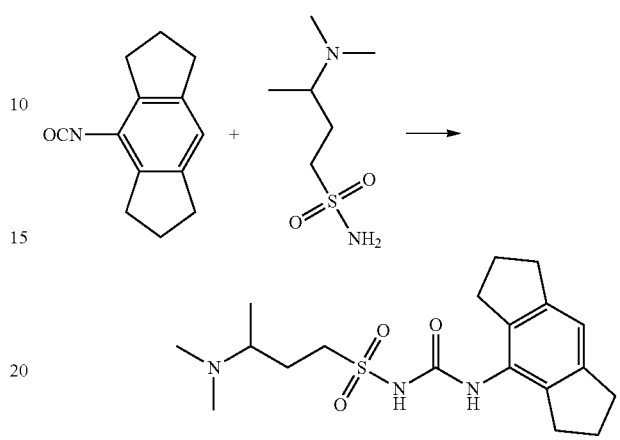

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(dimethylamino)butane-1-sulfonamide (Intermediate P43) to afford the title compound (3 mg, 10%) as a white solid.

$^1$H NMR (Methanol-$d_4$) δ 6.89 (s, 1H), 3.35 (m, 2H), 2.83 (m, 9H), 2.65 (s, 6H), 2.36-2.13 (m, 1H), 2.13-1.82 (m, 5H), 1.34-1.17 (m, 3H).

LCMS: m/z 380 (M+H)$^+$ (ES$^+$); 378 (M−H)$^-$ (ES$^-$).

Example 79: 1-(2-Ethyl-6-oxa-2-azaspiro[3.4]octan-7-yl)-N-((1,2,3,5,6,7-hexahydro-s-indacen-4-yl)carbamoyl)methanesulfonamide, potassium salt

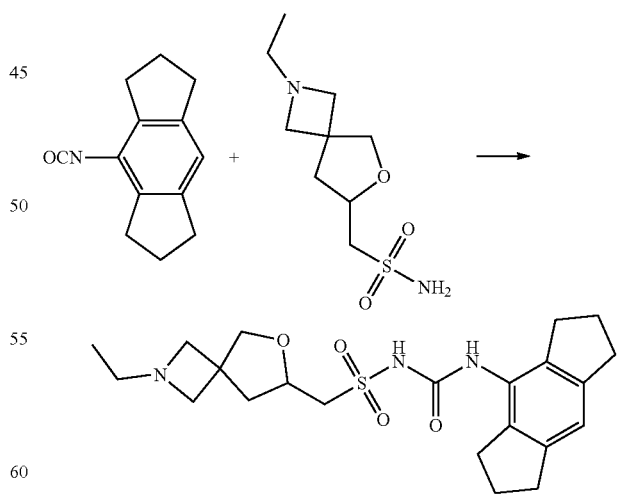

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (2-ethyl-6-oxa-2-azaspiro[3.4]octan-7-yl)methanesulfonamide (Intermediate P44) to afford the title compound (8 mg, 30%) as a white solid.

$^1$H NMR (Methanol-$d_4$) δ 6.88 (s, 1H), 4.36 (dd, 1H), 3.98 (d, 1H), 3.84 (dd, 1H), 3.69 (s, 3H), 3.53 (dd, 1H), 3.37 (d, 1H), 2.83 (m, 10H), 2.74-2.58 (m, 1H), 2.49 (dd, 1H), 2.23-2.12 (m, 1H), 2.04 (m, 4H), 1.03 (m, 3H).

LCMS: m/z 434 (M+H)$^+$ (ES$^+$); 432 (M-H)$^-$ (ES$^-$).

Example 80: N-((1,2,3,5,6,7-Hexahydro-s-indacen-4-yl)carbamoyl)-1-(2-methyl-6-oxa-2-azaspiro[3.4]octan-7-yl)methanesulfonamide, Potassium Salt

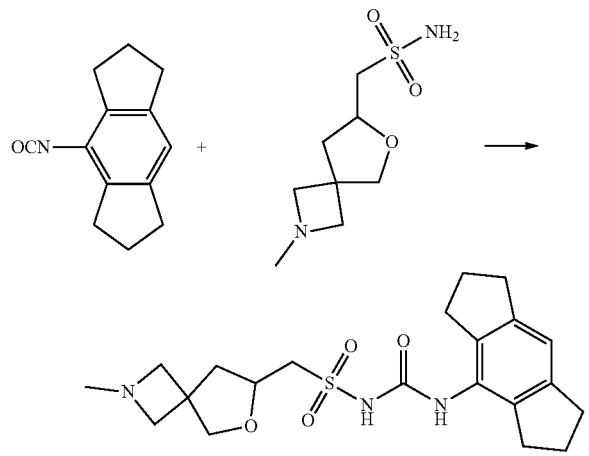

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (2-methyl-6-oxa-2-azaspiro[3.4]octan-7-yl)methanesulfonamide (Intermediate P45) to afford the title compound (8 mg, 25%) as a white solid.

$^1$H NMR (Methanol-$d_4$) δ 6.88 (s, 1H), 4.32 (p, 1H), 3.96 (d, 1H), 3.82 (d, 1H), 3.67-3.44 (m, 5H), 3.37 (m, 1H), 2.83 (m, 8H), 2.52-2.34 (m, 1H), 2.45 (s, 3H), 2.16-1.91 (m, 5H).

LCMS: m/z 420 (M+H)$^+$ (ES$^+$); 418 (M-H)$^-$ (ES$^-$).

Example 81: 3-(Dimethylamino)-N-((1,2,3,5,6,7-hexahydro-s-indacen-4-yl) carbamoyl)-2,2-dimethylpropane-1-sulfonamide, potassium salt

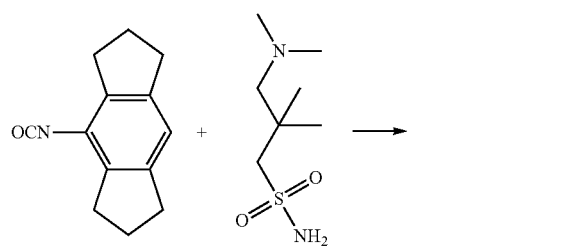

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(dimethylamino)-2,2-dimethylpropane-1-sulfonamide (Intermediate P46) to afford the title compound (7 mg, 15%) as a white solid.

$^1$H NMR (Methanol-$d_4$) δ 6.92 (s, 1H), 3.44 (s, 2H), 3.32 (m, 6H), 3.21 (s, 2H), 2.84 (m, 8H), 2.05 (m, 4H), 1.29 (s, 6H).

LCMS: m/z 394 (M+H)$^+$ (ES$^+$); 392 (M-H)$^-$ (ES$^-$).

Example 82: 4-(Dimethylamino)-N-((1,2,3,5,6,7-hexahydro-s-indacen-4-yl) carbamoyl)butane-1-sulfonamide, potassium salt

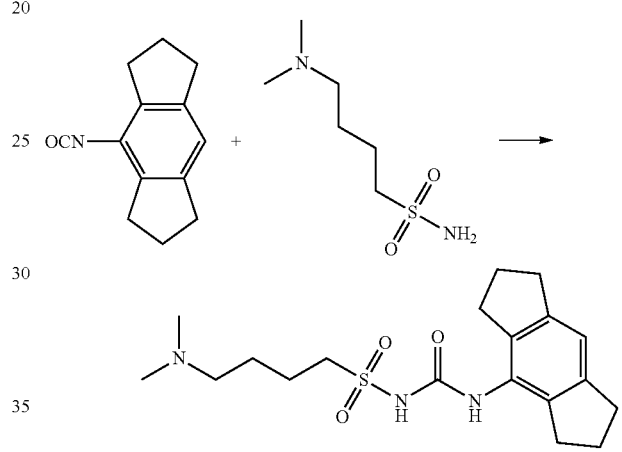

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 4-(dimethylamino)butane-1-sulfonamide (Intermediate P47) to afford the title compound (18 mg, 27%) as a white solid.

$^1$H NMR (Methanol-$d_4$) δ 6.89 (s, 1H), 3.28 (m, 2H), 2.94 (t, 2H), 2.83 (m, 8H), 2.66 (s, 6H), 2.03 (m, 4H), 1.85 (m, 4H).

LCMS: m/z 380 (M+H)$^+$ (ES$^+$); 378 (M-H)$^-$ (ES$^-$).

Example 83: N-((1,2,3,5,6,7-Hexahydro-s-indacen-4-yl)carbamoyl)-1-(1-methylpiperidin-3-yl)methanesulfonamide, Potassium Salt

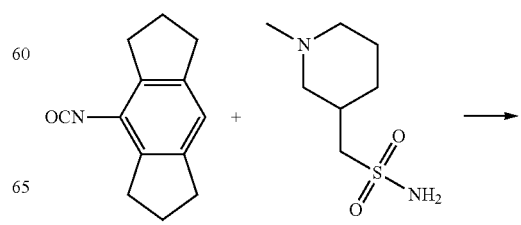

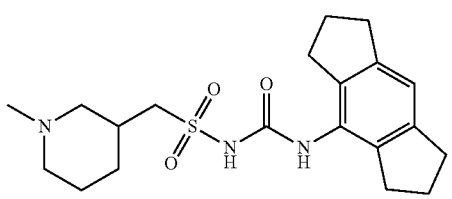

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-methylpiperidin-3-yl)methanesulfonamide (Intermediate P48) to afford the title compound (19 mg, 11%) as a white solid.

$^1$H NMR (Methanol-d$_4$) δ 6.88 (s, 1H), 3.29-3.06 (m, 2H), 3.01 (d, 2H), 2.83 (m, 9H), 2.55-2.29 (m, 1H), 2.30 (s, 3H), 2.16-1.82 (m, 5H), 1.82-1.57 (m, 2H), 1.31-1.13, 2H).

LCMS: m/z 392 (M+H)$^+$ (ES$^+$); 390 (M−H)$^−$ (ES$^−$).

Example 84: 1-(1-Ethylpiperidin-3-yl)-N-((1,2,3,5,6,7-hexahydro-s-indacen-4-yl)carbamoyl)methanesulfonamide, potassium salt

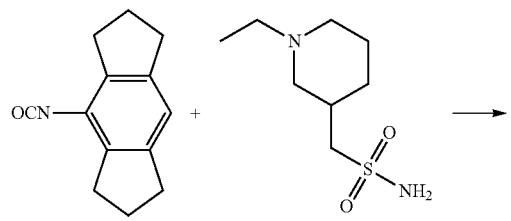

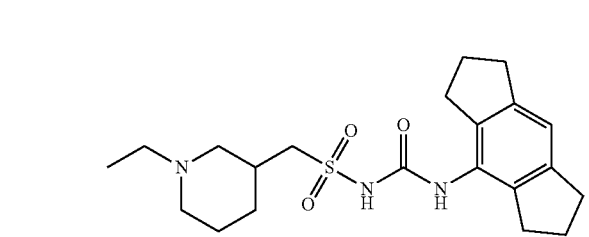

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-ethylpiperidin-3-yl)methanesulfonamide (Intermediate P49) to afford the title compound (45 mg, 28%) as a white solid.

$^1$H NMR (Methanol-d$_4$) δ 6.88 (s, 1H), 3.26-3.11 (m, 2H), 3.00 (m, 3H), 2.83 (m, 9H), 2.74-2.29 (m, 2H), 2.04 (m, 4H), 1.97-1.55 (m, 3H), 1.34 (m, 1H), 1.28 (t, 3H), 1.13 (m, 1H).

LCMS: m/z 406 (M+H)$^+$ (ES$^+$); 404 (M−H)$^−$ (ES$^−$).

Example 85: 1-((1S)-2-Amino-7,7-dimethylbicyclo[2.2.1]heptan-1-yl)-N-((1,2,3,5,6,7-hexahydro-s-indacen-4-yl)carbamoyl)methanesulfonamide, TFA Salt

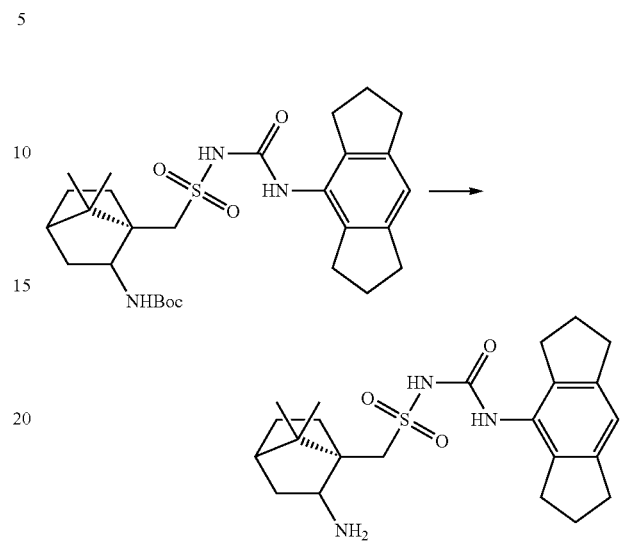

Tert-butyl ((1S)-1-((N-((1,2,3,5,6,7-hexahydro-s-indacen-4-yl)carbamoyl)sulfamoyl) methyl)-7,7-dimethylbicyclo[2.2.1]heptan-2-yl)carbamate, potassium salt (Intermediate P50) (100 mg, 0.19 mmol) was stirred in DCM (0.3 mL) and TFA (0.3 mL) for 2.5 hours. Then the reaction mixture was concentrated and submitted for purification by reversed phase column chromatography (see "Experimental Methods", "Purification Method") to afford the title compound (1 mg, 1%) as a white solid.

$^1$H NMR (Methanol-d$_4$) δ 6.89 (s, 1H), 3.67-3.44 (m, 2H), 2.82 (m, 8H), 2.41 (m, 1H), 2.03 (m, 4H), 1.94-1.53 (m, 4H), 1.49-1.06 (m, 3H), 0.97 (m, 6H).

LCMS: m/z 432 (M+H)$^+$ (ES$^+$); 430 (M−H)$^−$ (ES$^−$).

Example 86: 4-(Azetidin-1-yl)-N-((1,2,3,5,6,7-hexahydro-s-indacen-4-yl) carbamoyl)butane-1-sulfonamide, Potassium Salt

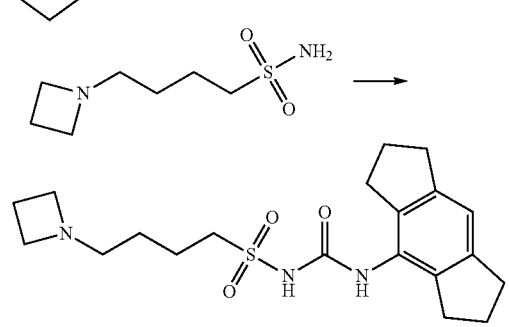

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 4-(azetidin-1-yl)butane-1-sulfonamide (Intermediate P51) to afford the title compound (1 mg, 3%) as a white solid.

LCMS: m/z 392 (M+H)⁺ (ES⁺); 390 (M–H)⁻ (ES⁻).

Example 87: 1-(Azetidin-1-ylmethyl)-N-((1,2,3,5,6,7-hexahydro-s-indacen-4-yl)carbamoyl)cyclopropane-1-sulfonamide, potassium salt

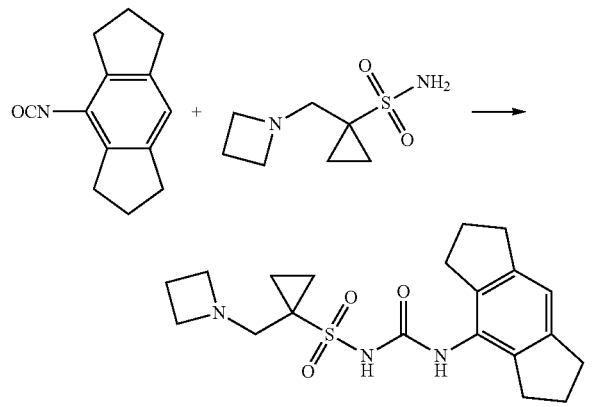

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 1-(azetidin-1-ylmethyl)cyclopropane-1-sulfonamide (Intermediate P52) to afford the title compound (15 mg, 37%) as a white solid.

$^1$H NMR (Methanol-$d_4$) δ 6.93 (s, 1H), 4.09 (m, 4H), 2.84 (m, 8H), 2.65 (s, 2H), 2.40 (m, 2H), 2.05 (m, 4H), 1.40 (s, 2H), 0.97 (s, 2H).

LCMS: m/z 390 (M+H)⁺ (ES⁺); 388 (M–H)⁻ (ES⁻).

Example 88: N-((1,2,3,5,6,7-Hexahydro-s-indacen-4-yl)carbamoyl)-2-(pyrrolidin-1-yl)ethane-1-sulfonamide, Potassium Salt

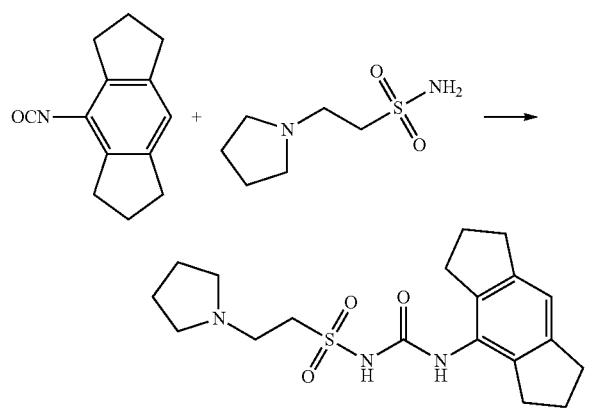

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(pyrrolidin-1-yl)ethane-1-sulfonamide (Intermediate P53) to afford the title compound (25 mg, 20%) as a white solid.

$^1$H NMR (Methanol-$d_4$) δ 6.88 (s, 1H), 3.46 (s, 2H), 3.09 (s, 2H), 2.81 (m, 12H), 2.03 (m, 4H), 1.86 (m, 4H).

LCMS: m/z 378 (M+H)⁺ (ES⁺); 376 (M–H)⁻ (ES⁻).

Example 89: N-((1,2,3,5,6,7-Hexahydro-s-indacen-4-yl)carbamoyl)-2-(2-methylazetidin-1-yl)ethane-1-sulfonamide, Potassium Salt

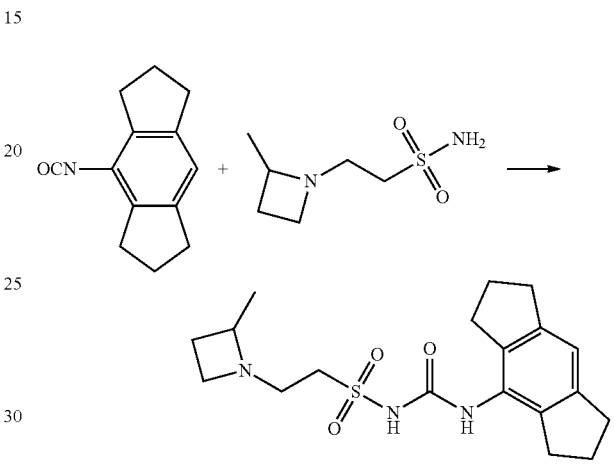

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(2-methylazetidin-1-yl)ethane-1-sulfonamide (Intermediate P54) to afford the title compound (35 mg, 42%) as a white solid.

$^1$H NMR (Methanol-$d_4$) δ 6.91 (s, 1H), 4.21 (q, 1H), 3.90 (td, 1H), 3.84-3.63 (m, 2H), 3.56-3.33 (m, 3H), 2.84 (m, 8H), 2.52-2.30 (m, 1H), 2.18-1.95 (m, 5H), 1.45 (d, 3H).

LCMS: m/z 378 (M+H)⁺ (ES⁺); 376 (M–H)⁻ (ES⁻).

Example 90: 2-(3-Fluoroazetidin-1-yl)-N-((1,2,3,5,6,7-hexahydro-s-indacen-4-yl)carbamoyl)ethane-1-sulfonamide, Potassium Salt

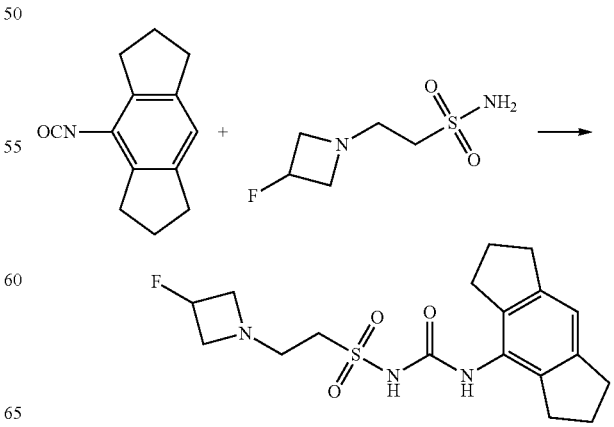

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(3-fluoroazetidin-1-yl)ethane-1-sulfonamide (Intermediate P55) to afford the title compound (6 mg, 5%) as a white solid.

$^1$H NMR (Methanol-$d_4$) δ 6.87 (s, 1H), 3.81-3.53 (m, 2H), 3.31 (m, 1H), 3.19-3.04 (m, 1H), 3.04-2.91 (m, 2H), 2.83 (s, 11H), 2.02 (m, 4H).

LCMS: m/z 382 (M+H)$^+$ (ES$^+$); 380 (M−H)$^-$ (ES$^-$).

Example 91: 2-(Azetidin-1-yl)-N-((1,2,3,5,6,7-hexahydro-s-indacen-4-yl) carbamoyl)propane-1-sulfonamide, Potassium Salt

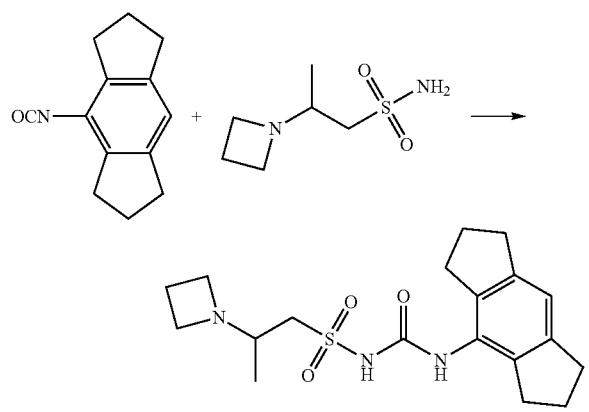

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(azetidin-1-yl)propane-1-sulfonamide (Intermediate P56) to afford the title compound (21 mg, 20%) as a white solid.

$^1$H NMR (Methanol-$d_4$) δ 6.87 (s, 1H), 3.58-3.38 (m, 4H), 3.07-2.93 (m, 2H), 2.83 (m, 9H), 2.05 (m, 6H), 1.22 (d, 3H).

LCMS: m/z 378 (M+H)$^+$ (ES$^+$); 376 (M−H)$^-$ (ES$^-$).

Example 92: Methyl 3-(N-((1,2,3,5,6,7-hexahydro-s-indacen-4-yl) carbamoyl)sulfamoyl)propanoate, potassium salt

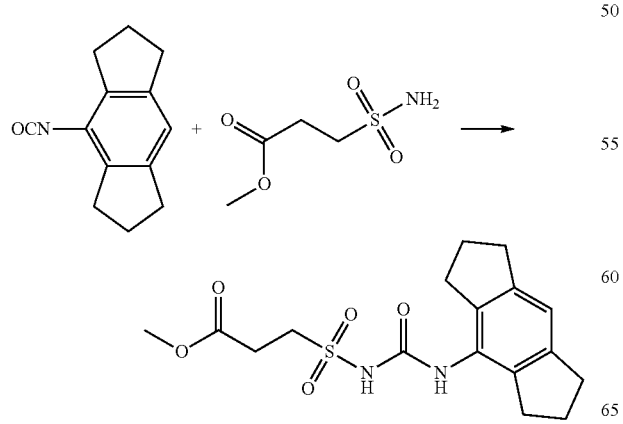

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and methyl 3-sulfamoylpropanoate (Intermediate P57) to afford the title compound (60 mg, 44%) as a white solid.

$^1$H NMR (Methanol-$d_4$) δ 6.87 (s, 1H), 3.68 (s, 3H), 3.48 (t, 2H), 2.95-2.68 (m, 10H), 2.04 (m, 4H).

LCMS: m/z 367 (M+H)$^+$ (ES$^+$); 365 (M−H)$^-$ (ES$^-$).

Example 43: N-((1,2,3,5,6,7-Hexahydro-s-indacen-4-yl)carbamoyl)-1-(1-isopropylpiperidin-3-yl)methanesulfonamide, Potassium Salt

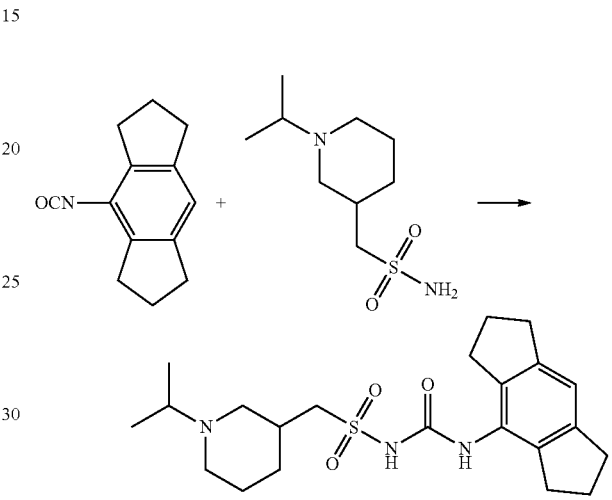

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-isopropylpiperidin-3-yl)methanesulfonamide (Intermediate P58) to afford the title compound (34 mg, 34%) as a white solid.

$^1$H NMR (Methanol-$d_4$) δ 6.88 (s, 1H), 3.58 (d, 1H), 3.25-3.06 (m, 2H), 2.83 (m, 10H), 2.77-2.50 (m 2H), 2.39 (m, 1H), 2.02 (m, 5H), 1.94-1.59 (m 2H), 1.33 (m, 1H), 1.25 (d, 6H).

LCMS: m/z 420 (M+H)$^+$ (ES$^+$); 418 (M−H)$^-$ (ES$^-$).

Example 94: N-(3-(N-((1,2,3,5,6,7-Hexahydro-s-indacen-4-yl)carbamoyl) sulfamoyl)propyl)-3-methoxy-N-methylpropanamide, Potassium Salt

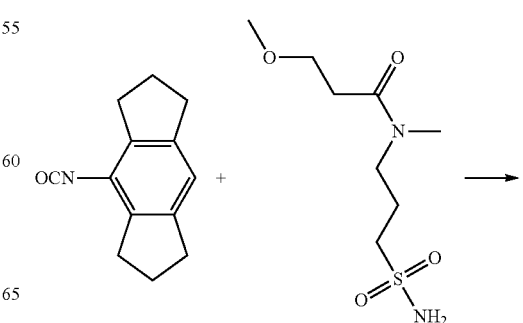

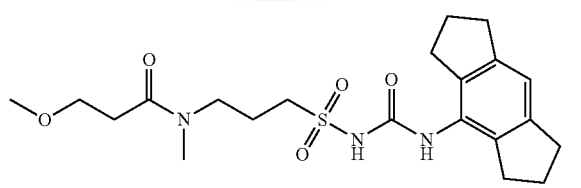

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-methoxy-N-methyl-N-(3-sulfamoylpropyl)propanamide (Intermediate P59) to afford the title compound (7 mg, 9%) as a white solid.

$^1$H NMR (Methanol-$d_4$) δ 6.87 (s, 1H), 3.64 (m, 2H), 3.61-3.47 (m, 2H), 3.21 (m, 2H), 3.07 (s, 3H), 2.94 (s, 3H), 2.82 (m, 8H), 2.65 (m, 2H), 2.03 (m, 6H).

LCMS: m/z 438 (M+H)$^+$ (ES$^+$); 436 (M−H)$^−$ (ES$^−$).

Example 95: N-(3-(N-((1,2,3,5,6,7-Hexahydro-s-indacen-4-yl)carbamoyl) sulfamoyl)propyl)-N-methylisobutyramide, Potassium Salt

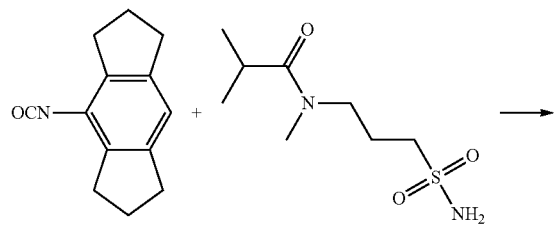

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and N-methyl-N-(3-sulfamoylpropyl)isobutyramide (Intermediate P60) to afford the title compound (22 mg, 17%) as a white solid.

$^1$H NMR (Methanol-$d_4$) δ 6.87 (s, 1H), 3.52 (q, 2H), 3.20 (dd, 1H), 3.09, 2.95 (d, 3H), 2.82 (m, 8H), 2.37 (dt, 2H), 2.02 (m, 7H), 1.62 (qd, 2H), 1.06-0.77 (m, 3H).

LCMS: m/z 422 (M+H)$^+$ (ES$^+$); 420 (M−H)$^−$ (ES$^−$).

Example 96: N-(3-(N-((1,2,3,5,6,7-Hexahydro-s-indacen-4-yl)carbamoyl) sulfamoyl)propyl)-N-methylformamide, Potassium Salt

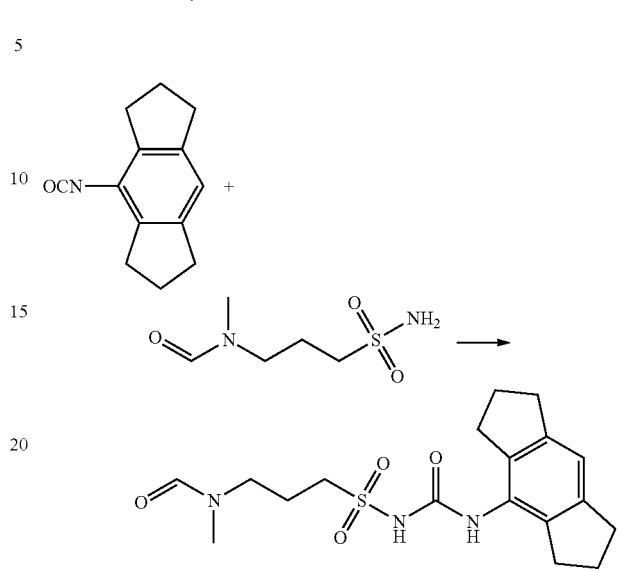

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and N-methyl-N-(3-sulfamoylpropyl)formamide (Intermediate P61) to afford the title compound (29 mg, 13%) as a white solid.

$^1$H NMR (Methanol-$d_4$) δ 8.04 (d, 1H), 6.87 (s, 1H), 3.48 (td, 2H), 3.25-3.09 (m, 2H), 3.00, 2.95 (d, 3H), 2.95-2.70 (m, 8H), 2.03 (m, 6H).

LCMS: m/z 380 (M+H)$^+$ (ES$^+$); 378 (M−H)$^−$ (ES$^−$).

Example 97: 3-(N-((1,2,3,5,6,7-Hexahydro-s-indacen-4-yl)carbamoyl) sulfamoyl)-N,N-dimethylpropanamide, Potassium Salt

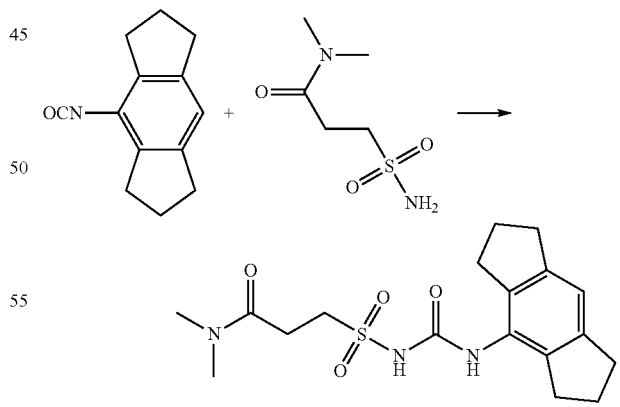

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and N,N-dimethyl-3-sulfamoylpropanamide (Intermediate P62) to afford the title compound (19 mg, 41%) as a white solid.

¹H NMR (Methanol-d₄) δ 6.87 (s, 1H), 3.58-3.38 (m, 2H), 3.09 (s, 3H), 2.93 (s, 3H), 2.83 (m, 10H), 2.02 (p, 4H).
LCMS: m/z 380 (M+H)⁺ (ES⁺); 378 (M–H)⁻ (ES⁻).

Example 98: 3-(Benzyl(isopropyl)amino)-N-((1,2,3,5,6,7-hexahydro-s-indacen-4-yl)carbamoyl)propane-1-sulfonamide, potassium salt

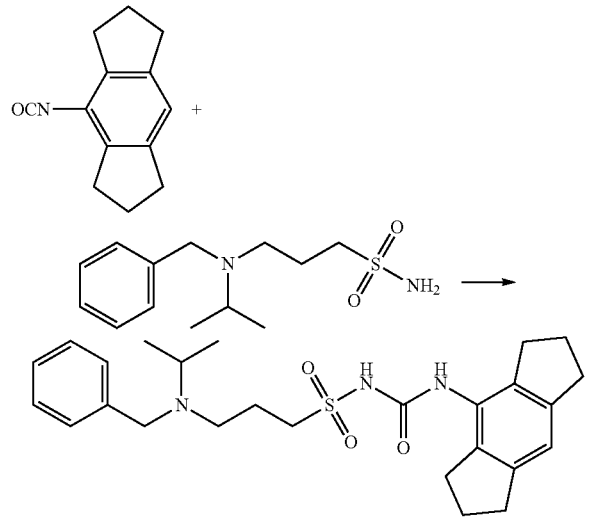

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 3-(benzyl(isopropyl)amino)propane-1-sulfonamide (Intermediate P63) to afford the title compound (82 mg, 24%) as a white solid.

¹H NMR (Methanol-d₄) δ 7.55-7.16 (m, 5H), 6.89 (s, 1H), 3.59 (s, 2H), 3.28-3.17 (m, 1H), 3.12-3.00 (m, 2H), 2.81 (dt, 8H), 2.58 (t, 2H), 2.01 (m, 6H), 1.05 (d, 6H).
LCMS: m/z 470 (M+H)⁺ (ES⁺); 468 (M–H)⁻ (ES⁻).

Example 99: Methyl (3-(N-((1,2,3,5,6,7-hexahydro-s-indacen-4-yl) carbamoyl)sulfamoyl)propyl)(methyl)carbamate, potassium salt

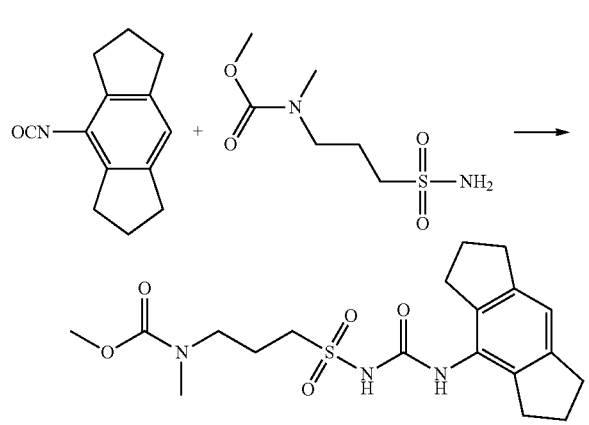

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and methyl methyl(3-sulfamoylpropyl)carbamate (Intermediate P64) to afford the title compound (4 mg, 13%) as a white solid.

¹H NMR (Methanol-d₄) δ 6.87 (s, 1H), 3.66 (s, 3H), 3.40 (t, 2H), 3.24-3.14 (m, 2H), 2.92 (s, 3H), 2.82 (m, 8H), 2.02 (p, 6H).
LCMS: m/z 410 (M+H)⁺ (ES⁺); 408 (M–H)⁻ (ES⁻).

Example 100: N-((1,2,3,5,6,7-Hexahydro-s-indacen-4-yl)carbamoyl)-3-(isopropylamino)propane-1-sulfonamide, Potassium Salt

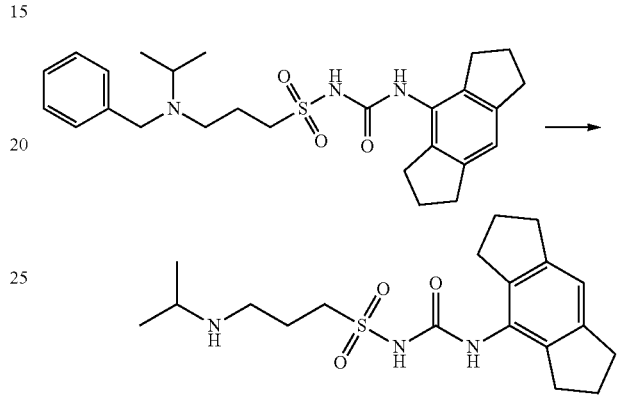

Prepared as described for N-((1,2,3,5,6,7-hexahydro-s-indacen-4-yl)carbamoyl)-3-(methylamino)propane-1-sulfonamide, potassium salt (Example 69), using 3-(benzyl(isopropyl)amino)-N-((1,2,3,5,6,7-hexahydro-s-indacen-4-yl) carbamoyl)propane-1-sulfonamide, potassium salt (Example 98) to afford the title compound (59 mg, 87%) as a white solid.

¹H NMR (Methanol-d₄) δ 6.88 (s, 1H), 3.26-3.19 (m, 1H), 3.08 (m, 2H), 2.83 (m, 10H), 2.02 (td, 6H), 1.12 (d, 6H).
LCMS: m/z 380 (M+H)⁺ (ES⁺); 378 (M–H)⁻ (ES⁻).

Example 101: 3-(Dimethylamino)-N-((4-fluoro-2,6-diisopropylphenyl) carbamoyl)propane-1-sulfonamide, potassium salt

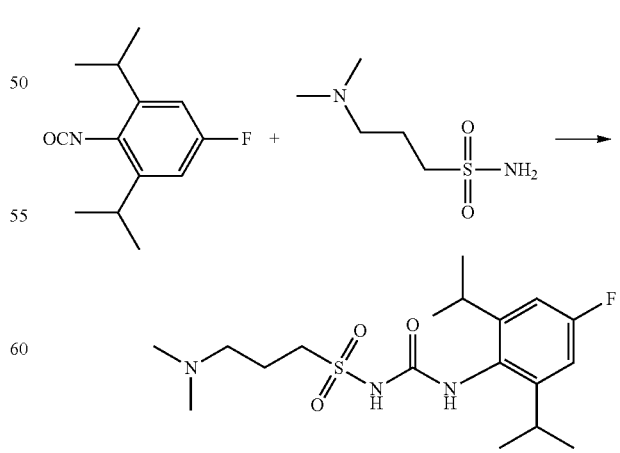

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 5-fluoro-2-isocyanato-1,3-diisopropylbenzene (Intermediate A10) and 3-(dimethylamino)propane-1-sulfonamide (Intermediate P65) to afford the title compound (10 mg, 24%) as a white solid.

$^1$H NMR (Methanol-d$_4$) δ 6.83 (d, 2H), 3.26 (m, 2H), 3.02 (t, 2H), 2.67 (s, 6H), 2.14 (m, 2H), 1.29 (m, 2H), 1.19 (d, 12H).

LCMS: m/z 388 (M+H)$^+$ (ES$^+$); 386 (M–H)$^-$ (ES$^-$).

Example 102: 2-(2,2-Dimethylazetidin-1-yl)-N-((1,2,3,5,6,7-hexahydro-s-indacen-4-yl)carbamoyl)ethane-1-sulfonamide, potassium salt

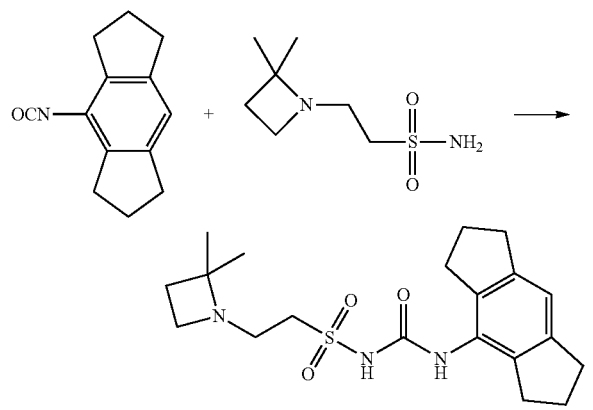

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(2,2-dimethylazetidin-1-yl)ethane-1-sulfonamide, TFA salt (Intermediate P66) to afford the title compound (66 mg, 56%) as a white solid.

$^1$H NMR (Methanol-d$_4$) δ 6.88 (s, 1H), 3.46 (t, 2H), 3.09 (dd, 2H), 2.83 (m, 10H), 2.03 (m, 6H), 1.38 (d, 6H).

LCMS: m/z 392 (M+H)$^+$ (ES$^+$); 390 (M–H)$^-$ (ES$^-$).

Example 103: 2-(2,4-Dimethylazetidin-1-yl)-N-((1,2,3,5,6,7-hexahydro-s-indacen-4-yl)carbamoyl)ethane-1-sulfonamide, potassium salt

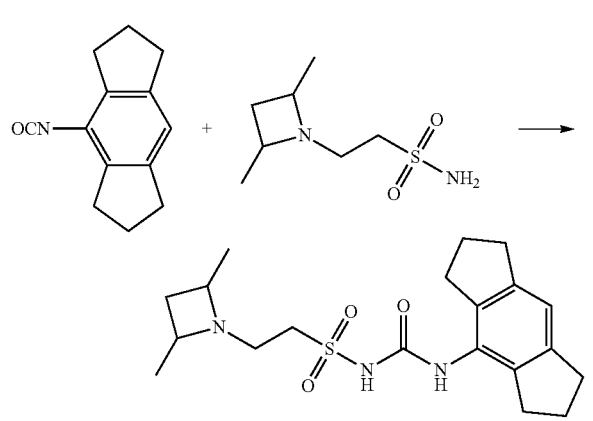

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(2,4-dimethylazetidin-1-yl)ethane-1-sulfonamide, TFA salt (Intermediate P67) to afford the title compound (33 mg, 20%) as a white solid.

$^1$H NMR (Methanol-d$_4$) δ 6.89 (s, 1H), 3.51 (m, 2H), 3.12 (m, 4H), 2.84 (m, 8H), 2.06 (dt, 6H), 1.26 (t, 6H).

LCMS: m/z 392 (M+H)$^+$ (ES$^+$); 390 (M–H)$^-$ (ES$^-$).

Example 104: N-((1,2,3,5,6,7-Hexahydro-s-indacen-4-yl)carbamoyl)-2-(2-isopropylazetidin-1-yl)ethane-1-sulfonamide, Potassium Salt

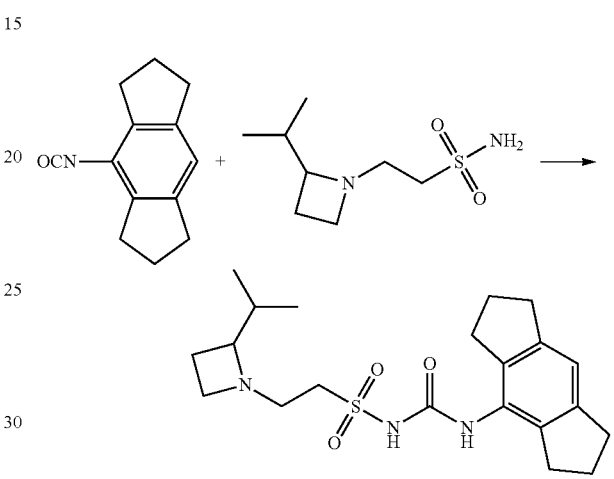

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and 2-(2-isopropylazetidin-1-yl)ethane-1-sulfonamide, TFA salt (Intermediate P68) to afford the title compound (17 mg, 11%) as a white solid.

$^1$H NMR (Methanol-d$_4$) δ 6.87 (s, 1H), 3.45 (m, 1H), 3.26 (m, 1H), 3.03 (q, 2H), 2.83 (m, 11H), 2.15 (m, 1H), 2.03 (m, 4H), 1.95-1.68 (m, 2H), 0.95 (d, 3H), 0.82 (d, 3H).

LCMS: m/z 406 (M+H)$^+$ (ES$^+$); 404 (M–H)$^-$ (ES$^-$).

Example 105: N-((1,2,3,5,6,7-Hexahydro-s-indacen-4-yl)carbamoyl)-1-(1-methylpyrrolidin-2-yl)methanesulfonamide, Potassium Salt

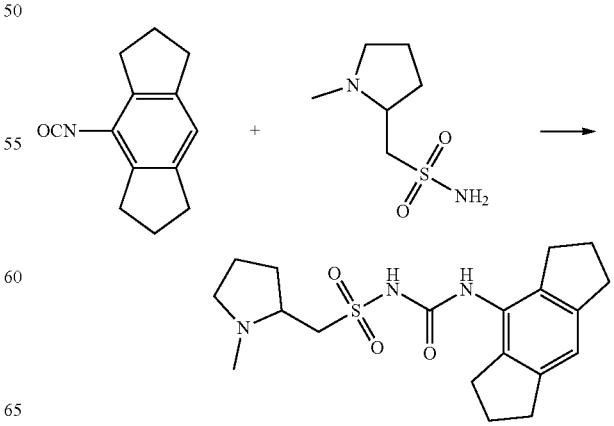

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-methylpyrrolidin-2-yl)methanesulfonamide (Intermediate P69) to afford the title compound (38 mg, 45%) as a white solid.

$^1$H NMR (Methanol-$d_4$) δ 6.87 (s, 1H), 3.71 (dd, 1H), 3.21-3.00 (m, 3H), 2.83 (m, 10H), 2.42 (d, 3H), 2.31 (m, 1H), 2.13-1.94 (m, 4H), 1.81 (m, 2H).

LCMS: m/z 378 (M+H)$^+$ (ES$^+$); 376 (M−H)$^-$ (ES$^-$).

Example 106: 1-(1-Ethylpyrrolidin-2-yl)-N-((1,2,3,5,6,7-hexahydro-s-indacen-4-yl)carbamoyl)methanesulfonamide, potassium salt

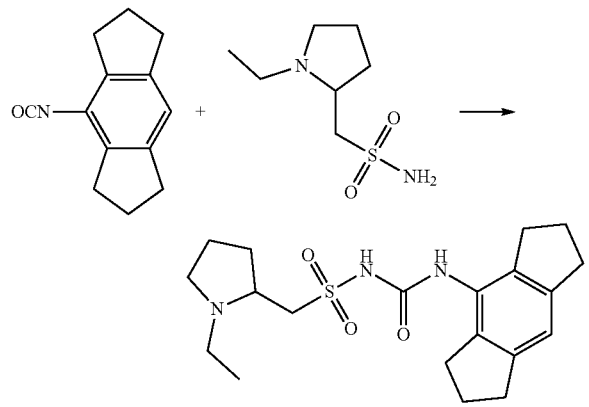

Prepare as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-ethylpyrrolidin-2-yl)methanesulfonamide (Intermediate P70) to afford the title compound (36 mg, 37%) as a white solid.

$^1$H NMR (Methanol-$d_4$) δ 6.89 (s, 1H), 3.78-3.56 (m, 1H), 3.26-3.14 (m, 3H), 2.94-2.75 (m, 10H), 2.60 (dt, 2H), 2.34 (m, 1H), 2.03 (m, 4H), 1.97-1.82 (m, 2H), 1.21 (td, 3H).

LCMS: m/z 392 (M+H)$^+$ (ES$^+$); 390 (M−H)$^-$ (ES$^-$).

Example 107: N-((1,2,3,5,6,7-Hexahydro-s-indacen-4-yl)carbamoyl)-1-(1-isopropylpyrrolidin-2-yl)methanesulfonamide, Potassium Salt

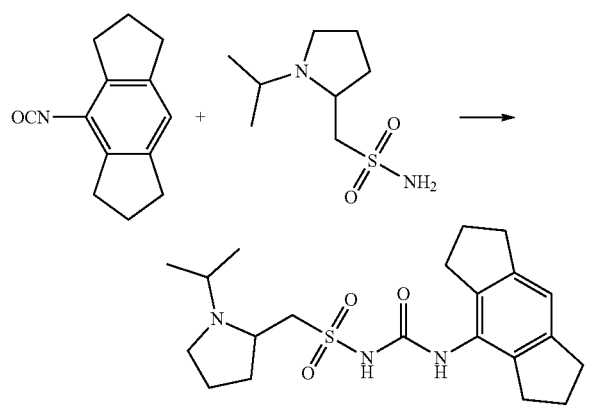

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-isopropylpyrrolidin-2-yl)methanesulfonamide (Intermediate P71) to afford the title compound (101 mg, 40%) as a white solid.

$^1$H NMR (Methanol-$d_4$) δ 6.89 (s, 1H), 3.79-3.54 (m, 2H), 3.44 (q, 1H), 3.08 (dt, 1H), 2.94 (dd, 1H), 2.82 (m, 10H), 2.22 (ddt, 1H), 2.13-1.97 (m 4H), 1.89 (m 2H), 1.21 (ddd, 6H).

LCMS: m/z 406 (M+H)$^+$ (ES$^+$); 404 (M−H)$^-$ (ES$^-$).

Example 108: 3-(Dimethylamino)-N-((4-chloro-2,6-diisopropylphenyl) carbamoyl)propane-1-sulfonamide, potassium salt

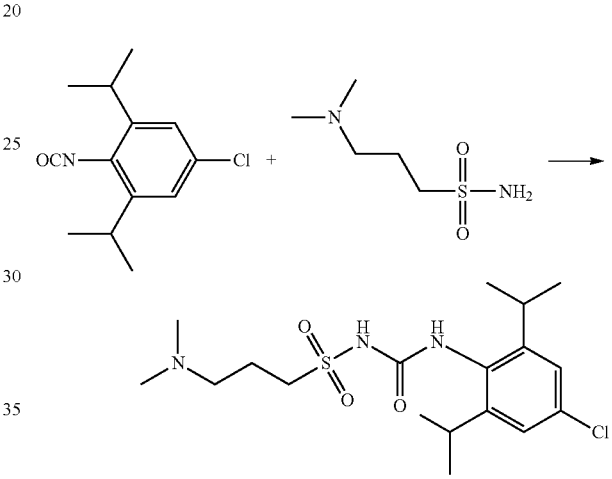

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 5-chloro-2-isocyanato-1,3-diisopropylbenzene (Intermediate A9) and 3-(dimethylamino)propane-1-sulfonamide (Intermediate P65) to afford the title compound (15 mg, 34%) as a white solid.

$^1$H NMR (Methanol-$d_4$) δ 7.09 (d, 2H), 3.26 (m, 2H), 2.86 (t, 2H), 2.54 (s, 6H), 2.10 (m, 2H), 1.19 (d, 14H).

LCMS: m/z 404 (M+H)$^+$ (ES$^+$); 402 (M−H)$^-$ (ES$^-$).

Example 109: N-((1,2,3,5,6,7-Hexahydro-s-indacen-4-yl)carbamoyl)-1-(1-isopropylpiperidin-2-yl)methanesulfonamide, Potassium Salt

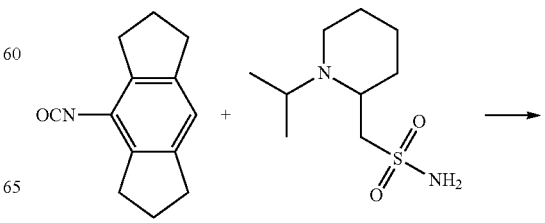

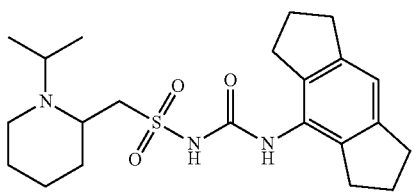

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-isopropylpiperidin-2-yl)methanesulfonamide (Intermediate P72) to afford the title compound (11 mg, 8%) as a white solid.

$^1$H NMR (Methanol-d$_4$) δ 6.90 (s, 1H), 4.05 (m, 1H), 3.88-3.67 (m, 2H), 3.58 (dd, 1H), 3.04 (t, 1H), 2.83 (m, 9H), 2.23 (m, 1H), 2.03 (m, 5H), 1.81 (d, 3H), 1.62 (m, 1H), 1.33 (dd, 6H).

LCMS: m/z 420 (M+H)$^+$ (ES$^+$); 418 (M–H)$^-$ (ES$^-$).

Example 110: 1-(1-Ethylpiperidin-2-yl)-N-((1,2,3,5,6,7-hexahydro-s-indacen-4-yl)carbamoyl)methanesulfonamide, potassium salt

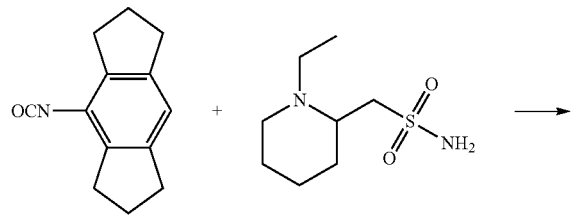

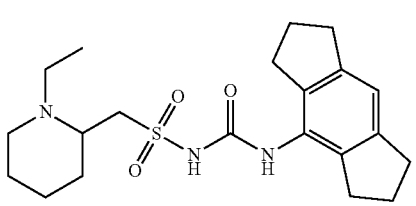

Prepared as described for N-ethyl-N-(4-(N-((1,2,3,5,6,7-hexahydro-s-indacen-4-yl) carbamoyl)sulfamoyl)cyclohexyl)acetamide, potassium salt (Example 63) using 4-isocyanato-1,2,3,5,6,7-hexahydro-s-indacene (Intermediate A1) and (1-ethylpiperidin-2-yl)methanesulfonamide (Intermediate P73) to afford the title compound (2 mg, 1%) as a white solid.

$^1$H NMR (Methanol-d$_4$) δ 6.89 (s, 1H), 4.07 (m, 1H), 3.79-3.48 (m, 2H), 3.21-2.99 (m, 3H), 2.83 (m, 9H), 2.03 (m, 6H), 1.74 (m, 3H), 1.59 (s, 1H), 1.26 (t, 3H).

LCMS: m/z 406 (M+H)$^+$ (ES$^+$); 404 (M–H)$^-$ (ES$^-$).

Example 111: N-((1,2,3,5,6,7-Hexahydro-s-indacen-4-yl)carbamoyl)-1-(1-isopropyl-1H-pyrazol-3-yl)methanesulfonamide

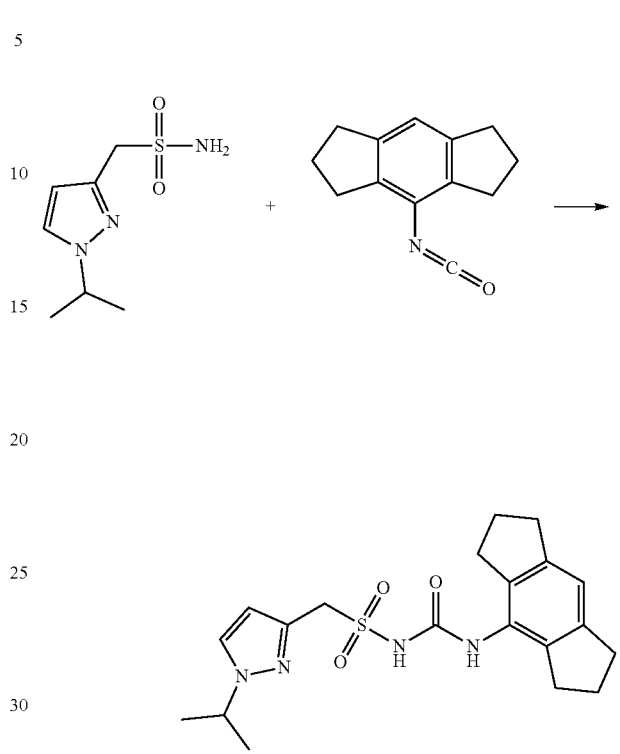

Prepared according to the general procedure of N-((1,2,3,5,6,7-hexahydro-s-indacen-4-yl)carbamoyl)-1-(1-methyl-1H-pyrazol-4-yl)methanesulfonamide (Example 35) from (1-isopropyl-1H-pyrazol-3-yl)methanesulfonamide (Intermediate P74) and 4-isocyanato-1,2,3,5,6,7-hexahydro-s-indacene (Intermediate A1) to afford the title compound (14 mg, 24%) as a white solid.

$^1$H NMR (DMSO-d6) δ 10.11 (s, 1H), 7.89 (s, 1H), 7.78 (d, J=2.3 Hz, 1H), 6.96 (s, 1H), 6.26 (d, J=2.3 Hz, 1H), 4.65 (s, 2H), 4.47 (sept, J=6.7 Hz, 1H), 2.82 (t, J=7.4 Hz, 4H), 2.74 (t, J=7.4 Hz, 4H), 1.99 (p, J=7.4 Hz, 4H), 1.40 (d, J=6.7 Hz, 6H).

LCMS; m/z 403.4 (M+H)$^+$ (ES$^+$).

Example 112: N-((2-(2-Cyanopyridin-4-yl)-4-fluoro-6-isopropylphenyl) carbamoyl)-1-(pyridin-3-yl)methanesulfonamide

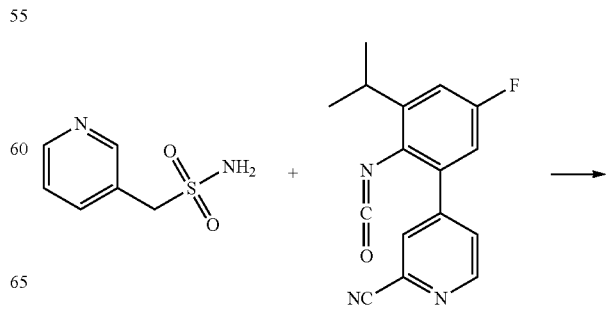

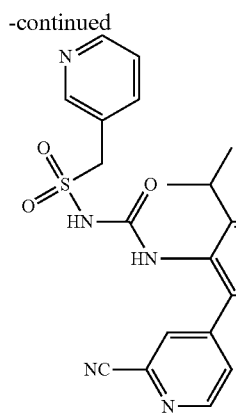

To a solution of pyridin-3-ylmethanesulfonamide (70 mg, 406.49 μmol, 1 eq) in THF (5 mL) was added t-BuONa (39 mg, 406.49 μmol, 1 eq) and 4-(5-fluoro-2-isocyanato-3-isopropylphenyl)picolinonitrile (Intermediate A3) (114 mg, 406.49 μmol, 1 eq). The mixture was stirred at 25° C. for 30 minutes. The reaction mixture was concentrated under reduced pressure. The residue was purified by prep-HPLC (column: Phenomenex Gemini C18, 150 mm*25 mm*10 μm; mobile phase: [A: water (0.05% ammonium hydroxide v/v); B: MeCN]; B %: 5%-35%, 11.5 min) to give the title compound (68 mg, 37% yield, 100% purity on LCMS) as a white solid.

$^1$H NMR (DMSO-d$_6$): δ 8.77 (d, 1H), 8.50 (d, 1H), 8.37 (s, 1H), 8.10 (s, 1H), 7.86 (br s, 1H), 7.79 (d, 1H), 7.61-7.45 (m, 1H), 7.33-7.27 (m, 2H), 7.19-7.02 (m, 1H), 4.31 (s, 2H), 3.24-3.18 (m, 1H) and 1.20-1.06 (m, 6H).

LCMS: m/z 454.3 (M+H)$^+$ (ES$^+$).

EXAMPLES—BIOLOGICAL STUDIES

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 g/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.

1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% CO$_2$
4. Add 5 μl nigericin (Sigma #N7143) (FAC 5 μM) to all wells
5. Incubate for 1 hr at 37° C. and 5% CO$_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|----|----|----|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950 (10 uM) Compound 8-point half-log dilution
Low Drug free control

The results of the pyroptosis assay performed are summarised in Table 1 below as THP IC$_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1βg/ml of LPS in 96-well, clear bottom cell culture plate (Corning #3585)

2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add 10 μl Nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 1 below as HWB $IC_{50}$.

TABLE 1

NLRP3 inhibitory activity in THP-1 Cells (≤10 μM = '+', ≤2.0 μM = '++', ≤1.6 μM = '+++', ≤1.2 μM = '++++', ≤0.8 μM = '+++++', ND = not determined).
NLRP3 inhibitory activity in HWB (≤10 μM = '●', ≤7.5 μM = '●●', ≤5.0 μM = '●●●', ≤1.0 μM = '●●●●', ND = not determined).

| EXAMPLE | THP $IC_{50}$ | HWB $IC_{50}$ |
| --- | --- | --- |
| 1 | +++ | ●●●● |
| 2 | + | ND |
| 3 | +++++ | ●●●● |
| 4 | +++++ | ND |
| 5 | +++ | ND |
| 6 | + | ND |
| 7 | +++ | ND |
| 8 | +++++ | ●●●● |
| 9 | + | ND |
| 10 | ++++ | ND |
| 11 | +++++ | ●● |
| 12 | +++++ | ND |
| 13 | +++++ | ●●● |
| 14 | +++++ | ●●● |
| 15 | ++ | ND |
| 16 | ++ | ND |
| 17 | +++ | ND |
| 18 | + | ND |
| 19 | +++ | ND |
| 20 | +++++ | ●●● |
| 21 | ++++ | ND |
| 22 | + | ND |
| 23 | +++++ | ●●●● |
| 24 | ++++ | ND |
| 25 | + | ND |
| 26 | + | ND |
| 27 | +++++ | ●●●● |
| 28 | +++++ | ●●●● |
| 29 | +++++ | ●●●● |
| 30 | +++++ | ●●● |
| 31 | +++++ | ●●● |
| 32 | +++++ | ND |
| 33 | ++++ | ND |
| 34 | +++++ | ●●● |
| 35 | +++++ | ●●● |
| 36 | +++++ | ●●●● |
| 37 | +++++ | ●●●● |
| 38 | + | ND |
| 39 | + | ND |
| 40 | + | ND |
| 41 | +++++ | ND |
| 42 | +++++ | ND |
| 43 | +++++ | ND |
| 44 | +++++ | ●●●● |
| 45 | +++++ | ND |
| 46 | + | ND |
| 47 | +++++ | ND |

TABLE 1-continued

NLRP3 inhibitory activity in THP-1 Cells (≤10 μM = '+', ≤2.0 μM = '++', ≤1.6 μM = '+++', ≤1.2 μM = '++++', ≤0.8 μM = '+++++', ND = not determined).
NLRP3 inhibitory activity in HWB (≤10 μM = '●', ≤7.5 μM = '●●', ≤5.0 μM = '●●●', ≤1.0 μM = '●●●●', ND = not determined).

| EXAMPLE | THP $IC_{50}$ | HWB $IC_{50}$ |
| --- | --- | --- |
| 48 | +++++ | ●●● |
| 49 | + | ND |
| 50 | +++++ | ND |
| 51 | +++++ | ND |
| 52 | ++++ | ND |
| 53 | +++++ | ●●●● |
| 54 | + | ND |
| 55 | + | ND |
| 56 | + | ND |
| 57 | + | ND |
| 58 | +++++ | ●●●● |
| 59 | +++++ | ●●●● |
| 60 | + | ND |
| 61 | +++++ | ●●●● |
| 62 | +++++ | ●●●● |
| 63 | + | ND |
| 64 | + | ND |
| 65 | + | ND |
| 66 | + | ND |
| 67 | +++++ | ● |
| 68 | ++++ | ND |
| 69 | ++++ | ND |
| 70 | +++++ | ●●● |
| 71 | +++++ | ● |
| 72 | +++ | ●●●● |
| 73 | +++++ | ●●● |
| 74 | +++++ | ●●● |
| 75 | +++++ | ND |
| 76 | +++ | ND |
| 77 | + | ●● |
| 78 | +++++ | ●●●● |
| 79 | +++ | ND |
| 80 | +++++ | ●●● |
| 81 | ++++ | ●●● |
| 82 | ++ | ●●● |
| 83 | ++++ | ●●●● |
| 84 | +++++ | ●●●● |
| 85 | + | ND |
| 86 | + | ND |
| 87 | ++ | ND |
| 88 | +++ | ND |
| 89 | +++++ | ●●●● |
| 90 | +++++ | ●●● |
| 91 | +++++ | ●●●● |
| 92 | +++++ | ●● |
| 93 | +++++ | ●●●● |
| 94 | ++ | ND |
| 95 | +++++ | ●●● |
| 96 | ++++ | ND |
| 97 | +++++ | ●● |
| 98 | +++ | ND |
| 99 | ++++ | ND |
| 100 | ++++ | ND |
| 101 | + | ND |
| 102 | +++++ | ●●●● |
| 103 | +++++ | ●●●● |
| 104 | +++++ | ●●●● |
| 105 | +++++ | ●●●● |
| 106 | +++++ | ●●●● |
| 107 | +++++ | ●●●● |
| 108 | + | ND |
| 109 | +++++ | ●●●● |
| 110 | +++++ | ●●●● |
| 111 | +++++ | ●● |
| 112 | + | ND |

PK Protocol

Pharmacokinetic parameters were determined in male Sprague Dawley rats (Charles River, UK, 250-350 g; or Vital River Laboratory Animal Technology Co Ltd, Beijing, China, 7-9 weeks old). Animals were individually housed during the study and maintained under a 12 h light/dark cycle.

For intravenous administration, compounds were formulated as a solution in water or DMSO:PBS [10:90] in 2 mL/kg dosing volume and administered via tail vein. For oral administration, compounds were formulated as a solution in DMSO:water [10:90] in 5 mL/kg dosing volume and administered orally.

Serial blood samples (about 120-300 μL) were taken from each animal at each of 8 time-points post dose (0.083, 0.25, 0.5, 1, 2, 4, 8 and 24 h) or at each of 12 time-points post dose (0.03, 0.1, 0.17, 0.25, 0.5, 1, 2, 4, 6, 8, 12 and 24 h) or pre-dose and at each of 9 time-points post dose (0.25, 0.5, 1, 2, 4, 6, 8, 12 and 24 h). Samples were held on ice for no longer than 30 minutes before centrifugation (10,000 rpm (8,385 g) for 3 minutes; or 5,696 rpm (3,000 g) for 15 minutes) for plasma generation. Plasma was frozen on dry ice prior to bioanalysis. PK parameters were generated from LC-MS/MS data using Dotmatics or Phoenix WinNonlin 6.3 software.

TABLE 2

PK data (intravenous administration)

| Example No | Dose (mg/kg) | AUC (ng · hr/mL) | $T_{1/2}$ (hr) | $V_{dss}$ (L/kg) | Cl (mL/min/kg) |
|---|---|---|---|---|---|
| 3 | 1 | 1181.1 | 1.5 | 0.79 | 14.2 |
| 8 | 1 | 2346.4 | 1.1 | 0.49 | 7.1 |
| 29 | 1 | 2776.5 | 1.3 | 0.53 | 6.0 |
| 37 | 1 | 591.0 | 0.9 | 0.55 | 28.2 |

TABLE 3

PK data (oral administration)

| Example No | Dose (mg/kg) | $C_{max}$ (ng/mL) | AUC (ng · hr/mL) | $T_{max}$ (hr) | $T_{1/2}$ (hr) | Cl/F (mL/min/kg) | Bioavailability |
|---|---|---|---|---|---|---|---|
| 3 | 3 | 819.0 | 2271.3 | 0.42 | 1.8 | 22.6 | 64.1 |

As is evident from the results presented in Table 1, surprisingly in spite of the structural differences versus the prior art compounds, the compounds of the invention show high levels of NLRP3 inhibitory activity in the pyroptosis assay and in particular in the human whole blood assay.

As is evident from the results presented in Tables 2 and 3, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

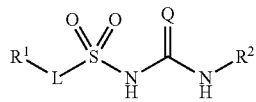

Formula (I)

or a pharmaceutically acceptable salt or solvate thereof, wherein:

Q is O;

L is a $C_1$-$C_{12}$ hydrocarbylene group which is saturated or a combination of saturated and aromatic, wherein the hydrocarbylene group may be straight-chained or branched, or include cyclic groups, wherein the hydrocarbylene group may optionally be substituted, and wherein the hydrocarbylene group may optionally include one or more heteroatoms N, O or S in its carbon skeleton;

$R^1$ is —$NR^3R^4$, —$OR^5$, —$C(=NR^6)R^7$, —$(CO)R^8$, —CN, —$N_3$, a quaternary ammonium group and its counterion, or an optionally substituted heterocycle;

$R^3$, $R^4$, $R^5$, $R^6$, $R^7$ and $R^8$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

or L and $R^3$, or L and $R^4$, or $R^3$ and $R^4$ together with the nitrogen atom to which they are attached form a 3- to 12-membered saturated or unsaturated cyclic group, wherein the cyclic group may optionally be substituted;

or L and $R^5$ together with the oxygen atom to which they are attached form a 3- to 12-membered saturated or unsaturated cyclic group, wherein the cyclic group may optionally be substituted;

or L and $R^6$, or L and $R^7$, or $R^6$ and $R^7$ together with the —(C=N)— group to which they are attached form a 3- to 12-membered saturated or unsaturated cyclic group, wherein the cyclic group may optionally be substituted;

or L and $R^8$ together with the —(C=O)— group to which they are attached form a 3- to 12-membered saturated or unsaturated cyclic group, wherein the cyclic group may optionally be substituted; and $R^2$ is a cyclic group substituted at the α and α' positions, wherein $R^2$ may optionally be further substituted;

provided that the atom of L which is attached to the sulfur atom of the sulfonylurea group is a carbon atom and is not a ring atom of any cyclic group; and provided that the compound of formula (I) is not

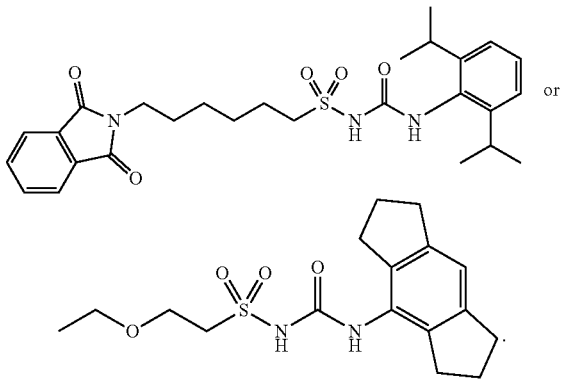

2. The compound or the pharmaceutically acceptable salt or solvate thereof as claimed in claim 1, wherein L is a $C_1$-$C_8$ hydrocarbylene group which is saturated or aromatic or a combination thereof, wherein the hydrocarbylene group may be straight-chained or branched, or include cyclic groups, and wherein the hydrocarbylene group may optionally be substituted with one or more substituents independently selected from halo, —CN, —N(R$^9$)$_2$, —OR$^9$ or oxo (=O) groups, wherein R$^9$ is independently selected from a hydrogen atom or a C$_1$-C$_3$ alkyl group.

3. The compound or the pharmaceutically acceptable salt or solvate thereof as claimed in claim 1, wherein R$^1$ is —NR$^3$R$^4$, and R$^3$ and R$^4$ are each independently hydrogen or a C$_1$-C$_6$ alkyl, C$_2$-C$_6$ alkenyl, C$_2$-C$_6$ alkynyl, C$_3$-C$_6$ cycloalkyl, phenyl or benzyl group, each of which may optionally be substituted with one or more substituents independently selected from halo, —CN, —N(R$^9$)$_2$, —OR$^9$ or oxo (=O) groups, wherein R$^9$ is independently selected from a hydrogen atom or a C$_1$-C$_3$ alkyl group.

4. The compound or the pharmaceutically acceptable salt or solvate thereof as claimed in claim 1, wherein R$^1$ is —OR$^5$, and R$^5$ is hydrogen or a C$_1$-C$_6$ alkyl, C$_2$-C$_6$ alkenyl, C$_2$-C$_6$ alkynyl, C$_3$-C$_6$ cycloalkyl, phenyl or benzyl group, each of which may optionally be substituted with one or more substituents independently selected from halo, —CN, —N(R$^9$)$_2$, —OR$^9$ or oxo (=O) groups, wherein R$^9$ is independently selected from a hydrogen atom or a C$_1$-C$_3$ alkyl group.

5. The compound or the pharmaceutically acceptable salt or solvate thereof as claimed in claim 1, wherein R$^1$ is —C(=NR$^6$)R$^7$, and R$^6$ and R$^7$ are each independently hydrogen or a C$_1$-C$_6$ alkyl, C$_2$-C$_6$ alkenyl, C$_2$-C$_6$ alkynyl, C$_3$-C$_6$ cycloalkyl, phenyl or benzyl group, each of which may optionally be substituted with one or more substituents independently selected from halo, —CN, —N(R$^9$)$_2$, —OR$^9$ or oxo (=O) groups, wherein R$^9$ is independently selected from a hydrogen atom or a C$_1$-C$_3$ alkyl group.

6. The compound or the pharmaceutically acceptable salt or solvate thereof as claimed in claim 1, wherein R$^1$ is —(CO)R$^8$, and R$^8$ is hydrogen or a C$_1$-C$_6$ alkyl, C$_2$-C$_6$ alkenyl, C$_2$-C$_6$ alkynyl, C$_3$-C$_6$ cycloalkyl, phenyl or benzyl group, each of which may optionally be substituted with one or more substituents independently selected from halo, —CN, —N(R$^9$)$_2$, —OR$^9$ or oxo (=O) groups, wherein R$^9$ is independently selected from a hydrogen atom or a C$_1$-C$_3$ alkyl group.

7. The compound or the pharmaceutically acceptable salt or solvate thereof as claimed in claim 1, wherein R$^1$ is —(CO)R$^8$, and L and R$^8$ together with the —(C=O)— group to which they are attached form a 4-, 5- or 6-membered saturated cyclic group, wherein the cyclic group may optionally include one heteroatom N, O or S in its carbon skeleton, and wherein the cyclic group may optionally be substituted with one or more substituents independently selected from halo, —CN, —N(R$^9$)$_2$, —OR$^9$, C$_1$-C$_3$ alkyl, C$_1$-C$_3$ alkylene or oxo (=O) groups, wherein R$^9$ is independently selected from a hydrogen atom or a C$_1$-C$_3$ alkyl group.

8. The compound or the pharmaceutically acceptable salt or solvate thereof as claimed in claim 1, wherein R$^2$ is an aryl or a heteroaryl group, wherein the aryl or the heteroaryl group is substituted at the α and α' positions, and wherein R$^2$ may optionally be further substituted.

9. The compound or the pharmaceutically acceptable salt or solvate thereof as claimed in claim 8, wherein R$^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, and wherein R$^2$ may optionally be further substituted.

10. The compound or the pharmaceutically acceptable salt or solvate thereof as claimed in claim 1, wherein R$^2$ is a cyclic group substituted at the α-position with a monovalent heterocyclic group or a monovalent aromatic group, wherein a ring atom of the heterocyclic or aromatic group is directly attached to the α-ring atom of the cyclic group, wherein the heterocyclic or aromatic group may optionally be substituted, and wherein the cyclic group is further substituted at the α' position and may optionally be further substituted.

11. The compound or the pharmaceutically acceptable salt or solvate thereof as claimed in claim 1, wherein the compound is selected from the group consisting of:

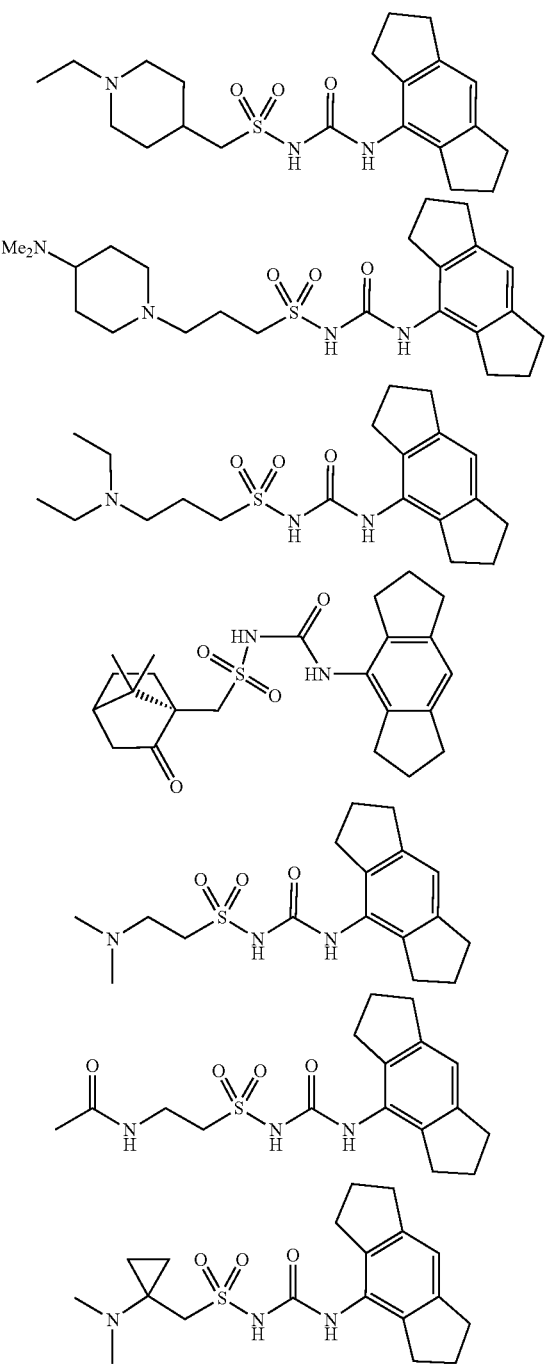

287
-continued
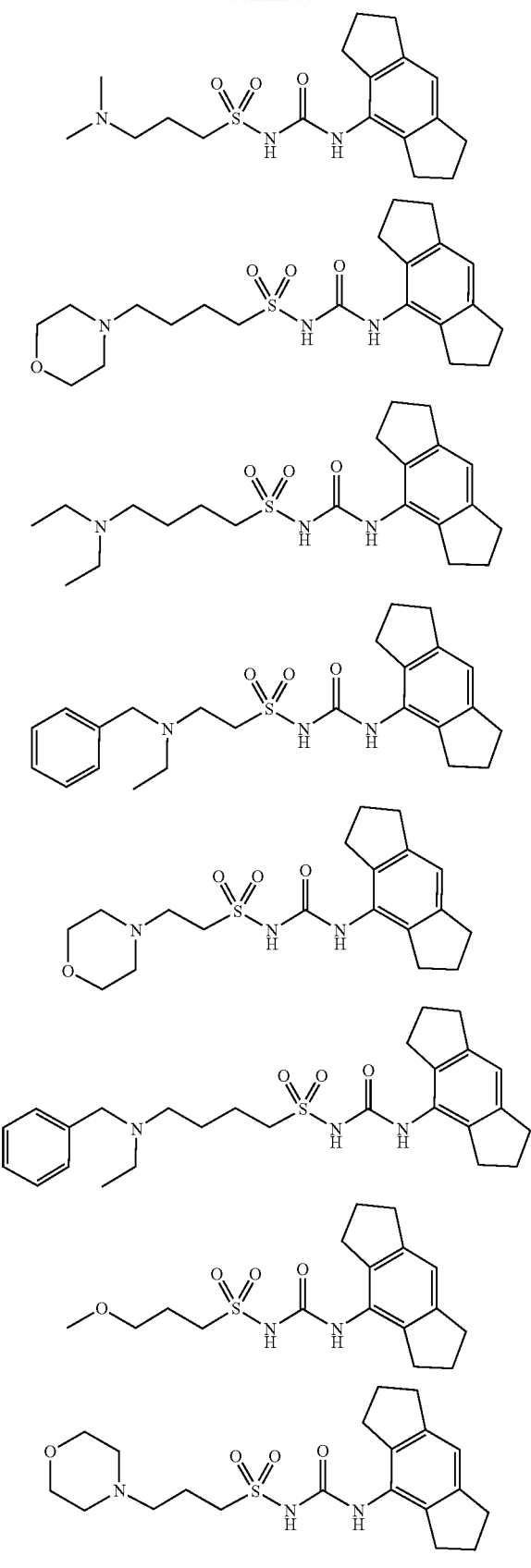
288
-continued
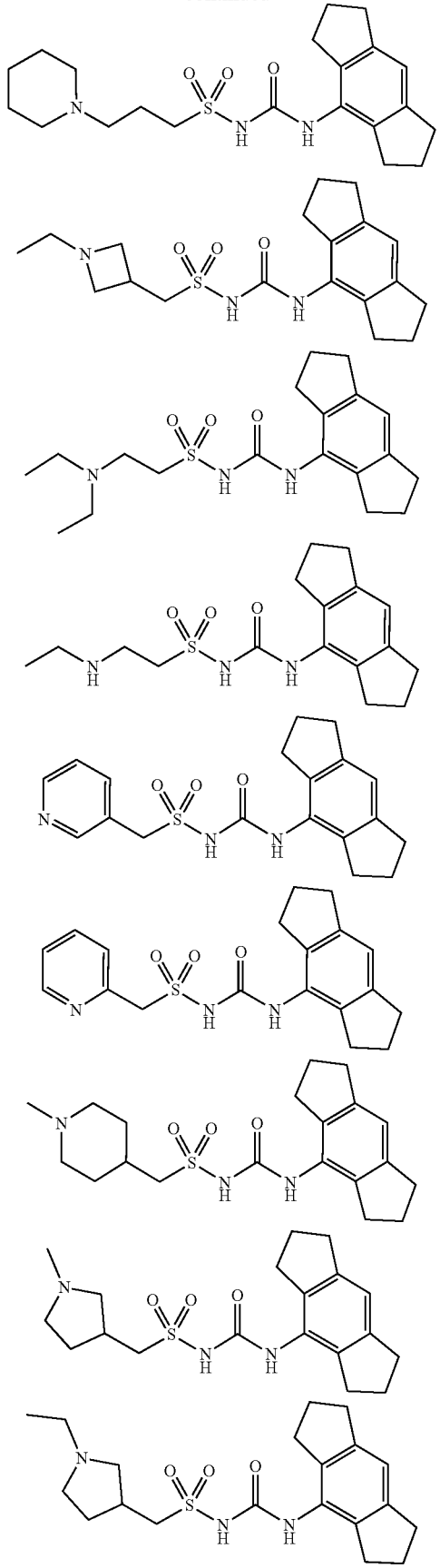

289
-continued
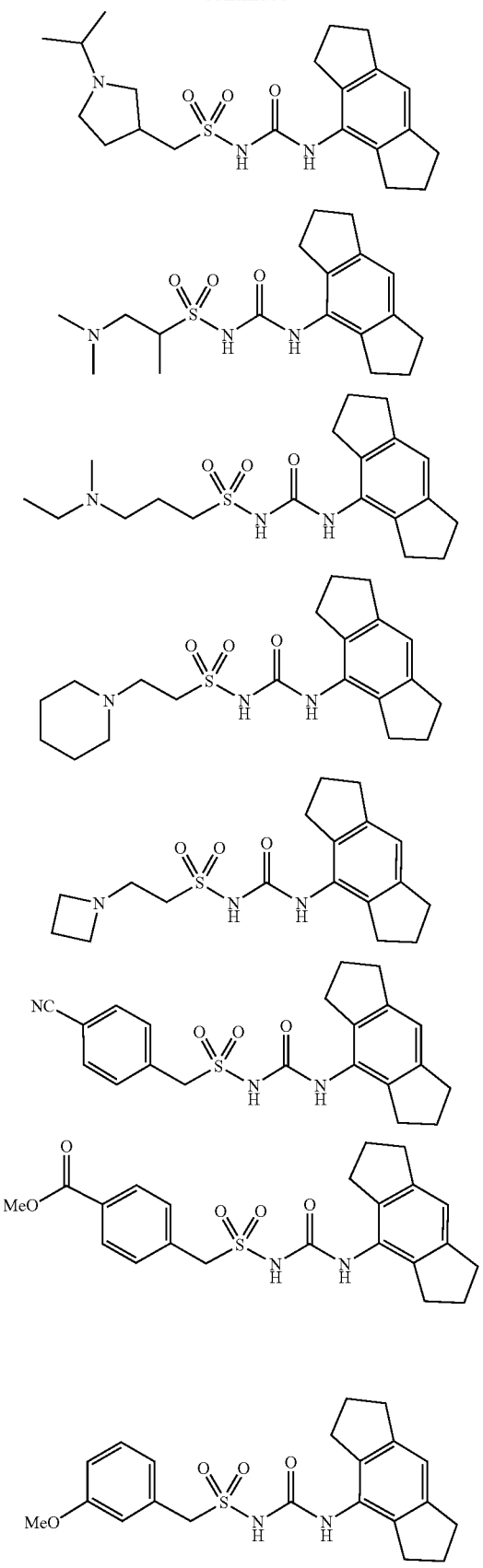
290
-continued
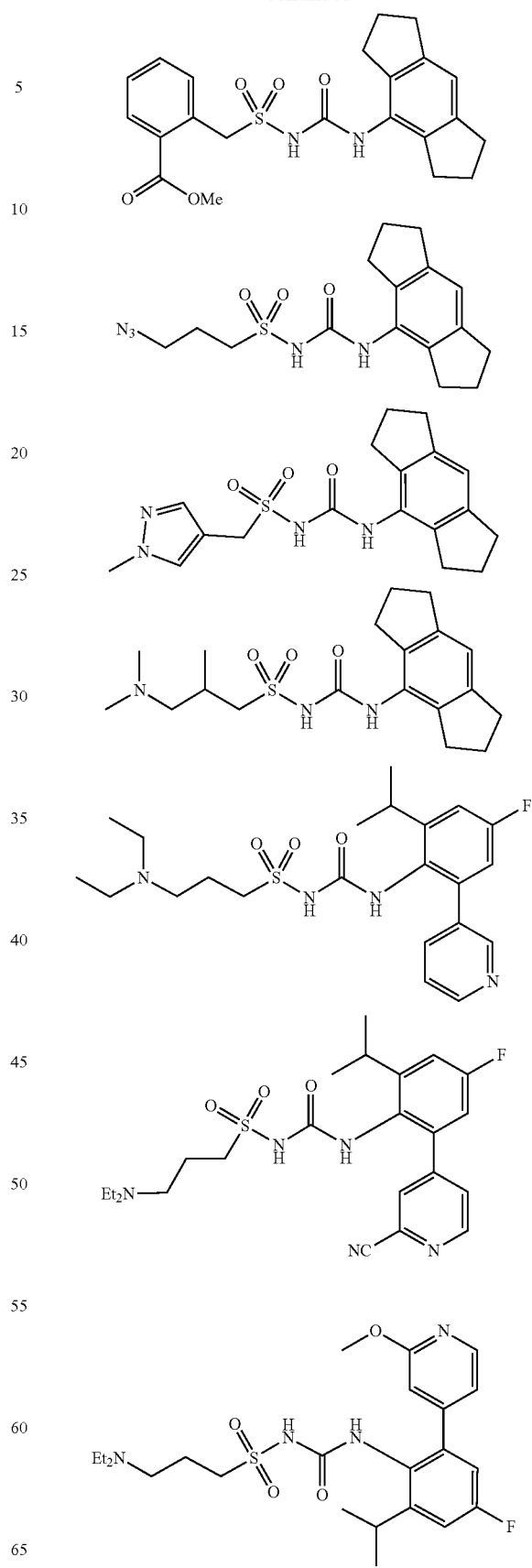

291
-continued
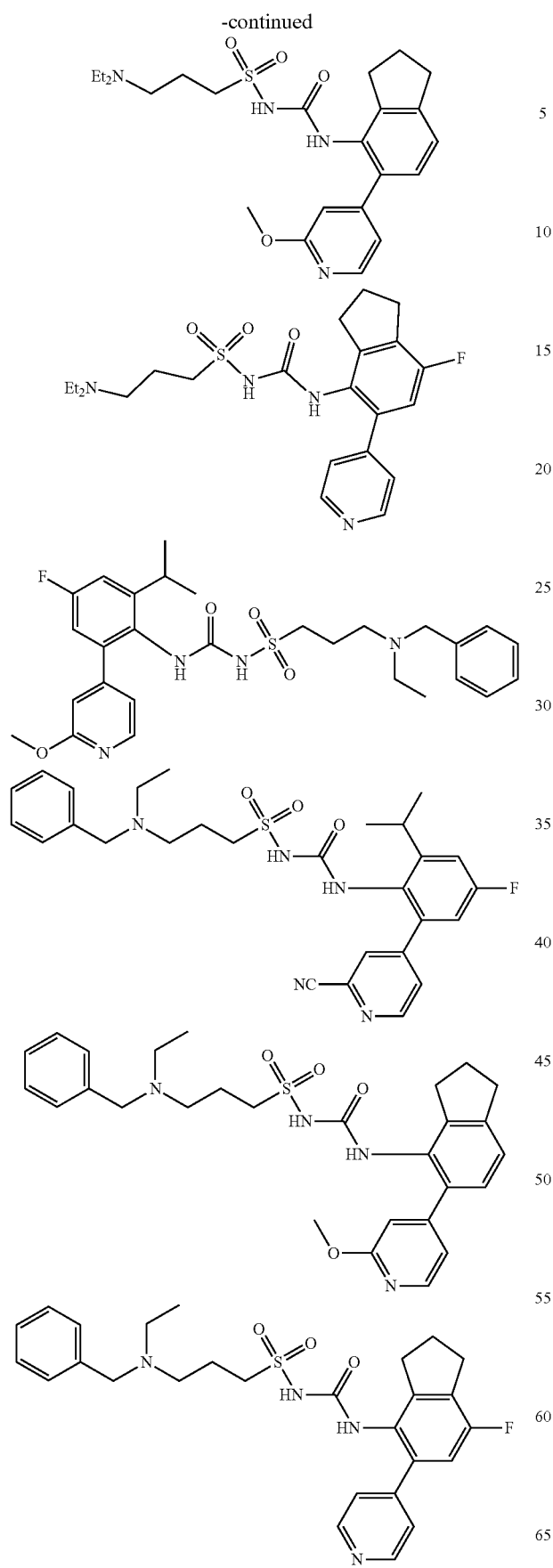
292
-continued
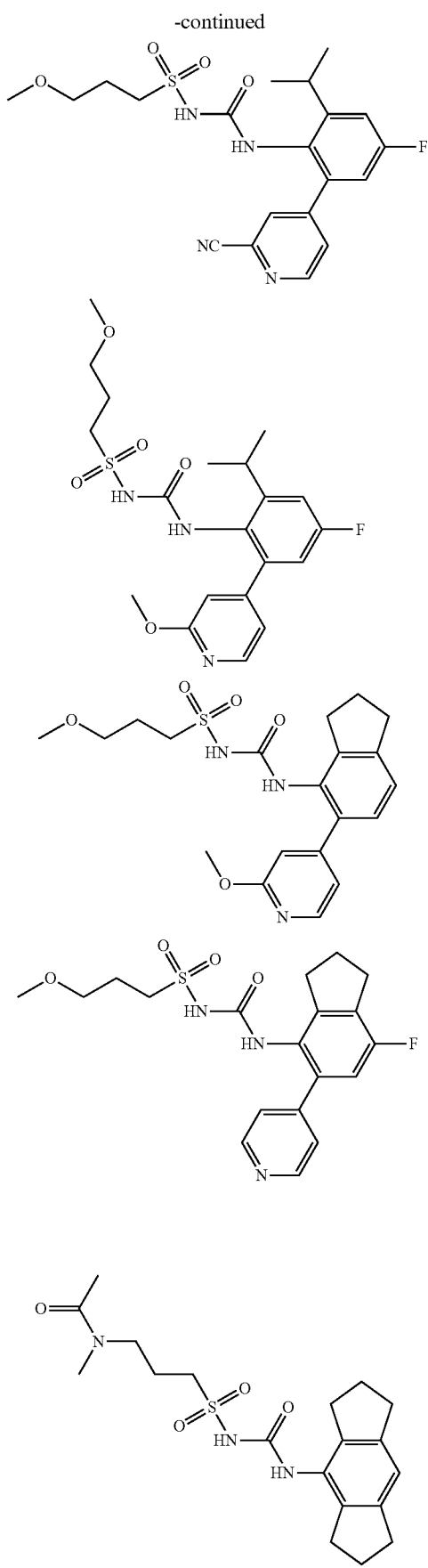

293
-continued
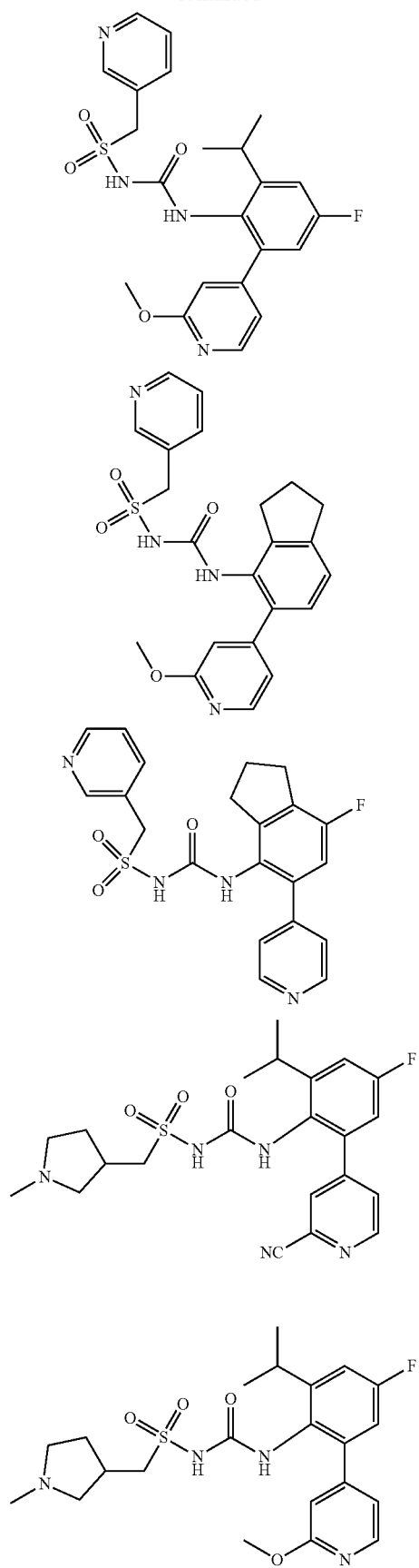
294
-continued
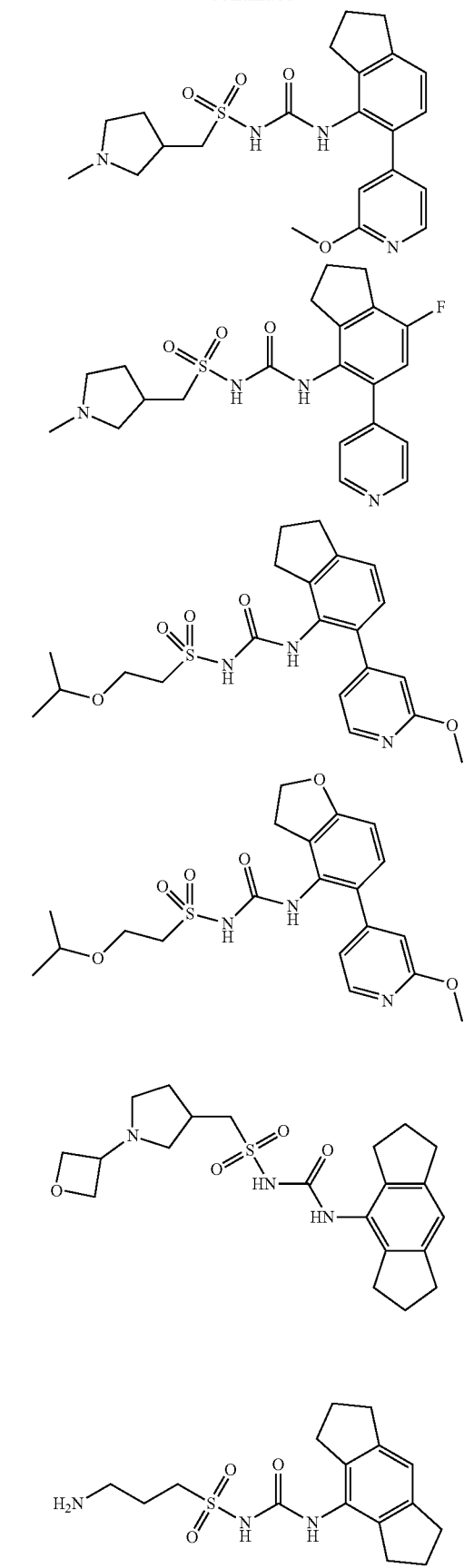

295
-continued
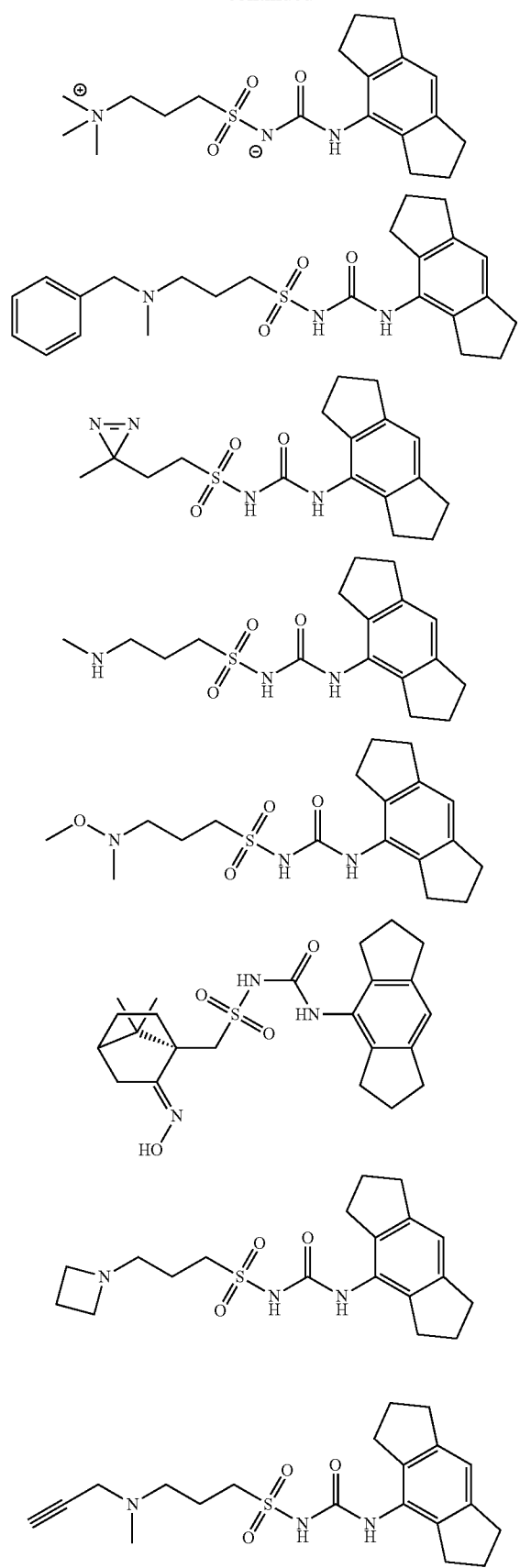
296
-continued
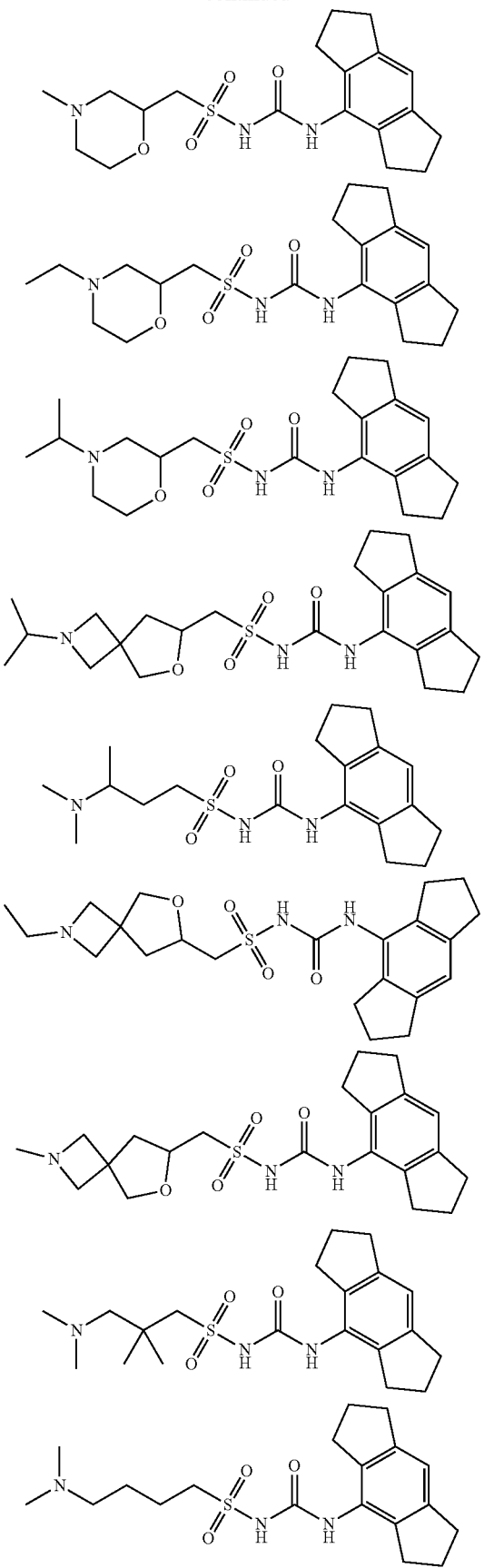

297
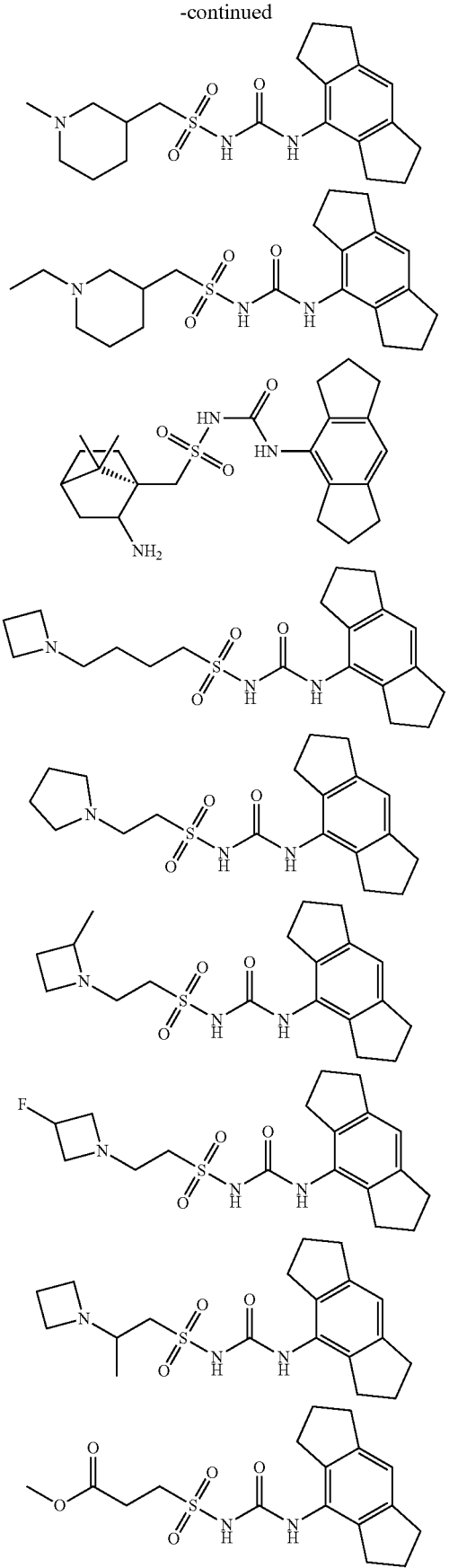
298
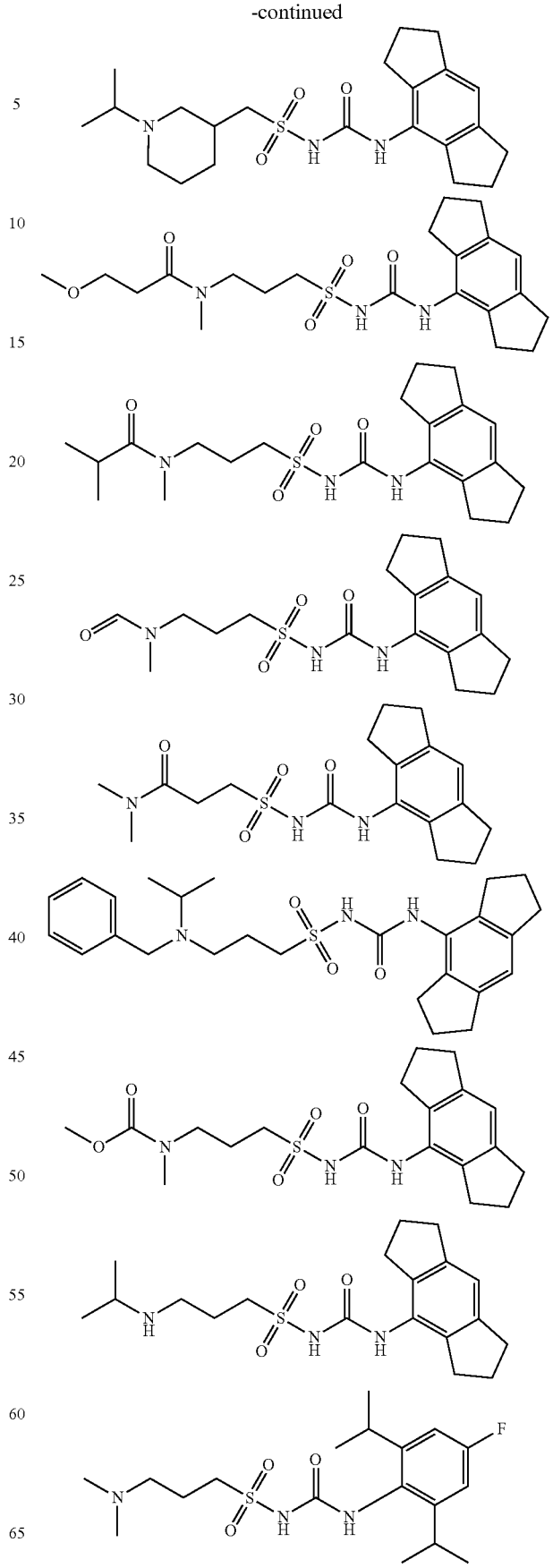

299
-continued

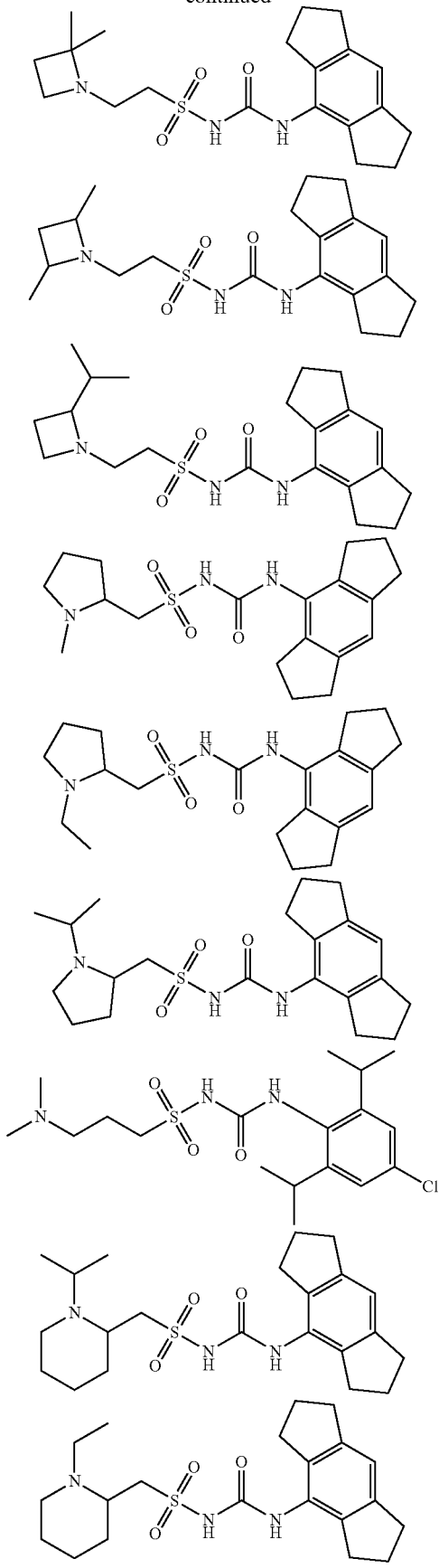

300
-continued

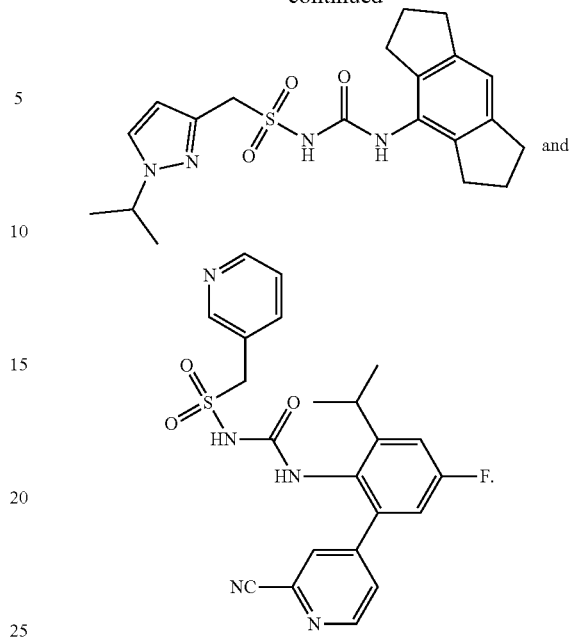

12. A pharmaceutical composition comprising the compound or the pharmaceutically acceptable salt or solvate thereof as claimed in claim 1, and a pharmaceutically acceptable excipient.

13. A method of treating, delaying onset of, or reducing risk of a disease, disorder or condition in a subject, the method comprising a step of administering an effective amount of the compound or the pharmaceutically acceptable salt or solvate thereof as claimed in claim 1 to the subject, thereby treating, delaying onset of, or reducing risk of the disease, disorder or condition, wherein the disease, disorder or condition is responsive to NLRP3 inhibition.

14. The method as claimed in claim 13, wherein the disease, disorder or condition is selected from:
  (i) inflammation;
  (ii) an auto-immune disease;
  (iii) cancer;
  (iv) an infection;
  (v) a central nervous system disease;
  (vi) a metabolic disease;
  (vii) a cardiovascular disease;
  (viii) a respiratory disease;
  (ix) a liver disease;
  (x) a renal disease;
  (xi) an ocular disease;
  (xii) a skin disease;
  (xiii) a lymphatic condition;
  (xiv) a psychological disorder;
  (xv) graft versus host disease;
  (xvi) allodynia; or
  (xvii) any disease where an individual has been determined to carry a germline or somatic non-silent mutation in NLRP3.

15. The method as claimed in claim 13, wherein the disease, disorder or condition is selected from:
  (i) cryopyrin-associated periodic syndromes (CAPS);
  (ii) Muckle-Wells syndrome (MWS);
  (iii) familial cold autoinflammatory syndrome (FCAS);
  (iv) neonatal onset multisystem inflammatory disease (NOMID);

(v) familial Mediterranean fever (FMF);
(vi) pyogenic arthritis, pyoderma gangrenosum and acne syndrome (PAPA);
(vii) hyperimmunoglobulinemia D and periodic fever syndrome (HIDS);
(viii) Tumour Necrosis Factor (TNF) Receptor-Associated Periodic Syndrome (TRAPS);
(ix) systemic juvenile idiopathic arthritis;
(x) adult-onset Still's disease (AOSD);
(xi) relapsing polychondritis;
(xii) Schnitzler's syndrome;
(xiii) Sweet's syndrome;
(xiv) Behcet's disease;
(xv) anti-synthetase syndrome;
(xvi) deficiency of interleukin 1 receptor antagonist (DIRA); or
(xvii) haploinsufficiency of A20 (HA20).

16. The method as claimed in claim 13, wherein the compound or the pharmaceutically acceptable salt or solvate thereof is administered as a pharmaceutical composition further comprising a pharmaceutically acceptable excipient.

17. A method of inhibiting NLRP3 in a subject, comprising administering the compound or the pharmaceutically acceptable salt or solvate thereof as claimed in claim 1 to the subject thereby inhibiting NLRP3.

18. A method of analysing inhibition of NLRP3 or an effect of inhibition of NLRP3 by a compound, comprising contacting a cell or non-human animal with the compound or the pharmaceutically acceptable salt or solvate thereof as claimed in claim 1, and analysing inhibition of NLRP3 or an effect of inhibition of NLRP3 in the cell or non-human animal by the compound or the pharmaceutically acceptable salt or solvate thereof.

19. A prodrug of a compound of formula (I):

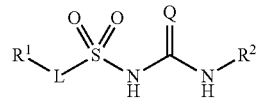

Formula (I)

or a pharmaceutically acceptable salt or solvate thereof, wherein:

Q is O;

L is a $C_1$-$C_{12}$ hydrocarbylene group which is saturated or aromatic or a combination thereof, wherein the hydrocarbylene group may be straight-chained or branched, or include cyclic groups, wherein the hydrocarbylene group may optionally be substituted, and wherein the hydrocarbylene group may optionally include one or more heteroatoms N, O or S in its carbon skeleton;

$R^1$ is $-NR^3R^4$, $-OR^5$, $-C(=NR^6)R^7$, $-(CO)R^8$, $-CN$, $-N_3$, a quaternary ammonium group and its counterion, or an optionally substituted heterocycle;

$R^3$, $R^4$, $R^5$, $R^6$, $R^7$ and $R^8$ are each independently hydrogen or a saturated or unsaturated $C_1$-$C_{10}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton;

or L and $R^3$, or L and $R^4$, or $R^3$ and $R^4$ together with the nitrogen atom to which they are attached form a 3- to 12-membered saturated or unsaturated cyclic group, wherein the cyclic group may optionally be substituted;

or L and $R^5$ together with the oxygen atom to which they are attached form a 3- to 12-membered saturated or unsaturated cyclic group, wherein the cyclic group may optionally be substituted;

or L and $R^6$, or L and $R^7$, or $R^6$ and $R^7$ together with the $-(C=N)-$ group to which they are attached form a 3- to 12-membered saturated or unsaturated cyclic group, wherein the cyclic group may optionally be substituted;

or L and $R^8$ together with the $-(C=O)-$ group to which they are attached form a 3- to 12-membered saturated or unsaturated cyclic group, wherein the cyclic group may optionally be substituted; and $R^2$ is a cyclic group substituted at the α and α' positions, wherein $R^2$ may optionally be further substituted;

provided that the atom of L which is attached to the sulfur atom of the sulfonylurea group is a carbon atom and is not a ring atom of any cyclic group; and provided that the compound of formula (I) is not

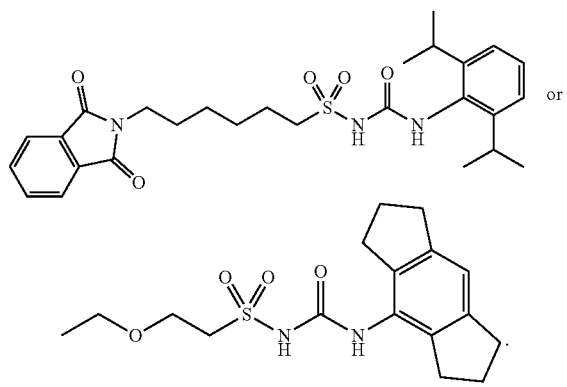

20. A method of treating, delaying onset of, or reducing risk of a disease, disorder or condition in a subject, the method comprising a step of administering an effective amount of the prodrug or the pharmaceutically acceptable salt or solvate thereof as claimed in claim 19 to the subject, thereby treating, delaying onset of, or reducing risk the disease, disorder or condition, wherein the disease, disorder or condition is responsive to NLRP3 inhibition.

* * * * *